(12) United States Patent
Smith

(10) Patent No.: US 7,759,367 B2
(45) Date of Patent: Jul. 20, 2010

(54) PHARMACEUTICAL COMPOSITIONS AND THEIR USES

(75) Inventor: Terence Smith, Truro (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 1389 days.

(21) Appl. No.: 10/497,518

(22) PCT Filed: Dec. 6, 2002

(86) PCT No.: PCT/GB02/05542

§ 371 (c)(1),
(2), (4) Date: Feb. 9, 2005

(87) PCT Pub. No.: WO03/047577

PCT Pub. Date: Jun. 12, 2003

(65) Prior Publication Data

US 2006/0100249 A1     May 11, 2006

(30) Foreign Application Priority Data

Dec. 6, 2001    (GB) ................................ 0129260.6

(51) Int. Cl.
*A61K 31/44*    (2006.01)
*C07D 213/62*    (2006.01)
*C07D 213/78*    (2006.01)

(52) U.S. Cl. ........................ 514/351; 514/345; 546/298
(58) Field of Classification Search ................. 514/351; 546/298
See application file for complete search history.

(56) References Cited

U.S. PATENT DOCUMENTS

| 5,972,919 | A | * | 10/1999 | Carling et al. | ............... 514/171 |
| 6,133,255 | A | | 10/2000 | Harrison et al. | |
| 6,403,596 | B1 | * | 6/2002 | Liverton et al. | ............. 514/256 |
| 6,734,212 | B2 | * | 5/2004 | Zhu et al. | ................... 514/535 |
| 7,309,810 | B2 | * | 12/2007 | Takai et al. | ..................... 800/3 |

FOREIGN PATENT DOCUMENTS

| DE | 19643037 A1 | 4/1998 |
| EP | 0802195 A2 | 10/1997 |
| JP | 52-83761 A | 7/1977 |
| JP | 55-31072 A | 3/1980 |
| JP | 10-504285 A | 4/1998 |
| RU | 2166959 | 4/1995 |
| WO | WO 94/25469 A1 | 11/1994 |
| WO | WO 95/01357 A1 | 1/1995 |
| WO | WO-95/35308 A1 | 12/1995 |
| WO | WO 96/10023 A1 | 4/1996 |
| WO | WO 96/33974 A1 | 10/1996 |
| WO | WO 97/18163 A1 | 5/1997 |
| WO | WO 97/28135 A1 | 8/1997 |
| WO | WO 97/34878 A1 | 9/1997 |
| WO | WO 97/43276 A1 | 11/1997 |
| WO | WO 98/38173 A1 | 9/1998 |
| WO | WO 98/50384 A1 | 11/1998 |
| WO | WO 98/55480 A1 | 12/1998 |
| WO | WO 99/31062 A1 | 6/1999 |
| WO | WO 00/01376 A2 | 1/2000 |
| WO | WO 00/07988 A1 | 2/2000 |
| WO | WO 01/96308 A1 | 12/2001 |

OTHER PUBLICATIONS

Rothuizen et al. Journal of Neuroimmunology. 1999, vol. 99, Issue 1, pp. 131-141.*
Ransohoff, R.M. Journal of Clinical Investigation. 2006, vol. 116, No. 9, pp. 2313-2316.*
Vippagunta et al. Advanced Drug Delivery Reviews. 2001, vol. 48, pp. 3-26.*
Rosenberg et al., Proc. Natl. Acad. Sci, vol. 88, pp. 4865-4869, (1991).
Smith et al., Neuroreport, vol. 5, pp. 1009-1011, (1994).
Dreyer et al., E. J. of Neuroscience, vol. 7, pp. 2502-2507, (1995).
Ushijima et al., E. J. of Neuroscience, vol. 7, pp. 1353-1359, (1995).
Sindou et al., J. of Neurological Sciences, vol. 126, pp. 133-137, (1994).
Muller et al., E. J. of Pharmacology, vol. 226, pp. 209-214, (1992).
Lipton, S., Neurology, vol. 42, pp. 1403-1405, (1992).
Hardin-Pouzet et al., GLIA, vol. 20, pp. 79-85, (1997).
Gahring et al., Neurology, vol. 48, pp. 494-500, (1997).
Brusa et al., Science, vol. 270, pp. 1677-1680, (1995).
Sheardown et al., Science, vol. 247, pp. 571-574.
Turski et al., J. of Pharm. and Exp. Therapeutics, vol. 260, No. 2, pp. 742-747, (1992).
Kotlinska et al., Pharm. Bio. and Behavior, vol. 60, No. 1, pp. 119-124, (1998).
Yoshiyama et al., J. of Pharm. and Exp. Therapeutics, vol. 280, No. 2, pp. 894-904, (1997).
Gray et al., Neuroscience Letters, vol. 268, pp. 127-130, (1999).
Fujita et al., Yakugaku Zasshi, vol. 110, No. 6, pp. 449-452, (1990), Abstract only.
Castillo et al., The Lancet, vol. 349, pp. 79-83, (1997).
Nadin et al., Tetrahedron Letters, vol. 40, pp. 4073-4076, (1999).
Meldrum, B., Brain Research Reviews, vol. 18, pp. 293-314, (1993).
Arias et al., J. of Neuro. Research, vol. 41, pp. 561-566, (1995).
Cha et al., Neuroscience Letters, vol. 132, pp. 55-58, (1991).
Nelson et al., Proc. Natl. Acad. Sci., vol. 87, pp. 269-273, (1990).
Earl et al., Journal of Organic Chemistry, vol. 49, pp. 4786-4800 (1984).
Adachi et al., Chemical Abstracts, vol. 131, Abstract No. 58848, 1999 (abstract of WO 99/31062).
El-Kholy et al., Journal of the Chemical Society, pp. 4490-4498, 1961.
Fujita et al., Yakugaku Zasshi, vol. 110, No. 6, pp. 449-452, (1990).
D. A. Kharkevich, Pharmacology, Moscow, Meditsina, 1987, pp. 47-48.

(Continued)

Primary Examiner—Sreeni Padmanabhan
Assistant Examiner—Samira Jean-Louis
(74) Attorney, Agent, or Firm—Birch, Stewart, Kolasch & Birch, LLP

(57) ABSTRACT

The present invention relates to compositions comprising 1,2-dihydropiridin-2-one compounds and an immunoregulatory or anti-inflammatory agent. The compositions are useful for the prevention or the treatment of neurodegenerative diseases, for example demyelinating disorders.

22 Claims, 2 Drawing Sheets

OTHER PUBLICATIONS

Figure 1:
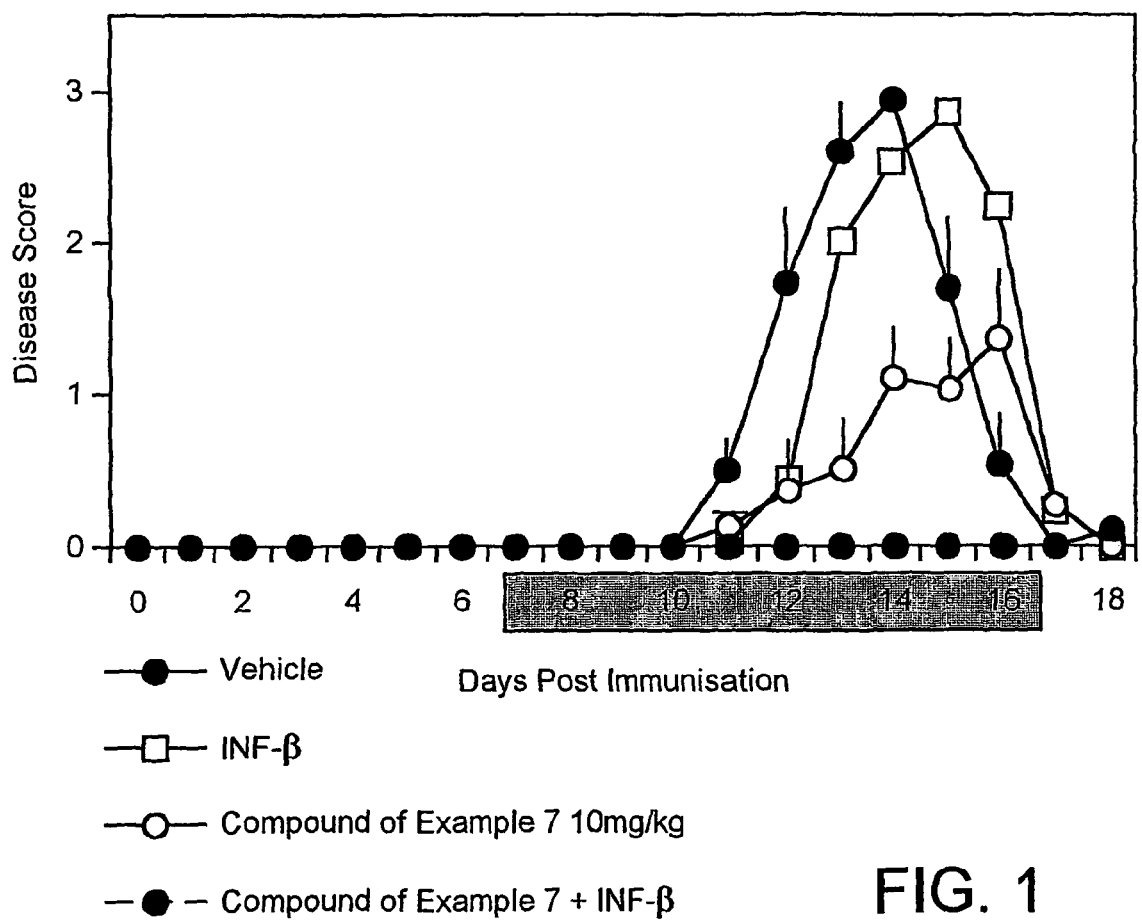

D.G. Belikov, Pharmaceutical Chemistry, Moscow, Vyshaya Shkola, 1993, vol. 1, pp. 43 to 47.

Prineas et al, "Demyelinating Diseases," in Greenfield's Neuropathology, Vol. 2, Chapter 13, eds. Graham et al., pp. 813-896 (Arnold, London, 1997).

Lassmann, "Cellular Damage and Repair in Multiple Sclerosis," in Myelin Biology and Disorders, ed. Lazzarina, vol. 2, pp. 733-762 (Elsevier Academic Press, 2004).

Wekerle et al., "Animal Models," *Ann. Neurol.*, 36:S47-S53 (1994).

* cited by examiner

PHARMACEUTICAL COMPOSITIONS AND THEIR USES

The present invention relates inter alia to the treatment of demyelinating disorders and neurodegenerative diseases and to compositions for such use.

The majority of excitatory synaptic responses in mammalian CNS are elicited by amino acids such as L-glutamate or L-aspartate, which participate in nerve functions including recognition, memory, movement, respiration, cardiovascular adjustment and sensation. In the expression of their physiological activity, an interaction with a specific receptor is important. These receptors can be classified into four different receptor subtypes. Three of these receptors are coupled to ionophores and are known as the N-methyl-D-aspartate (NMDA), the AMPA (α-amino-3-hydroxy-5-methyl-4-isoxazole-propionate), and the kainate receptors. The fourth receptor subtype is linked to phosphoinositol metabolism and is known as the metabotropic glutamate receptor.

The NMDA receptor is coupled to high conductance channels permeable to $Na^+$, $K^+$, and $Ca^{2+}$. It is modulated by glycine (coagonist) and polyamines (positive modulator) and is blocked in a use- and voltage dependent manner by $Mg^{2+}$. The functional NMDA receptor is thought to be formed as a pentameric subunit assembly consisting of subunit selection from NR1 (eight isoforms) and NR2 (four isoforms) families. The type of subunits forming the NMDA channel determine its biophysical properties and physiological function. The AMPA and kainate receptors are permeable to $Na^+$ and $K^+$ AMPA receptor-dependent ion channel is formed from four different subunits designated as GluR1 to GluR4 (in two alternative splice variants—flip and flop) in a tetrameric subunit assembly. Pharmacological properties of AMPA receptor-dependent ion channels are determined by the selection of subunits. Channel assemblies lacking GluR2 subunits are permeable to $Ca^{2+}$ in addition to $Na^+$- and $K^+$-permeability. In situ hybridization has revealed different expression of glutamate receptor subunits throughout the brain and during development.

The amino acid as an excitatory neurotransmitter has been known to induce neurotoxicity by, for example, abnormal excitation of central nerves. It has been noted that the said toxicity is as serious as being accompanied by the death of nerve cells causing various nervous diseases. Main nervous diseases which have been known are cerebral ischemia, head injury, spinal injury, Alzheimer's disease, Parkinson's disease, amyotrophic lateral sclerosis (ALS), Huntington's chorea, AIDS nervous disturbance, epilepsy, neurodegeneration observed after the state of hypoxia, mental disorder, mobility disturbance, pain, spasticity, nervous disturbance by toxin in food, various neurodegenerative diseases, various mental diseases, chronic pain, migraine, carcinomatous pain and pain caused by diabetic nervous disturbance. They are serious diseases where many mechanisms of onset, etc. have not yet been clarified and effective therapeutic pharmaceutical agents have not yet been found, but it is believed that they are closely related to excessive release/accumulation of excitatory neurotransmitters, changes in expressing pattern of receptors, etc. For example, it has been reported that glutamate concentration in cerebrospinal fluid increases in stroke, cerebral ischemia, head injury and spinal injury. There is a report that neuropathy occurs when glutamate, NMDA, AMPA, kainate, etc. are excessively applied to nerve cells. There are reports that, in Alzheimer's disease, β-amyloid protein enhances the neurotoxicity of glutamate and that it promotes the release of glutamate. In the case of Parkinson's disease, there are reports that L-dopa hydroxide activates the AMPA receptor and enhances the neurotoxicity. There is another report that L-dopa promotes the generation of free radicals resulting in a rise of oxidative stress. In the case of Huntington's chorea, it is reported that a substance which inhibits the release of glutamate is effective in improving the symptoms. In the case of ALS, there are many reports showing the participation of glutamate in its pathology. There are some cases where the AIDS patients suffer from recognition nerve function deficiency and, even in such a nerve disease, participation of glutamate is suggested. For example, it is reported that gp 120 which is a glycoprotein in an envelope of HIV virus suppresses the incorporation of glutamate by astrocytes while a substance which inhibits the release of glutamate suppresses the neurodegeneration by gp 120. With regard to allergic encephalomyelitis, there is a report that, in the mice where the said inflammation takes place, enzyme which decomposes glutamate incorporated from outside of cells is deficient. Olivopontocerebellar atrophy is a disease which is sometimes combined with Parkinson's disease and an antibody to GluR2 which is a subunit constituting the AMPA receptor has been found and the relation between olivopontocerebellar atrophy and AMPA receptor is suggested. With regard to a report for epilepsy, it is reported that, in the mice which are unable to construct the GluR2 in AMPA receptor, $Ca^{2+}$ permeability of the AMPA receptor increases whereby it is apt to cause a sudden onset resulting in death. Besides the above, it is reported that NBQX (2,3-dihydroxy-6-nitro-7-sulfamoylbenz[f]quinoxaline) and other inhibiting compounds to AMPA receptors have antianxiety and anticonvulsant action and there is also a report for the connection of AMPA receptor/kainate receptor with urinary disturbance, drug abuse, pain, etc.

Therapeutic approaches to neurodegerative diseases and demyelinating disorders have proven largely unsatisfactory despite, in the case of the latter, the use of immunosuppressive agents such as corticosteroids and cyclophosphamide, which although providing limited benefit to patients, can be associated with potentially serious side effects. The introduction of interferon preparations has provided efficacy in the treatment of certain demyelinating disorders (e.g. multiple sclerosis). The beneficial effects are related to the immunomodulatory actions of the interferons. However, as benefits are apparent in only a portion of the subgroup of patients classified as suitable for treatment, then the problem remains that management of the disease remains insufficient with such preparations. The limited efficacy of current immunomodulatory therapies in demyelinating disorders (e.g. multiple sclerosis) may be related the failure of these agents to combat the oligodendroglial, neuronal and axonal degeneration associated with the disease.

It can be expected that the substances showing an antagonistic action to excitatory neurotransmitters are useful for the therapy of the above-mentioned diseases. It is presently expected that substances having an antagonistic action to non-NMDA receptors such as AMPA receptor and kainate receptor will be particularly useful. For example, it is reported that inhibitors of the interaction of glutamate with the AMPA and/or kainate receptor complex are useful in treating demyelinating disorders (WO00/01376). In addition it is reported that AMPA and/or kainate receptor antagonists were effective in ameliorating experimental autoimmune encephalomyelitis (EAE), an animal model which reproduces many of the pathological and clinical features of multiple sclerosis. Whilst the neuroprotective potential of AMPA and/or kainate receptor antagonists is recognised in the neuronal/axonal degeneration resulting from hypoxia/ischemia, hypoglycemia, convulsions and head or spinal cord trauma, these data

[WO00/01376] were the first to provide evidence in support of the involvement of glutamate in the pathogenesis of demyelinating disorders. In addition, the improved clinical outcome in EAE associated with AMPA and/or kainate receptor antagonist therapy was independent of anti-inflammatory or immunomodulatory effects, suggesting an alternative mechanism of action involving oligodendroglial and neuronal/axonal protection.

A solution to the problem of the lack of clinical efficacy of current therapies in demyelinating disorders is to use a combination of an immunoregulatory or anti-inflammatory agent and a neuroprotective, axonal protective and/or oligodendroglial protective agent. Thus, an object of the present invention is to investigate and find compounds which inhibit AMPA receptor(s) and/or kainate receptor(s) which when combined with an immuomodulatory or anti-inflammatory agent suppresses the neurotoxicity, axonal toxicity and oligodendroglial toxicity of excitatory neurotransmitters and achieves a protective action as pharmaceutical agents being useful as therapeutic, preventing or improving agents for various neurodegenerative and demyelinating diseases.

The present inventors have now provided evidence (whereby the reversal of paralysis in an in vivo model of a demyelinating and neurodegenerative disorder is achieved) in support of the pronounced clinical benefit in the therapy of neurodegenerative and demyelinating disorders using a combination of an AMPA and/or kainate receptor antagonist with an immunoregulatory agent, which is greater than the anticipated additive effect of either agent alone.

Thus in one aspect the invention provides a composition comprising
I) a compound as described in the text herein, and
II) an immunoregulatory or an anti-inflammatory agent.

Compounds of the present invention include 1,2-dihydropyridin-2-one compounds such as e.g. 3-(2-Cyanophenyl)-1-phenyl-5-(2-pyridyl)-1,2-dihydropyridin-2-one, 3-(2-Cyanophenyl)-5-(2-pyridyl)-1-(3-pyridyl)-1,2-dihydropyridin-2-one, 3-(2-Fluoro-3-pyridyl)-5-(2-pyridyl)-1-phenyl-1,2-dihydropyridin-2-one, 3-(2-Fluoro-3-pyridyl)-5-(2-pyridyl)-1-(3-pyridyl)-1,2-dihydropyridin-2-one, 3-(2-Cyanophenyl)-1-phenyl-5-(2-pyrimidinyl)-1,2-dihydropyridin-2-one, 3-(2-Cyanophenyl)-1-(3-pyridyl)-5-(2-pyrimidinyl)-1,2-dihydropyridin-2-one, 3-(2-Fluoropyridin-3-yl)-1-phenyl-5-(2-pyrimidinyl)-1,2-dihydropyridin-2-one, 3-(2-Cyanopyridin-3-yl )-1-phenyl-5-(2-pyrimidinyl)-1,2-dihydropyridin-2-one.

Further compounds of the invention and their synthesis are described below and in the accompanying representative examples.

The composition, as defined herein, may further comprise a pharmaceutically acceptable carrier or excipient.

According to the present invention immunoregulation can be defined as the control of specific immune responses and interactions between cells of lymphoid and myeloid lineage; in addition immunoregulation can include immunosuppression and immunomodulation, where immunosuppression can be defined as the prevention or interference with the development of an immunologic response and can include myelosuppression, and where immunomodulation can be defined as the adjustment of the immune response to a desired level. According to the present invention anti-inflammatory can be defined as the reduction of inflammation. Immunoregulatory or anti-inflammatory agents according to the invention can be e.g. an interferon (IFN; IFN-beta-1a e.g. Rebif and Avonex; IFN-beta-1b e.g., Betaseron and Betaferon; IFN-alpha-2a e.g. Alphaferone; IFN-alpha-2b e.g. Viraferon), a corticotrophin (e.g. Acthar; Cortrosyn), a synthetic steriod (e.g. dexamethasone e.g. Decadron; prednisolone e.g. Delta-Cortef; methylprednisolone e.g. A-Methapred, Solu-Medreol), a chemotherapeutic agent (e.g. mitozantrone e.g. Novantrone; cyclophosphamide e.g. Cytoxan, Neosar; paclitaxel e.g. Taxol; methotrexate e.g. Floex), azothioprine (e.g.Imuran), cyclosporine (e.g. Sandimmune, Neoral), penicillamine (e.g. Depen), aphosophodiesterase inhibitor (e.g. Cilomilast, Roflumilast), an antibody or vaccine against a leukocyte, endothelial or glial cell surface molecule (e.g. an integrin or adhesion molecule (e.g. Antegren (natalizumab)); T-cell receptor or costimulatory molecule) a synthetic polypeptide (e.g. glatiramer acetate, copolymer-1, Copaxone; alteredpeptide ligand) a tolerance-inducing agent (e.g. myelin basic protein), a tissue matrix metalloproteinase MMP inhibitor (e.g. hydroxamic acid-based inhibitors of MMPs), a cytokine or chemokine inhibitor or receptor antagonist (e.g. tumour necrosis factor (TNF) inhibitor e.g. Thalidomide; a TNF-receptor immunoglobulin fusion protein), a non-steroidal anti-inflammatory agent (e.g. an inhibitor of a phospholipase, cyclo-oxygenase (e.g. salicylic acid, acetaminiphen, indomethacin (e.g. Indocin), suldinac (e.g. Clinoril), femanates (e.g. Ponstel, Tolectin, Toradol, Voltarin), Arylproprionic acid derivatives (e.g. Ibuprofen, Naproxen), rofecoxib (e.g. Vioxx), celecoxib (e.g. Celebrex)) or lippoxygense (e.g. Zileuton; a receptor antagonist of a leukotriene (e.g., Zafirlukast, Motelukast), prostaglandin, platelet activating factor (PAF) thomboxane (e.g. Seratrodast); an anti-histamine).

Thus, in a further aspect, the invention provides a composition as defined herein, for use in the prevention or treatment neurodegenerative disease. All references to neurodegenerative disease may be acute or chronic. Compositions of the present invention may be used in human and veterinary medicine. Treatments may be prophylactic or may be in respect of existing conditions. Accordingly, the compositions of the present invention are useful in the therapeutic, prevention and improvement of various nervous diseases and are useful, for example, as therapeutic and preventive agents for acute neurodegenerative diseases (such as cerebral vascular accident of acute stage, head injury, spinal injury (such as spinal cord lesion), neuropathy by hypoxia or hypoglycemia), chronic neurodegenerative diseases (such as Alzheimer's disease, Parkinson's disease, Huntington's chorea, amyotrophic lateral sclerosis and spinocerebellar degeneration), epilepsy, hepatic enephalopathy, peripheral neuropathy, Parkinson's syndrome, spastic paralysis, pain, neuralgia, schizophrenia, anxiety, drug abuse, nausea, vomiting, urinary disturbance, visual disturbance (paropsia) due to glaucoma, auditory disturbance (paracusis) due to antibiotics, food poisoning, infectious encephalomyelitis (such as cerebrospinal meningitis (e.g. HIV cerebrospinal meningitis)), cerebrovascular dementia, dementia or nervous symptoms due to meningitis.

In this text, the neurodegenerative disease can be a demyelinating disorder. The term "demyelinating disorder" is used herein to include any disorder that results in a reduced level of myelination for example, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV-myelopathy, HTLV-myelopathy, progressive multifocal leucoencephalopathy, or a secondary demyelinating disorder—i.e. where bystander myelin loss occurs as a consequence of a secondary pathological insult. Examples of secondary demyelinating diseases are CNS lupus erythematodes, polyarteritis nodosa, Sjoegren's syndrome, sarcoid granuloma or isolated cerebral vasculitis.

Indeed, neurodegeneration, the major correlate of permanent clinical disability in multiple sclerosis occurs acutely during active demyelinating and can lead to in excess of 75% axonal loss in the chronic phase of disease. Similarly, neuronal and axonal degeneration are also a pathological component of the acute and chronic EAE models.

The compound of the present invention herein and an immunoregulatory or anti-inflammatory agent can be used separately, simultaneously or sequentially to treat a neurodegenerative disease, for example a demyelinating disorder. It can provide synergistically effective combination.

Throughout this text, the prevention and/or treatment of any disease or disorder means any effect which mitigates any damage or any medial disorder, to any extend, and includes preventions and/or treatments themselves. Further, the term 'treatment' means any amelioration of disease, disorder, syndrome, condition, pain, symptom, or a combination of two or more thereof.

Therefore, the invention further provides use of a compound as described herein and an immunoregulatory or anti-inflammatory agent in the manufacture of a medicament for the prevention or treatment of neurodegenerative disease. The neurodegenerative disease can be a demyelinating disorder. In such use, the compound as described herein and the immunoregulatory or anti-inflammatory agent can be administered separately, simultaneously or sequentially.

Further provided is a method for the prevention or treatment of neurodegenerative disease, the method comprising administration to a patient, a composition as defined herein. The patient is preferably in need of such administration. The methods of the invention can be carried out to prevent or treat, for example, a demyelinating disorder. In such methods the immunoregulatory or anti-inflammatory agent can be administered separately, simultaneously or sequentially.

The compositions of the present invention are administered, or used, or manufactured for use in a quantity sufficient to prevent and/or treat the symptoms of the condition, disease or disorder. For all aspects of the invention, particularly medical ones, the administration of the composition has a dosage regime which will ultimately be determined by the attending physician and will take into consideration such factors as the compound being used, animal type, age, weight, severity of symptoms, method of administration, adverse reactions and/or other contraindications. Specific dosage ranges can be determined by standard design clinical trials with patient progress and recovery being fully monitored. Such trials may use an escalating dose design using a low percentage of the maximum tolerated doses in animals as the starting dose in man.

The physiologically acceptable compounds, in compositions of the invention may be administered for periods of continuous therapy, for example a week or more, a month or more, a year or more, or indefinitely.

A still further aspect of the invention provides a kit comprising: a first container comprising a compound as defined herein according to the invention and a second container comprising an immunoregulatory or anti-inflammatory agent, optionally with instructions for use and which kit can further comprise a pharmaceutically acceptable carrier or excipient (combined with the compound in the first container and/or the agent in the second container, or separate to both).

Compounds of the invention can be represented by the following formula, a salt thereof or hydrates thereof.

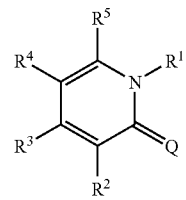

(I)

In the formula, Q indicates NH, O or S; and $R^1$, $R^2$, $R^3$, $R^4$ and $R^5$ are the same as or different from each other and each indicates hydrogen atom, a halogen atom, a $C_{1-6}$ alkyl group or a group represented by the formula —X-A (wherein X indicates a single bond, an optionally substituted $C_{1-6}$ alkylene group, an optionally substituted $C_{2-6}$ alkenylene group, an optionally substituted $C_{2-6}$ alkynylene group, —O—, —S—, —CO—, —SO—, —$SO_2$—, —N($R^6$)—, —N($R^7$)—CO—, —CO—N($R^8$)—, —N($R^9$)—$CH_2$—, —$CH_2$—N($R^{10}$)—, —$CH_2$—CO—, —CO—$CH_2$—, —N($R^{11}$)—S(O)$_m$—, —S(O)$_n$—N($R^{12}$)—, —$CH_2$—S(O)$_p$—, —S(O)$_q$—$CH_2$—, —$CH_2$—O—, —O—$CH_2$—, —N($R^{13}$)—CO—N($R^{14}$)— or —N($R^{15}$)—CS—N($R^{16}$)— (wherein $R^6$, $R^7$, $R^8$, $R^9$, $R^{10}$, $R^{11}$, $R^{12}$, $R^{13}$, $R^{14}$, $R^{15}$ and $R^{16}$ indicate hydrogen atom, a $C_{1-6}$ alkyl group or a $C_{1-6}$ alkoxy group; and m, n, p and q indicates an integer of 0, 1 or 2 independently); and A indicates a $C_{3-8}$ cycloalkyl group, a $C_{3-8}$ cycloalkenyl group, a 5 to 14 membered non-aromatic heterocyclic group, a $C_{6-14}$ aromatic hydrocarbocyclic group, or a 5 to 14 membered aromatic heterocyclic group which may be substituted respectively, provided that 3 groups among $R^1$, $R^2$, $R^3$, $R^4$ and $R^5$ are always the same as or different from each other and each indicates —X-A; and the residual 2 groups always indicate hydrogen atom, a halogen atom or a $C_{1-6}$ alkyl group). In the above-mentioned definition, the cases where (1) Q is O; $R^1$ and $R^5$ are hydrogen atoms; and $R^2$, $R^3$ and $R^4$ are phenyl groups, (2) Q is O; $R^1$ and $R^4$ are hydrogen atoms; and $R^2$, $R^3$ and $R^5$ are phenyl groups, and (3) Q is O; $R^1$ and $R^2$ are hydrogen atoms; and $R^3$, $R^4$ and $R^5$ are phenyl groups, are excluded.

That is, the present invention relates to (1) the compound represented by the above formula (I), a salt thereof or hydrates thereof; (2) the compound according to the above (1), a salt thereof or hydrates thereof, which is represented by the formula:

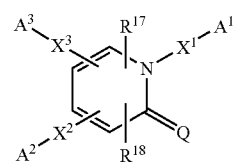

(II)

wherein Q indicates NH, O or S; $X^1$, $X^2$ and $X^3$ are the same as or different from each other and each indicates a single bond, an optionally substituted $C_{1-6}$alkylene group, an optionally substituted $C_{2-6}$ alkenylene group, an optionally substituted $C_{2-6}$ alkynylene group, —O—, —S—, —CO—, —SO—, —$SO_2$—, —N($R^6$)—, —N($R^7$)—CO—, —CO—N($R^8$)—, —N($R^9$)—$CH_2$—, —$CH_2$—N($R^{10}$)—, —$CH_2$—CO—, —CO—$CH_2$—, —N($R^{11}$)—S(O)$_m$—, —S(O)$_n$—N($R^{12}$)—, —$CH_2$—S(O)$_p$—, —S(O)$_q$—$CH_2$—, —$CH_2$—O—, —O—$CH_2$—, —N($R^{13}$)—CO—N($R^4$)— or —N(R$^{15}$)—CS—N(R$^{6}$)— (wherein R$^{6}$, R$^{7}$, R$^{8}$, R$^{9}$, R$^{10}$, R$^{11}$, R$^{12}$, R$^{13}$, R$^{14}$, R$^{15}$ and R$^{16}$ indicate hydrogen atom, a C$_{1-6}$ alkyl group or a C$_{1-6}$ alkoxy group; and m, n, p and q are independent of each other and each indicates an integer of 0, 1 or 2); A$^{1}$, A$^{2}$ and A$^{3}$ are the same as or different from each other and each indicates an optionally substituted C$_{3-8}$ cycloalkyl group, C$_{3-8}$ cycloalkenyl group, 5 to 14-membered non-aromatic heterocyclic group, C$_{6-14}$ aromatic hydrocarbocyclic group or 5 to 14-membered aromatic heterocyclic group; and R$^{17}$ and R$^{18}$ are the same as or different from each other and each indicates hydrogen atom, a halogen atom or a C$_{1-6}$ alkyl group; (3) the compound according to the above (2), a salt thereof or hydrates thereof, wherein X$^{1}$, X$^{2}$ and X$^{3}$ are (1) single bond, (2) a C$_{1-6}$ alkylene group, a C$_{2-6}$ alkenylene group or a C$_{2-6}$ alkynylene group which may be optionally substituted respectively with one or more groups selected from the following substituent group a, (3) —O—, (4) —S—, (5) —CO—, (6) —SO—, (7) —SO$_{2}$—, (8) —N(R$^{6}$)—, (9) —N(R$^{7}$)—CO—, (10) —CO—N(R$^{8}$)—, (11) —N(R$^{9}$)—CH$_{2}$—, (12) —CH$_{2}$—N(R$^{10}$)—, (13) —CH$_{2}$—CO—, (14) —CO—CH$_{2}$—, (15) —N(R$^{11}$)—S(O)$_{m}$—, (16) —S(O)$_{n}$—N(R$^{12}$)—, (17) —CH$_{2}$—S(O)$_{p}$—, (18) —S(O)$_{q}$—CH$_{2}$—, (19) —CH$_{2}$—O—, (20) —O—CH$_{2}$—, (21) —N(R$^{13}$)—CO—N(R$^{14}$)— or (22) —N(R$^{15}$)—CS—N(R$^{16}$)—(wherein R$^{6}$, R$^{7}$, R$^{8}$, R$^{9}$, R$^{10}$, R$^{11}$, R$^{12}$, R$^{13}$, R$^{14}$, R$^{15}$ and R$^{16}$, m, n, p and q have the same meanings as defined above); and A$^{1}$, A$^{2}$ and A$^{3}$ are a C$_{3-8}$ cycloalkyl group, a C$_{3-8}$ cycloalkenyl group, a 5- to 14-membered non-aromatic heterocyclic group, a C$_{6-14}$ aromatic hydrocarbocyclic group or a 5- to 14-membered aromatic heterocyclic group which may be optionally substituted with one or more groups selected from the following substituent group b (the substituent group a: the group consisting of hydroxy group, a halogen atom and nitrile group; and the substituent group b: the group consisting of (1) hydroxy group, (2) a halogen atom, (3) nitrile group, (4) nitro group, (5) a C$_{1-6}$ alkyl group, a C$_{2-6}$ alkenyl group or a C$_{2-6}$ alkynyl group which may be optionally substituted respectively with one or more groups selected from the group consisting of hydroxy group, nitrile group, a halogen atom, a C$_{1-6}$ alkylamino group, a di-(C$_{1-6}$ alkyl)amino group, a C$_{2-6}$ alkenylamino group, a di(C$_{2-6}$ alkenylamino) group, a C$_{2-6}$ alkynylamino group, a di(C$_{2-6}$ alkynylamino) group, an N—C$_{1-6}$ alkyl-N—C$_{2-6}$ alkenylamino group, an N—C$_{1-6}$ alkyl-N—C$_{2-6}$ alkynylamino group, an N—C$_{2-6}$ alkenyl-N—C$_{2-6}$ alkynylamino group, an aralkylamino group, a TBDMS oxy group, a C$_{1-6}$ alkylsulfonylamino group, a C$_{1-6}$ alkylcarbonyloxy group, a C$_{2-6}$ alkenylcarbonyloxy group, a C$_{2-6}$ alkynylcarbonyloxy group, an N—C$_{1-6}$ alkylcarbamoyl group, an N—C$_{2-6}$ alkenylcarbamoyl group and an N—C$_{1-6}$ alkynylcarbamoyl group, (6) a C$_{1-6}$ alkoxy group, a C$_{2-6}$ alkenyloxy group or a C$_{2-6}$ alkynyloxy group which may be optionally substituted respectively with one or more groups selected from the group consisting of a C$_{1-6}$ alkylamino group, an aralkyloxy group and hydroxy group, (7) a C$_{1-6}$ alkylthio group, a C$_{2-6}$ alkenylthio group or a C$_{2-6}$ alkynylthio group which may be optionally substituted respectively with one or more groups selected from the group consisting of hydroxy group, nitrile group, a halogen atom, a C$_{1-6}$ alkylamino group, an aralkyloxy group, a TBDMS oxy group, a C$_{1-6}$ alkylsulfonylamino group, a C$_{1-6}$ alkylcarbonyloxy group and a C$_{1-6}$ alkylcarbamoyl group, (8) a carbonyl group substituted with a group selected from the group consisting of a C$_{1-6}$ alkoxy group, amino group, a C$_{1-6}$ alkylamino group, a di(C$_{1-6}$ alkyl) amino group, a C$_{2-6}$ alkenylamino group, a di(C$_{2-6}$ alkenyl) amino group, a C$_{2-6}$ alkynylamino group, a di(C$_{2-6}$ alkynyl) amino group, an N—C$_{1-6}$ alkyl-N—C$_{2-6}$ alkenylamino group, an N—C$_{1-6}$ alkyl-N—C$_{2-6}$ alkynylamino group and an N—C$_{2-6}$ alkenyl-N—C$_{2-6}$ alkynylamino group, (9) amino group which may be optionally substituted with one or two groups selected from the group consisting of a C$_{1-6}$ alkyl group, a C$_{2-6}$ alkenyl group, a C$_{2-6}$ alkynyl group, a C$_{1-6}$ alkylsulfonyl group, a C$_{2-6}$ alkenylsulfonyl group, a C$_{2-6}$ alkynylsulfonyl group, a C$_{1-6}$ alkylcarbonyl group, a C$_{2-6}$ alkenylcarbonyl group and a C$_{2-6}$ alkynylcarbonyl group, (10) a C$_{1-6}$ alkylsulfonyl group, (11) a C$_{2-6}$ alkenylsulfonyl group, (12) a C$_{2-6}$ alkynylsulfonyl group, (13) a C$_{1-6}$ alkylsulfinyl group, (14) a C$_{2-6}$ alkenylsulfinyl group, (15) a C$_{2-6}$ alkynylsulfinyl group, (16) a formyl group, (17) a C$_{3-8}$ cycloalkyl group or a C$_{3-8}$ cycloalkenyl group which may be optionally substituted respectively with one or more groups selected from the group consisting of hydroxy group, a halogen atom, nitrile group, a C$_{1-6}$ alkyl group, a C$_{1-6}$ alkyloxy group, a C$_{1-6}$ alkyloxy C$_{1-6}$ alkyl group and an aralkyl group, (18) a 5- to 14-membered non-aromatic heterocyclic group which may be optionally substituted with one or more groups selected from the group consisting of hydroxy group, a halogen atom, nitrile group, a C$_{1-6}$ alkyl group, a C$_{1-6}$ alkyloxy group, a C$_{1-6}$ alkyloxy C$_{1-6}$ alkyl group and an aralkyl group, (19) a C$_{6-14}$ aromatic hydrocarbocyclic group which may be optionally substituted with one or more groups selected from the group consisting of hydroxy group, a halogen atom, nitrile group, a C$_{1-6}$ alkyl group, a C$_{1-6}$ alkyloxy group, a C$_{1-6}$ alkyloxy C$_{1-6}$ alkyl group and an aralkyl group, and (20) a 5- to 14-membered aromatic heterocyclic group which may be optionally substituted with one or more groups selected from the group consisting of hydroxy group, a halogen atom, nitrile group, a C$_{1-6}$ alkyl group, a C$_{1-6}$ alkyloxy group, a C$_{1-6}$ alkyloxy C$_{1-6}$ alkyl group and an aralkyl group); (4) the compound according to the above (2), a salt thereof or hydrates thereof, wherein A$^{1}$, A$^{2}$ and/or A$^{3}$ are the same as or different from each other and each is an optionally substituted C$_{3-8}$ cycloalkyl, C$_{3-8}$ cycloalkenyl or 5- to 14-membered non-aromatic heterering; (5) the compound according to the above (2), a salt thereof or hydrates thereof, wherein A$^{1}$, A$^{2}$ and/or A$^{3}$ are the same as or different from each other and each is an optionally substituted C$_{6-14}$ aromatic hydrocarbon ring or a 5- to 14-membered aromatic heterering; (6) the compound according to the above (2), a salt thereof or hydrates thereof, wherein A$^{1}$, A$^{2}$ and A$^{3}$ are the same as or different from each other and each represents phenyl group, pyrrolyl group, pyridyl group, pyridazinyl group, pyrimidinyl group, pyrazinyl group, thienyl group, thiazolyl group, furyl group, naphthyl group, quinolyl group, iso-quinolyl group, indolyl group, benzimidazolyl group, benzothiazolyl group, benzoxazolyl group, imidazopyridyl group, carbazolyl group, cyclopentyl group, cyclohexyl group, cyclohexenyl group, dioxinyl group, adamantyl

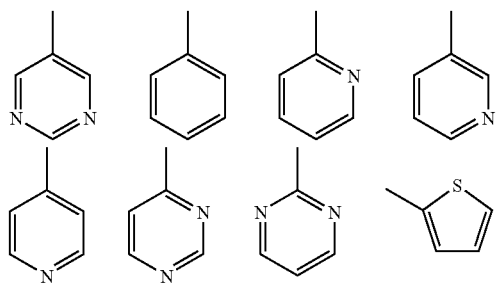

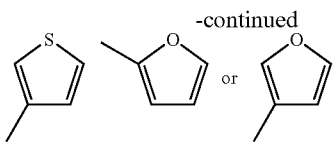

group, pyrrolidinyl group, piperidinyl group, piperazinyl group or morpholyl group which may optionally have one or more substituents, respectively; (7) the compound according to the above (2), a salt thereof or hydrates thereof, wherein $A^1$, $A^2$ and $A^3$ are the same as or different from each other and each is a group represented by the formula:

which may be substituted; (8) the compound according to the above (2), a salt thereof or hydrates thereof, wherein $A^1$, $A^2$ and $A^3$ are the same as or different from each other and each is optionally substituted with hydroxyl group, a halogen atom, amino group or nitrile group; (9) the compound according to the above (7), a salt thereof or hydrates thereof, wherein the substituents of $A^1$, $A^2$ and $A^3$ are the same as or different from each other and each is hydroxyl group, a halogen atom or, amino group, nitrile group or nitro group; (10) the compound according to the above (1) or (2), a salt thereof or hydrates thereof, wherein Q is oxygen; (11) the compound according to the above (1) or (2), a salt thereof, hydrates thereof, wherein $X^1$, $X^2$ and $X^3$ are the same as or different from each other and each represents single bond, —CH$_2$—, —CH(OH)—, —CH$_2$—CH$_2$—, —CH=CH—, —C≡C—, —O— or —CO—; (12) the compound according to the above (2), a salt thereof or hydrates thereof, wherein $X^1$, $X^2$ and $X^3$ are single bonds; (13) the compound according to the above (2), a salt thereof or hydrates thereof, wherein $R^{17}$ and $R^{18}$ are the same as or different from each other and each represents hydrogen atom, fluorine, chlorine, bromine, iodine, methyl group, ethyl group, n-propyl group or iso-propyl group; (14) the compound according to the above (2), a salt thereof or hydrates thereof, wherein $R^{17}$ and $R^{18}$ represent hydrogen atom; (15) the compound according to the above (1) or (2), a salt thereof or hydrates thereof, which is represented by the formula:

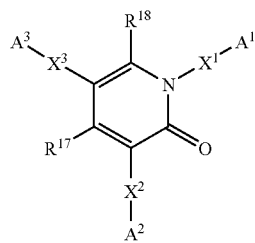

(III)

wherein $X^1$, $X^2$, $X^3$, $A^1$, $A^2$, $A^3$, $R^{17}$ and $R^{18}$ have the same meanings as defined in the above (2); (16) the compound according to the above (15), a salt thereof or hydrates thereof, wherein $A^1$, $A^2$ and $A^3$ are same as or different from each other and each represents an optionally substituted $C_{6-14}$ aromatic hydrocarbon ring or 5- to 14-membered aromatic heteroring; (16) the compound according to the above (15), a salt thereof or hydrates thereof, wherein $A^1$, $A^2$ and $A^3$ are same as or different from each other and each represents an optionally substituted $C_{6-14}$ aromatic hydrocarbon ring or 5- to 14-membered aromatic heteroring; (17) the compound according to the above (15), a salt thereof or hydrates thereof, wherein $A^1$, $A^2$ and $A^3$ are the same as or different from each other and each represents an optionally substituted phenyl group, pyrrolyl group, pyridyl group, pyridazinyl group, pyrimidinyl group, pyrazinyl group, thienyl group, thiazolyl group, furyl group, naphthyl group, quinolyl group, iso-quinolyl group, indolyl group, benzimidazolyl group, benzothiazolyl group, benzoxazolyl group, imidazopyridyl group, carbazolyl group, cyclopentyl group, cyclohexyl group, cyclohexenyl group, dioxinyl group, adamantyl group, pyrrolidinyl group, piperidinyl group, piperazinyl group or morpholyl group; (18) the compound according to the above (15), a salt thereof or hydrates thereof, wherein $A^1$, $A^2$ and $A^3$ are the same as or different from each other and each represents a group represented by the following formula:

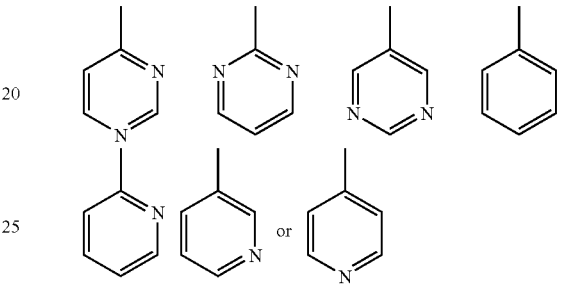

which may be substituted; (19) the compound according to the above (15), a salt thereof or hydrates thereof, wherein the bonding site of the substituent at $A^1$, $A^2$ and/or $A^3$ are α-position of the carbon atom bonding to the group $X^1$, $X^2$ and $X^3$, respectively; (20) the compound according to the above (15), a salt thereof or hydrates thereof, wherein $X^1$, $X^2$ and $X^3$ are single bonds; (21) the compound according to the above (15), a salt thereof or hydrates thereof, wherein $R^{17}$ and $R^{18}$ are hydrogen atoms; (22) the compound according to the above (1), a salt thereof or hydrates thereof, which is any one of compounds selected from: 3-(2-cyanophenyl)-5-(2-methylsulfonylaminophenyl)-1-phenyl-1,2-dihydropyridin-2-one; 3-(2-chloro-3-pyridyl)-5-(2-pyridyl)-1-phenyl-1,2-dihydropyridin-2-one; 3-(2-cyanophenyl)-5-(2-pyridyl)-1-phenyl-1, 2-dihydropyridin-2-one; 3-(2-cyanophenyl)-5-(2-pyridyl)-1-(3-nitrophenyl)-1,2-dihydropyridin-2-one; 3-(2-cyanophenyl)-5-(2-pyridyl)-1-(3-aminophenyl)-1,2-dihydropyridin-2-one; 3-(2-cyanophenyl)-5-(2-pyridyl)-1-(3-methylsulfonylaminophenyl)-1,2-dihydropyridin-2-one; 3-(2-cyanophenyl)-5-(2-pyridyl)-1-(3-methylaminophenyl)-1,2-dihydropyridin-2-one; 3-(2-cyanophenyl)-5-(2-pyridyl)-1-(3-dimethylaminophenyl)-1,2-dihydropyridin-2-one; 3-(2-cyanophenyl)-5-(2-pyridyl)-1-[3-(5-methoxymethyl-2-oxazolidinon-3-yl)-phenyl]-1,2-dihydropyridin-2-one; 3-(2-cyanophenyl)-5-(2-pyridyl)-1-(3-methoxycarbonylphenyl)-1,2-dihydropyridin-2-one; 3-(2-cyanophenyl)-5-(2-pyridyl)-1-(3-methylaminocarbonylphenyl)-1,2-dihydropyridin-2-one; 3-(2-cyano-3-pyridyl)-5-(2-pyridyl)-1-phenyl-1,2-dihydropyridin-2-one; 3-(2-chlorophenyl)-5-(2-pyridyl)-1-(4-hydroxyphenyl)-1,2-dihydropyridin-2-one; 3-(2-chlorophenyl)-5-(2-pyridyl)-1-(4-dimethylaminoethoxyphenyl)-1,2-dihydropyridin-2-one; 3-(2-cyanophenyl)-5-(2-pyridyl)-1-(3-formylphenyl)-1,2-dihydropyridin-2-one; 3-(2-cyanophenyl)-5-(2-pyridyl)-1-(3-hydroxymethylphenyl)-1,2-dihydropyridin-2-one; 3-(2-cyanophenyl)-5-(2-pyridyl)-1-(3-cyanomethylphenyl)-1,2-dihydropyridine-2-one; 3-(2-cyanophenyl)-5-(2-pyridyl)-1-(3-acetylaminomethylphenyl)-1,2-dihydropyridin-2-one;

3-(2-cyanophenyl)-5-(2-pyridyl)-1-(3-methylsulfonylaminomethylphenyl)-1,2-dihydropyridin-2-one; 3-(2-cyanophenyl)-5-(2-pyridyl)-1-(3-acetoxymethylphenyl)-1,2-dihydropyridin-2-one; 3-(2-cyanophenyl)-5-(2-pyridyl)-1-(4-methylthiophenyl)-1,2-dihydropyridin-2-one; 3-(2-cyanophenyl)-5-(2-pyridyl)-1-(4-methylsulfonylphenyl)-1,2-dihydropyridin-2-one; 3-(2-cyanophenyl)-5-(2-formylthiophen-3-yl)-1-phenyl-1,2-dihydropyridin-2-one; 3-(2-cyanophenyl)-5-(2-diethylaminomethylthiophen-3-yl)-1-phenyl-1,2-dihydropyridin-2-one; 3-(2-cyanophenyl)-5-(2-hydroxymethylthiophen-3-yl)-1-phenyl-1,2-dihydropyridine-2-one; 3-(2-cyanophenyl)-5-(2-pyridyl)-1-benzyl-1,2-dihydropyridin-2-one; 3-(2-cyanophenyl)-5-(2-pyridyl)-1-(3-pyridyl)-1,2-dihydropyridin-2-one; 3-(2-cyanophenyl)-5-phenyl-(2-pyridyl)-1,2-dihydropyridin-2-one; 3-(2-cyanophenyl)-1,5-diphenyl-1,2-dihydropyridin-2-one; 3-(2-cyanophenyl)-5-(2-methoxyphenyl)-1-phenyl-1,2-dihydropyridin-2-one; 3-(2-cyanophenyl)-5-(3,4-dimethoxyphenyl)-1-phenyl-1,2-dihydropyridin-2-one; 3-(2-cyanophenyl)-5-(thiophen-3-yl)-1-phenyl-1,2-dihydropyridin-2-one; 3-(2-cyanophenyl)-5-(2-fluorophenyl)-1-phenyl-1,2-dihydropyridin-2-one; 3-(2-cyanophenyl)-5-(thiophen-2-yl)-1-phenyl-1,2-dihydropyridin-2-one; 3-(2-cyanophenyl)-5-(3-furyl)-1-phenyl-1,2-dihydropyridin-2-one; 3-(2-cyanophenyl)-5-(2-furyl)-1-phenyl-1,2-dihydropyridin-2-one; 3-(2-chlorophenyl)-5-(2-pyridyl)-1-phenyl-1,2-dihydropyridin-2-one, 3-(2-methoxycarbonylphenyl)-5-(2-pyridyl)-1-phenyl-1,2-dihydropyridin-2-one; 3-phenyl-5-(2-pyridyl)-1-phenyl-1,2-dihydropyridin-2-one; 3-(2-fluorophenyl)-5-(2-pyridyl)-1-phenyl-1,2-dihydropyridin-2-one; 3-(2-chlorophenyl)-5-(2-pyridyl)-1-(3-methoxyphenyl)-1,2-dihydropyridin-2-one; 3-(2-fluoro-3-pyridyl)-5-(2-pyridyl)-1-phenyl-1,2-dihydropyridin-2-one; 3-(2-methoxy-5-pyridyl)-5-(2-pyridyl)-1-phenyl-1,2-dihydropyridin-2-one; 3-(2-fluoro-3-pyridyl)-5-(2-pyridyl)-1-(3-methoxyphenyl)-1,2-dihydropyridin-2-one; 3-(2-fluoro-3-pyridyl)-5-(2-pyridyl)-1-(3-fluorophenyl)-1,2-dihydropyridin-2-one; 3-(2-cyanophenyl)-5-(2-pyridyl)-1-(4-fluorophenyl)-1,2-dihydropyridin-2-one; 3-(2-cyanophenyl)-5-(2-pyridyl)-1-(3-fluorophenyl)-1,2-dihydropyridin-2-one; 3-(2-cyanophenyl)-5-(2-pyridyl)-1-(4-methoxyphenyl)-1,2-dihydropyridin-2-one; 3-(2-cyanophenyl)-5-(2-pyridyl)-1-(3-methoxyphenyl)-1,2-dihydropyridin-2-one; 3-phenyl-5-(2-pyridyl)-1-(3-fluorophenyl)-1,2-dihydropyridin-2-one; 3-(2-chlorophenyl)-5-(2-pyridyl)-1-(4-fluorophenyl)-1,2-dihydropyridin-2-one; 3-(2-cyanophenyl)-5-(2-pyridyl)-1-(4-formylphenyl)-1,2-dihydropyridin-2-one; 3-(2-cyanophenyl)-5-(2-pyridyl)-1-(2-formylphenyl)-1,2-dihydropyridin-2-one; 3-(2-cyanophenyl)-5-(2-pyridyl)-1-(3-chlorophenyl)-1,2-dihydropyridin-2-one; 3-(2-cyanophenyl)-5-(2-pyridyl)-1-(3-tolyl)-1,2-dihydropyridin-2-one; 3-(2-cyanophenyl)-5-(2-pyridyl)-1-(3-trifluoromethylphenyl)-1,2-dihydropyridin-2-one; 3-(2-cyanophenyl)-5-(2-pyridyl)-1-(thiophen-3-yl)-1,2-dihydropyridin-2-one; 3-(2-cyanophenyl)-5-(2-pyridyl)-1-(3-furyl)-1,2-dihydropyridin-2-one; 3-(2-cyanophenyl)-5-(2-pyridyl)-1-(4-tolyl)-1,2-dihydropyridin-2-one; 3-(2-cyanophenyl)-5-(2-pyridyl)-1-(4-trifluoromethylphenyl)-1,2-dihydropyridin-2-one; 3-(2-cyanophenyl)-5-(2-pyridyl)-1-(2-methoxypyridin-5-yl)-1,2-dihydropyridin-2-one; 3-(2-cyanophenyl)-5-(2-pyridyl)-1-(pyrimidin-5-yl)-1,2-dihydropyridin-2-one; 3-(2-cyanophenyl)-5-(2-pyridyl)-1-(3-benzyloxymethylpyridin-5-yl)-1,2-dihydropyridin-2-one; 3-(2-cyanophenyl)-5-(2-pyridyl)-1-(2-ethylthiopyridin-5-yl)-1,2-dihydropyridin-2-one; 3-(2-cyanophenyl)-5-(2-pyridyl)-1-(4-pyridyl)-1,2-dihydropyridin-2-one; 3-(2-cyanophenyl)-5-(2-pyridyl)-1-(3-methoxypyridin-5-yl)-1,2-dihydropyridin-2-one; 3-(2-cyanophenyl)-5-(2-pyridyl)-1-(2-chloropyridin-5-yl)-1,2-dihydropyridin-2-one; 3-(2-cyanophenyl)-5-(2-pyridyl)-1-(2-fluoropyridin-5-yl)-1,2-dihydropyridin-2-one; 3-(2-cyanophenyl)-5-(2-pyridyl)-1-(2-methoxyphenyl)-1,2-dihydropyridin-2-one; 3-phenyl-5-(2-pyridyl)-1-(3-pyridyl)-1,2-dihydropyridin-2-one; 3-(2-chlorophenyl)-5-(2-pyridyl)-1-(3-pyridyl)-1,2-dihydropyridin-2-one; 3-(thiophen-3-yl)-5-(2-pyridyl)-1-(3-pyridyl)-1,2-dihydropyridin-2-one; 3-(2,6-dimethylphenyl)-5-(2-pyridyl)-1-(3-pyridyl)-1,2-dihydropyridin-2-one; 3-(2-cyanothiophen-3-yl)-5-(2-pyridyl)-1-(3-pyridyl)-1,2-dihydropyridin-2-one; 3-(2-fluoro-3-pyridyl)-5-(2-pyridyl)-1-(3-pyridyl)-1,2-dihydropyridin-2-one; 3-(2-chlorophenyl)-5-(2-pyridyl)-1-(3-hydroxyphenyl)-1,2-dihydropyridin-2-one; 3-(2-chlorophenyl)-5-(2-pyridyl)-1-(3-dimethylaminoethoxyphenyl)-1,2-dihydropyridin-2-one; 3-(2-chlorophenyl)-5-(2-pyridyl)-1-(3-dimethylaminopropoxyphenyl)-1,2-dihydropyridin-2-one; 3-(2-cyanophenyl)-5-(2-pyridyl)-1-(2-hydroxymethylphenyl)-1,2-dihydropyridin-2-one; 3-(2-cyanophenyl)-5-(2-pyridyl)-1-(4-cyanomethylphenyl)-1,2-dihydropyridin-2-one; 3-(2-cyanophenyl)-5-(2-pyridyl)-1-(2-cyanomethylphenyl)-1,2-dihydropyridin-2-one; 3-(2-cyanophenyl)-5-(6-diethylaminomethyl-2-pyridyl)-1-phenyl-1,2-dihydropyridin-2-one; 3-(2-cyanophenyl)-1-phenyl-5-(2-pyrimidinyl)-1,2-dihydropyridin-2-one; 3-(2-hydroxypyridin-6-yl)-1-phenyl-5-(2-pyridyl)-1,2-dihydropyridin-2-one; 1-(2-aminobenzothiazol-6-yl)-3-(2-cyanophenyl)-5-(2-pyridyl)-1,2-dihydropyridin-2-one; 3-(2-cyanophenyl)-5-(2-pyridyl)-1-(1-benzyl-1,2,5,6-tetrahydropyridin-3-yl)-1,2-dihydropyridin-2-one; 3-[2-(5-methyl-1,2,4-oxadiazol-3-yl)phenyl]-1-phenyl-5-(2-pyridyl)-1,2-dihydropyridin-2-one; 3-(2-cyanophenyl)-5-(6-methylpyridin-2-yl)-1-phenyl-1,2-dihydropyridin-2-one; 3-(2-cyanophenyl)-5-(5-methylpyridin-2-yl)-1-phenyl-1,2-dihydropyridin-2-one; 3-(2-cyanophenyl)-5-(3-hydroxypyridin-2-yl)-1-phenyl-1,2-dihydropyridin-2-one; 3-(2-cyanophenyl)-1-phenyl-5-(2-thiazolyl)-1,2-dihydropyridin-2-one; 3-(2-cyanophenyl)-5-(6-methoxypyridin-2-yl)-1-phenyl-1,2-dihydropyridin-2-one; 1-(4-aminophenyl)-3-(2-cyanophenyl)-5-(2-pyridyl)-1,2-dihydropyridin-2-one; 1-(3-aminophenyl)-3-(2-cyanophenyl)-5-(2-pyrimidinyl)-1,2-dihydropyridin-2-one; 3-(2-cyanophenyl)-5-(2-pyridyl)-1-(3-amino-4-methylphenyl)-1,2-dihydropyridin-2-one; 3-(2-cyanophenyl)-1-(3-dimethylaminoethoxyphenyl)-5-(2-pyridyl)-1,2-dihydropyridin-2-one; 3-(2-cyanophenyl)-1-(3-piperidinoethoxyphenyl)-5-(2-pyridyl)-1,2-dihydropyridin-2-one; 3-(2-cyanophenyl)-1-(3-pyrrolidinoethoxyphenyl)-5-(2-pyridyl)-1,2-dihydropyridin-2-one; 3-(2-cyanophenyl)-1-(3-diisoproylaminoethoxyphenyl)-5-(2-pyridyl)-1,2-dihydropyridin-2-one; 3-(2-cyanophenyl)-1-[3-(4-piperidinobutoxy)phenyl]-5-(2-pyridyl)-1,2-dihydropyridin-2-one; 3-(2-cyanophenyl)-1-(4-nitrophenyl)-5-(2-pyridyl)-1,2-dihydropyridin-2-one; 1-phenyl-5-(2-pyridyl)-3-(2-thiazolyl)-1,2-dihydropyridin-2-one; 3-(2-cyanophenyl)-1-(3-pyridyl)-5-(2-pyrimidinyl)-1,2-dihydropyridin-2-one; 3-(2-fluoropyridin-3-yl)-1-phenyl-5-(2-pyrimidinyl)-1,2-dihydropyridin-2-one; 3-(2-cyanopyridin-3-yl)-1-phenyl-5-(2-pyrimidinyl)-1,2-dihydropyridin-2-one; 3-(2-cyanophenyl)-1-(3-nitrophenyl)-5-(2-pyrimidinyl)-1,2-dihydropyridin-2-one; 3-(2-nitrophenyl)-1-phenyl-5-(2-pyridyl)-1,2-dihydropyridin-2-one; 3-(2-formylthiophen-3-yl)-5-(2-pyridyl)-1-phenyl-1,2-dihydropyridin-2-one; 3-(2-cyanophenyl)-5-(2-pyridyl)-1-(2-naphthyl)-1,2-dihydropyridin-2-one; 3-(2-cyanophenyl)-5-(2-pyridyl)-1-(1-naphthyl)-1,2-dihydropyridin-2-one; 5-(2-aminopyridin-6-yl)-3-(2- cyanophenyl)-1-phenyl-1,2-dihydropyridin-2-one; 5-(6-bromopyridin-2-yl)-3-(2-cyanophenyl)-1-phenyl-1,2-dihydropyridin-2-one; 3-(2-cyanophenyl)-5-(2-morphorinopyridin-6-yl)-1-phenyl-1,2-dihydropyridin-2-one; 3-(2-cyanophenyl)-1-(3-hydroxyphenyl)-5-(2-pyridyl)-1,2-dihydropyridin-2-one; 3-(2-cyanophenyl)-1-[3-(4-piperidyloxy)]phenyl-5-(2-pyridyl)-1,2-dihydropyridin-2-one; 1-[3-(N-acetylpiperidin-4-yl-oxy)phenyl]-3-(2-cyanophenyl)-5-(2-pyridyl)-1,2-dihydropyridin-2-one; 3-(2-cyanophenyl)-1-[3-(1-methylsulfonylpiperidin-4-yl-oxy) phenyl]-5-(2-pyridyl)-1,2-dihydropyridin-2-one; 1-[3-(N-methylpiperidin-4-yl-oxy)phenyl]-3-(2-cyanophenyl)-5-(2-pyridyl)-1,2-dihydropyridin-2-one; 3-(6-chloro-1H-benzimidazol-2-yl)-5-(2-pyridyl)-1-phenyl-1,2-dihydropyridin-2-one; 3-(2-cyanophenyl)-5-(2-pyridyl)-1-(3-nitro-4-methylphenyl)-1,2-dihydropyridin-2-one; 3-(2-cyanothiophen-3-yl)-5-(2-pyridyl)-1-phenyl-1,2-dihydropyridin-2-one; 3-[2-(5-oxazolyl)phenyl]-1-phenyl-5-(2-pyridyl)-1,2-dihydropyridin-2-one; 3-[2-(5-oxazolyl) thiophen-3-yl]-1-phenyl-5-(2-pyridyl)-1,2-dihydropyridin-2-one; and 3-(2-ethoxycarbonylvinylthiophen-3-yl)-5-(2-pyridyl)-1-phenyl-1,2-dihydropyridin-2-one; (23) a pharmaceutical composition comprising a compound represented by the following formula, a salt thereof or hydrates thereof:

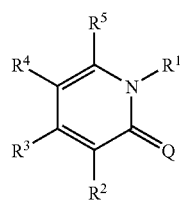

(I)

in the formula, Q indicates NH, O or S; and $R^1$, $R^2$, $R^3$, $R^4$ and $R^5$ are the same as or different from each other and each indicates hydrogen atom, a halogen atom, a $C_{1-6}$ alkyl group or the formula —X-A (wherein X indicates a single bond, a $C_{1-6}$ alkylene group which may optionally have substituents, a $C_{2-6}$ alkenylene group which may optionally have substituents, a $C_{2-6}$ alkynylene group which may optionally have substituents, —O—, —S—, —CO—, —SO—, —SO$_2$—, —N($R^6$)—, —N($R^7$)—CO—, —CO—N($R^8$)—, —N($R^9$)—CH$_2$—, —CH$_2$—N($R^{10}$)—, —CH$_2$—CO—, —CO—CH$_2$—, —N($R^{11}$)—S(O)$_m$—, —S(O)$_n$—N($R^{12}$)—, —CH$_2$—S(O)$_p$—, —S(O)$_q$—CH$_2$—, —CH$_2$—O—, —O—CH$_2$—, —N($R^{13}$)—CO—N($R^{14}$)— or —N($R^{15}$)—CS—N($R^{16}$)— (wherein $R^6$, $R^7$, $R^8$, $R^9$, $R^{10}$, $R^{11}$, $R^{12}$, $R^{13}$, $R^{14}$, $R^{15}$ and $R^{16}$ indicates hydrogen atom, a $C_{1-6}$ alkyl group or a $C_{1-6}$ alkoxy group; and m, n, p and q are independent of each other and each indicates an integer of 0, 1 or 2); and A indicates an optionally substituted $C_{3-8}$ cycloalkyl group, $C_{3-8}$ cycloalkenyl group, 5- to 14-membered non-aromatic heterocyclic group, $C_{6-14}$ aromatic hydrocarbocyclic group or 5- to 14-membered aromatic heterocyclic group), provided that 3 groups among $R^1$, $R^2$, $R^3$, $R^4$ and $R^5$ are always the same as or different from each other and each indicates —X-A; and the residual 2 groups always indicate hydrogen atom, a halogen atom or a $C_{1-6}$ alkyl group; (24) the pharmaceutical composition according to the above (23), wherein it is an inhibitor to an α-amino-3-hydroxy-5-methyl-4-isoxazoleupropionic acid (hereinafter, referred to as "AMPA") receptor and/or a kainate receptor; (25) the pharmaceutical composition according to the above (23), wherein it is an inhibitor to an AMPA receptor; (26) the pharmaceutical composition according to the above (23), wherein it is an inhibitor to an kainate receptor; (27) the pharmaceutical composition according to the above (23), which is a therapeutic or preventive agent for the diseases in which an AMPA receptor or a kainate receptor is participated; (28) the pharmaceutical composition according to the above (23), which is a therapeutic or preventive agent for the diseases in which an AMPA receptor is participated; (29) the pharmaceutical composition according to the above (23), which is a therapeutic or preventive agent for acute neurodegenerative disease; (30) the pharmaceutical composition according to the above (23), which is a therapeutic or preventive agent for cerebrovascular disorders at acute stage, head injury, spinal injury, neuropathy by hypoxia or hypoglycemia; (31) the pharmaceutical composition according to the above (23), which is a therapeutic or preventive agent for chronic neurodegenerative disease; (32) the pharmaceutical composition according to the above (23), which is a therapeutic or preventive agent for Alzheimer's disease, Parkinson's disease, Huntington's chorea, amyotrophic lateral sclerosis or spinocerebellar degeneration; (33) the pharmaceutical composition according to the above (23), which is an agent for treating or preventing epilepsy, hepatic encephalopathy, peripheral neuropathy, Parkinson's syndrome, spastic paralysis, pain, neuralgia, schizophrenia, anxiety, drug abuse, nausea, vomiting, urinary disturbance, paropsia caused by glaucoma, paracusis caused by antibiotics or food poisoning; (34) the pharmaceutical composition according to the above (23), which is an agent for treating or preventing infectious encephalomyelitis, cerebrovascular senile dementia or dementia or neurosis caused by cerebrospinal meningitis; (35) the pharmaceutical composition according to the above (34), wherein the infectious encephalomyelitis is HIV encephalomyelitis; (36) the pharmaceutical composition according to the above (23), which is an agent for treating or preventing demyelinating disease; (37) the pharmaceutical composition according to the above (36), wherein the demyelinating disease is encephalitis, acute disseminated encephalomyelitis, multiple sclerosis, acute demyelinating polyneuropathy, Guillain-Barre syndrome, chronic inflammatory demyelinating polyneuropathy, Marchifava-Bignami disease, central pontine myelinolysis, neuromyelitis optica, Devic disease, Balo disease, HIV myelopathy, HTLV myelopathy, progressive multifocal leukoencephalopathy or secondary demyelinating disease; (38) the pharmaceutical composition according to the above (37), wherein the secondary demyelinating disease is CNS lupus-erythematodes, polyarteritis nodosa, Sjoegren's syndrome, sarcoidosis or isolated cerebral vasculitis; and the like.

The present invention provides a process for preventing or treating diseases in which AMPA receptor or kainate receptor is participated, by dosing a pharmacologically effective dose of the compound represented by the formula (I), a salt thereof or hydrates thereof and an immunoregulatory or an anti-inflammatory agent to a patient.

As hereunder, meanings of the symbols, terms, etc. mentioned in the specification of this application will be explained, whereby the present invention will be illustrated in detail.

As "acute neurodegenerative affection" in the present invention, for example, acute stroke (subarachnoid hemorrhage, cerebral infarction and the like), head injury, spinal cord lesion, neuropathy caused by hypoxia, neuropathy caused by hypoglycemia and the like are mentioned. As "chronic neurodegenerative affection", for example, Alzheimer's disease, Parkinson's disease, Huntington's chorea, amyotrophic lateral sclerosis, spinocerebellar degeneration and the like are mentioned. As "infectious encephalomyelitis", for example, HIV encephalomyelitis is mentioned, and as "demyelinating disease", for example, encephalitis, acute disseminated encephalomyelitis, multiple sclerosis, acute demyelinating polyneuropathy, Guillain-Barre syndrome, chronic inflammatory demyelinating polyneuropathy, Marchifava-Bignami disease, central pontine myelinolysis, neuromyelitis optica, Devic disease, Balo disease, HIV myelopathy, HTLV myelopathy, progressive multifocal leukoencephalopathy, secondary demyelinating disease and the like are mentioned. As "the secondary demyelinating disease" mentioned above, for example, CNS lupus erythematodes, polyarteritis nodosa, Sjoegren's syndrome, sarcoidosis, isolated cerebral vasculitis and the like are mentioned.

The term "and/or" used in the present invention is used in the meaning that both cases in case of "and" and in case of "or" are included.

Incidentally, in the specification of this application, although structural formula of a compound may express a certain isomer for the sake of convenience, the present invention covers all isomers such as geometrical isomers resulting from the structure of the compound, optical isomers due to asymmetric carbon, stereo isomers, rotamers and tautomers as well as a mixture of isomers and the present invention is not limited to the description of the formula given for the sake of convenience but may be another isomer or may be a mixture. Accordingly, although it is possible that an asymmetric carbon atom is present in a molecule and accordingly that optically active substance and racemic substance may be present, the present invention is not limited thereto but covers any of them. Further, crystal polymorphism may be present but, again, there is no limitation, any of single crystal form or a mixture will do. The compound (I) or its salt related to the present invention may be an anhydride or a hydrate, and either of them are included in the scope of claim for patent in the present invention. The metabolite which is generated by decomposing the compound (I) related to the present invention in vivo, and the prodrug of the compound (I) or its salt related to the present invention produce are also included in the scope of claim for patent in the present invention.

The "halogen atom" used in the present invention indicates fluorine, chlorine, bromine, iodine and the like.

The "$C_{1-6}$ alkyl group" used in the present invention indicates an alkyl group having 1 to 6 carbons, and examples include linear chain or branched chain alkyl groups such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, and the like.

The "$C_{2-6}$ alkenyl group" used in the present invention indicates an alkenyl group having 2 to 6 carbons, and examples of the preferable group include vinyl group, allyl group, 1-propenyl group, 2-propenyl group, iso-propenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, 1,6-hexadienyl group, and the like.

The "$C_{2-6}$ alkynyl group" used in the present invention indicates an alkynyl group having 2 to 6 carbons, and examples of the preferable group include ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group, 1,6-hexadiynyl group, and the like.

The "$C_{1-6}$ alkoxy group" used in the present invention indicates an alkoxy group having 1 to 6 carbons, and examples include methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropoxy group, 1,2-dimethylpropoxy group, 2,2-dimethylpropoxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 1,3-dimethylbutoxy group, 2-methylpentoxy group, 3-methylpentoxy group, hexyloxy group, and the like.

The "$C_{2-6}$ alkenyloxy group" used in the present invention indicates an alkenyloxy group having 2 to 6 carbons, and examples of the preferable group include vinyloxy group, allyloxy group, 1-propenyloxy group, 2-propenyloxy group, iso-propenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,6-hexadienyloxy group, and the like.

The "$C_{3-8}$ cycloalkyl group" used in the present invention indicates a cycloalkyl group composed of 3 to 8 carbon atoms, and examples include cyclopropyl group, cyclobutyl group, cyclopentyl group, cyclohexyl group, cycloheptyl group, cyclooctyl group, and the like.

The "$C_{3-8}$ cycloalkenyl group" used in the present invention indicates a $C_{3-8}$ cycloalkenyl group composed of 3 to 8 carbon atoms, and examples include cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-1-yl, 1,4-cyclohexadien-3-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl, 1,3,6-cyclooctatrien-6-yl group, and the like.

The "5 to 14 membered non-aromatic heterocyclic group" used in the present invention means a mono-cyclic type, di-cyclic type or tri-cyclic type 5 to 14 membered non-aromatic heterocyclic group which contains one or more of hetero atoms selected from a group which consists of nitrogen atom, sulfur atom and oxygen atom. Specific examples in the group include, for example, pyrrolidinyl group, pyrrolinyl group, piperidyl group, piperazinyl group, imidazolidinyl group, pyrazolidinyl group, morpholinyl group, tetrahydrofuryl group, tetrahydropyranyl group, dihydrofuryl group, dihydropyranyl group, imidazolinyl group, oxazolinyl group, and the like. Further, a group derived from a pyridone ring and a non-aromatic condensed ring (for example, a group derived from a phthalimide ring, a succinimide ring, and the like) are also included in the non-aromatic heterocyclic group.

The "$C_{6-14}$ aromatic hydrocarbocyclic group" and the "aryl group" used in the present invention mean an aromatic hydrocarbocyclic group which is composed of 6 to 14 carbon atoms, and a mono-cyclic group, and a condensed group of a di-cyclic group, a tri-cyclic group and the like are also included. Specific examples in the group include phenyl group, indenyl group, 1-naphthyl group, 2-naphthyl group, azulenyl group, heptalenyl group, biphenyl group, indathenyl group, acenaphthyl group, fluorenyl group, phenalenyl group, phenanthrenyl group, anthracenyl group, cyclopenta-cyclooctenyl group, benzocyclooctenyl group etc.

The "5 to 14 membered aromatic heterocyclic group" and the "heteroaryl group" used in the present invention mean a mono-cyclic type, di-cyclic type, or tri-cyclic type 5 to 14 membered aromatic heterocyclic group which contains one or more of hetero atoms selected from a group which consists of nitrogen atom, sulfur atom and oxygen atom. For example, specific examples in the group include 1) aromatic heterocyclic groups containing nitrogen such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, iso-indolyl group, indolizinyl group, prenyl group, indazolyl group, quinolyl group, iso-quinolyl group, quinoliziyl group, phthalazyl group, naphthylidinyl group, quinoxalyl group, quinazolinyl group, cynnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group, pyrazolopyridinyl group etc.; 2) aromatic heterocyclic groups containing sulfur such as thienyl group and benzothienyl group; 3) aromatic heterocyclic groups containing oxygen such as furyl group, pyranyl group, cyclopentapyranyl group, benzofuryl group and iso-benzofuryl group etc.; and 4) aromatic heterocyclic groups containing 2 or more of different hetero atoms such as thiazolyl group, iso-thiazolyl group, benzothiazolyl group, bennzothiadiazolyl group, phenothiazinyl group, isoxazolyl group, furazanyl group, phenoxazinyl group, oxazolyl group, isoxazoyl group, benzoxazolyl group, oxadiazolyl group, pyrazoloxadiazolyl group, imidazothiazolyl group, thienofuranyl group, furopyrrolyl group and pyridoxadinyl group etc.

The groups indicated by A, $A^1$, $A^2$ and $A^3$ in the formula (I) and (II) in the present invention indicate independently an optionally substituted $C_{3-8}$ cycloalkyl group, an optionally substituted $C_{3-8}$ cycloalkenyl group, an optionally substituted 5 to 14 membered non-aromatic heterocyclic group, an optionally substituted $C_{6-14}$ aromatic hydrocarbocyclic group or an optionally substituted 5 to 14 membered aromatic heterocyclic group, and each of the groups has the same meanings as the above definitions, respectively. The preferable group in A, $A^1$, $A^2$ and $A^3$ is not specifically limited, but the more preferable group includes phenyl group, pyrrolyl group, pyridyl group, pyridazinyl group, pyrimidinyl group, pyrazinyl group, thienyl group, thiazolyl group, furyl group, naphthyl group, quinolyl group, iso-quinolyl group, indolyl group, benzimidazolyl group, benzothiazolyl group, benzoxazolyl group, imidazopyridyl group, carbazolyl group, cyclopentyl group, cyclohexyl group, cyclohexenyl group, dioxinyl group, adamantyl group, pyrrolidinyl group, piperidyl group, piperazinyl group and morpholinyl group which may be substituted, respectively, etc. The more preferable group includes a group represented by the formula:

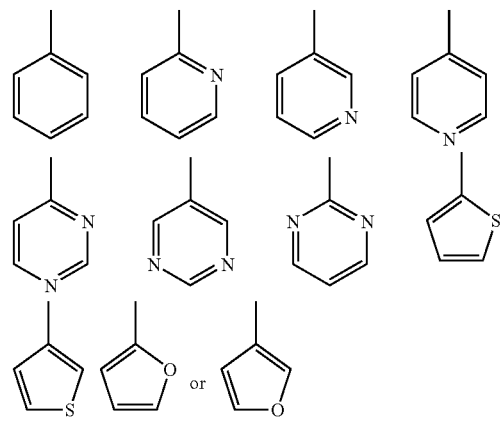

which may optionally have one or more substituents respectively, etc., and the most preferable group includes a group represented by the formula:

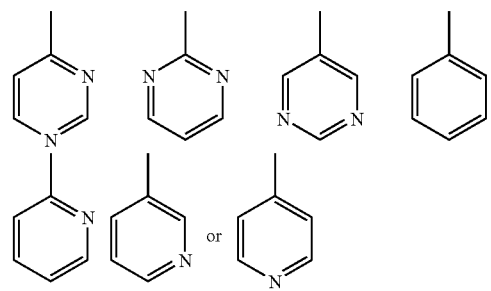

which may optionally have substituents respectively, etc.

Examples of the preferable group in the "substituent" of the groups indicated by A, $A^1$, $A^2$ and $A^3$ in the formula (I) and (II) include a group such as hydroxy group, a halogen atom, nitrile group, nitro group, a $C_{1-6}$ alkyl group, $C_{2-6}$ alkenyl group, $C_{2-6}$ alkynyl group, $C_{1-6}$ alkoxy group, $C_{2-6}$ alkenyloxy group, $C_{2-6}$ alkynyloxy group, $C_{1-6}$ alkylthio group, $C_{2-6}$ alkenylthio group, $C_{2-6}$ alkynylthio group, amino group, a substituted carbonyl group, $C_{1-6}$ alkylsulfonyl group, $C_{2-6}$ alkenylsulfonyl group, $C_{2-6}$ alkynylsulfonyl group, $C_{1-6}$ alkylsulfinyl group, $C_{2-6}$ alkenylsulfinyl group, $C_{2-6}$ alkynylsulfinyl group, formyl group, aralkyl group, heteroarylalkyl group, aralkyloxy group, heteroarylalkyloxy group, $C_{3-8}$ cycloalkyl group, $C_{3-8}$ cycloalkenyl group, 5 to 14 membered non-aromatic heterocyclic group, $C_{6-14}$ aromatic hydrocarbon group, 5 to 14 membered aromatic heterocyclic group etc., which may be substituted, respectively.

Examples of the preferable group in the "halogen atom" include fluorine atom, chlorine atom, bromine atom, iodine atom etc., and the more preferable example includes fluorine atom, chlorine atom and bromine atom.

Examples of the preferable group in the "$C_{1-6}$ alkyl group which may optionally have substituents" include methyl group, ethyl group, n-propyl group, iso-propyl group, n-butyl group, iso-butyl group, tert-butyl group, n-pentyl group, iso-pentyl group, neopentyl group, n-hexyl group, 1-methylpropyl group, 1,2-dimethylpropyl group, 2-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, 3-methylpentyl group etc. Examples of the preferable group in the "$C_{2-6}$ alkenyl group which may optionally have substituents" include a vinyl group, allyl group, 1-propenyl group, iso-propenyl group, 1-buten-1-yl group, 1-buten-2-yl group, 1-buten-3-yl group, 2-buten-1-yl group, 2-buten-2-yl group etc., which may be substituted, respectively. Examples of the preferable group in the "$C_{2-6}$ alkynyl group which may optionally have one or more substituents" include an ethynyl group, 1-propynyl group, 2-propynyl group, butynyl group, pentynyl group, hexynyl group etc., which may be substituted, respectively. Further, preferable examples of the "substituents" in the "which may optionally have one or more substituents" include 1 or more groups selected from hydroxy group, nitrile group, a halogen atom, an N—$C_{1-6}$ alkylamino group, an N,N-di-$C_{1-6}$ alkylamino group, an N—$C_{2-6}$ alkenylamino group, an N,N-di-$C_{2-6}$alkenylamino group, an N—$C_{2-6}$ alkynylamino group, an N,N-di-$C_{2-6}$ alkynylamino group, a $C_{6-14}$ aromatic hydrocarbocyclic group (for example, phenyl group etc.), a 5 to 14 membered aromatic heterocyclic group (for example, thienyl group, furyl group, pyridyl group, pyridazinyl group, pyrimidinyl group, pyrazinyl group etc.), an aralkyloxy group, a heteroaryloxy group, a TBDMS-oxy group, a $C_{1-6}$ alkylsulfonylamino group, a $C_{2-6}$ alkenylsulfonylamino group, a $C_{2-6}$ alkynylsulfonylamino group, a $C_{1-6}$ alkylcarbonyloxy group, a $C_{2-6}$ alkenylcarbonyloxy group, a $C_{2-6}$ alkynylcarbonyloxy group, a $C_{1-6}$ alkylcarbamoyl group, a $C_{2-6}$ alkenylcarbamoyl group, a $C_{2-6}$ alkynylcarbamoyl group, and the like.

Preferable examples in the "$C_{1-6}$ alkoxy group which may optionally have substituents" include methoxy group, ethoxy group, n-propoxy group, iso-propoxy group, sec-propoxy group, n-butoxy group, iso-butoxy group, sec-butoxy group, tert-butoxy group, n-pentoxy group, iso-pentoxy group, sec-pentoxy group, tert-pentoxy group, n-hexoxy group, iso-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group, 3-methylpentoxy group, hexyloxy group etc. Preferable examples in the "$C_{2-6}$ alkenyloxy group which may optionally have substituents" include vinyloxy group, allyloxy group, 1-propenyloxy group, iso-propenyloxy group, 1-buten-1-yloxy group, 1-buten-2-yloxy group, 1-buten-3-yloxy group, 2-buten-1-yloxy group, 2-buten-2-yloxy group etc. Preferable examples in the "$C_{2-6}$ alkynyloxy group which may optionally have substituents" include ethynyloxy group, 1-propynyloxy group, 2-propynyloxy group, butynyloxy group, pentynyloxy group, hexynyloxy group etc. Further, preferable examples of the "substituent" in the "which may optionally have substituents" include 1 or more groups selected from an $C_{1-6}$ alkylamino group, an aralkyloxy group, hydroxy group, and the like.

Respectively preferable examples in the "$C_{1-6}$ alkylthio group which may optionally have substituents", "$C_{2-6}$ alkenylthio group which may optionally have substituents" and "$C_{2-6}$ alkynylthio group which may optionally have substituents" include a $C_{1-6}$ alkylthio group (for example, methylthio group, ethylthio group, n-propylthio group, iso-propylthio group, n-butylthio group, iso-butylthio group, tert-butylthio group, n-pentylthio group, iso-pentylthio group, neopentylthio group, n-hexylthio group etc.) which may be optionally substituted by 1 or more groups selected from the group consisting of hydroxy group, a halogen atom, nitrile group and nitro group, a $C_{2-6}$ alkenylthio group (for example, vinylthio group, allylthio group, 1-propenylthio group, iso-propenylthio group, 1-buten-1-ylthio group, 1-buten-2-ylthio group, 1-buten-3-ylthio group, 2-buten-1-ylthio group, 2-buten-2-ylthio group etc.) and a $C_{2-6}$ alkynylthio group (for example, ethynylthio group, 1-propynylthio group, 2-propynylthio group, butynylthio group, pentynylthio group, hexynylthio group etc.).

Preferable examples in the "carbonyl group which was substituted" include a group which is represented by the formula —CO—W (examples of W in the formula include a $C_{1-6}$ alkyl group, a $C_{2-6}$ alkenyl group, a $C_{2-6}$ alkynyl group, a $C_{1-6}$ alkoxy group, amino group, an N—$C_{1-6}$ alkylamino group, an N,N-di($Ci_{1-6}$ alkyl)amino group, an N—$C_{2-6}$ alkenylamino group, an N,N-di($C_{2-6}$ alkenyl)amino group, an N—$C_{2-6}$ alkynylamino group, an N,N-di($C_{2-6}$ alkynyl)amino group, an N—$C_{1-6}$ alkyl-N—$C_{2-6}$ alkenylamino group, an N—$C_{1-6}$ alkyl-N—$C_{2-6}$ alkynylamino group, an N—$C_{2-6}$ alkenyl-N—$C_{2-6}$ alkynylamino group etc.).

Examples of the "substituent" in the "amino group which may optionally have substituents" include 1 or 2 groups selected from a $C_{1-6}$ alkyl group, $C_{2-6}$ alkenyl group, $C_{2-6}$ alkynyl group, $C_{1-6}$ alkylsulfonyl group, $C_{2-6}$ alkenylsulfonyl group, $C_{2-6}$ alkynylsulfonyl group, $C_{1-6}$ alkylcarbonyl group, $C_{2-6}$ alkenylcarbonyl group, $C_{2-6}$ alkynylcarbonyl group etc., which may be substituted, respectively. Preferable examples in the "substituent" of the $C_{1-6}$ alkyl group, $C_{2-6}$ alkenyl group, $C_{2-6}$ alkynyl group, $C_{1-6}$ alkylsulfonyl group, $C_{2-6}$ alkenylsulfonyl group, $C_{2-6}$ alkynylsulfonyl group, $C_{1-6}$ alkylcarbonyl group, $C_{2-6}$ alkenylcarbonyl group and $C_{2-6}$ alkynylcarbonyl group include hydroxy group, a halogen atom, nitrile group, a $C_{1-6}$ alkoxy group, a $C_{1-6}$ alkylthio group etc. Specifically preferable examples in the "amino group which may optionally have substituents" in particular include methylamino group, ethylamino group, n-propylamino group, iso-propylamino group, n-butylamino group, iso-butylamino group, tert-butylamino group, n-pentylamino group, iso-pentylamino group, neopentylamino group, n-hexylamino group, 1-methylpropylamino group, 1,2-dimethylpropylamino group, 2-ethylpropylamino group, 1-methyl-2-ethylpropylamino group, 1-ethyl-2-methylpropylamino group, 1,1,2-trimethylpropylamino group, 1-methylbutylamino group, 2-methylbutylamino group, 1,1-dimethylbutyllamino group, 2,2-dimethylbutylamino group, 2-ethylbutylamino group, 1,3-dimethylbutylamino group, 2-methylpentylamino group, 3-methylpentylamino group, N,N-dimethylamino group, N,N-diethylamino group, N,N-di(n-propyl)amino group, N,N-di(iso-propyl)amino group, N,N-di(n-butyl)amino group, N,N-di(iso-butyl)amino group, N,N-di(tert-butyl)amino group, N,N-di(n-pentyl)amino group, N,N-di(iso-pentyl)amino group, N,N-di(neopentyl)amino group, N,N-di(n-hexyl)amino group, N,N-di(1-methylpropyl)amino group, N,N-di(1,2-dimethylpropyl)amino group, N-methyl-N-ethylamino group, N-ethyl-N-(n-propyl)amino group, N-ethyl-N-(iso-propyl)amino group, vinylamino group, allylamino group, (1-propenyl)amino group, iso-propenylamino group, (1-buten-1-yl)amino group, (1-buten-2-yl)amino group, (1-buten-3-yl)amino group, (2-buten-1-yl)amino group, (2-buten-2-yl)amino group, N,N-divinylamino group, N,N-diallylamino group, N,N-di(1-propenyl)amino group, N,N-di(iso-propenyl)amino group, N-vinyl-N-allylamino group, ethynylamino group, 1-propynylamino group, 2-propynylamino group, butynylamino group, pentynylamino group, hexynylamino group, N,N-diethynylamino group, N,N-di(1-propynyl)amino group, N,N-di(2-propynyl)amino group, N,N-dibutynylamino group, N,N-dipentynylamino group, N,N-dihexynylamino group, hydroxymethylamino group, 1-hydroxyethylamino group, 2-hydroxyethylamino group, 3-hydroxy-n-propylamino group, methylsulfonylamino group, ethylsulfonylamino group, n-propylsulfonylamino group, iso-propylsulfonylamino group, n-butylsulfonylamino group, tert-butylsulfonylamino group, vinylsulfonylamino group, allylsulfonylamino group, iso-propenylsulfonylamino group, iso-pentenylsulfonylamino group, ethynylsulfonylamino group, methylcarbonylamino group, ethylcarbonylamino group, n-propylcarbonylamino group, iso-propylcarbonylamino group, n-butylcarbonylamino group, tert-butylcarbonylamino group, vinylcarbonylamino group, allylcarbonylamino group, iso-propenylcarbonylamino group, iso-pentenylcarbonylamino group, ethynylcarbonylamino group etc.

Respectively preferable examples in the "$C_{1-6}$ alkylsulfonyl group which may optionally have one or more substituents", "$C_{2-6}$ alkenylsulfonyl group which may optionally have one or more substituents", "$C_{2-6}$ alkynylsulfonyl group which may optionally have one or more substituents", "$C_{1-6}$ alkylsulfinyl group which may optionally have one or more substituents", "$C_{2-6}$ alkenylsulfinyl group which may optionally have one or more substituents" and "$C_{2-6}$ alkynylsulfinyl group which may optionally have one or more substituents" include methylsulfonyl group, ethylsulfonyl group, n-propylsulfonyl group, iso-propylsulfonyl group, n-butylsulfonyl group, tert-butylsulfonyl group, vinylsulfonyl group, allylsulfonyl group, iso-propenylsulfonyl group, iso-pentenylsulfonyl group, ethynylsulfonyl group, methylsulfinyl group, ethylsulfinyl group, n-propylsulfinyl group, iso-propylsulfinyl group, n-butylsulfinyl group, tert-butylsulfinyl group, vinylsulfinyl group, allylsulfinyl group, iso-propenylsulfinyl group, iso-pentenylsulfinyl group, ethynylsulfinyl group etc.

Preferable examples in the "aralkyl group" and "heteroarylalkyl group" include benzyl group, phenethyl group, naphthylmethyl group, naphthylethyl group, pyridylmethyl group, pyridylethyl group, thienylmethyl group, thienylethyl group etc., preferable examples in the "aralkyloxy group" include benzyloxy group, phenethyloxy group, phenylpropoxy group, naphthylmethyloxy group, naphthylethyloxy group, naphthylpropyloxy group etc., and preferable examples in the "heteroarylalkyloxy group" include pyridylmethyloxy group, pyrazinylmethyloxy group, pyrimidinylmethyloxy group, pyrrolylmethyloxy group, imidazolylmethyloxy group, pyrazolylmethyloxy group, quinolylmethyloxy group, iso-quinolylmethyloxy group, furfuryloxy group, thienylmethyloxy group, thiazolylmethyloxy group etc.

Preferable examples in the "$C_{3-8}$ cycloalkyl group which may optionally have one or more substituents" and "$C_{3-8}$ cycloalkenyl group which may optionally have one or more substituents" include a $C_{3-8}$ cycloalkyl group (for example, cyclopropyl group, cyclobutyl group, cyclopentyl group, cyclohexyl group, cycloheptyl group, and the like) and a $C_{3-8}$ cycloalkenyl group (for example, cyclopropenyl group, cyclopropenyl group, cyclobutenyl group, cyclopentenyl group, cyclohexenyl group, cycloheptenyl group, and the like) which may be optionally substituted respectively by 1 or more groups selected from hydroxy group, a halogen atom, nitrile group, a $C_{1-6}$ alkyl group (for example, methyl group, ethyl group, n-propyl group, iso-propyl group, n-butyl group, iso-butyl group, tert-butyl group, n-pentyl group, iso-pentyl group, neopentyl group, n-hexyl group etc.), a $C_{1-6}$ alkoxy group (for example, methoxy group, ethoxy group, n-propoxy group, iso-propoxy group, sec-propoxy group, n-butoxy group, iso-butoxy group, sec-butoxy group, tert-butoxy group, n-pentoxy group, iso-pentoxy group, sec-pentoxy group, tert-pentoxy group, n-hexoxy group etc.), a $C_{1-6}$ alkoxy $C_{1-6}$ alkyl group, an aralkyl group (for example, benzyl group, phenethyl group, naphthylmethyl group, naphthylethyl group etc.), and the like.

Preferable examples of the "5 to 14 membered non-aromatic heterocyclic group", "$C_{6-14}$ aromatic hydrocarbocyclic group" and "5 to 14 membered aromatic heterocyclic group" in "optionally substituted 5 to 14 membered non-aromatic heterocyclic group", "optionally substituted $C_{6-14}$ aromatic hydrocarbocyclic group" and "optionally substituted 5 to 14 membered aromatic heterocyclic group" are not specifically limited, but the more preferable "5 to 14 membered non-aromatic heterocyclic group" includes pyrrolidinyl group, pyrrolinyl group, piperidyl group, piperazinyl group, imidazolidinyl group, pyrazolidinyl group, morpholinyl group, phthalimidoyl group, a succinimidoyl group etc.; the more preferable "$C_{6-14}$ aromatic hydrocarbocyclic group" includes phenyl group, indenyl group, naphthyl group, azulenyl group, heptalenyl group, biphenyl group etc.; the more preferable "5 to 14 membered aromatic heterocyclic group" includes pyrrolyl group, pyridyl group, pyridazinyl group, pyrimidinyl group, pyrazinyl group, pyrazolyl group, imidazolyl group, thienyl group, furyl group, thiazolyl group, iso-thiazolyl group, quinolyl group, iso-quinolyl group, indolyl group, benzimidazolyl group, benzothiazolyl group, benzoxazolyl group, carbazolyl group, dioxinyl group etc., respectively. Further, preferable examples of the "substituent" in the "which may optionally have one or more substituents" include 1 or more groups selected from hydroxy group, a halogen atom (for example, fluorine atom, chlorine atom, bromine atom, iodine atom etc.), nitrile group, a $C_{1-6}$ alkyl group (for example, methyl group, ethyl group, n-propyl group, iso-propyl group, n-butyl group, iso-butyl group, tert-butyl group, n-pentyl group, iso-pentyl group, neopentyl group, n-hexyl group etc.), a $C_{1-6}$ alkoxy group (methoxy group, ethoxy group, n-propoxy group, iso-propoxy group, sec-propoxy group, n-butoxy group, iso-butoxy group, sec-butoxy group, tert-butoxy group, n-pentoxy group, iso-pentoxy group, sec-pentoxy group, tert-pentoxy group, n-hexoxy group etc.), a $C_{1-6}$ alkoxy $C_{1-6}$ alkyl group (for example, methoxymethyl group, methoxyethyl group, ethoxymethyl group, ethoxyethyl group etc.), an aralkyl group (for example, benzyl group, phenethyl group, naphthylmethyl group, naphthylethyl group etc.), and the like. Further, an amino group, a cyclic amino group, and an alkoxyamino group which may optionally have substituents are also preferable as the substituents.

Q indicates NH, O or S in the formula (I) and (II), and is preferably O.

The groups indicated by X, $X^1$, $X^2$ and $X^3$ in the present invention indicate the same or different single bonding, an optionally substituted $C_{1-6}$ alkylene group, an optionally substituted $C_{2-6}$ alkenylene group, an optionally substituted $C_{2-6}$ alkynylene group, —O—, —S—, —CO—, —SO—, —SO$_2$—, —N(R$^6$)—, —N(R$^7$)—CO—, —CO—N(R$^8$)—, —N(R$^9$)—CH$_2$—, —CH$_2$—N(R$^{10}$)—, —CH$_2$—CO—, —CO—CH$_2$—, —N(R$^{11}$)—S(O)$_m$—, —S(O)$_n$—N(R$^{12}$)—, —CH$_2$—S(O)$_p$—, —S(O)$_q$—CH$_2$—, —CH$_2$—O—, —O—CH$_2$—, —N(R$^{13}$)—CO—N(R$^{14}$)— or —N(R$^{15}$)—

CS—N(R$^{16}$)— (wherein R$^6$, R$^7$, R$^8$, R$^9$, R$^{10}$, R$^{11}$, R$^{12}$, R$^{13}$, R$^{14}$, R$^{15}$ and R$^{16}$ indicate hydrogen atom, a C$_{1-6}$ alkyl group or a C$_{1-6}$ alkoxy group; and m, n, p and q indicates an integer of 0, 1 or 2 independently).

Specifically preferable examples in the above "C$_{1-6}$ alkylene group" is an alkenylene group having 1 to 3 carbons, and examples include —CH$_2$—, —(CH$_2$)$_2$—, —CH(CH$_3$)—, —(CH$_2$)$_3$—, —CH(CH$_3$)—CH$_2$—, —CH$_2$—CH(CH$_3$)— etc. Specifically preferable examples in the above "C$_{2-6}$ alkenylene group" is an alkenylene group having 2 or 3 carbons, and examples include —CH═CH—, —CH═CH—CH$_2$—, —CH$_2$—CH═CH—, —C(CH$_3$)═CH—, —CH═C(CH$_3$)— etc. Specifically preferable examples in the above "C$_{2-6}$ alkynylene group" is an alkynylene group having 2 or 3 carbons, and examples include —C≡C—, —C≡C—CH$_2$—, —CH$_2$—C≡C— etc. Preferable examples in the substituent indicated by X, X$^1$, X$^2$ and X$^3$ in the "C$_{1-6}$ alkylene group which may optionally have one or more substituents", "C$_{2-6}$ alkenylene group which may optionally have one or more substituents" or "C$_{2-6}$ alkynylene group which may optionally have one or more substituents" include a halogen atom (for example, fluorine atom, chlorine atom, bromine atom, iodine atom etc.), hydroxy group, nitrile group, nitro group etc.

The preferable C$_{1-6}$ alkyl group represented by the R$^6$, R$^7$, R$^8$, R$^9$, R$^{10}$, R$^{11}$, R$^{12}$, R$^{13}$, R$^{14}$, R$^{15}$ and R$^{16}$ includes methyl group, ethyl group, n-propyl group, iso-propyl group, n-butyl group, tert-butyl group etc., and the preferable C$_{2-6}$ alkyloxy group includes methoxy group, ethoxy group, n-propoxy group, iso-propoxy group, n-butoxy group, tert-butoxy group etc.

The preferable group in X, X$^1$, X$^2$ and X$^3$ in the above formula (I) and (II) includes single bond, —CH$_2$—, —CH(OH)—, —CH(CN)—, —CH$_2$—CH$_2$—, —CH(OH)—CH$_2$—, —CH(CN)—CH$_2$—, —CH$_2$—CH(OH)—, —CH$_2$—CH(CN)—, —CH═CH—, —CH═CH—CH$_2$—, —CH═CH—CH(OH)—, —CH═CH—CH(CN)—, —CH(OH)—CH═CH—, —CH(CN)—CH═CH—, —C≡C—, —O—, —S—, —SO—, —SO$_2$—, —CO—, —NH—CO—NH—, —NH—CS—NH—, and the like; the more preferable group includes single bond, —CH$_2$—, —CH(OH)—, —CH(CN)—, —CH$_2$—CH$_2$—, —CH(OH)—CH$_2$—, —CH(CN)—CH$_2$—, —CH$_2$—CH(OH)—, —CH$_2$—CH(CN)—, —CH═CH—, —C≡C—, —CO—, and the like; the further preferable group are —CH$_2$—, —CH(OH)—, —CO—, and a single bond is most preferable.

The preferable mode of in the compound according to the present invention represented by the formula:

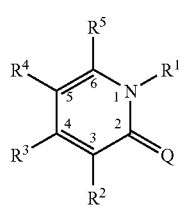

(I)

(wherein Q, R$^1$, R$^2$, R$^3$, R$^4$ and R$^5$ have the same meanings as defined above), a salt thereof or hydrates thereof is not specifically limited. Among them, the preferable mode includes the compound, a salt thereof or hydrates thereof, wherein R$^1$ (namely, 1-position of a pyridone ring) is a group represented by the formula —X-A (X and A have the same meanings as defined above), two of the residual R$^2$, R$^3$, R$^4$ and R$^5$ are a group represented by the formula —X-A (X and A have the same meanings as defined above), and the other two are hydrogen atom, a halogen atom or a C$_{1-6}$ alkyl group; namely, the compound represented by the formula:

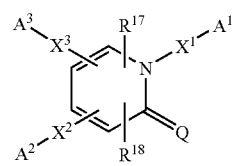

(II)

(wherein Q, X$^1$, X$^2$, X$^3$, A$^1$, A$^2$, A$^3$, R$^{17}$ and R$^{18}$ have the same meanings as defined above), a salt thereof or hydrates thereof. The more preferable mode includes the compound, a salt thereof or hydrates thereof, wherein Q is oxygen in the above formula (II); namely, the pyridone compound represented by the formula:

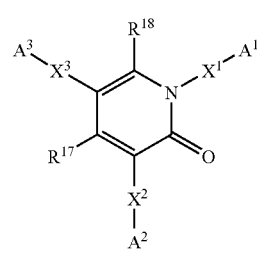

(III)

(wherein X$^1$, X$^2$, X$^3$, A$^1$, A$^2$, A$^3$, R$^{17}$ and R$^{18}$ have the same meanings as defined above), a salt thereof or hydrates thereof. The further preferable mode includes the compound, a salt thereof or hydrates thereof, wherein R$^{17}$ and R$^{18}$ are hydrogen atoms in the above formula (III); namely, 1,3,5-substituted pyridone compound represented by the formula:

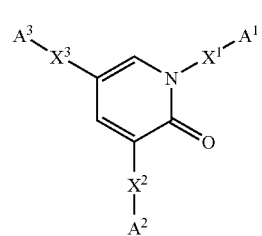

(IV)

(wherein X$^1$, X$^2$, X$^3$, A$^1$, A$^2$ and A$^3$ have the same meanings as defined above), a salt thereof or hydrates thereof. The most preferable mode includes the compound, a salt thereof or hydrates thereof, wherein X$^1$, X$^2$ and X$^3$ are single bonds in the above formula (IV); namely, 1,3,5-substituted pyridone compound represented by the formula:

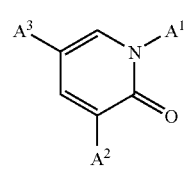

(V)

(wherein A$^1$, A$^2$ and A$^3$ have the same meanings as defined above), a salt thereof or hydrates thereof The preferable groups in A$^1$, A$^2$ and A$^3$ are as in the above exemplification.

There is no particular limitation for "a salt" in the specification of the present application so far as it forms a salt with the compound of the present invention and is a pharmacologically acceptable one. Preferably, salt with a hydrogen halide (such as hydrofluoride, hydrochloride, hydrobromide and hydroiodide, etc.), salt with an inorganic acid (such as sulfate, nitrate, perchlorate, phosphate, carbonate and bicarbonate, etc.), salt with an organic carboxylic acid (such as acetate, trifluoroacetate, oxalate, maleate, tartrate, fumarate and citrate, etc.), salt with an organic sulfonic acid (such as methanesulfonate, trifluoromethanesulfonate, ethanesulfonate, benzenesulfonate, toluenesulfonate and camphor-sulfonate, etc.), salt with an amino acid (such as aspartate and glutamate, etc.), salt with a quaternary amine, salt with an alkaline metal (such as sodium salt and potassium salt, etc.) and salt with an alkaline earth metal (such as magnesium salt and calcium salt, etc.). More preferred examples of the "pharmacologically acceptable salt" are hydrochloride and oxalate etc.

Representative manufacturing methods for the compounds represented by the above formula (I) and (II) according to the present invention will be illustrated as hereunder.

Production process 1

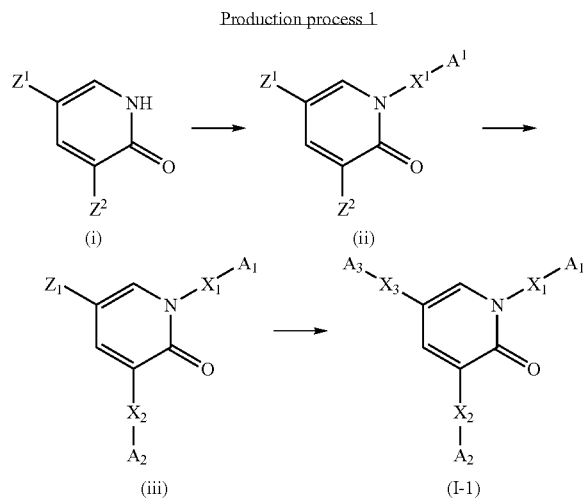

Wherein $A^1$, $A^2$ and $A^3$ may be the same as or different from each other and each indicates optionally substituted $C_{3-8}$ cycloalkyl group, the $C_{3-8}$ cycloalkenyl group, 5- to 14-membered non-aromatic heterocyclic group, $C_{6-14}$ aromatic hydrocarbocyclic group or 5- to 14-membered aromatic heterocyclic group; $Z^1$ and $Z^2$ are the same as or different from each other and each represents halogen atoms; and $X^1$, $X^2$ and $X^3$ have the same meanings as defined above. In the present production process, the most preferable $A^1$, $A^2$ and $A^3$ are optionally substituted $C_{6-14}$ aromatic hydrocarbocyclic group or 5- to 14-membered aromatic heterocyclic group. The above-mentioned production process 1 is a process of producing the compound (I-1) which is related to the present invention, by introducing $A^1$, $A^2$ and $A^3$ in the pyridone compound which has the substituents $Z^1$ and $Z^2$. Namely, the compound (I-1) which is related to the present invention can be produced by the process that the pyridone compound (i) which has the substituents $Z^1$ and $Z^2$ and an aryl boronic acid compound are provided to a coupling reaction using a copper compound to obtain the compound (ii), and then $A^2$ and $A^3$ are introduced in the compound (ii) by carrying out the coupling reaction with an organometallic reagent using a transition metal catalyst or an organoboron compound, preferably carrying out the coupling reaction with an aryl tin derivative, an aryl zinc derivative or an aryl boronic acid derivative, using a palladium catalyst. The preferable aryl boronic acid compound which is used for the reaction of producing the compound (ii) differs depending on a starting raw material, a solvent used and the like, and is not specifically limited unless the reaction is not disturbed, but the aryl boronic acid compound which has a group corresponding to $A^1$ introduced as an aryl group, such as preferably a phenyl boronic acid compound which may be optionally substituted, a heterocyclic boronic acid compound which may be optionally substituted, or the like, can be used. Preferable result can be also obtained by the present reaction in the presence of a base, and at this time, the base used differs depending on a starting raw material, a solvent used and the like. When the base is used in the coupling reaction of the present reaction, it is not specifically limited, and preferably triethylamine, pyridine, tetramethylethylenediamine and the like. Preferable examples of the copper compound used include copper acetate, di-μ-hydroxobis[(N,N,N',N'-tetramethylethylenediamine)copper (II)] chloride, and the like. The more preferable result can be obtained by carrying out the reaction of producing the compound (ii) from (i) in the presence of a solvent. The solvent used differs usually depending on a starting raw material, a reagent and the like, and is not specifically limited so long as it is inert to the reaction and dissolves the raw material in a certain amount. Preferably, dichloromethane, tetrahydrofuran, ethyl acetate and the like may be proposed. Further, the present reaction is preferably carried out under atmosphere of oxygen or in air flow, and good results (the reduction of the reaction time and the improvement of yield etc.) can be obtained thereby. The aryl tin compound, the aryl zinc compound or the aryl boronic acid compound which is used for the reaction of producing the compound (I-1) by introducing $A^2$ and $A^3$ in the compound (ii) differs depending on a starting raw material, a solvent used and the like, and is not specifically limited unless the reaction is not disturbed, but a phenyl tin compound which may be optionally substituted, a heterocyclic tin compound which may be optionally substituted, a phenyl zinc compound which may be optionally substituted, a heterocyclic zinc compound which may be optionally substituted, a phenyl boronic acid compound, a heterocyclic boronic acid compound which may be optionally substituted, an aryl tin compound, an aryl zinc compound or an aryl boronic acid compound which has a group corresponding to $A^2$ or $A^3$ introduced as an aryl group, can be preferably used. Preferable results can be also obtained by the present reaction in the presence of a base, and at this time, the base used differs depending on a starting raw material, a solvent used and the like. Further, it is not specifically limited, unless the reaction is not disturbed, and preferably cesium carbonate, sodium carbonate, potassium carbonate, and the like. The palladium catalyst used is not specifically limited in usual, and known palladium catalysts such as tetrakistriphenylphosphine palladium and the like are preferably mentioned. The reaction of producing the compound (I-1) by introducing $A^2$ and $A^3$ in the compound (ii) is preferably carried out in the presence of a solvent from the viewpoints of operation property and stirring property, and the solvent used is not specifically limited in usual, but dimethylformamide, toluene, xylene, benzene and the like are preferably mentioned. The reaction temperature is not specifically limited, and usually room temperature, or under refluxing by heating, and preferably 50 to 160° C. In addition to them, the compound (I-1) related to the present invention can be also produced by the process that the pyridone compound (iii) after introduction of $A^1$ and $A^2$ is introduced to an organoboron compound or an organometallic reagent, preferably a boronic acid compound, a tin compound or a zinc compound, and the derivative is provided to a coupling reaction with a halogenated aryl derivative using a transition metal catalyst, preferably a palladium catalyst.

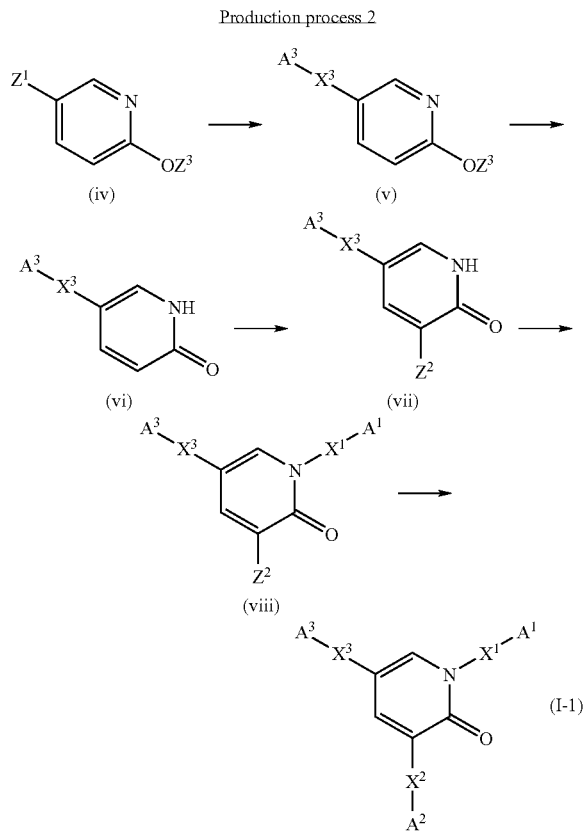

Wherein $X^1$, $X^2$, $X^3$, $A^1$, $A^2$, $A^3$, $Z^1$ and $Z^2$ indicate the same meanings as defined above; and $Z^3$ indicates a protecting group of hydroxy group of an alcohol (for example, a $C_{1-6}$ alkyl group, a benzyl group and the like). In the present production process, the most preferable $A^1$, $A^2$ and $A^3$ are optionally substituted $C_{6-14}$ aromatic hydrocarbocyclic group or 5- to 14-membered aromatic heterocyclic group. The compound (I-1) according to the present invention can be also produced by introducing $A^1$, $A^2$ and $A^3$ to the pyridine compound (IV) having substituents $Z^1$ and —$OZ^3$. The reaction of producing the compound (V) by introducing $A^3$ to the compound (IV) can be carried out by providing to the coupling reaction with an organometallic reagent or an organoboron compound using a transition metal catalyst, preferably by providing the compound (IV) to the coupling reaction with an aryl tin derivative, an aryl zinc derivative, or an aryl boronic acid derivative in the presence of a base, using a palladium catalyst. The aryl tin derivative, the aryl zinc derivative or the aryl boronic acid derivative used for the present reaction differs depending on a starting raw material, a solvent used and the like, and is not specifically limited unless the reaction is not disturbed, but a phenyl tin derivative which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted, an aryl tin derivative, an aryl zinc derivative or an aryl boronic acid derivative which has a group corresponding to $A^3$ introduced as an aryl group, can be preferably used. The base used differs depending on a starting raw material, a solvent used and the like and is not specifically limited unless the reaction is not disturbed, but preferably cesium carbonate, sodium carbonate, potassium carbonate, and the like. The palladium catalyst used is not specifically limited in usual, and known palladium complex such as tetrakistriphenylphosphine palladium and the like are preferably mentioned. Further, the present reaction is preferably carried out in the presence of a solvent from the viewpoints of operation property and stirring property. The solvent used differs depending on a starting material, a solvent used and the like, and those which dissolve the starting material to a certain degree are not specifically limited unless the reaction is not disturbed, but dimethylformamide, toluene, xylene, benzene and the like are preferably mentioned. The reaction temperature is not specifically limited, and usually room temperature, or under refluxing by heating, and preferably 50 to 160° C. The reaction of producing the pyridone compound (vi) by de-protecting of $Z^3$ can be carried out by some known processes, and for example, a conventional process described in T. W. Greene and P. G. M. Wuts "Protecting groups in organic synthesis $2^{nd}$ Edition (1991)" is mentioned as the representative process. The reaction of producing the pyridone compound (vii) by introducing the substituent $Z^2$ to the compound (vi) can be usually carried out by a known halogenation method. The halogenating agent differs depending on a starting raw material, a solvent used and the like and is not specifically limited unless the reaction is not disturbed, but a bromination agent such as acetic acid-bromine, N-bromosuccinimide or the like, an iodination agent such as iodine, N-iodosuccinimide or the like, and the like are preferably used. The compound (viii) can be produced by providing the compound (vii) and an aryl boronic acid derivative to the coupling reaction using a copper compound and by introducing $A^1$. The aryl boronic acid derivative used is not specifically limited in usual, and an aryl boronic acid derivative which may be optionally substituted, a heterocyclic boronic acid derivative which may be optionally substituted, and an aryl boronic acid derivative which has a group corresponding to $A^1$ introduced as an aryl group, can be used. Preferable result can be also obtained by the present reaction in the presence of a base, and at this time, the base used differs depending on a starting raw material, a solvent used and the like. Further, the base is not specifically limited, and preferably triethylamine, pyridine, tetramethylethylenediamine and the like. Preferable examples of the copper compound used include copper acetate, di-μ-hydroxo-bis[(N,N,N',N'-tetramethylethylenediamine)copper (II)] chloride, and the like. Further, the present reaction is preferably carried out in the presence of a solvent. The solvent used differs usually depending on a starting raw material, a reagent and the like, and is not specifically limited so long as it is inert to the reaction and dissolves the starting materials in a certain amount, but is preferably dichloromethane, tetrahydrofuran, ethyl acetate and the like. Further, the present reaction is preferably carried out under atmosphere of oxygen or in air flow, and good results (the reduction of the reaction time and the improvement of yield etc.) can be obtained thereby. The final step of producing the compound (I-1) related to the present invention can be carried out by providing the compound (viii) to the coupling reaction with an organometallic reagent or an organoboron compound using a transition metal catalyst, preferably by providing to the coupling reaction with an aryl tin derivative, an aryl zinc derivative or an aryl boronic acid derivative using a palladium catalyst, and by introducing $A^2$ to the compound (viii). The aryl tin derivative, the aryl zinc derivative or the aryl boronic acid derivative which is used is not specifically limited usually, and a phenyl tin derivative which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted, an aryl tin derivative, an aryl zinc derivative or an aryl boronic acid derivative which has a group corresponding to $A^2$ introduced as an aryl group, can be preferably used.

The sequential reaction of producing (I-1) from (viii) which was mentioned in the production process 2 can also obtain a preferable result in the presence of a base, and at this time, the base used differs depending on a starting raw material, a solvent used and the like. Further, it is not specifically limited, unless the reaction is not disturbed, and preferably cesium carbonate, sodium carbonate, potassium carbonate, and the like. The palladium catalyst used is not specifically limited in usual, and known palladium catalysts such as tetrakistriphenylphosphine palladium and the like are preferably mentioned. Further, a more preferable result can be obtained by carrying out the present reaction in the presence of a solvent, and the solvent used is not specifically limited in usual, and the solvent used differs depending on a starting raw material, a reagent and the like, and the solvent which does not disturb the reaction and dissolves the starting raw material to a certain degree is not specifically limited, but is preferably dimethylformamide, toluene, xylene, benzene and the like. The reaction temperature is not specifically limited, and usually room temperature, or under refluxing by heating, and preferably 50 to 160° C. In addition to them, the compound (I-1) related to the present invention can be also produced by the process that the pyridone compound (viii) after introduction of $A^1$ is introduced to an organoboron compound or an organometallic reagent, preferably a boronic acid compound, a tin compound or a zinc compound, and the derivative is provided to a coupling reaction with a halogenated aryl derivative using a transition metal catalyst, preferably a palladium catalyst.

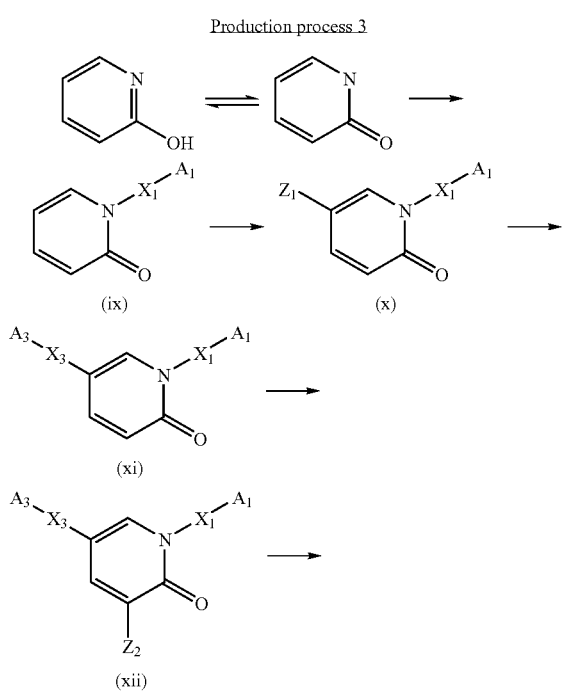

Production process 3

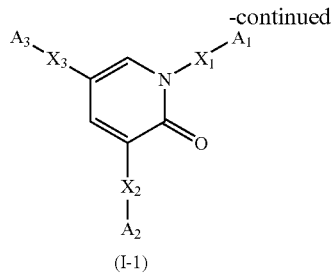

-continued (I-1)

Wherein $X^1$, $X^2$, $X^3$, $A^1$, $A^2$, $A^3$, $Z^1$ and $Z^2$ have the same meanings as defined above, and each of the most preferable group of $A^1$, $A^2$ and $A^3$ in the present production process is the $C_{6-14}$ aromatic hydrocarbocyclic group or the 5 to 14 membered aromatic heterocyclic group which may optionally have one or more substituents, respectively. The compound (I-1) according to the present invention can be also produced by introducing $A^1$, $A^2$ and $A^3$ to 2-hydroxypyridine. The reaction of producing the compound (ix) can be conducted by providing an aryl boronic acid derivative to the coupling reaction using a copper compound, the Ullmann reaction with a halogenated aryl derivative, or a substitution reaction for the halogenated aryl derivative and by introducing $A^1$ to 2-hydroxypyridine. The aryl boronic acid derivative used in the coupling reaction differs usually depending on a starting raw material, a reagent and the like, and is not specifically limited unless the reaction is not disturbed. The aryl boronic acid derivative having a group corresponding to $A^1$ introduced as an aryl group such as a phenyl boronic acid derivative which may be optionally substituted, a heterocyclic boronic acid derivative which may be optionally substituted, and the like can be preferably used. Preferable results can be also obtained by the present reaction in the presence of a base, and at this time, the base used differs depending on a starting raw material, a solvent used and the like. Further, the base is not specifically limited unless the reaction is not disturbed, but is preferably triethylamine, pyridine, tetramethylethylenediamine and the like. Preferable examples of the copper compound used include copper acetate, di-µ-hydroxo-bis[(N,N,N',N'-tetramethylethylenediamine) copper (II)] chloride, and the like. Further, the present reaction is preferably carried out in the presence of a solvent. The solvent used differs usually depending on a starting raw material, a reagent and the like, and the solvent which does not disturb the reaction and dissolves the starting raw material to a certain degree is not specifically limited, but is preferably dichloromethane, tetrahydrofuran, ethyl acetate and the like. Further, the present reaction is preferably carried out under atmosphere of oxygen or in air flow, and good results (the reduction of the reaction time and the improvement of yield etc.) can be obtained thereby. The Ullmann reaction is carried out at 60° C. to under refluxing by heating, preferably 100 to 200° C. in the presence of a base such as potassium carbonate, sodium carbonate or sodium acetate, using copper or a copper compound such as copper iodide, copper chloride, copper bromide or the like, which is not specifically limited usually. The solvent used differs depending on a starting raw material, a reagent and the like, and the solvent which does not disturb the reaction and dissolves the starting raw material to a certain degree is not specifically limited, but is preferably dimethylformamide, toluene, xylene, tetralin, dichlorobenzene, nitrobenzene and the like. The substitution reaction with the halogenated aryl derivative is not specifically limited, but carried out under ice-cooling to under refluxing by heating, preferably at room temperature to 60° C. in a solvent such as tetrahydrofuran or dimethylformamide or the like, using a base such as potassium carbonate, sodium hydride, potassium hydride, sodium butoxide, or potassium butoxide or the like. The reaction of producing the compound (x) by introducing the substituent $Z^1$ to the compound (ix) can be usually carried out by known halogenation method. The halogenating agent used differs depending on a starting raw material, a solvent used and the like, and is not specifically limited, unless the reaction is not disturbed, but a bromination agent such as acetic acid-bromine, N-bromosuccinimide or the like, an iodination agent such as iodine, N-iodosuccinimide or the like, and the like are preferably used. The reaction of producing the compound (xi) by introducing $A^3$ to the compound (x) can be usually carried out by providing the compound (x) to the coupling reaction with an organometallic reagent or an organoboron compound using a transition metal catalyst, preferably by providing it to the coupling reaction with an aryl tin derivative, an aryl zinc derivative, or an aryl boronic acid derivative in the presence of a base, using a palladium catalyst. The aryl tin derivative, the aryl zinc derivative or the aryl boronic acid derivative which is used for the present reaction is not specifically limited usually, but an aryl tin derivative, an aryl zinc derivative or an aryl boronic acid derivative having a group corresponding to $A^3$ introduced as an aryl group such as a phenyl tin derivative. which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted, can be preferably used. The base used differs depending on a starting raw material, a solvent used and the like and is not specifically limited unless the reaction is not disturbed, but preferably cesium carbonate, sodium carbonate, potassium carbonate, and the like. The palladium catalyst used is not specifically limited in usual, and known palladium catalysts such as tetrakistriphenylphosphine palladium and the like are preferably mentioned. Further, the present reaction is preferably carried out in the presence of a solvent from the viewpoints of operation property and stirring property. The solvent used differs depending on a starting material, a solvent used and the like, and the solvent which does not disturb the reaction and dissolves the starting material to a certain degree is not specifically limited, but is preferably dimethylformamide, toluene, xylene, benzene and the like. The reaction temperature is not specifically limited, and usually room temperature, or under refluxing by heating, and preferably 50 to 160° C. The reaction of producing the compound (xii) by introducing the substituent $Z^2$ to the compound (xi) can be usually carried out by known halogenation method. The halogenating agent used differs depending on a starting raw material, a solvent used and the like, and is not specifically limited, unless the reaction is not disturbed, but a bromination agent such as acetic acid-bromine, N-bromosuccinimide or the like, an iodination agent such as iodine, N-iodosuccinimide or the like, and the like are preferably used. The final step of producing the compound (I-1) related to the present invention can be carried out by providing the compound (xii) to the coupling reaction with an organometallic reagent or an organoboron compound using a transition metal catalyst, preferably by providing it to the coupling reaction with an aryl tin derivative, an aryl zinc derivative or an aryl boronic acid derivative using a palladium catalyst, and by introducing $A^2$ to the compound (xii). The aryl tin derivative, the aryl zinc derivative or the aryl boronic acid derivative which is used differs depending on a starting raw material, a solvent used and the like, and is not specifically limited unless the reaction is not disturbed. The aryl tin derivative, aryl zinc derivative or aryl boronic acid derivative having a group corresponding to $A^2$ introduced as an aryl group, such as a phenyl tin derivative which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted, can be used. At this time, the base used differs depending on a starting raw material, a solvent used and the like, and is not specifically limited unless the reaction is not disturbed, but is preferably cesium carbonate, sodium carbonate, potassium carbonate, and the like. The palladium catalyst used differs depending on a starting raw material, a solvent used and the like, and is not specifically limited unless the reaction is not disturbed, but known palladium catalysts such as tetrakistriphenylphosphine palladium and the like are mentioned. Further, a more preferable result can be obtained by carrying out the present reaction in the presence of a solvent, and the solvent used is not specifically limited in usual, but is preferably dimethylformamide, toluene, xylene, benzene and the like. The reaction temperature is not specifically limited, and usually room temperature, or under refluxing by heating, and preferably 50 to 160° C. In addition to them, the compound (I-1) related to the present invention can be also produced by the process that the compound (xii) is introduced to an organoboron compound or an organometallic reagent, preferably a boronic acid derivative, a tin compound or a zinc compound or the like, and the derivative is provided to a coupling reaction with a halogenated aryl derivative using a transition metal catalyst, preferably a palladium catalyst.

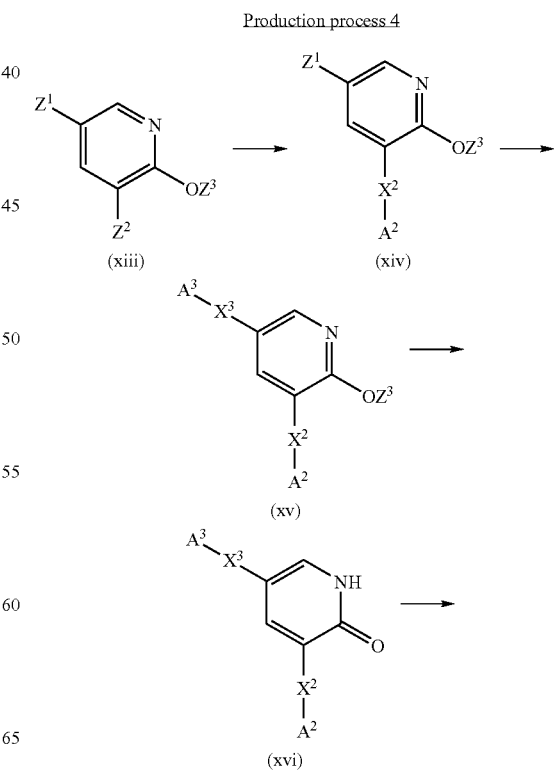

Production process 4

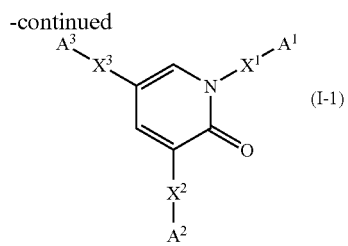

(I-1)

Wherein $X^1$, $X^2$, $X^3$, $A^1$, $A^2$ $A^3$, $Z^1$, $Z^2$ and $Z^3$ have the same meanings as defined above, and each of the most preferable group of $A^1$, $A^2$ and $A^3$ in the present production process is the $C_{6-14}$ aromatic hydrocarbocyclic group or the 5 to 14 membered aromatic heterocyclic group which may optionally have substituents, respectively. The compound (I-1) related to the present invention can be also produced by introducing $A^1$, $A^2$ and $A^3$ to the compound (xiii) having the substituents $Z^1$, $Z^2$ and —$OZ^3$. The reaction of producing the compound (xiv) by introducing $A^2$ to the compound (xiii) can be conducted by providing the compound (xiii) to the coupling reaction with an organometallic reagent or an organoboron compound using a transition metal catalyst, preferably by providing it to the coupling reaction with an aryl tin derivative, an aryl zinc derivative, or an aryl boronic acid derivative in the presence of a base, using a palladium catalyst. The aryl tin compound, aryl zinc compound or aryl boronic acid derivative used in the present reaction differs usually depending on a starting raw material, a reagent and the like, and is not specifically limited unless the reaction is not disturbed. The aryl tin compound, aryl zinc compound or aryl boronic acid derivative having a group corresponding to $A^2$ introduced as an aryl group, such as a phenyl tin derivative which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted and the like can be used. The base used differs depending on a starting raw material, a solvent used and the like and is not specifically limited unless the reaction is not disturbed, but is cesium carbonate, sodium carbonate, potassium carbonate, and the like. The palladium catalyst used differs depending on a starting raw material, a solvent used and the like and is not specifically limited unless the reaction is not disturbed, but known palladium catalysts such as tetrakistriphenylphosphine palladium and the like are mentioned. Further, the present reaction is preferably carried out in the presence of a solvent from the viewpoints of operation property and stirring property. The solvent used differs depending on a starting material, a solvent used and the like, and the solvent which does not disturb the reaction and dissolves the starting material to a certain degree is not specifically limited, but is preferably dimethylformamide, toluene, xylene, benzene and the like. The reaction temperature is not specifically limited, and usually room temperature, or under refluxing by heating, and preferably 50 to 160° C. The reaction of producing the compound (xv) by introducing the substituent $A^3$ to the compound (xiv) can be carried out by providing the compound (xiv) to the coupling reaction with an organometallic reagent or an organoboron compound using a transition metal catalyst, preferably by providing it to the coupling reaction with an aryl tin compound, aryl zinc compound, or aryl boronic acid derivative in the presence of a base, using a palladium catalyst. The aryl tin compound, aryl zinc compound or aryl boronic acid derivative used in the present reaction differs usually depending on a starting raw material, a reagent and the like, and is not specifically limited unless the reaction is not disturbed. The aryl tin compound, aryl zinc compound or aryl boronic acid derivative having a group corresponding to $A^3$ introduced as an aryl group, such as a phenyl tin derivative which may be optionally substituted, a heterocyclic tin derivative which may be optionally substituted, a phenyl zinc derivative which may be optionally substituted, a heterocyclic zinc derivative which may be optionally substituted, a phenyl boronic acid derivative, a heterocyclic boronic acid derivative which may be optionally substituted and the like can be preferably used. The base used differs depending on a starting raw material, a solvent used and the like and is not specifically limited unless the reaction is not disturbed, but is preferably cesium carbonate, sodium carbonate, potassium carbonate, and the like. The palladium catalyst used is not specifically limited usually, but known palladium catalysts such as tetrakistriphenylphosphine palladium and the like are preferably mentioned. Further, the present reaction is preferably carried out in the presence of a solvent from the viewpoints of operation property and stirring property. The solvent used differs depending on a starting material, a solvent used and the like, and the solvent which does not disturb the reaction and dissolves the starting material to a certain degree is not specifically limited, but is preferably dimethylformamide, toluene, xylene, benzene and the like. The reaction temperature is not specifically limited, and usually room temperature, or under refluxing by heating, and preferably 50 to 160° C. The reaction of producing the pyridone compound (xvi) by de-protecting the removal of $Z^3$ can be carried out by some known processes, and for example, a conventional process described in T. W. Greene and P. G. M. Wuts "Protecting groups in organic synthesis $2^{nd}$ Edition (1991)" is mentioned as the representative process. The final step of producing the compound (I-1) related to the present invention can be conducted by providing the compound (xvi) and an aryl boronic acid derivative to the coupling reaction using a copper compound, the Ullmann reaction with a halogenated aryl derivative, or a substitution reaction for the halogenated aryl derivative and by introducing $A^1$. The aryl boronic acid derivative used differs depending on a starting raw material, a solvent used and the like, and is not specifically limited unless the reaction is not disturbed. The aryl boronic acid derivative having a group corresponding to $A^1$ introduced as an aryl group, such as a phenyl boronic acid derivative which may be optionally substituted, a heterocyclic boronic acid derivative which may be optionally substituted and the like can be used. Preferable result can be also obtained by the present reaction in the presence of a base, and at this time, the base used differs depending on a starting raw material, a solvent used and the like. Further, the base is not specifically limited unless the reaction is not disturbed, but is preferably triethylamine, pyridine, tetramethylethylenediamine and the like. Preferable examples of the copper compound used include copper acetate, di-µ-hydroxo-bis[(N,N,N',N'-tetramethylethylenediamine) copper (II)] chloride, and the like. Further, the present reaction is preferably carried out in the presence of a solvent. The solvent used differs usually depending on a starting raw material, a reagent and the like, and the solvent which does not disturb the reaction and dissolves the starting raw material to a certain-degree is not specifically limited, but is preferably dichloromethane, tetrahydrofuran, ethyl acetate and the like. Further, the present reaction is preferably carried out under atmosphere of oxygen or in air flow, and good results (the reduction of the reaction time and the improvement of yield etc.) can be obtained thereby. The Ullmann reaction is carried out at 60° C. to under refluxing by heating, preferably 100 to 200° C. in the presence of a base such as potassium carbonate, sodium carbonate or sodium acetate, using copper or a copper compound such as copper iodide, copper chloride, copper bromide or the like, which is not specifically limited usually. The solvent used differs depending on a starting raw material, a reagent and the like, and the solvent which does not disturb the reaction and dissolves the starting raw material to a certain degree is not specifically limited, but is preferably dimethylformamide, toluene, xylene, tetralin, dichlorobenzene, nitrobenzene and the like. The substitution reaction with the halogenated aryl derivative is not specifically limited, but carried out under ice-cooling to under refluxing by heating, preferably at room temperature to 60° C. in a solvent such as tetrahydrofuran or dimethylformamide or the like, using a base such as potassium carbonate, sodium hydride, potassium hydride, sodium butoxide, or potassium butoxide or the like.

In the above production process, the production intermediate represented by the formula:

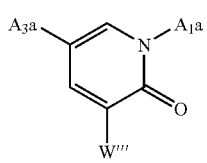

(Wherein $A^{1a}$ and $A^{3a}$ are the same as or different from each other and each indicate a $C_{6-14}$ aromatic hydrocarbocyclic group or 5 to 14 membered aromatic heterocyclic group which may be optionally substituted, respectively, and W''' indicates a halogen atom) can be also produced by the following method (Production process 5).

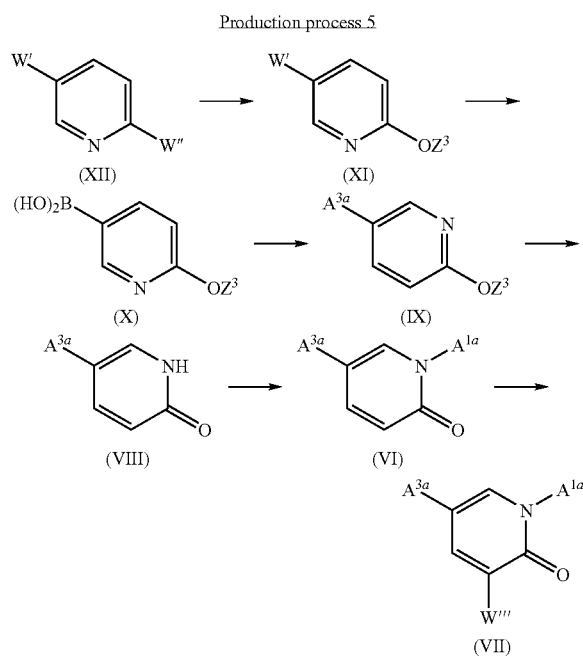

W', W'' and W''' in the above formula indicate the same or different halogen atom, and the most preferable atom is bromine atom.

The compound (XII) can be easily produced according to known methods or corresponding methods, and further, can be easily obtained as a commercially available substance. The step of producing the compound (XI) from the compound (XII) is a step of reacting the compound (XII) with the base represented by the formula $Z^3OM$ (M indicates an alkali metal atom). The base differs depending on a starting raw material, a solvent used and the like, and is not specifically limited unless the reaction is not disturbed, but is preferably sodium alkoxide, and preferably sodium methoxide, sodium ethoxide and the like in particular. In this case, it is preferable to carry out the reaction in an alcohol corresponding to the alkoxide used, and for example, it is preferable to carry out in methanol in case of using sodium methoxide and ethanol in case of using sodium ethoxide, etc.

The step of producing the compound (X) from the compound (XI) is a step of reacting the compound (XI) with trimethoxyborane in the presence of a base. The base used differs depending on a starting raw material, a solvent used and the like, and is not specifically limited unless the reaction is not disturbed, but is preferably n-butyllithium and the like. The solvent used differs depending on a starting raw material, a solvent used and the like, and the solvent which does not disturb the reaction and dissolves the starting material to a certain degree is not specifically limited, but is preferably ethers such as tetrahydrofuran, and the like. When n-butyllithium is used as a base, the reaction can be terminated by an acid such as hydrochloric acid, or the like according to a conventional method.

The step of producing the compound (IX) from the compound (X) is a step of carrying out the coupling reaction of the compound (X) with a halogenoaryl or a halogenoheteroaryl which corresponds to the substituent $A^{3a}$ introduced, in the presence of a base and a palladium catalyst and producing the compound (IX). The palladium catalyst used is not specifically limited, but palladium acetate/triphenylphosphine catalyst and the like can be mentioned as the preferable example. The base used differs depending on a starting raw material, a solvent used and the like, and is not specifically limited unless the reaction is not disturbed, but is preferably cesium carbonate, sodium carbonate, potassium carbonate, and the like. Further, the present step is preferably carried out in the presence of a solvent from the viewpoints of operation property and stirring property. The solvent used differs depending on a starting raw material, a solvent used and the like, and the solvent which does not disturb the reaction and dissolves the starting material to a certain degree is not specifically limited, but is preferably 1,2-dimethoxyethane, dimethylformamide, toluene, xylene, benzene and the like. The reaction temperature is not specifically limited, and usually room temperature, or under refluxing by heating, and preferably 50 to 160° C.

The step of producing the compound (VIII) from the compound (IX) is a step of submitting to the reaction of protecting the removal of $Z^3$ of the compound (IX). The present step can be carried out by some known processes, and for example, a method of refluxing the compound (IX) by heating in the presence of an acid (preferably, hydrochloric acid and the like) is mentioned. Additionally, for example, a conventional process described in T. W. Greene and P. G. M. Wuts "Protecting groups in organic synthesis $2^{nd}$ Edition (1991)" is mentioned as the representative process.

The step of producing the compound (VI) from the compound (VIII) is a step of submitting the compound (VIII) and the aryl boronic acid derivative represented by the formula $A^{1a}B(OH)_2$ to the coupling reaction using a copper compound and introducing $A^{1a}$. The aryl boronic acid derivative used is not specifically limited usually. The aryl boronic acid derivative which has a group corresponding to $A^{1a}$ introduced as an aryl group, such as a phenyl boronic acid derivative which may be optionally substituted, a heterocyclic boronic acid derivative which may be optionally substituted and the like can be used. Preferable result can be also obtained by the present reaction in the presence of a base, and at this time, the base used differs depending on a starting raw material, a solvent used and the like. Further, the base is not specifically limited unless the reaction is not disturbed, but is preferably triethylamine, pyridine, tetramethylethylenediamine and the like. Preferable examples of the copper compound used include copper acetate, di-μ-hydroxobis[(N,N,N',N'-tetramethylethylenediamine)copper (II)] chloride, and the like. Further, the present reaction is preferably carried out in the presence of a solvent. The solvent used differs usually depending on a starting raw material, a reagent and the like, and the solvent which does not disturb the reaction and dissolves the starting raw material to a certain degree is not specifically limited, but is preferably N,N-dimethylformamide, dichloromethane, tetrahydrofuran, ethyl acetate and the like. Further, the present reaction is preferably carried out under atmosphere of oxygen or in air flow, and good results (the reduction of the reaction time and the improvement of yield etc.) can be obtained thereby.

The step of producing the compound (VII) from the compound (VI) is a step of submitting the compound (VI) to the halogenation reaction. The halogenation reaction can be usually carried out by known halogenation methods. The halogenating agent used differs depending on a starting raw material, a solvent used and the like, and is not specifically limited unless the reaction is not disturbed, but is preferably a bromination agent such as acetic acid-bromine, N-bromosuccinimide or the like, an iodination agent such as iodine, N-iodosuccinimide or the like, and the like.

According to the above production process 5, the production intermediates (VI) and (VII) can be produced in high yield. Further, when the production intermediates of the compounds related to the present invention are produced according to the production processes, the contamination of a copper compound to the final product can be easily prevented, and the compounds of the present invention satisfying the point of safety (toxicity and the like) can be provided. Accordingly, the production processes are extremely excellent production processes from the viewpoints of yield and safety, experimentally and industrially. The novel compound represented by the formula:

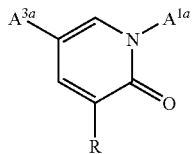

(wherein $A^{1a}$ and $A^{3a}$ are the same as defined above; and R indicates hydrogen atom or a halogen atom) or a salt thereof is useful as the production intermediate in the production of the compound (I) according to the present invention or a salt thereof. In the formula (XIII), the preferable examples in $A^{1a}$ and $A^{3a}$ may be the same as or different from each other, and each includes phenyl group, pyridyl group, pyridazinyl group, pyrimidinyl group, pyrazinyl group, thienyl group, thiazolyl group, furyl group, naphthyl group, quinolyl group, iso-quinolyl group, indolyl group, benzimidazolyl group, benzothiazolyl group, benzoxazolyl group, imidazopyridyl group, carbazolyl group etc., which may optionally have one or more substituents, respectively. The more preferable examples may be the same as or different from each other, and each includes a phenyl group, pyridyl group, pyrimidinyl group, thienyl group, furyl group etc., which may optionally have one or more substituents, respectively. Further, the preferable examples in R in particular are hydrogen atom or bromine atom.

The substituents on $A^1$, $A^2$ and $A^3$ in the compound represented by the formula:

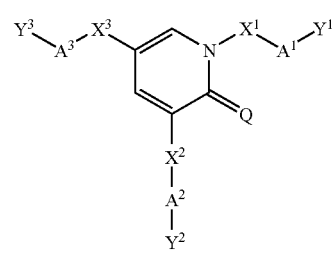

(wherein Q, $X^1$, $X^2$, $X^3$, $A^1$, $A^2$ and $A^3$ have the same meanings as defined above; $Y^1$, $Y^2$ and $Y^3$ indicates the same or different substituent; and each of the most preferable group in $A^1$, $A^2$ and $A^3$ is a $C_{6-14}$ aromatic hydrocarbocyclic group or 5 to 14 membered aromatic heterocyclic group which may optionally have one or more substituents, respectively) can be converted by various reactions. For example, the representative processes are as below. (1) When $Y^1$, $Y^2$ and/or $Y^1$, $Y^2$ and/or $Y^3$ are/is nitro group(s), various reactions are known for changing to a functional group from a nitro group, although there is no particular limitation for the method and for the resulting substance, a method of changing to an amine derivative by a reduction reaction may be exemplified. Although there is usually no particular limitation for the reduction condition, preferred conditions are a method where iron, zinc or tin is used under acidic conditions, a hydrogenation method where palladium, rhodium, ruthenium, platinum or a complex thereof is used as a catalyst. When the amine derivative produced by the said reduction reaction is used, it is possible to further change to an amide compound, a carbamate compound, a sulfonamide compound, a halogen compound, a substituted amine compound etc., easily. (2) When $Y^1$, $Y^2$ and/or $Y^3$ are/is alkoxy group(s), an example for changing to a functional group from an alkoxy group is a method to change to an alcohol derivative by means of deprotection. The alcohol derivative which is prepared by the said method may be easily changed to an ester compound by a dehydrating condensation with carboxylic acid derivative or by a reaction with an acid chloride or may be easily changed to an ether compound by a Mitsunobu reaction or by a condensation reaction with a halogen compound. (3) When $Y^1$, $Y^2$ and/or $Y^3$ are/is aldehyde group(s), various reactions are known for changing to a functional group from an aldehyde group and, although there is no particular limitation for the method therefor and the resulting substance by the change, an example is a method of changing to a carboxylic acid derivative by an oxidation reaction. The carboxylic acid derivative prepared by the said method may be easily changed further to an ester compound, a ketone compound, etc. In addition, starting from the said aldehyde derivative, it is possible to easily manufacture an alcohol derivative by a reduction reaction, an amine derivative by a reductive amination reaction, a secondary alcohol compound by an addition reaction with an organic metal reagent and various alkyl derivatives by a Wittig reaction. (4) When $Y^1$, $Y^2$ and/or $Y^3$ are/is halogen atom(s), an example for changing to a functional group from a halogen atom as substituents is a method of changing to a nitrile derivative by a substitution reaction. Besides the above, it is also possible to easily change to various kinds of compounds via, for example, an organolithium compound, an organomagnesium compound, an organotin compound or an organoboronic acid derivative etc.

The above-mentioned methods are the methods for the manufacture of the compound (I) of the present invention. The starting compound in the above-mentioned methods may form a salt or a hydrate and there is no particular limitation for such salt and hydrate so far as they do not inhibit the reaction. When the compound (I) of the present invention is obtained in a free substance, it may be changed to a state of a salt by conventional methods. Further, various isomers (for example, a geometrical isomer, an enantiomer based on an asymmetric carbon, a rotamer, a stereoisomer, a tautomer, and the like) which are obtained for the compound (I) related to the present invention are purified by using usual separation procedures, for example, such as recrystallization, a diastereomer salt method, an enzymolysis method, various chromatographies (for example, thin layer chromatography, column chromatography, gas chromatography, and the like), and can be separated.

The present invention includes within its scope pharmaceutically acceptable compositions useful in treating demyelinating disorders which comprise an inhibitor of the present invention. The inhibitor will usually be provided in combination with a pharmaceutically acceptable carrier. It may be used in any suitable form, provided that it can still act in inhibiting the interaction of glutamate with the AMPA receptor complex. For example, pharmaceutically acceptable salts, esters, hydrates, etc. may often be used.

A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier. Preferably it will be provided in unit dosage form. It will normally be provided in a sealed, sterile container e.g. in an ampoule, a vial, a bottle, a blister pack, etc.

Different drug delivery systems can be used to administer pharmaceutical compositions of the present invention, depending upon the desired route of administration. Such systems include tablets, diluted powder, fine granules, granules, coated tablets, capsules, syrup, troche, inhalation preparation, suppositories, injections, ointments, eye ointments, eye drops, nasal preparations, ear drops, cataplasma and lotions by means of conventional methods. In the manufacture of the pharmaceutical preparations, it is possible to use commonly used fillers, binders, disintegrating agent, lubricants, coloring agents, corrigents and, if necessary, stabilizers, emulsifiers, absorption promoters, surfactant, pH adjusting agents, antiseptics, antioxidants, etc. and, after compounding with the ingredients commonly used as materials for the pharmaceutical preparations, it is made into pharmaceutical preparations by a common method. Examples of the components therefor are 1) animal and plant oil such as soybean oil, beef tallow and synthetic glyceride; 2) hydrocarbon such as liquid paraffin, squalane and solid paraffin; 3) ester oil such as octyldodecyl myristate and isopropyl myristate; 4) higher alcohol such as cetostearyl alcohol and behenyl alcohol; 5) silicone resin; 6) silicone oil; 7)surfactant such as polyoxyethylene fatty acid ester, sorbitan fatty acid ester, glycerol fatty acid ester, polyoxyethylene sorbitan fatty acid ester, polyoxyethylene hydrogenated castor oil and polyoxyethylene-polyoxypropylene block copolymer; 8) water-soluble high-molecular substance such as hydroxyethyl cellulose, polyacrylic acid, carboxyvinyl polymer, polyethylene glycol, polyvinylpyrrolidone and methylcellulose; 9) lower alcohol such as ethanol and isopropanol; 10) polyhydric alcohol such as glycerol, propylene glycol, dipropylene glycol and sorbitol; 11) saccharide such as glucose and sucrose; 12) inorganic powder such as silicic acid anhydride, aluminum magnesium silicate and aluminum silicate; 13) and pure water. Applicable examples of (1) a filler are lactose, corn starch, pure sugar, glucose, mannitol, sorbitol, crystalline cellulose and silicon dioxide; those of (2) a binder are polyvinyl alcohol, polyvinyl ether, methyl cellulose, ethyl cellulose, gum arabic, tragacanth, gelatin, shellac, hydroxypropyl methyl cellulose, hydroxypropyl cellulose, polyvinylpyrrolidone, polypropylene glycol-polyoxyethylene block copolymer, meglumine, calcium citrate, dextrin and pectin; those of (3) a disintegrating agent are starch, agar, gelatin powder, crystalline cellulose, calcium carbonate, sodium bicarbonate, calcium citrate, dextrin, pectin and carboxymethyl cellulose calcium; those of (4) a lubricant are magnesium stearate, talc, polyethylene glycol, silica and hydrogenated plant oil; those of (5) a coloring agent are those which are allowed to add to pharmaceuticals; those of (6) a corrigent are cocoa powder, menthol, aromatic powder, peppermint oil, borneol and cinnamon powder; and those of (7) an antioxidant are those which are permitted to be added to pharmaceuticals, such as ascorbic acid, α-tocopherol and the like, are respectively used.

(1) In the manufacture of preparations for oral use, the compound of the present invention or a pharmacologically acceptable salt is mixed with a filler and, if necessary, further with a binder, a disintegrating agent, a lubricant, a coloring agent, a corrigent, etc. and the mixture is made into diluted powder, fine particles, granules, tablets, coated tablets, capsules, etc. by a common method. (2) In case of tablets and coated tablets, there is of course no problem that such tablets and granules are sugar-coated, gelatin-coated, or appropriately coated upon necessity. (3) In case of the manufacture of liquid preparations such as syrup, injection preparations and eye drops, a pH adjusting agent, a solubilizer, an isotonizing agent, etc. and, if necessary, a solubilizing aid, a stabilizer, buffer, suspending agent, antioxidant etc. are added, and then made into pharmaceutical preparations by a common method. It can be made as a freeze drying product, and injections can be dosed in vena, subcutis, and muscle. Preferable examples in a suspending agent include methyl cellulose, polysorbate 80, hydroxyethyl cellulose, gum arabic, tragacanth powder, sodium carboxymethyl cellulose, polyoxyethylene sorbitan monolaurate, and the like; preferable examples in a resolving aid include polyoxyethylene hardened castor oil, polysorbate 80, nicotinic acid amide, polyoxyethylene sorbitan monolaurate, and the like; preferable examples in a stabilizer include sodium sulfite, meta sodium sulfite, ether, and the like; preferable examples in a preservative include methyl p-oxybenzoate, ethyl p-oxybenzoate, sorbic acid, phenol, cresol, chlorocresol and the like. Further, (4) in case of external use, there is no particular limitation for a method of manufacturing a pharmaceutical preparation, but a common method is used for the manufacture. Thus, with regard to a base material used, various materials which are commonly used for pharmaceuticals, quasi drugs, cosmetics, etc. may be used. Specific examples of the base material used are animal/plant oil, mineral oil, ester oil, waxes, higher alcohols, fatty acids, silicone oil, surfactant, phospholipids, alcohols, polyhydric alcohols, water-soluble high-molecular substances, clay minerals and pure water and, if necessary, it is possible to add pH adjusting agent, antioxidant, chelating agent, antiseptic antifungal, coloring agent, perfume, etc. If necessary, it is further possible to compound other components such as a component having a differentiation-inducing action, blood flow promoter, bactericide, anti-inflammatory agent, cell activator, vitamins, amino acid, moisturizer and keratin solubilizing agent.

Dose of the pharmaceutical agent according to the present invention varies depending upon degree of symptom, age, sex, body weight, dosage form, type of salt, sensitivity to the pharmaceuticals, specific type of the disease, etc. and, in the case of adults, the daily dose is usually about 30 μg to 10 g, preferably, 100 μg to 5 g or, more preferably, 100 μg to 100 mg in the case of oral administration while, in the case of administration by injection, it is usually about 30 μg to 1 g, preferably 100 μg to 500 mg or, more preferably, 100 μg to 30 mg. That is administered once daily or dividedly for several times a day.

EXAMPLES

The following Reference Examples, Examples and in vivo Examples are exemplary, and not intended to limit the present invention. One skilled in the art may make various variations of the Reference Examples, Examples and in vivo Examples as well as of the claims of the invention to fully utilize the invention. These variations shall be included in claims of the invention.

Referential Example 1

5-Bromo-3-iodo-1,2-dihydropyridin-2-one

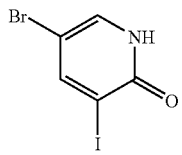

2-Amino-5-bromopyridine (CAS No. 1072-97-5) (300 g) was dissolved in a mixed solvent consisting of 1000 ml of acetic acid and 200 ml of water, 30 ml of concentrated sulfuric acid were gradually dropped thereinto under stirring. Then, 79.1 g of periodic acid hydrate and 176 g of iodine were added thereto, followed by stirring at 80° C. for 4 hours. To the reaction mixture were added periodic acid hydrate (40 g) and iodine (22 g), followed by further stirring at 80° C. for 2 hours. After cooling to room temperature, the reaction mixture was poured onto ice (3000 ml) and neutralized to pH 7.0 with 5N aqueous sodium hydroxide. The resulting crystals were collected by filtration, dissolved in a mixed solvent of ethyl acetate/diethyl ether, successively washed with aqueous sodium thiosulfate, water, 1N aqueous sodium hydroxide and brine, and dried over anhydrous magnesium sulfate. Then, the solvent was evaporated, to give 392 g of 2-amino-5-bromo-3-iodopyridine (yield: 76%). 2-Amino-5-bromo-3-iodopyridine (100 g) was gradually added to 300 ml of concentrated sulfuric acid under ice-cooling. After the reaction mixture was stirred at room temperature for 2 hours, it was ice-cooled again. 35 g of sodium nitrite were gradually added thereto, followed by stirring at room temperature for 3 days and nights. The reaction solution was poured onto ice (3000 ml) and neutralized to pH 4.0 with sodium hydroxide. The resulting crystals were collected by filtration, washed with water and warm air-dried at 60° C. for one day and night, to give 102 g (quantitative) of the title compound.

$^1$H-NMR (400 MHz, CDCl$_3$); δ (ppm) 7.60 (d, 1H), 8.14 (d, 1H).

Referential Example 2

5-Bromo-1-phenyl-3-iodo-1,2-dihydropyridin-2-one

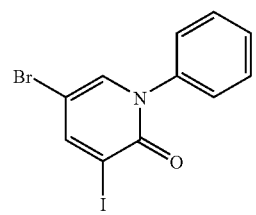

5-Bromo-3-iodo-1,2-dihydropyridin-2-one (10.0 g) obtained in Referential Example 1, 10.0 g of phenylboronic acid and 8.1 g of copper acetate were suspended in 500 ml of dichloromethane. 15 ml of triethylamine were added thereto, followed by stirring at room temperature for 5 days and nights. To the reaction solution were added 200 ml of water and 50 ml of aqueous ammonia, followed by stirring vigorously. Then the insoluble matters were filtered off through Celite, the filtrate was extracted with dichloromethane, the extract was dried over anhydrous magnesium sulfate. The solvent was evaporated, and the residue was recrystallized from ethyl acetate/hexane, to give 6.54 g (yield: 52%) of the title compound.

$^1$H-NMR (400 MHz, CDCl$_3$); δ (ppm) 7.34-7.38 (m, 2H), 7.44-7.52 (m, 3H), 7.53 (d, 1H), 8.10 (d, 1H).

Referential Example 3

5-Bromo-3-(2-cyanophenyl)-1-phenyl-1,2-dihydropyridin-2-one

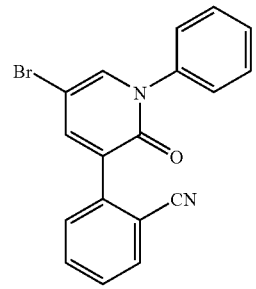

5-Bromo-1-phenyl-3-iodo-1,2-dihydropyridin-2-one (11.69 g) obtained in Referential Example 2, 8.0 g of 2-(2-cyanophenyl)-1,3,2-dioxaborinate and 16.0 g of cesium carbonate were suspended in 150 ml of dimethylformamide. 3.0 g of tetrakistriphenylphosphine palladium were added thereto, followed by stirring at 80° C. in nitrogen atmosphere for 2 hours. The reaction solution was poured into water, the mixture was extracted with ethyl acetate, the extract was successively washed with water and brine and dried over anhydrous magnesium sulfate. Then, the solvent was evaporated, and the residue was purified by a silica gel column chromatography (hexane/ethyl acetate system), followed by recrystallizing from ethyl acetate/hexane, to give 5.67 g (yield: 52%) of the title compound.

$^1$H-NMR (400 MHz, CDCl$_3$); δ (ppm) 7.42-7.54 (m, 6H), 7.61-7.65 (m, 4H), 7.66 (d, 1H), 7.74-7.77 (m, 1H).

Referential Example 4

5-(2-Pyridyl)-1,2-dihydropdin-2-one

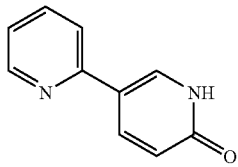

2,5-Diboromopyridine [CAS No. 624-28-2] (400 g) was added to 3500 ml of a 28% methanolic solution of sodium methoxide, the mixture was stirred at 60° C. for 3 hours and allowed to cool, the reaction solution was poured into 3 liters of water, the mixture was extracted with 9000 ml of diethyl ether, the extract was washed with a saturated saline solution for three times and dried over anhydrous magnesium sulfate and the solvent was evaporated in vacuo. The residue was dissolved in 2 liters of dimethylformamide, 900 g of tri-N-butyl-(2-pyridyl) tin [CAS No. 59020-10-9] and 20 g of tetrakistriphenylphosphine palladium and mixture was stirred at 120° C. in a nitrogen atmosphere for 3 hours. The reaction solution was allowed to cool and poured into 3 liters of water, the mixture was extracted with 10 liters of diethyl ether, the extract was successively washed with a saturated sodium bicarbonate solution and a saturated saline solution and the solvent was evaporated in vacuo. A 48% aqueous solution (800 ml) of hydrogen bromide was added to the residue and the mixture was stirred at 110° C. for 3 hours. After allowing to cool, the reaction solution was washed with 3 liters of diethyl ether, poured into 2 liters of ice, adjusted to pH 11.0 with a 5N sodium hydroxide solution and washed with 3 liters of diethyl ether again. The aqueous layer was adjusted to pH 7.0 and extracted with dichloromethane. The crude crystals prepared by evaporating the solvent in vacuo were washed with a mixed solvent consisting of diethyl ether and hexane to give 201.5 g (yield: 69%) of the title compound.

$^1$H-NMR (400 MHz, CDCl$_3$); δ (ppm) 6.72 (d, 1H), 7.20 (ddd, 1H), 7.50-7.54 (m, 1H), 7.73 (dt, 1H), 8.12-8.15 (m, 1H), 8.19 (dd, 1H), 8.60-8.64 (m, 1H).

Referential Example 5

3-Bromo-5-(2-pyridyl)-1,2-dihydropyridin-2-one

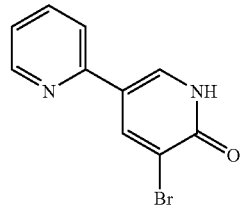

5-(2-Pyridyl)-1,2-dihydropyridin-2-one (201.5 g) obtained in Referential Example 4 was dissolved in 1300 ml of dimethylformamide, 208.3 g of N-bromosuccimide were added thereto and the mixture was stirred at room temperature for 2 hours. The reaction mixture was poured into 4 liters of ice water and the precipitate was filtered and dried with warm air at 50° C. for two days and nights to give 230 g (yield: 79%) of the title compound.

$^1$H-NMR (400 MHz, CDCl$_3$); δ (ppm) 7.21-7.26 (m, 1H), 7.52 (d, 1H), 7.75 (dt, 1H), 8.21 (d, 1H), 8.61-8.64 (m, 1H), 8.67 (d, 1H).

Referential Example 6

3-Bromo-5-(2-pyridyl)-1-(3-pyridyl)-1,2-dihydropyridin-2-one

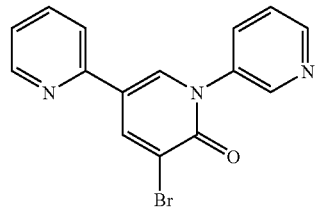

Dichloromethane (300 ml) was added to 18.75 g of 3-bromo-5-(2-pyridyl)-1,2-dihydropyridin-2-one obtained in Referential Example 5 and 18.36 of 3-pyridineboronic acid, then 3.47 g of di-µ-hydroxo-bis[(N,N,N',N'-tetramethylethylenediamine) copper (II)] chloride were added and the mixture was stirred in an oxygen atmosphere for 4 days and nights. The reaction solution was purified by an NH silica gel short column (eluted by ethyl acetate), the solvent was evaporated in vacuo and the resulting crude crystals were washed with diethyl ether to give 24.26 g (yield: 99%) of the title compound.

$^1$H-NMR (400 MHz, CDCl$_3$); δ (ppm) 7.23-7.26 (m, 1H), 7.47-7.51 (m, 1H), 7.52-7.56 (m, 1H), 7.77 (dt, 1H), 7.87-7.91 (m, 1H), 8.19 (d, 1H), 8.53 (d, 1H), 8.59-8.62 (m, 1H), 8.71-8.75 (m, 2H).

Referential Example 7

1-(2-Pyridyl)-1,2-dihydropyridin-2-one

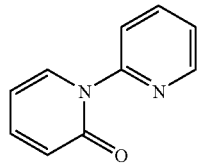

25 ml of a dimethylformamide solution containing 4.00 g of 2(1H)-pyridone and 8.00 g of 2-bromopyridine was incorporated with 3.80 g of potassium carbonate and 0.51 g of cuprous iodide, followed by stirring at 120° C. for 2 hours. After the mixture was returned to room temperature, water was added thereto. The mixture was extracted with ethyl acetate, and the ethyl acetate layer was washed with water and brine, and then dried over magnesium sulfate. The solvent was evaporated, and the residue was purified by silica gel chromatography (ethyl acetate/hexane=1:1), to give 1.58 g of the title compound as a pale yellow wax.

$^1$H-NMR (400 MHz, CDCl$_3$); δ (ppm) 6.31 (dt, 1H), 6.67 (d, 1H), 7.33 (ddd, 1H), 7.40 (ddd, 1H), 7.82-7.90 (m, 2H), 7.96 (dd, 1H), 8.57 (dd, 1H).

Referential Example 8

1-(2-Pyridyl)-5-bromo-1,2-dihydropyridin-2-one

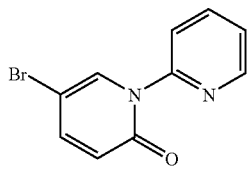

Under ice-cooling, 15 ml of a dimethylformamide solution containing 1.50 g of 1-(2-pyridyl)-1,2-dihydropyridin-2-one was incorporated with 1.60 g of N-bromosuccinic acid imide. The mixture was stirred at room temperature for 2 hours, and then diluted with water and extracted with ethyl acetate. The organic layer was washed with water and brine, and then dried over magnesium sulfate. The solvent was evaporated, and the residue was purified by silica gel chromatography (ethyl acetate/hexane=1:3), to give 1.13 g of the title compound as a pale brown powder.

$^1$H-NMR (400 MHz, CDCl$_3$); δ (ppm) 6.57 (d, 1H), 7.34 (ddd, 1H), 7.42 (dd, 1H), 7.85 (dt, 1H), 7.97 (dd, 1H), 8.10 (d, 1H), 8.57 (dd, 1H).

Referential Example 9

1-(2-Pyridyl)-5-(2-pyridyl)-1,2-dihydropyridin-2-one

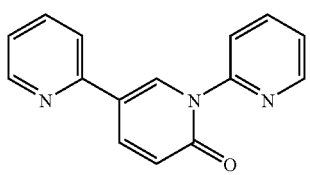

2.5 ml of a dimethylformamide solution containing 0.10 g of 1-(2-pyridyl)-5-bromo-1,2-dihydropyridin-2-one and 0.30 g of 2-tributyl stannyl pyridine was incorporated with 0.05 g of dichlorobistriphenylphosphine palladium, followed by stirring at 130° for 2 hours. The mixture was returned to room temperature, followed by diluting with water and extracting with ethyl acetate. The organic layer was washed with water and brine, and then dried over magnesium sulfate. The solvent was evaporated, and the residue was purified by silica gel chromatography (ethyl acetate), to give 0.076 g of the title compound as a pale yellow powder.

$^1$H-NMR (400 MHz, CDCl$_3$); δ (ppm) 6.77 (d, 1H), 7.22 (dd, 1H), 7.36 (dd, 1H), 7.61 (d, 1H), 7.76 (dt, 1H), 7.87 (dt, 1H), 7.97 (d, 1H), 8.12 (dd, 1H), 8.60-8.65 (m, 2H), 8.67 (d, 1H).

Referential Example 10

1-(2-Pyridyl)-5-(2-pyridyl)-3-bromo-1,2-dihydropyridin-2-one

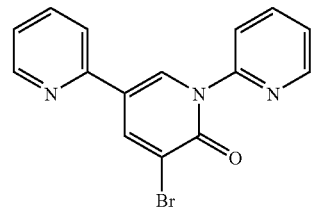

2 ml of a dimethylformamide solution containing 0.07 g of 1-(2-pyridyl)-5-(2-pyridyl)-1,2-dihydropyridin-2-one was incorporated with 0.07 g of N-bromosuccinic acid imide, under stirring and ice-cooling. After stirring the mixture at room temperature for 2 hours, it was diluted with water and extracted with ethyl acetate. The organic layer was washed with water and brine, and then dried over magnesium sulfate. The solvent was evaporated, and the residue was purified by silica gel chromatography (ethyl acetate/hexane=3:1), to give 0.05 g of the title compound as a pale brown powder.

$^1$H-NMR (400 MHz, DMSO-d$_6$); δ (ppm) 7.33 (ddd, 1H), 7.58 (ddd, 1H), 7.83-7.88 (m, 2H), 7.97 (dd, 1H), 8.07 (dt, 1H), 8.59-8.62 (m, 1H), 8.65-8.80 (m, 1H), 8.72 (d, 1H), 8.81 (d, 1H).

Referential Example 11

3,5-Dibromo-2-methoxypyridine

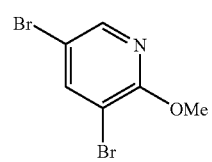

80 ml of a 28% sodium methoxide solution was incorporated with 30.0 g of 2,3,5-tribromopyridine under ice-cooling, followed by stirring at 50° C. for 2 hours. The reaction solution was diluted with water and extracted with diethyl ether. The organic layer was washed with brine, and then dried over anhydrous magnesium sulfate. The solvent was evaporated, and the residue was purified by silica gel chromatography (ethyl acetate/hexane=1:20), to give 18.5 g of the title compound.

$^1$H-NMR (400 MHz, CDCl$_3$); δ (ppm) 3.99 (s, 3H), 7.93 (d, 1H), 8.14 (d, 1H).

Referential Example 12

3-(2-Pyridyl)-5-bromo-2-methoxypyridine

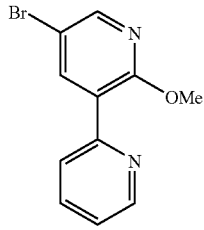

100 ml of a dimethylformamide solution containing 6.3 g of 3,5-dibromo-2-methoxypyridine and 8.1g of 2-tributyl stannyl pyridine was incorporated with 1.0 g of tetrakistriphenylphosphine palladium, followed by stirring at 120° C. for 2 hours in nitrogen atmosphere. After the mixture was returned to room temperature, the solvent was evaporated, and the residue was extracted with ethyl acetate. The organic layer was washed with water and brine, and then dried over magnesium sulfate. The solvent was evaporated, and the residue was purified by silica gel chromatography (ethyl acetate/hexane=1:3), to give 2.8 g of the title compound as a pale yellow powder.

$^1$H-NMR (400 MHz, CDCl$_3$); δ (ppm) 4.02 (s, 3H), 7.31 (dd, 1H), 7.80 (dt, 1H), 8.02 (ddd, 1H), 8.25 (d, 1H), 8.40 (d, 1H), 8.71-8.74 (m, 1H).

Referential Example 13

3-(2-Pyridyl)-5-phenyl-2-(1H)-pyridone

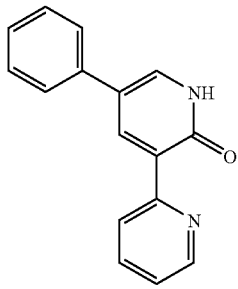

A mixture of 1.0 g of 3-(2-pyridyl)-5-bromo-2-methoxypyridine, 0.9 g of phenylboronic acid, 0.3 g of dichlorobistriphenylphosphine palladium and 2 ml of triethylamine was stirred at 120° C. for 1.5 hours in 30 ml of xylene in nitrogen atmosphere. The mixture was returned to room temperature, diluted with ethyl acetate, washed with water and brine, and dried over magnesium sulfate. The solvent was evaporated, and the residue was incorporated with 47% hydrobromic acid and heated at 70° C. for 1 hour. The reaction solution was ice-cooled, diluted with water, and neutralized with potassium carbonate. The resulting precipitates were collected by filtration, washed with water and ether, and then air-dried, to give 0.5 g of the title compound as a pale yellow powder.

$^1$H-NMR (400 MHz, DMSO-d$_6$); δ (ppm) 7.30-7.37 (m, 2H), 7.43 (dd, 2H), 7.62 (d, 2H), 7.82-7.90 (m, 1H), 7.87 (d, 1H), 8.64-8.69 (m, 2H), 8.57 (d, 1H), 12.30(brs, 1H).

Referential Example 14

1-Phenyl-3-nitro-5-(2-pyridyl)-1,2-dihydropyridin-2-one

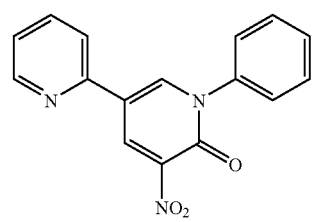

(14a) 3-Nitro-1-phenyl-1,2-dihydropyridin-2-one 5 g of 2-hydroxy-3-nitropyridine, 7.14 g of phenylboronic acid, 2.6 g of copper (II) acetate, 9.9 ml of triethylamine and 5.8 ml of pyridine were added to 100 ml of tetrahydrofuran, followed by stirring overnight. The reaction mixture was poured into aqueous ammonia, and extracted with ethyl acetate. The organic layer was washed with water, dried, and concentrated. The residue was suspended into ether, and collected by filtration, to give 4.71 g of the title compound.

$^1$H-NMR (400 MHz, CDCl$_3$); δ (ppm) 6.39 (dd, 1H), 7.36-7.40 (m, 2H), 7.49-7.54 (m, 3H), 7.73 (dd, 1H), 8.38 (dd, 1H).

(14b) 5-Bromo-3-nitro-1-phenyl-1,2-dihydropyridin-2-one 10 ml of a dimethylformamide solution containing 1 g of 3-nitro-1-phenyl-1,2-dihydropyridin-2-one was incorporated with 988 mg of N-bromosuccinimide, followed by stirring at room temperature overnight. Further, it was stirred at 50° C. for 3 hours. The reaction mixture was poured into ice-water, and the resulting precipitates were collected by filtration, to give 1.27 g of the title compound.

$^1$H-NMR (400 MHz, CDCl$_3$); δ (ppm) 7.36-7.39 (m, 2H), 7.50-7.57 (m, 3H), 7.88 (d, 1H), 8.42 (d, 1H).

(14c) 3-Nitro-1-phenyl-5-(2-pyridyl)-1,2-dihydropyridin-2-one 1.27 g of 5-bromo-3-nitro-1-phenyl-1,2-dihydropyridin-2-one, 2.38 g of 2-tri-n-butyl stannyl pyridine and 248 mg of tetrakistriphenylphosphine palladium were added to 20 ml of xylene, followed by stirring at 120° C. overnight in nitrogen atmosphere. The reaction mixture was purified by silica gel chromatography (ethyl acetate/hexane system), to give 638 mg of the title compound.

$^1$H-NMR (400 MHz, CDCl$_3$); δ (ppm) 7.28 (ddd, 1H), 7.45-7.63 (m, 6H), 7.80 (dt, 1H), 8.61 (ddd, 1H), 8.63 (d, 1H), 9.03 (d, 1H).

Referential Example 15

3-Amino-1-phenyl-5-(2-pyridyl)-1,2-dihydropdridin-2-one

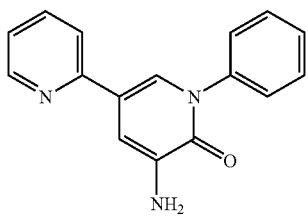

100 mg of 10% palladium-carbon was added to 20 ml of an ethanol solution containing 546 mg of 3-nitro-1-phenyl-5-(pyridin-2-yl)-1,2-dihydropyridin-2-one, followed by stirring overnight in hydrogen atmosphere. The reaction mixture was filtered through silica gel and concentrated, to give 411 mg of the title compound.

$^1$H-NMR (400 MHz, CDCl$_3$); δ (ppm) 4.36-4.42 (m, 1H), 7.18 (dd, 1H), 7.28 (d, 1H), 7.44-7.54 (m, 6H), 7.61 (d, 1H), 7.70 (dt, 1H), 8.57-8.60 (m, 1H).

Referential Example 16

3-(2-Cyanophenyl)-5-(methoxycarbonyl)-1-phenyl-1,2-dihydropyridin-2-one

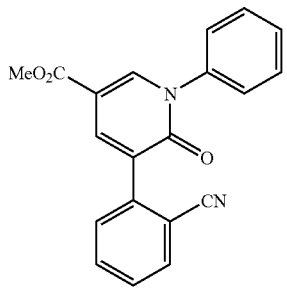

6 g of methyl 5-bromo-6-hydroxynicotinate synthesized by a known method from 6-hydroxynicotinic acid, and 6.3 g of phenylboronic acid were dissolved in 200 ml of tetrahydrofuran. To the mixture were added 939 mg of copper acetate and 1 ml of pyridine, followed by stirring at room temperature for 3 nights. Aqueous ammonia was added to the reaction solution, and the solution was extracted with chloroform. The organic layer was washed with brine, and then dried over anhydrous magnesium sulfate. The solvent was evaporated, and the residue obtained as a solid was washed with diethyl ether, to give 7.35 g of 3-bromo-5-(methoxycarbonyl)-1-phenyl-1,2-dihydropyridin-2-one as white crystals. 5 g of the product was dissolved in 100 ml of dimethylformamide, followed by adding 4.6 g of 2-(2-cyanophenyl)-1,3,2-dioxaborinate, 7.9 g of cesium carbonate and 375 mg of tetrakistriphenylphosphine palladium, and stirring at 140° C. for 1 hour in nitrogen atmosphere. After cooling to room temperature, the reaction mixture was poured into water, and extracted with ethyl acetate. Then, the extract was successively washed with water and brine, and dried over anhydrous magnesium sulfate. Then, the solvent was evaporated, and the residue was purified by silica gel chromatography (hexane/ethyl acetate system), to give 3.23 g of the title compound.

$^1$H-NMR (400 MHz, CDCl$_3$); δ (ppm) 3.89 (s, 3H), 7.42-7.55 (m, 6H), 7.61-7.66 (m, 2H), 7.75 (dd, 1H), 8.14 (d, 1H), 8.35 (d, 1H).

Referential Example 17

3-(2-Chlorophenyl)-5-hydroxymethyl-1-phenyl-1,2-dihydropyridin-2-one

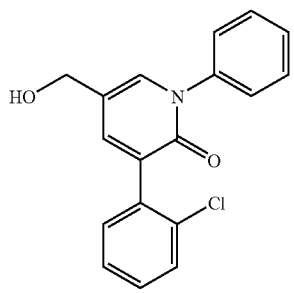

36 mg of 3-(2-chlorophenyl)-5-methoxycarbonyl-1-phenyl-1,2-dihydropyridin-2-one synthesized by the method of Referential Example 3 from 3-bromo-5-methoxycarbonyl-1-phenyl-1,2-dihydropyridin-2-one and 2-chlorophenylboronic acid, was dissolved in 20 ml of toluene. After cooling to –78° C., 0.1 ml diisobutyl aluminum hydride (1.5 M tetrahydrofuran solution) was added dropwise thereinto. While heating from –78° C. to room temperature, the mixture was stirred overnight. Then, 1N hydrochloric acid was added thereto, followed by stirring. The mixture was neutralized with an aqueous solution of sodium hydrogen carbonate; and then extracted with ethyl acetate. Then, the extract was successively washed with water and brine, and dried over anhydrous magnesium sulfate. Then, the solvent was evaporated, and the residue was purified by silica gel chromatography (hexane/ethyl acetate system), to give 12 mg of the titles compound.

$^1$H-NMR (400 MHz, CDCl$_3$); δ (ppm) 4.48 (s, 2H), 7.25-7.29 (m, 3H), 7.37-7.51 (m, 8H).

ESI-Mass; 312 [M$^+$+H]

Referential Example 18

3-Methoxycarbonyl-5-(2-pyridyl)-1-phenyl-1,2-dihydropyridin-2-one

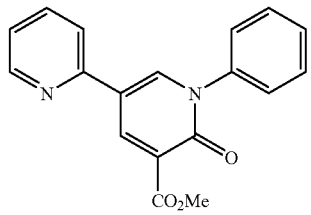

4.5 g of methyl 5-bromo-2-hydroxynicotinate synthesized by a known method from 2-hydroxynicotinic acid, and 4.7 g of phenylboronic acid were dissolved in 200 ml of tetrahydrofuran. To the mixture were added 705 mg of copper acetate and 1 ml of pyridine, followed by stirring at room temperature for 3 nights in a flow of air. Aqueous ammonia water was added to the reaction solution, and the solution was extracted with chloroform. The organic layer was washed with brine, and dried over anhydrous magnesium sulfate. The solvent was evaporated, and the residue obtained as a solid was washed with diethyl ether, to obtain 3.59 g of 5-bromo-3-methoxycarbonyl-1-phenyl-1,2-dihydropyridin-2-one as white crystals. 3.2 g of the product was dissolved in 100 ml of dimethylformamide, to which 7.7 g of tri-N-butyl-(2-pyridyl)tin [CAS No. 59020-10-9] and 240 mg of tetrakistriphenylphosphine palladium were added, followed by stirring at 110° C. for 3 hours in nitrogen atmosphere. After cooling to room temperature, the reaction solution was poured into water, extracted with ethyl acetate. Then, the extract was successively washed with water and brine, dried over anhydrous magnesium sulfate, and then filtered through NH silica gel and silica gel. Then, the filtrate was evaporated, and the resulting precipitates were washed with ether and hexane, and dried, to give 1.59 g of the title compound.

$^1$H-NMR (400 MHz, CDCl$_3$); δ (ppm) 3.95 (s, 3H), 7.22 (ddd, 1H), 7.42-7.54 (m, 5H), 7.62 (dt, 1H), 7.76 (td, 1H), 8.52 (d, 1H), 8.58 (ddd, 1H), 8.85 (d, 1H).

Referential Example 19

3-(2-Cyanophenyl)-5-nitro-1-phenyl-1,2-dihydropyridin-2-one

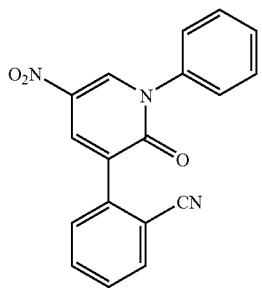

(19a) 5-Nitro-1-phenyl-1,2-dihydroperidin-2-one 5.93 g of the title compound was obtained in accordance with the method used for Referential Example (14a), from 5 g of 2-hydroxy-5-nitropyridine.

$^1$H-NMR (400 MHz, CDCl$_3$); δ (ppm) 6.67 (d, 1H), 7.39-7.43 (m, 2H), 7.53-7.59 (m, 3H), 8.18 (dd, 1H), 8.68 (dd, 1H).

(19b) 3-Bromo-5-nitro-1-phenyl-1,2-dihydropyridin-2-one 4.72 g of the title compound was obtained in accordance with the method used for Referential Example (14b), from 5.93 g of 5-nitro-1-phenyl-1,2-dihydropyridin-2-one.

$^1$H-NMR (400 MHz, CDCl$_3$); δ (ppm) 7.38-7.42 (m, 2H), 7.54-7.58 (m, 3H), 8.59-8.61 (m, 1H), 8.66-8.68 (m, 1H).

(19c) 5-Nitro-3-(2-cyanophenyl)-1-phenyl-1,2-dihydroperidin-2-one 758 mg of the title compound was obtained in accordance with the method used for Referential Example 3, from 3 g of 3-bromo-5-nitro-1-phenyl-1,2-dihydropyridin-2-one.

$^1$H-NMR (400 MHz, CDCl$_3$); δ (ppm) 7.47-7.63 (m, 7H), 7.68 (dt, 1H), 7.80 (ddd, 1H), 8.38 (d, 1H), 8.78 (d, 1H).

Referential Example 20

5-Amino-3-(2-cyanophenyl)-1-phenyl-1,2-dihydropyridin-2-one

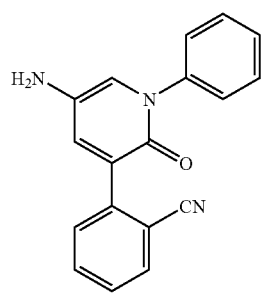

414 mg of the title compound was obtained in accordance with the method used for Referential Example 15, from 708 mg of 5-nitro-3-(2-cyanophenyl)-1-phenyl-1,2-dihydropyridin-2-one.

$^1$H-NMR (400 MHz, CDCl$_3$); δ (ppm) 6.99 (d, 1H), 7.39-7.49 (m, 7H), 7.60 (dt, 1H), 7.73 (d, 1H), 7.75 (d, 1H).

Example 1

3-(2-Cyanophenyl)-5-(2-nitrophenyl)-1-phenyl-1,2-dihydropyridin-2-one

5-Bromo-3-(2-cyanophenyl)-1-phenyl-1,2-dihydropyridin-2-one (100 mg), 60 mg of 2-nitrophenylboronic acid and 130 mg of cesium carbonate were suspended in 10 ml of dimethylformamide, then 20 mg of tetrakistriphenylphosphine palladium were added and the mixture was stirred at 120° C. in a nitrogen atmosphere for 4 hours. After allowing to cool, the reaction solution was poured into water, the mixture was extracted with ethyl acetate, the extract was dried over anhydrous magnesium sulfate, the solvent was evaporated in vacuo and the residue was purified by a silica gel column chromatography (hexane-ethyl acetate system) to give 35 mg of the title compound.

$^1$H-NMR (400 MHz, CDCl$_3$); δ (ppm) 7.40-7.80 (m, 14H), 7.97 (dd, 1H).

Example 2

5-(2-Aminophenyl)-3-(2-cyanophenyl)-1-phenyl-1,2-dihydropyridin-2-one 3-(2-Cyanophenyl)-5-(2-nitrophenyl)-1-phenyl-1,2-dihydropyridin-2-one (32 mg) was dissolved in 15 ml of ethyl acetate, 5 mg of 10% palladium-carbon (water-containing substance) were added and the mixture was stirred at room temperature in a hydrogen atmosphere for 15 minutes. The catalyst was filtered off and the solvent was evaporated in vacuo to give 20 mg of the title compound.

¹H-NMR (400 MHz, CDCl₃); δ (ppm) 3.95 (bs, 2H), 6.76 (dd, 1H), 6.80 (dt, 1H), 7.14 (dd, 1H), 7.17 (dt, 1H), 7.41-7.55 (m, 6H), 7.59 (d, 1H), 7.62 (dt, 1H), 7.74-7.82 (m, 2H), 7.88 (d, 1H).

Example 3

3-(2-Cyanophenyl)-5-(2-methylsulfonylaminophenyl)-1-phenyl-1,2-dihydropyridin-2-one 5-(2-Aminophenyl)-3-(2-cyanophenyl)-1-phenyl-1,2-dihydropyridin-2-one (16 mg) was dissolved in 10 ml of dimethylformamide, then 0.05 ml of triethylamine and 3 drops of methanesulfonyl chloride were added and the mixture was stirred at room temperature for one hour. Ethyl acetate was added to the reaction solution, the mixture was washed with water and a saturated saline solution, the solvent was evaporated in vacuo and the residue was purified by a silica gel column chromatography (hexane-ethyl acetate system) to give 5 mg of the title compound.
¹H-NMR (400 MHz, CDCl₃); δ (ppm) 2.19 (s, 3H), 6.88-6.95 (m, 1H), 7.08-7.15 (m, 1H), 7.38-7.55 (m, 8H), 7.61 (dt, 1H), 7.69-7.76 (m, 3H), 7.91 (d, 1H), 7.92-7.97 (m, 1H).

Example 4

3-(2-Chloro-3-pyridyl)-5-(2-pyridyl)-1-phenyl-1,2-dihydropyridin-2-one

3-Iodo-5-(2-pyridyl)-1-phenyl-1,2-dihydropyridin-2-one (200 mg) synthesized by the same method as mentioned in Referential Example 6, 130 mg of 2-chloro-3-pyridyl boronic acid and 250 mg of cesium carbonate were suspended in 10 ml of dimethylformamide, 40 mg of tetrakistriphenylphosphine palladium were added and the mixture was stirred at 100° C. in a nitrogen atmosphere for 3 hours. After allowing to cool, the reaction solution was poured into water, the mixture was extracted with ethyl acetate, the extract was dried over anhydrous magnesium sulfate, the solvent was evaporated in vacuo and the residue was purified by a silica gel column chromatography (hexane-ethyl acetate system) to give 143 mg of the title compound.
¹H-NMR (400 MHz, CDCl₃); δ (ppm) 7.20-7.24 (m, 1H), 7.31 (dd, 1H), 7.44-7.59 (m, 6H), 7.75 (dt, 1H), 7.91 (dd, 1H), 8.25 (d, 1H), 8.33 (d, 1H), 8.41 (dd, 1H), 8.59-9.62 (m, 1H).

Example 5

3-(2-Cyanophenyl)-5-(2-pyridyl)-2-methoxypyridine

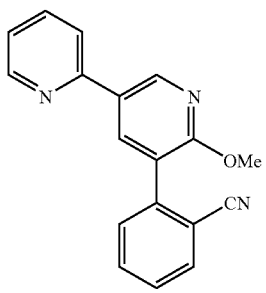

Tetrakistriphenylphosphine palladium (0.15 g) was added to a mixed solution of 0.50 g of 5-(2-pyridyl)-3-bromo-2-methoxypyridine, 0.42 g of 2-(2-cyanophenyl)-1,3,2-dioxaborinate, 0.82 g of cesium carbonate and 20 ml of dimethylformamide and the mixture was stirred at 140° C. in a nitrogen atmosphere for 5 hours. After cooling to room temperature, ethyl acetate was added thereto, the mixture was washed with water and a saturated saline solution and dried over magnesium sulfate. The solvent was concentrated in vacuo and the residue was purified by a silica gel column chromatography (ethyl acetate:hexane=1:3) to give 0.36 of the title compound as pale yellow powder.
¹H-NMR (CDCl₃, 400 MHz); δ (ppm) 4.03 (3H, s), 7.24-7.28 (1H, m), 7.46-7.51 (1H, ddd), 7.57 (1H, dd), 7.65-7.69 (1H, ddd), 7.72-7.82 (3H, m), 8.31 (1H, d), 8.66-8.69 (1H, m), 8.83 (1H, d).

Example 6

3-(2-Cyanophenyl)-5-(2-pyridyl)-2(1H)-pyridone

Chlorotrimethylsilane (0.1 ml) was added to a suspension of 0.20 g of 3-(2-cyanophenyl)-5-(2-pyridyl)-2-methoxypyridine and 0.12 g of sodium iodide in 10 ml of acetonitrile and the mixture was stirred at room temperature for 3 hours. A saturated sodium bicarbonate solution was added to the mixture followed by extracting with ethyl acetate. The ethyl acetate layer was washed with water and a saturated saline solution and dried over magnesium sulfate. The solvent was concentrated in vacuo and the residue was purified by a silica gel column chromatography (ethyl acetate:hexane=1:1) to give 0.11 g of the title compound in pale yellow powder.
¹H-NMR (DMSO-d₆, 400 MHz); δ (ppm) 7.26-7.30(1H, ddd), 7.55-7.60(1H, ddd), 7.6(1H, dd), 7.74-7.79(1H, ddd), 7.80-7.86(1H, ddd), 7.89-7.94(2H, m), 8.28(1H, d), 8.37(1H, d), 8.56-8.59(1H, m).

Example 7

3-(2-Cyanophenyl)-1-phenyl-5-(2-pyridyl)-1,2-dihydropyridin-2-one

A suspension of 0.11 g of 3-(2-cyanophenyl)-5-(2-pyridyl)-2(1H)-pyridone, 0.12 g of phenyl boronic acid 0.1 g of copper acetate and 0.3 ml of triethylamine in 10 ml of methylene chloride was stirred at room temperature for overnight. To this were added 5 ml of concentrated aqueous ammonia, 10 ml of water and 40 ml of ethyl acetate and the organic layer was separated, washed with water and a saturated saline solution and dried over magnesium sulfate. The solvent was concentrated in vacuo and the residue was purified by a silica gel column chromatography (ethyl acetate:hexane=1:2) to give 0.06 g of the title product as pale yellow powder.
¹H-NMR (DMSO-d₆, 400 MHz); δ (ppm) 7.29-7.33(1H, m), 7.48-7.63(6H, m), 7.71-7.75(1H, dd), 7.76-7.88(2H, m), 7.92-7.95(1H, m), 8.01(1H, d), 8.48(1H, d), 8.54(1H, d), 8.58-8.61(1H, m).

Example 8

3-(2-Cyanophenyl)-5-(2-pyridyl)-1-(3-nitrophenyl)-1,2-dihydropyridin-2-one

The title compound was obtained in the same manner as in Example 7.
¹H-NMR (400 MHz, CDCl₃); δ (ppm) 7.24-7.28 (m, 1H), 7.49 (dt, 1H), 7.63-7.81 (m, 6H), 7.95-7.98 (m, 1H), 8.31-8.37 (m, 3H), 8.45(t, 1H), 8.60-8.63 (m, 1H).

Example 9

3-(2-Cyanophenyl)-5-(2-pyridyl)-1-(3-aminophenyl)-1,2-dihydropyridin-2-one

Iron powder (180 mg) and 342 mg of ammonium chloride were added to a solution of 317 mg of 3-(2-cyanophenyl)-5-(2-pyridyl)-1-(3-nitrophenyl)-1,2-dihydropyridin-2-one in a mixture of 10 ml of 2-propanol and 5 ml of water followed by refluxing for 4 hours. The reaction mixture was concentrated, partitioned in ethyl acetate-water, the organic layer was washed with water, dried and concentrated and the residue was purified by a silica gel column chromatography (ethyl acetate/hexane system) to give 235 mg of the title compound as a pale yellow solid.

$^1$H-NMR (400 MHz, CDCl$_3$); δ (ppm) 3.84 (s, 2H), 6.75 (dd, 1H), 6.82-6.87 (m, 2H), 7.20 (dd, 1H), 7.26-7.30 (m, 1H), 7.45 (td, 1H), 7.59-7.65 (m, 2H), 7.72-7.80 (m, 3H), 8.29 (s, 2H), 8.56-8.61 (m, 1H).

Example 10

3-(2-Cyanophenyl)-5-(2-pyridyl)-1-(3-methylsulfonylaminophenyl)-1,2-dihydropyridin-2-one Triethylamine (0.2 ml) was added to a solution of 31 mg of 3-(2-cyanophenyl)-5-(2-pyridyl)-1-(3-aminophenyl)-1,2-dihydropyridin-2-one in 2 ml of tetrahydrofuran, 0.1 ml of methanesulfonic acid chloride was dropped thereinto with ice cooling and the mixture was stirred for 10 minutes. To this were added 2 ml of 2N sodium hydroxide, the mixture was stirred at room temperature for 5 minutes and partitioned to ethyl acetate-water, the organic layer was washed with water, dried and concentrated and the residue was purified by a silica gel column chromatography (ethyl acetate-hexane system) to give 38 mg of the title compound as a pale yellow amorphous substance.

$^1$H-NMR (400 MHz, CDCl$_3$); δ (ppm) 2.93 (s, 3H), 4.00-4.09 (m, 1H), 7.22-7.31 (m, 3H), 7.36 (t, 1H), 7.43 (t, 1H), 7.46 (dd, 1H), 7.61 (dt, 1H), 7.65 (td, 1H), 7.73-7.78 (m, 3H), 8.27 (d, 1H), 8.31 (d, 1H), 8.59-8.61 (m, 1H).

Example 11

3-(2-Cyanophenyl)-5-(2-pyridyl)-1-(3-methylaminophenyl)-1,2-dihydropyridin-2-one Paraformaldehyde (41 mg) and 119 mg of triacetoxy sodium borohydride were added to a solution of 50 mg of 3-(2-cyanophenyl)-5-(2-pyridyl)-1-(3-aminophenyl)-1,2-dihydropyridin-2-one in 3 ml of acetic acid followed by stirring at room temperature for one night. To this was added an aqueous solution of sodium bicarbonate, the mixture was extracted with ethyl acetate, the organic layer was washed with water, dried and concentrated and the residue was purified by a silica gel column chromatography (ethyl acetate/hexane system) to give 11 mg of the title compound as a pale yellow solid.

$^1$H-NMR (400 MHz, CDCl$_3$); δ (ppm) 2.00 (s, 3H), 7.11-7.14 (m, 1H), 7.21 (ddd, 1H), 7.35 (t, 1H), 7.44-7.49 (m, 2H), 7.59 (d, 1H), 7.66 (td, 1H), 7.70-7.77 (m, 4H), 8.25 (d, 1H), 8.51 (s, 1H), 8.58-8.61 (m, 1H).

Example 12

3-(2-Cyanophenyl)-5-(2-pyridyl)-1-(3-dimethylaminophenyl)-1,2-dihydropyridin-2-one Paraformaldehyde (41 mg) and 119 mg of triacetoxy sodium borohydride were added to a solution of 50 mg of 3-(2-cyanophenyl)-5-(2-pyridyl)-1-(3-aminophenyl)-1,2-dihydropyridin-2-one in 3 ml of acetic acid followed by stirring at room temperature for 6 hours. To this were further added 41 mg of paraformaldehyde and 119 mg of triacetoxy sodium borohydride, the mixture was stirred for one night, an aqueous solution of sodium bicarbonate was added thereto, the mixture was extracted with ethyl acetate, the organic layer was washed with water, dried and concentrated and the residue was purified by a silica gel column chromatography (ethyl acetate/hexane system) to give 38 mg of the title compound as a pale yellow amorphous substance.

$^1$H-NMR (400 MHz, CDCl$_3$); δ (ppm) 2.99 (s, 6H), 6.77-6.80 (m, 3H), 7.18-7.21 (m, 1H), 7.32-7.37 (m, 1H), 7.44(t, 1H), 7.59-7.64 (m, 2H), 7.71-7.83 (m, 3H), 8.32 (s, 2H), 8.58-8.60 (m, 1H).

Example 13

3-(2-Cyanophenyl)-5-(2-pyridyl)-1-[3-(5-methoxymethyl-2-oxazolidinon-3-yl)-phenyl]-1,2-dihydropyridin-2-one Glycidyl methyl ether (0.01 ml) and 22 mg of magnesium periodate were added to a solution of 38 mg of 3-(2-cyanophenyl)-5-(2-pyridyl)-1-(3-aminophenyl)-1,2-dihydropyridin-2-one in 6 ml of acetonitrile followed by stirring at room temperature. After 2 hours, 0.01 ml of glycidyl methyl ether and 22 mg of magnesium periodate were further added thereto and the mixture was stirred at room temperature for 1 hour and then stirred at 50° C. for 1 hour more. The reaction mixture was partitioned to ethyl acetate-water, the organic layer was washed with water, dried and concentrated, the residue was dissolved in 6 ml of tetrahydrofuran, 32 mg of carbonyldiimidazole were added thereto and the mixture was heated to reflux for 2 hours. This was partitioned to ethyl acetate-water, the organic layer was washed with water, dried and concentrated and the residue was purified by a preparative thin layer chromatography (ethyl acetate/hexane system) to give 21 mg of the title compound as a pale yellow solid.

$^1$H-NMR (400 MHz, CDCl$_3$); δ (ppm) 3.43 (s, 3H), 3.64 (dd, 2H), 3.97 (dd, 1H), 4.09 (t, 1H), 4.77 (ddd, 1H), 7.22 (ddd, 1H), 7.29 (ddd, 1H), 7.46 (td, 1H), 7.53 (t, 1H), 7.59-7.79 (m, 7H), 8.30 (d, 1H), 8.31 (d, 1H), 8.58-8.61 (m, 1H).

Example 14

3-(2-Cyanophenyl)-5-(2-pyridyl)-1-(3-methoxycarbonylphenyl)-1,2-dihydropyridin-2-one The title compound was obtained in the same manner as in Example 7.

$^1$H-NMR (400 MHz, CDCl$_3$); δ (ppm) 3.94 (s, 3H), 7.23 (ddd, 1H), 7.47 (td, 1H), 7.59-7.68 (m, 4H), 7.73-7.80 (m, 3H), 7.88-7.91 (m, 2H), 8.31 (d, 1H), 8.32 (d, 1H), 8.59-8.61 (m, 1H).

Example 15

3-(2-Cyanophenyl)-5-(2-pyridyl)-1-(3-methylaminocarbonylphenyl)-1,2-dihydropyridin-2-one 3-(2-Cyanophenyl)-5-(2-pyridyl)-1-(3-methoxycarbonylphenyl)-1,2-dihydropyridin-2-one (10 mg) was added to 6 ml of a 40% methanolic solution of methylamine followed by stirring at room temperature for one night. The reaction solution was concentrated in vacuo to give 10 mg of the title compound as a pale yellow solid.

¹H-NMR (400 MHz, CDCl₃); δ (ppm) 3.00 (d, 3H), 6.51 (brs, 1H), 7.23 (ddd, 1H), 7.47 (td, 1H), 7.58-7.68 (m, 4H), 7.73-7.80 (m, 3H), 7.88-7.91 (m, 2H), 8.31 (d, 1H), 8.32 (d, 1H), 8.59-8.61 (m, 1H).

Example 16

3-(2-Cyano-3-pyridyl)-5-(2-pyridyl)-1-phenyl-1,2-dihydropyridin-2-one (Route 1)
3-(2-Chloro-3-pyridyl)-5-(2-pyridyl)-1-phenyl-1,2-dihydropyridin-2-one (281 mg) was dissolved in 20 ml of dimethylformamide, 170 mg of copper cyanide were added and the mixture was stirred at 130° C. for 10 hours. The reaction solution was cooled to room temperature, aqueous ammonia and ethyl acetate were added, the organic layer was partitioned, washed with water and dried over anhydrous sodium sulfate, the drying agent was filtered off, the filtrate was concentrated in vacuo and the residue was purified by a silica gel column chromatography (hexane-ethyl acetate system) to give 120 mg of the title compound as a colorless amorphous substance.

(Route 2)
3-Bromo-5-(2-pyridyl)-1-phenyl-1,2-dihydropyridin-2-one (2.9 g) synthesized by the same method as mentioned in Referential Example 6 was dissolved in 200 ml of xylene, 5 ml of bis(tributyl tin) and 400 mg of tetrakistriphenylphosphine palladium were added and the mixture was stirred at 140° C. for 2 hours. 3-Bromo-2-cyanopyridine (3.2 g) and 100 mg of tetrakistriphenylphosphine palladium were added thereto and the mixture was stirred at 140° C. for 2 hours. Tetrakistriphenylphosphine palladium (1.0 g) and 800 mg of copper iodide were divided into four and added every 1 hour, then 2 g of 3-bromo-2-cyanopyridine were added thereto and the mixture was stirred at 140° C. for one night. The reaction solution was cooled to room temperature, water and ethyl acetate were added thereto, the organic layer was partitioned, washed with water and dried over anhydrous sodium sulfate, the drying agent was filtered off, the filtrate was concentrated in vacuo and the residue was purified by a silica gel column chromatography (hexane-ethyl acetate system) to give 1.8 g of the title compound as a colorless amorphous substance.

¹H-NMR (400 MHz, CDCl₃); δ (ppm) 7.24 (ddd, 1H), 7.47-5.57 (m, 6H), 7.63 (d, 1H), 7.68 (td, 1H), 8.22 (dd, 1H), 8.37 (dd, 1H), 8.43 (d, 1H), 8.59-8.61 (m, 1H), 8.69 (dd, 1H).
ESI-Mass; 351 [M⁺+H]

Example 17

3-(2-Chlorophenyl)-5-(2-pyridyl)-1-(4-methoxyphenyl)-1,2-dihydropyridin-2-one

The title compound was obtained in the same manner as in Example 4.
¹H-NMR (400 MHz, CDCl₃); δ (ppm) 3.84 (s, 3H), 6.98-7.03 (m, 2H), 7.19 (ddd, 1H), 7.28-7.33 (m, 2H), 7.40-7.46 (m, 2H), 7.46-7.51 (m, 2H), 7.53-7.57 (m, 1H), 7.72 (ddd, 1H), 8.12 (d, 1H), 8.29 (d, 1H), 8.57-8.61 (m, 1H).

Example 18

3-(2-Chlorophenyl)-5-(2-pyridyl)-1-(4-hydroxyphenyl)-1,2-dihydropyridin-2-one 3-(2-Chlorophenyl)-5-(2-pyridyl)-1-(4-methoxyphenyl)-1,2-dihydropyridin-2-one (440 mg) was dissolved in 5 ml of 48% hydrobromic acid and heated to reflux for 1 hours. After the reaction solution was allowed to cool at room temperature, it was diluted with a saturated aqueous solution of sodium bicarbonate and extracted with ethyl acetate. The organic layer was washed with water and dried over anhydrous magnesium sulfate. The drying agent was filtered off and the filtrate was concentrated in vacuo and purified by a silica gel column chromatography (hexane-ethyl acetate system) to give 292 mg of the title compound.
¹H-NMR (400 MHz, CDCl₃); δ (ppm) 6.67-6.73 (m, 2H), 7.12-7.18 (m, 2H), 7.19-7.24 (m, 1H), 7.30-7.38 (m, 2H), 7.47-7.53 (m, 2H), 7.56 (d, 1H), 7.70 (s, 1H), 7.73 (ddd, 1H), 8.18 (d, 1H), 8.26 (d, 1H), 8.57-8.62 (m, 1H).

Example 19

3-(2-Chlorophenyl)-5-(2-pyridyl)-1-(4-dimethylaminoethoxyphenyl)-1,2-dihydropyridin-2-one 3-(2-Chlorophenyl)-5-(2-pyridyl)-1-(4-hydroxyphenyl)-1,2-dihydropyridin-2-one (82 mg) and 57 mg of N,N-dimethylaminoethyl chloride were dissolved in 2 ml of dimethylformamide, 55 mg of potassium carbonate were added thereto at 60° C. and the mixture was stirred for one night. The reaction solution was diluted with water and extracted with ethyl acetate. The organic layer was washed with a saturated saline solution and dried over anhydrous magnesium sulfate. The drying agent was filtered off and the filtrate was concentrated in vacuo and purified by an NH silica gel column chromatography (hexane-ethyl acetate system) to give 27 mg of the title compound.
¹H-NMR (400 MHz, CDCl₃); δ (ppm) 2.55 (s, 6H), 2.76 (t, 2H), 4.11 (t, 2H), 6.99-7.05 (m, 2H), 7.19 (ddd, 1H), 7.26-7.34 (m, 2H), 7.39-7.45 (m, 2H), 7.45-7.51 (m, 2H), 7.55 (d, 1H), 7.72 (ddd, 1H), 8.12 (d, 1H), 8.28 (d, 1H), 8.57-8.61 (m, 1H).

Example 20

3-(2-Cyanophenyl)-5-(2-pyridyl)-1-(3-formylphenyl)-1,2-dihydropyridin-2-one

The title compound was obtained in the same manner as in Example 7.
¹H-NMR (400 MHz, CDCl₃); δ (ppm) 7.24 (ddd, 1H), 7.84 (ddd, 1H), 7.63 (d, 1H), 7.66 (ddd, 1H), 7.72 (dd, 1H), 7.75-7.82 (m, 3H), 7.84-7.88 (m, 1H), 8.00 (ddd, 1H), 8.05-8.08 (m, 1H), 8.32 (d, 1H), 8.35 (d, 1H), 8.59-8.62 (m, 1H), 10.08 (s, 1H).

Example 21

3-(2-Cyanophenyl)-5-(2-pyridyl)-1-(3-hydroxymethylphenyl)-1,2-dihydropyridin-2-one 3-(2-Cyanophenyl)-5-(2-pyridyl)-1-(3-formylphenyl)-1,2-dihydropyridin-2-one (585 mg) was dissolved in 20 ml of methanol, 260 mg of sodium borohydride were added with ice cooling and the mixture was stirred at room temperature for one night. The reaction solution was diluted with ethyl acetate, washed with a saturated saline solution and dried over anhydrous magnesium sulfate. The drying agent was filtered off and the filtrate was concentrated in vacuo and purified by an NH silica gel column chromatography (ethyl acetate). The resulting crude crystals were recrystallized from ethyl acetate-diethyl ether to give 320 mg of the title compound.
¹H-NMR (400 MHz, DMSO-d₆); δ (ppm) 4.60 (d, 2H), 5.37 (t, 1H), 7.29-7.33 (m, 1H), 7.42-7.47 (m, 2H), 7.48-7.55

(m, 2H), 7.59 (ddd, 1H), 7.73 (dd, 1H), 7.78 (dd, 1H), 7.83 (ddd, 1H), 7.94 (dd, 1H), 8.01 (d, 1H), 8.48 (d, 1H), 8.52 (d, 1H), 8.57-8.61 (m, 1H).

Example 22

3-(2-Cyanophenyl)-5-(2-pyridyl)-1-(3-cyanomethylphenyl)-1,2-dihydropyridin-2-one 3-(2-Cyanophenyl)-5-(2-pyridyl)-1-(3-hydroxyphenyl)-1,2-dihydropyridin-2-one (53 mg) was dissolved in 2 ml of tetrahydrofuran, then 60 µl of triethylamine and 20 µl of methanesulfonyl chloride were added thereto with ice cooling and the mixture was stirred at room temperature for 3 hours. The reaction solution was diluted with an aqueous solution of sodium bicarbonate and extracted with ethyl acetate and the extract was dried over anhydrous magnesium sulfate. The drying agent was filtered off, the filtrate was concentrated in vacuo, the resulting residue was dissolved in 1 ml of dimethyl sulfoxide, 3 mg of sodium cyanide were added and the mixture was stirred at room temperature for 1 hour. The reaction solution was diluted with ethyl acetate, washed with an aqueous solution of sodium bicarbonate and a saturated saline solution and dried over anhydrous magnesium sulfate. The drying agent was filtered off, the filtrate was concentrated in vacuo and the resulting crude crystals were recrystallized from ethyl acetate-diethyl ether-hexane to give 12 mg of the title compound.

$^1$H-NMR (400 MHz, CDCl$_3$); δ (ppm) 3.85 (s, 2H), 7.21-7.26 (m, 1H), 7.41-7.81 (m, 10H), 8.29-8.32 (m, 2H), 8.59-8.62 (m, 1H).

The following compounds were prepared by the same manner as in the above Example 22.

Example 23

3-(2-Cyanophenyl)-5-(2-pyridyl)-1-(3-acetylaminomethylphenyl)-1,2-dihydropyridin-2-one $^1$H-NMR (400 MHz, CDCl$_3$); δ (ppm) 2.04 (s, 3H), 4.47-4.52 (m, 2H), 7.22 (ddd, 1H), 7.37-7.53 (m, 5H), 7.61 (d, 1H), 7.65 (ddd, 1H), 7.72-7.81 (m, 3H), 8.28 (d, 1H), 8.31 (d, 1H), 8.59-8.62 (m, 1H).

Example 24

3-(2-Cyanophenyl)-5-(2-pyridyl)-1-(3-methylsulfonylaminomethylphenyl)-1,2-dihydropyridin-2-one $^1$H-NMR (400 MHz, CDCl$_3$); δ (ppm) 2.91 (s, 3H), 4.36 (d, 2H), 5.00-5.06 (m, 1H), 7.22 (ddd, 1H), 7.43-7.49 (m, 3H), 7.50-7.55 (m, 2H), 7.61 (ddd, 1H), 7.64 (ddd, 1H), 7.73-7.79 (m, 3H), 8.28-8.31 (m, 2H), 8.60 (ddd, 1H).

Example 25

3-(2-Cyanophenyl)-5-(2-pyridyl)-1-(3-acetoxymethylphenyl)-1,2-dihydropyridin-2-one To 56 mg of 3-(2-cyanophenyl)-5-(2-pyridyl)-1-(3-hydroxymethylphenyl)-1,2-dihydropyridin-2-one were added 1 ml of acetic anhydride and 1 ml of pyridine and the mixture was stirred at room temperature for one night. The reaction solution was concentrated in vacuo and purified by an NH silica gel chromatography (hexane-ethyl acetate system) to give 30 mg of the title compound.

$^1$H-NMR (400 MHz, CDCl$_3$); δ (ppm) 2.13 (s, 3H), 5.18 (s, 2H), 7.23 (ddd, 1H), 7.44-7.56 (m, 5H), 7.60-7.67 (m, 2H), 7.73-7.81 (m, 3H), 8.30-8.33 (m, 2H), 8.59-8.62 (m, 1H).

Example 26

3-(2-Cyanophenyl)-5-(2-pyridyl)-1-(4-methylthiophenyl)-1,2-dihydropyridin-2-one

The title compound was obtained in the same manner as in Example 7.

$^1$H-NMR (400 MHz, CDCl$_3$); δ (ppm) 2.53 (s, 3H), 7.21-7.24 (m, 1H), 7.36-8.79 (m, 10H), 8.28-8.32 (m, 2H), 8.59-8.61 (m, 1H).

Example 27

3-(2-Cyanophenyl)-5-(2-pyridyl)-1-(4-methylsulfonylphenyl)-1,2-dihydropyridin-2-one A 70% m-chloroperbenzoic acid (500 mg) was added little by little during 2 hours to a solution of 50 mg of 3-(2-cyanophenyl)-5-(2-pyridyl)-1-(4-methylthiophenyl)-1,2-dihydropyridin-2-one in 4 ml of methylene chloride followed by stirring with ice cooling. A saturated aqueous solution of sodium bicarbonate was added thereto, the mixture was partitioned to ethyl acetate-water, the organic layer was washed with water, dried and concentrated and the residue was purified by a silica gel column chromatography (ethyl acetate/hexane system) to give 5 mg of the title compound as a yellow solid.

$^1$H-NMR (400 MHz, CDCl$_3$); δ (ppm) 3.11 (s, 3H), 7.24-7.28 (m, 1H), 7.50 (dt, 1H), 7.61-7.82 (m, 7H), 8.20 (d, 2H), 8.30-8.33 (m, 2H), 8.60-8.63 (m, 1H).

Example 28

3-(2-Cyanophenyl)-5-(2-formylthiophen-3-yl)-1-phenyl-1,2-dihydropyridin-2-one

The title compound was prepared according to Example 1.

$^1$H-NMR (400 MHz, CDCl$_3$); δ (ppm) 7.29 (d, 1H), 7.42-7.57 (m, 6H), 7.65 (dt, 1H), 7.71 (d, 1H), 7.77-7.82 (m, 3H), 7.85 (d, 1H), 10.10 (s, 1H).

Example 29

3-(2-Cyanophenyl)-5-(2-diethylaminomethylthiophen-3-yl)-1-phenyl-1,2-dihydropyridin-2-one A solution of 20 mg of 3-(2-cyanophenyl)-5-(2-formylthiophen-3-yl)-1-phenyl-1,2-dihydropyridin-2-one, 0.1 ml of a 2M solution of diethylamine in tetrahydrofuran and 0.1 ml acetic acid in 2 ml of tetrahydrofuran was stirred at room temperature for 15 minutes, 20 mg of sodium triacetoxyborohydride were added and the mixture was stirred for 3 hours more. A 2N aqueous solution of sodium hydroxide was added thereto, the mixture was extracted with ethyl acetate and the organic layer was washed with water and a saturated saline solution and dried over magnesium sulfate. The solvent was concentrated in vacuo and the residue was purified by an NH silica gel column chromatography to give 15 mg of the title compound as white powder.

$^1$H-NMR (400 MHz, CDCl$_3$); δ (ppm) 1.38 (t, 6H), 2.99-3.20 (m, 4H), 4.57 (d, 2H), 7.07 (d, 1H), 7.40-7.58 (m, 8H), 7.60-7.67 (m, 2H), 7.77 (d, 1H), 7.87 (d, 1H).

Example 30

3-(2-Cyanophenyl)-5-(2-hydroxymethylthiophen-3-yl)-1-phenyl-1,2-dihydropyridin-2-one Sodium triacetoxyborohydride (10 mg) was added to a solution of 10 mg of 3-(2-cyanophenyl)-5-(2-formylthiophen-3-yl)-1-phenyl-1,2-dihydropyridin-2-one in 2 ml of tetrahydrofuran and the mixture was stirred for 1 hour. A 10% aqueous solution of sodium carbonate was added thereto, the mixture was extracted with ethyl acetate and the organic layer was washed with water and a saturated saline solution and dried over magnesium sulfate. The solvent was concentrated in vacuo and the residue was purified by an NH silica gel column chromatography to give 8 mg of the title compound as white powder.

$^1$H-NMR (400 MHz, CDCl$_3$): δ (ppm) 4.86 (s, 2H), 7.11 (d, 1H), 7.33 (d, 1H), 7.42-7.54 (m, 6H), 7.60-7.65 (m, 1H), 7.75 (d, 1H), 7.66-7.79 (m, 1H), 7.81-7.84 (m, 1H), 7.91 (d, 1H).
MS (ESI): 385 (MH$^+$)

Example 31

3-(2-Cyanophenyl)-5-(2-pyridyl)-1-benzyl-1,2-dihydropyridin-2-one 3-(2-Cyanophenyl)-5-(2-pyridyl)-2(1H)-pyridone (46 mg), 36 mg of benzyl alcohol and 88 mg of triphenylphosphine were dissolved in 2 ml of tetrahydrofuran, 147 mg of a 40% solution of diethylazo dicarboxylate in toluene were added with ice cooling and the mixture was stirred at room temperature for 1 hour. The reaction solution was concentrated in vacuo and purified by a silica gel chromatography (hexane-ethyl acetate system) to give 12 mg of the title compound.

$^1$H-NMR (400 MHz, CDCl$_3$); δ (ppm) 5.33 (s, 2H), 7.18 (ddd, 1H), 7.31-7.40 (m, 3H), 7.42-7.48 (m, 3H), 7.53 (dd, 1H), 7.64 (ddd, 1H), 7.68-7.79 (m, 3H), 8.18 (d, 1H), 8.30 (d, 1H), 8.56-8.60 (m, 1H).

Example 32

3-(2-Cyanophenyl)-5-(2-pyridyl)-1-(3-pyridyl)-1,2-dihydropyridin-2-one

3-Bromo-5-(2-pyridyl)-1-(3-pyridyl)-1,2-dihydropyridin-2-one (5.39 g) was dissolved in 200 ml of dimethylformamide, then 6.42 g of cesium carbonate, 3.69 g of 2-(2'-cyanophenyl)-1,3,2-dioxaborian and 949 mg of tetrakistriphenylphosphine palladium were added thereto and the mixture was stirred at 120° C. for 1 hour. The reaction solution was cooled to room temperature, water and ethyl acetate were added thereto, the organic layer was partitioned, washed with water and dried over anhydrous magnesium sulfate, the drying agent was filtered off, the filtrate was concentrated in vacuo and the residue was purified by a silica gel column chromatography (hexane-ethyl acetate system) to give 4.8 g of the title compound as a colorless amorphous substance.

$^1$H-NMR (400 MHz, CDCl$_3$); δ (ppm) 7.22-7.26 (m, 1H), 7.46-7.52 (m, 2H), 7.62 (dt, 1H), 7.66(td, 1H), 7.74-7.81 (m, 3H), 7.97 (ddd, 1H), 8.32 (s, 2H), 8.61 (ddd, 1H), 8.72 (dd, 1H), 8.80-8.81 (m, 1H).
ESI-Mass; 351 [M$^+$+H]

The following compounds were synthesized by the same method as mentioned in Example 1.

Example 33

3-(2-Pyridyl)-5-(2-cyanophenyl)-1-phenyl-1,2-dihydropyridin-2-one $^1$H-NMR (400 MHz, DMSO-d$_6$); δ (ppm) 7.35-7.40 (1H, m), 7.49-7.64 (5H, m), 7.77-7.81 (2H, m), 7.86 (1H, dt), 7.96 (1H, d), 8.22 (1H, d), 8.51 (1H, d), 8.66-8.71 (2H, m).

Example 34

3-(2-Cyanophenyl)-5-(3-pyridyl)-1-phenyl-1,2-dihydropyridin-2-one $^1$H-NMR (400 MHz, CDCl$_3$); δ (ppm) 7.38 (dd, 1H), 7.45-7.58 (m, 6H), 7.65 (ddd, 1H), 7.72 (d, 1H), 7.77-7.86 (m, 3H), 7.94 (d, 1H), 8.60 (dd, 1H), 8.79 (d, 1H).

Example 35

3-(2-Cyanophenyl)-5-(4-pyridyl)-1-phenyl-1,2-dihydropyridin-2-one $^1$H-NMR (400 MHz, CDCl$_3$); δ (ppm) 7.44 (dd, 2H), 7.46-7.58 (m, 6H), 7.66 (ddd, 1H), 7.81 (dd, 2H), 7.84 (d, 1H), 8.01 (d, 1H), 8.66 (dd, 2H).

Example 36

3-(2-Cyanophenyl)-5-(2-cyanophenyl)-1-phenyl-1,2-dihydropyridin-2-one $^1$H-NMR (400 MHz, CDCl$_3$);δ (ppm) 7.26-7.59 (m, 7H), 7.62-7.72 (m, 3H), 7.76-7.80 (m, 2H), 7.82-7.84 (m, 1H), 7.86-7.88 (m, 2H).
ESI-Mass; 374 [M$^+$+H]

Example 37

3,5-Diphenyl-1-(2-pyridyl)-1,2-dihydropyridin-2-one $^1$H-NMR (400 MHz, DMSO-d$_6$); δ (ppm) 7.36-7.40 (3H, m), 7.41-7.47 (4H, m), 7.52-7.56 (2H, m), 7.74-7.78 (2H, m), 7.84-7.90 (2H, m), 7.98-8.01 (1H, m), 8.11 (1H, d), 8.61-8.63 (1H, m).

Example 38

3-Phenyl-5-(2-cyanophenyl)-1-(2-pyridyl)-1,2-dihydropyridin-2-one $^1$H-NMR (400 MHz, DMSO-d$_6$); δ (ppm) 7.34-7.40 (2H, m), 7.40-7.50 (3H, m), 7.53 (2H, dd), 7.67 (1H, dt), 7.75-7.81 (2H, m), 7.83 (1H, d), 7.88 (1H, dt), 8.02 (1H, d), 8.15 (1H, d), 8.59-8.62 (1H, m).

Example 39

3-(2-Cyanophenyl)-5-phenyl-1-(2-pyridyl)-1,2-dihydropyridin-2-one $^1$H-NMR (400 MHz, DMSO-d$_6$); δ (ppm) 7.33-7.40 (2H, m), 7.41-7.50 (3H, m), 7.54-7.59 (2H, m), 7.65 (1H, dt), 7.75 (1H, dd), 7.80 (1H, dd), 7.88 (1H, dt), 7.96 (1H, d), 8.03 (1H, d), 8.23 (1H, d), 8.60-8.64 (1H, m).

Example 40

3-(2-Cyanophenyl)-5-(2-cyanophenyl)-1-(2-pyridyl)-1,2-dihydropyridin-2-one $^1$H-NMR (400 MHz, DMSO-d$_6$); δ (ppm) 7.36-7.40 (1H, m), 7.45-7.51 (2H, m), 7.61-7.66 (1H, m), 7.66-7.71 (2H, m), 7.75-7.80 (3H, m), 7.86-7.91 (2H, m), 8.05-8.09 (1H, m), 8.34 (1H, d), 8.59-8.62 (1H, m).

Example 41

3-(2-Cyanophenyl)-1,5-diphenyl-1,2-dihydropyridin-2-one $^1$H-NMR (400 MHz, CDCl$_3$); δ (ppm) 7.32-7.37 (m, 1H), 7.41-7.56 (m, 10H), 7.63 (td, 1H), 7.69 (d, 1H), 7.77-7.82 (m, 2H), 7.98 (d, 1H).
ESI-Mass; 349 [M$^+$+H]

Example 42

3-(2-Cyanophenyl)-5-(2-methoxyphenyl)-1-phenyl-1,2-dihydropyridin-2-one $^1$H-NMR (400 MHz, CDCl$_3$); δ (ppm) 3.88 (s, 3H), 6.95-7.04 (m, 3H), 7.29-7.54 (m, 7H), 7.58-7.64 (m, 1H), 7.71 (d, 1H), 7.74-7.79 (m, 2H), 7.95 (d, 1H).

Example 43

3-(2-Cyanophenyl)-5-(3,4-dimethoxyphenyl)-1-phenyl-1,2-dihydropyridin-2-one $^1$H-NMR (400 MHz, CDCl$_3$); δ (ppm) 3.91 (s, 3H), 3.94 (s, 3H), 6.92 (d, 1H), 7.00-7.02 (m, 1H), 7.04 (dd, 1H), 7.40-7.59 (m, 6H), 7.60-7.68 (m, 2H), 7.76-7.79 (m, 1H), 7.82-7.86 (m, 1H), 7.97 (d, 1H).

Example 44

3-(2-Cyanophenyl)-5-(thiophen-3-yl)-1-phenyl-1,2-dihydropyridin-2-one $^1$H-NMR (400 MHz, CDCl$_3$); δ (ppm) 7.24 (dd, 1H), 7.35 (dd, 1H), 7.41 (dd, 1H), 7.43-7.56 (m, 6H), 7.63 (dt, 1H), 7.70 (d, 1H), 7.76-7.81 (m, 2H), 7.96 (d, 1H).

Example 45

3-(2-Cyanophenyl)-5-(2-fluorophenyl)-1-phenyl-1,2-dihydropyridin-2-one $^1$H-NMR (400 MHz, CDCl$_3$); δ (ppm) 7.16 (ddd, 1H), 7.23 (dt, 1H), 7.29-7.36 (m, 1H), 7.42-7.54 (m, 6H), 7.60-7.67 (m, 2H), 7.74-7.81 (m, 3H), 7.92 (dd, 1H).

Example 46

3-(2-Cyanophenyl)-5-(thiophen-2-yl)-1-phenyl-1,2-dihydropyridin-2-one $^1$H-NMR (400 MHz, CDCl$_3$); δ (ppm) 7.07 (dd, 1H), 7.17 (dd, 1H), 7.25-7.28 (m, 1H), 7.43-7.56 (m, 6H), 7.64 (dt, 1H), 7.72 (d, 1H), 7.74-7.80 (m, 2H), 7.93 (d, 1H).

Example 47

3-(2-Cyanophenyl)-5-phenyl-1-(3-pyridyl)-1,2-dihydropyridin-2-one $^1$H-NMR (400 MHz, DMSO-d$_6$); δ (ppm) 7.32-7.39 (1H, m), 7.41-7.47 (2H, m), 7.52-7.65 (2H, m), 7.73-7.80 (4H, m), 7.94 (1H, d), 8.06-8.11 (1H, m), 8.20 (1H, d), 8.25 (1H, d), 8.68 (1H, dd), 8.83 (1H, d).

Example 48

3-(2-Cyanophenyl)-5-(3-furyl)-1-phenyl-1,2-dihydropyridin-2-one $^1$H-NMR (400 MHz, CDCl$_3$); δ (ppm) 6.55 (dd, 1H), 7.42-7.56 (m, 7H), 7.58 (d, 1H), 7.60-7.67 (m, 2H), 7.74-7.79 (m, 2H), 7.82 (d, 1H).

Example 49

3-(2-Cyanophenyl)-5-(2-furyl)-1-phenyl-1,2-dihydropyridin-2-one $^1$H-NMR (400 MHz, CDCl$_3$); δ (ppm) 7.12-7.24 (m, 2H), 7.42-7.55 (m, 6H), 7.58-7.65 (m, 3H), 7.66 (d, 1H), 7.74-7.77 (m, 2H).

Example 50

3-(2-Cyanophenyl)-5-(2,4-dimethoxypyrimidin-5-yl)-1-phenyl-1,2-dihydropyridin-2-one $^1$H-NMR (400 MHz, CDCl$_3$); δ (ppm) 4.03 (s, 3H), 4.07 (s, 3H), 7.42-7.57 (m, 5H), 7.60-7.70 (m, 3H), 7.75-7.80 (m, 2H), 7.86 (d, 1H), 8.29 (s, 1H).

Example 51

3-(2-Cyanophenyl)-5-(3-methoxypyridin-5-yl)-1-phenyl-1,2-dihydropyridin-2-one $^1$H-NMR (400 MHz, CDCl$_3$); δ (ppm) 3.92 (s, 3H), 7.30-7.34 (m, 1H), 7.44-7.58 (m, 6H), 7.65 (ddd, 1H), 7.72 (d, 1H), 7.77-7.84 (m, 2H), 7.95 (d, 1H), 8.28-8.33 (m, 1H), 8.36-8.40 (m, 1H).

Example 52

3-(2-Cyanophenyl)-5-(2-methoxyphenyl)-1-(3-pyridyl)-1,2-dihydropyridin-2-one $^1$H-NMR (400 MHz, CDCl$_3$); δ (ppm) 3.89 (s, 3H), 7.00 (d, 1H), 7.03-7.08 (ddd, 1H), 7.35-7.40 (m, 2H), 7.46-7.51 (ddd, 1H), 7.63-7.72 (m, 2H), 7.72 (d, 1H), 7.77-7.80 (dd, 1H), 7.82-7.88 (m, 1H), 7.95 (d, 1H), 8.47-8.52 (d, 1H), 8.75-8.80 (m, 1H), 8.96 (brs, 1H).

Example 53

3-(2-Cyanophenyl)-5-[2-methoxy-5-(2-cyanophenyl)phenyl]-1-(3-pyridyl)-1,2-dihydropyridin-2-one $^1$H-NMR (400 MHz, CDCl$_3$); δ (ppm) 3.97 (s, 3H), 7.12 (d, 1H), 7.41-7.50 (m, 2H), 7.54-7.62 (m, 3H), 7.62-7.68 (ddd, 2H), 7.70-7.80 (m, 5H), 8.03 (d, 1H), 8.32-8.38 (m, 1H), 8.71-8.76 (m, 1H), 8.93 (brs, 1H).

Example 54

3-(2-Cyanophenyl)-5-(3-methylpyridin-2yl)-1-phenyl-1,2-dihydropyridin-2-one $^1$H-NMR (400 MHz, CDCl$_3$); δ (ppm) 2.56 (s, 3H), 7.42-7.70 (m, 10H), 7.71-7.78 (m, 2H), 7.89-7.93 (m, 1H), 8.46-8.54 (m, 1H).

The following compounds were synthesized by the method which is the same as or according to the method mentioned in Example 4.

Example 55

3-(2-Methoxyphenyl)-5-(2-pyridyl)-1-phenyl-1,2-dihydropyridin-2-one $^1$H-NMR (DMSO-d$_6$, 400 MHz); δ (ppm) 3.76 (3H, s), 7.00 (1H, dt), 7.09 (1H, d), 7.25-7.40 (3H, m), 7.46-7.60 (4H, m), 7.76-7.84 (2H, m), 7.94 (1H, d), 8.23 (1H, d), 8.38 (1H, d), 8.55-8.58 (1H, m).

Example 56

3-(2-Methoxyphenyl)-5-(2-pyridyl)-1-(4-fluorophenyl)-1,2-dihydropyridin-2-one $^1$H-NMR (CDCl$_3$, 400 MHz); δ (ppm) 3.82 (3H, s), 6.97-7.05 (2H, m), 7.16-7.23 (2H, m), 7.24-7.32 (1H, m), 7.36 (1H, dt), 7.44 (1H, dd), 7.50-7.66 (2H, m), 7.74-7.90 (1H, m), 8.02-8.08 (1H, m), 8.18-8.45 (2H, m), 8.58-8.64 (1H, m).

Example 57

3-(2-Chlorophenyl)-5-(2-pyridyl)-1-phenyl-1,2-dihydropyridin-2-one $^1$H-NMR (CDCl$_3$, 400 MHz); δ (ppm) 6.76-6.81(2H, m), 6.86-6.91(1H, m), 7.17-7.22 (2H, m), 7.26-7.75 (5H, m), 7.61 (1H, d), 7.78-7.86 (1H, m), 8.11 (1H, d), 8.41 (1H, brs), 8.60-8.64 (1H, m).

Example 58

3-(2-Methoxycarbonylphenyl)-5-(2-pyridyl)-1-phenyl-1,2-dihydropyridin-2-one $^1$H-NMR (DMSO-d$_6$, 400 MHz); δ (ppm) 3.65 (3H, s), 7.28-7.32 (1H, m), 7.47-7.71 (8H, m), 7.78-7.86 (2H, m), 8.01-8.20 (1H, m), 8.33 (1H, d), 8.42 (1H, d), 8.58-8.60 (1H, m).

Example 59

3-(2-Methylaminocarbonylphenyl)-5-(2-pyridyl)-1-phenyl-1,2-dihydropyridin-2-one $^1$H-NMR (DMSO-d$_6$, 400 MHz); δ (ppm) 2.65 (3H, d), 7.26-7.31 (1H, m), 7.40-7.45 (1H, m), 7.46-7.53 (5H, m), 7.53-7.59(2H, m), 7.80-7.86 (1H, m), 7.96 (1H, d), 8.06-8.12 (1H, m), 8.22 (1H, d), 8.37 (1H, d), 8.57-8.60 (1H, m).

Example 60

3-(2-Tolyl)-5-(2-pyridyl)-1-phenyl-1,2-dihydropyridin-2-one $^1$H-NMR (DMSO-d$_6$, 400 MHz); δ (ppm) 2.24 (3H, s), 7.22-7.34 (4H, m), 7.47-7.60 (6H, m), 7.78-7.84 (1H, m), 7.99 (1H, d), 8.21-8.24 (1H, m), 8.44-8.47 (1H, m), 8.55-8.59 (1H, m).

Example 61

3-Phenyl-5-(2-pyridyl)-1-phenyl-1,2-dihydropyridin-2-one $^1$H-NMR (DMSO-d$_6$, 400 MHz); δ (ppm) 7.28-7.32 (1H, m), 7.35-7.40 (1H, m), 7.41-7.47 (2H, m), 7.49-7.54 (2H, m), 7.56-7.60 (3H, m), 7.76-7.86 (3H, m), 8.02 (1H, dd), 8.42 (1H, d), 8.44 (1H, d), 8.58-8.61 (1H, m).

Example 62

3-(2-Pyridyl)-5-(2-pyridyl)-1-phenyl-1,2-dihydropyridin-2-one $^1$H-NMR (DMSO-d$_6$, 400 MHz); δ (ppm) 7.29-7.40 (2H, m), 7.50-7.63 (5H, m), 7.80-7.88 (2H, m), 7.99 (1H, d), 8.50 (1H, d), 8.54 (1H, d), 8.62-8.66 (1H, m), 8.70-8.74 (1H, m), 9.31 (1H, d).

Example 63

3-(3-Cyanophenyl)-5-(2-pyridyl)-1-phenyl-1,2-dihydropyridin-2-one $^1$H-NMR (CDCl$_3$, 400 MHz); δ (ppm) 7.24 (ddd, 1H), 7.46-7.66 (m, 8H), 7.78 (td, 1H), 8.10 (dt, 1H), 8.16 (t, 1H), 8.25 (d, 1H), 8.31 (d, 1H), 8.61-8.63 (m, 1H).

Example 64

3-(4-Cyanophenyl)-5-(2-pyridyl)-1-phenyl-1,2-dihydropyridin-2-one $^1$H-NMR (CDCl$_3$, 400 MHz); δ (ppm) 7.22-7.26 (m, 1H), 7.47-7.60 (m, 6H), 7.70-7.78 (m, 3H), 7.95-7.98 (m, 2H), 8.26 (d, 1H), 8.33 (d, 1H), 8.61-8.63 (m, 1H).

Example 65

3-(3-Chlorophenyl)-5-(2-pyridyl)-1-phenyl-1,2-dihydropyridin-2-one $^1$H-NMR (CDCl$_3$, 400 MHz); δ (ppm) 7.21-7.36 (m, 3H), 7.47-7.76 (m, 5H), 7.58-7.60 (m, 1H), 7.71-7.75 (m, 2H), 7.84-7.87 (m, 1H), 8.23-8.26 (m, 2H), 8.60-8.63 (m, 1H).
ESI-Mass; 359 [M$^+$+H]

Example 66

3-(4-Chlorophenyl)-5-(2-pyridyl)-1-phenyl-1,2-dihydropyridin-2-one $^1$H-NMR (CDCl$_3$, 400 MHz); δ (ppm) 7.22 (ddd, 1H), 7.37-7.41 (m, 2H), 7.44-7.60 (m, 5H), 7.72-7.80 (m, 3H), 8.12-8.16 (m, 1H), 8.21-8.25 (m, 2H), 8.62 (ddd, 1H).
ESI-Mass; 359 [M$^+$+H]

Example 67

3-(3-Pyridyl)-5-(2-pyridyl)-1-phenyl-1,2-dihydropyridin-2-one $^1$H-NMR (CDCl$_3$, 400 MHz); δ (ppm) 7.22-7.52 (m, 1H), 7.33-7.37 (m, 1H), 7.45-7.57 (m, 5H), 7.59-7.61 (m, 1H), 7.56 (td, 1H), 8.24-8.27 (m, 2H), 8.30 (d, 1H), 8.59 (dd, 1H), 8.61-8.63 (m, 1H), 8.95-8.96 (m, 1H).
ESI-Mass; 326 [M$^+$+H]

Example 68

3-(2-Aminocarbonyl-3-pyridyl)-5-(2-pyridyl)-1-phenyl-1,2-dihydropyridin-2-one $^1$H-NMR (CDCl$_3$, 400 MHz); δ (ppm) 5.46 (brs, 1H), 7.19 (ddd, 1H), 7.39-7.53 (m, 6H), 7.55-7.58 (m, 1H), 7.58 (brs, 1H), 7.71 (ddd, 1H), 7.82 (dd, 1H), 8.08 (d, 1H), 8.21 (d, 1H), 8.57 (dd, 1H), 8.59 (ddd, 1H).

Example 69

3-(3-Methoxyphenyl)-5-(2-pyridyl)-1-phenyl-1,2-dihydropyridin-2-one $^1$H-NMR (CDCl$_3$, 400 MHz); δ (ppm) 3.84 (s, 3H), 6.92 (ddd, 1H), 7.20 (ddd, 1H), 7.31-7.38 (m, 2H), 7.42-7.55 (m, 6H), 7.57-7.59 (m, 1H), 7.73 (td, 1H), 8.23 (d, 1H), 8.24 (d, 1H), 8.60 (ddd, 1H).
ESI-Mass; 355 [M$^+$+H]

Example 70

3-(4-Methoxyphenyl)-5-(2-pyridyl)-1-phenyl-1,2-dihydropyridin-2-one $^1$H-NMR (CDCl$_3$, 400 MHz); δ (ppm) 3.85 (s, 3H), 6.94-6.98 (m, 2H), 7.20 (ddd, 1H), 7.42-7.55 (m, 5H), 7.57-7.60 (m, 1H), 7.73 (td, 1H), 7.77-7.81 (m, 2H), 8.18-8.20 (m, 2H), 8.59-8.20 (m, 1H).
ESI-Mass; 355 [M$^+$+H]

Example 71

3-(2-Fluorophenyl)-5-(2-pyridyl)-1-phenyl-1,2-dihydropyridin-2-one $^1$H-NMR (CDCl$_3$, 400 MHz); δ (ppm) 7.13-7.22 (m, 3H), 7.31-7.59 (m, 7H), 7.66 (td, 1H), 7.74 (td, 1H), 8.22 (dd, 1H), 8.29 (d, 1H), 8.58-8.60 (m, 1H).

Example 72

3-(3-Fluorophenyl)-5-(2-pyridyl)-1-phenyl-1,2-dihydropyridin-2-one $^1$H-NMR (CDCl$_3$, 400 MHz); δ (ppm) 7.03-7.08 (m, 1H), 7.21 (ddd, 1H), 7.35-7.63 (m, 9H), 7.74 (td, 1H), 8.23 (d, 1H), 8.27 (d, 1H), 8.59-8.62 (m, 1H).

Example 73

3-(4-Fluorophenyl)-5-(2-pyridyl)-1-phenyl-1,2-dihydropyridin-2-one $^1$H-NMR (CDCl$_3$, 400 MHz); δ (ppm) 7.08-7.14 (m, 2H), 7.21 (ddd, 1H), 7.44-7.60 (m, 6H), 7.74 (td, 1H), 7.78-7.83 (m, 2H), 8.21 (d, 1H), 8.22 (d, 1H), 8.60-8.62 (m, 1H).

Example 74

3-(2-Chlorophenyl)-5-(2-pyridyl)-1-(3-methoxyphenyl)-1,2-dihydropyridin-2-one $^1$H-NMR (CDCl$_3$, 400 MHz); δ (ppm) 3.84 (s, 3H), 6.96-7.01 (m, 1H), 7.04-7.11 (m, 2H), 7.17-7.23 (m, 1H), 7.26-7.34 (m, 2H), 7.40 (dd, 1H), 7.46-7.53 (m, 2H), 7.54-7.58 (m, 1H), 7.73 (ddd, 1H), 8.14 (d, 1H), 8.29 (d, 1H), 8.57-8.62 (m, 1H).

Example 75

3-(2,4-Dimethoxyphenyl)-5-(2-pyridyl)-1-phenyl-1,2-dihydropyridin-2-one $^1$H-NMR (CDCl$_3$, 400 MHz); δ (ppm) 3.93 (s, 6H), 6.93 (d, 1H), 7.19-7.23 (m, 1H), 7.33 (dd, 1H), 7.41-7.57 (m, 6H), 7.58-7.60 (m, 1H), 7.74 (td, 1H), 8.19 (d, 1H), 8.22 (d, 1H), 8.60-8.62 (m, 1H).
ESI-Mass; 385 [M$^+$+H]

Example 76

3-(2-Fluoro-3-pyridyl)-5-(2-pyridyl)-1-phenyl-1,2-dihydropyridin-2-one $^1$H-NMR (CDCl$_3$, 400 MHz); δ (ppm) 7.20-7.28 (m, 2H), 7.44-7.56 (m, 5H), 7.56-7.60 (m, 1H), 7.75 (td, 1H), 8.19-8.21 (m, 1H), 8.26 (ddd, 1H), 8.30 (d, 1H), 8.34 (t, 1H), 8.59-8.61 (m, 1H).
ESI-Mass; 344 [M$^+$+H]

Example 77

3-(2-Methoxy-5-pyridyl)-5-(2-pyridyl)-1-phenyl-1,2-dihydropyridin-2-one $^1$H-NMR (CDCl$_3$, 400 MHz); δ (ppm) 3.98 (s, 3H), 6.80 (d, 1H), 7.22 (ddd, 1H), 7.44-7.59 (m, 6H), 7.72-7.77 (m, 1H), 8.15 (dd, 1H), 8.21 (s, 2H), 8.50-8.52 (m, 1H), 8.59-8.62 (m, 1H).
ESI-Mass; 356 [M$^+$+H]

Example 78

3-(3-Cyano-2-pyridyl)-5-(2-pyridyl)-1-phenyl-1,2-dihydropyridin-2-one $^1$H-NMR (DMSO-d$_6$, 400 MHz): δ (ppm) 7.30-7.34 (ddd, 1H), 7.49-7.57 (m, 1H), 7.57-7.62 (m, 4H), 7.62-7.66 (dd, 1H), 7.82-7.87 (ddd, 1H), 8.02 (d, 1H), 8.39-8.43 (dd, 1H), 8.59-8.62 (m, 1H), 8.63 (d, 1H), 8.65 (d, 1H), 8.94-8.96 (m, 1H).

Example 79

3-(3-Cyano-2-pyridyl)-5-phenyl-1-(3-pyridyl)-1,2-dihydropyridin-2-one $^1$H-NMR (DMSO-d$_6$, 400 MHz): δ (ppm) 7.33-7.38 (m, 1H), 7.44 (d, 1H), 7.46 (d, 1H), 7.64 (d, 1H), 7.65 (d, 1H), 7.72-7.76 (m, 2H), 8.07-8.11 (m, 1H), 8.30 (d, 1H), 8.34 (d, 1H), 8.42 (dd, 1H), 8.68-8.71 (m, 1H), 8.82-8.84 (m, 1H), 8.86-8.93 (m, 1H).

Example 80

3-(2-Fluoro-3-pyridyl)-5-(2-pyridyl)-1-(3-methoxyphenyl)-1,2-dihydropyridin-2-one $^1$H-NMR (CDCl$_3$, 400 MHz); δ (ppm) 3.85 (s, 3H), 6.99-7.10 (m, 3H), 7.20-7.31 (m, 2H), 7.40-7.47 (m, 1H), 7.58 (d, 1H), 7.76 (ddd, 1H), 8.18-8.23 (m, 1H), 8.23-8.32 (m, 2H), 8.32-8.37 (m, 1H), 8.58-8.64 (m, 1H).

Example 81

3-(2-Methoxy-3-pyridyl)-5-(2-pyridyl)-1-phenyl-1,2-dihydropyridin-2-one

¹H-NMR (CDCl₃, 400 MHz); δ (ppm) 3.98 (s, 3H), 6.96 (dd, 1H), 7.18-7.22 (m, 1H), 7.44-7.59 (m, 6H), 7.74 (dt, 1H), 7.90 (dd, 1H), 8.17 (dd, 1H), 8.25-8.28 (m, 2H), 8.58-8.61 (m, 1H).

Example 82

3-(2-Fluoro-3-pyridyl)-5-(2-pyridyl)-1-(4-fluorophenyl)-1,2-dihydropyridin-2-one ¹H-NMR (CDCl₃, 400 MHz); δ (ppm) 7.18-7.30 (m, 4H), 7.46-7.52 (m, 2H), 7.58 (d, 1H), 7.76 (ddd, 1H), 8.20-8.27 (m, 2H), 8.29 (d, 1H), 8.31-8.35 (m, 1H), 8.59-8.64 (m, 1H).

Example 83

3-(2-Fluoro-3-pyridyl)-5-(2-pyridyl)-1-(pyrimidin-5-yl)-1,2-dihydropyridin-2-one ¹H-NMR (CDCl₃, 400 MHz); δ (ppm) 7.25-7.32 (m, 2H), 7.61 (d, 1H), 7.79 (ddd, 1H), 8.16-8.22 (m, 1H), 8.24-8.27 (m, 1H), 8.29 (d, 1H), 8.34-8.37 (m, 1H), 8.61-8.64 (m, 1H), 9.01 (s, 2H), 9.32 (s, 1H).

Example 84

3-(2-Fluoro-3-pyridyl)-5-(2-pyridyl)-1-(4-methylthophenyl)-1,2-dihydropyridin-2-one ¹H-NMR (CDCl₃, 400 MHz); δ (ppm) 2.53 (s, 3H), 7.20-7.28 (m, 2H), 7.36-7.43 (m, 4H), 7.57 (d, 1H), 7.75 (td, 1H), 8.19-8.27 (m, 2H), 8.28 (d, 1H), 8.33 (t, 1H), 8.59-8.61 (m, 1H).
ESI-Mass; 390 [M⁺+H]

Example 85

3-(2-Pyridin-5-yl)-5-(2-pyridyl)-1-phenyl-1,2-dihydropyridin-2-one

¹H-NMR (CDCl₃, 400 MHz); δ (ppm) 6.67 (d, 1H), 7.21-7.26 (m, 1H), 7.45-7.59 (m, 6H), 7.75 (td, 1H), 7.96 (dd, 1H), 8.14 (d, 1H), 8.26 (d, 1H), 8.32 (m, 1H), 8.62 (m, 1H).
ESI-Mass; 342 [M⁺+H]

Example 86

3-(2-Fluoro-3-pyridyl)-5-(2-pyridyl)-1-(2-methoxy-5-pyridyl)-1,2-dihydropyridin-2-one ¹H-NMR (CDCl₃, 400 MHz); δ (ppm) 4.00 (s, 3H), 6.88 (dd, 1H), 7.22-7.29 (m, 2H), 7.44-7.79 (m, 5H), 8.20-8.24 (m, 1H), 8.27-8.29 (m, 1H), 8.33-8.36 (m, 1H), 8.61 (ddd, 1H).

Example 87

3-(2-Fluoro-3-pyridyl)-5-phenyl-1-(3-pyridyl)-1,2-dihydropyridin-2-one

¹H-NMR (DMSO-d₆, 400 MHz): δ (ppm) 7.31-7.37 (m, 1H), 7.41-7.48 (m, 2H), 7.52-7.66 (m, 2H), 7.71-7.76 (m, 2H), 8.06-8.10 (m, 1H), 8.16-8.28 (m, 4H), 8.66-8.70 (m, 1H), 8.80-8.82 (m, 1H).

Example 88

3-(2-Fluoro-3-pyridyl)-5-(2-pyridyl)-1-(3-fluorophenyl)-1,2-dihydropyridin-2-one ¹H-NMR (CDCl₃, 400 MHz); δ (ppm) 7.17-7.33 (m, 5H), 7.48-7.55 (m, 1H), 7.56-7.61 (m, 1H), 7.76 (ddd, 1H), 8.20-8.27 (m, 2H), 8.29 (d, 1H), 8.32-8.35 (m, 1H), 8.59-8.63 (m, 1H).

Example 89

3-(2-Dimethylamino-3-pyridyl)-5-(2-pyridyl)-1-phenyl-1,2-dihydropyridin-2-one

¹H-NMR (CDCl₃, 400 MHz): δ (ppm) 1.70 (s, 6H), 7.19 (ddd, 1H), 7.41-7.60 (m, 7H), 7.71 (td, 1H), 7.82 (d, 1H), 8.08 (d, 1H), 8.21 (d, 1H), 8.57 (dd, 1H), 8.58-8.60 (m, 1H).
ESI-Mass; 369 [M⁺+H]

The following compounds were synthesized by the same method as mentioned in Example 7.

Example 90

3,5-Diphenyl-1-(2-pyridyl)-1,2-dihydropyridin-2-one

¹H-NMR (400 MHz, CDCl₃); δ (ppm) 7.33-7.40(3H, m), 7.41-7.47(4H, m), 7.54(2H, dd), 7.76(2H, dd), 7.86-7.90(2H, m), 7.99(1H, ddd), 8.11(1H, d), 8.61-8.64(1H, m).

Example 91

3-(2-Cyanophenyl)-5-(2-pyridyl)-1-(4-fluorophenyl)-1,2-dihydropyridin-2-one

¹H-NMR (400 MHz, CDCl₃); δ (ppm) 7.18-7.25 (m, 3H), 7.44-7.55 (m, 3H), 7.59-7.67 (m, 2H), 7.72-7.81 (m, 3H), 8.27-8.33 (m, 2H), 8.58-8.63 (m, 1H).

Example 92

3-(2-Cyanophenyl)-5-(2-pyridyl)-1-(3-fluorophenyl)-1,2-dihydropyridin-2-one

¹H-NMR (400 MHz, CDCl₃); δ (ppm) 7.15-7.25 (m, 2H), 7.28-7.36 (m, 2H), 7.44-7.54 (m, 2H), 7.58-7.68 (m, 2H), 7.72-7.82 (m, 3H), 8.28-8.33 (m, 2H), 8.57-8.63 (m, 1H).

Example 93

3-(2-Cyanophenyl)-5-(2-pyridyl)-1-(4-cyanophenyl)-1,2-dihydropyridin-2-one

¹H-NMR (400 MHz, CDCl₃); δ (ppm) 7.23-7.26 (m, 1H), 7.49 (dt, 1H), 7.61-7.86 (m, 9H), 7.28-8.30 (m, 2H), 8.60-8.62 (m, 1H).

Example 94

3-(2-Cyanophenyl)-5-(2-pyridyl)-1-(3-cyanophenyl)-1,2-dihydropyridin-2-one

¹H-NMR (400 MHz, CDCl₃); δ (ppm) 7.23-7.26 (m, 1H), 7.49 (dt, 1H), 7.61-7.89 (m, 9H), 8.30 (s, 2H), 8.60-8.62 (m, 1H).

Example 95

3-(2-Cyanophenyl)-5-(2-pyridyl)-1-(4-methoxyphenyl)-1,2-dihydropyridin-2-one $^1$H-NMR (400 MHz, CDCl$_3$); δ (ppm) 3.86 (s, 3H), 7.02 (d, 2H), 7.21 (ddd, 1H), 7.42-7.80 (m, 8H), 8.29 (d, 1H), 8.31 (d, 1H), 8.58-8.60 (m, 1H).

Example 96

3-(2-Cyanophenyl)-5-(2-pyridyl)-1-(3-methoxyphenyl)-1,2-dihydropyridin-2-one $^1$H-NMR (400 MHz, CDCl$_3$); δ (ppm) 3.85 (s, 3H), 6.95-7.03 (m, 1H), 7.06-7.10 (m, 2H), 7.20-7.22 (m, 1H), 7.41-7.81 (m, 7H), 8.31 (s, 2H), 8.59-8.61 (m, 1H).

Example 97

3-Phenyl-5-(2-pyridyl)-1-(3-fluorophenyl)-1,2-dihydropyridin-2-one $^1$H-NMR (400 MHz, CDCl$_3$); δ (ppm) 7.15-7.24 (m, 2H), 7.26-7.33 (m, 2H), 7.34-7.40 (m, 1H), 7.40-7.53 (m, 3H), 7.57-7.62 (m, 1H), 7.72-7.82 (m, 3H), 8.20-8.23 (m, 2H), 8.59-8.63 (m, 1H).

Example 98

3-Phenyl-5-(2-pyridyl)-1-(4-fluorophenyl)-1,2-dihydropyridin-2-one $^1$H-NMR (400 MHz, CDCl$_3$); δ (ppm) 7.18-7.24 (m, 3H), 7.34-7.39 (m, 1H), 7.40-7.45 (m, 2H), 7.46-7.52 (m, 2H), 7.57-7.61 (m, 1H), 7.72-7.77 (m, 1H), 7.77-7.82 (m, 2H), 8.19-8.23 (m, 2H), 8.59-8.62 (m, 1H).

Example 99

3-(2-Chlorophenyl)-5-(2-pyridyl)-1-(4-fluorophenyl)-1,2-dihydropyridin-2-one $^1$H-NMR (400 MHz, CDCl$_3$); δ (ppm) 7.16-7.24 (m, 3H), 7.29-7.35 (m, 2H), 7.45-7.54 (m, 4H), 7.56 (d, 1H), 7.70-7.76 (m, 1H), 8.12 (d, 1H), 8.28 (d, 1H), 8.58-8.62 (m, 1H).

Example 100

3-(2-Cyanophenyl)-5-(2-pyridyl)-1-(4-formylphenyl)-1,2-dihydropyridin-2-one $^1$H-NMR (400 MHz, CDCl$_3$); δ (ppm) 7.22-7.27 (m, 1H), 7.48 (ddd, 1H), 7.60-7.69 (m, 2H), 7.72-7.82 (m, 5H), 8.03-8.09 (m, 2H), 8.29 (d, 1H), 8.33 (d, 1H), 8.58-8.62 (m, 1H), 10.10 (s, 1H).

Example 101

3-(2-Cyanophenyl)-5-(2-pyridyl)-1-(2-formylphenyl)-1,2-dihydropyridin-2-one $^1$H-NMR (400 MHz, CDCl$_3$); δ (ppm) 7.20-7.25 (m, 1H), 7.44-7.52 (m, 2H), 7.61-7.70 (m, 3H), 7.73-7.83 (m, 4H), 8.06 (dd, 1H), 8.31 (d, 1H), 8.36 (d, 1H), 8.57-8.60 (m, 1H), 10.05 (s, 1H).

Example 102

3-(2-Cyanophenyl)-5-(2-pyridyl)-1-(3-chlorophenyl)-1,2-dihydropyridin-2-one $^1$H-NMR (400 MHz, CDCl$_3$); δ (ppm) 7.21-7.25 (m, 1H), 7.43-7.50 (m, 4H), 7.55-7.58 (m, 1H), 7.59-7.68 (m, 2H), 7.73-7.81 (m, 3H), 8.27-8.31 (m, 2H), 8.58-8.62 (m, 1H).

Example 103

3-(2-Cyanophenyl)-5-(2-pyridyl)-1-(3-tolyl)-1,2-dihydropyridin-2-one $^1$H-NMR (400 MHz, CDCl$_3$); δ (ppm) 2.43 (s, 3H), 7.20-7.23 (m, 1H), 7.26-7.35 (m, 3H), 7.39-7.48 (m, 2H), 7.60-7.66 (m, 2H), 7.72-7.81 (m, 3H), 8.31 (s, 2H), 8.58-8.61 (m, 1H).

Example 104

3-(2-Cyanophenyl)-5-(2-pyridyl)-1-(3-trifluoromethylphenyl)-1,2-dihydropyridin-2-one $^1$H-NMR (400 MHz, CDCl$_3$); δ (ppm) 7.22-7.25 (m, 1H), 7.47 (t, 1H), 7.61-7.82 (m, 9H), 8.31 (s, 2H), 8.59-8.62 (m, 1H).

Example 105

3-(2-Cyanophenyl)-5-(2-pyridyl)-1-(thiophen-3-yl)-1,2-dihydropyridin-2-one $^1$H-NMR (400 MHz, CDCl$_3$); δ (ppm) 7.22-7.25 (m, 1H), 7.37-7.49 (m, 3H), 7.59-7.67 (m, 3H), 7.74-7.80 (m, 3H), 8.27 (d, 1H), 8.40 (d, 1H), 8.60-8.62 (m, 1H).

Example 106

3-(2-Cyanophenyl)-5-(2-pyridyl)-1-(3-furyl)-1,2-dihydropyridin-2-one $^1$H-NMR (400 MHz, CDCl$_3$); δ (ppm) 6.83-6.86 (m, 1H), 7.19-7.26 (m, 1H), 7.48 (ddd, 1H), 7.52 (dd, 1H), 7.60-7.69 (m, 2H), 7.73-7.82 (m, 3H), 8.21 (d, 1H), 8.27-8.30 (m, 1H), 8.47 (d, 1H), 8.61-8.65 (m, 1H).

Example 107

3-(2-Cyanophenyl)-5-(2-pyridyl)-1-(4-tolyl)-1,2-dihydropyridin-2-one $^1$H-NMR (400 MHz, CDCl$_3$); δ (ppm) 2.41 (s, 3H), 7.18-7.22 (m, 1H), 7.30-7.46 (m, 5H), 7.59-7.65 (m, 2H), 7.71-7.80 (m, 3H), 8.29 (d, 1H), 8.31 (d, 1H), 8.58-8.60 (m, 1H).

Example 108

3-(2-Cyanophenyl)-5-(2-pyridyl)-1-(4-trifluoromethylphenyl)-1,2-dihydropyridin-2-one $^1$H-NMR (400 MHz, CDCl$_3$); δ (ppm) 7.22-7.25 (m, 1H), 7.48 (td, 1H), 7.61-7.82 (m, 9H), 8.30 (d, 1H), 8.32 (d, 1H), 8.59-8.61 (m, 1H).

Example 109

3-(2-Cyanophenyl)-5-(2-pyridyl)-1-(2-methoxypyridin-5-yl)-1,2-dihydropyridin-2-one $^1$H-NMR (400 MHz, CDCl$_3$); δ (ppm) 4.00 (s, 3H), 6.88 (d, 1H), 7.23 (ddd, 1H), 7.47 (td, 1H), 7.59-7.62 (m, 1H), 7.65 (td, 1H), 7.73-7.82 (m, 4H), 8.28-8.31 (m, 3H), 8.60 (ddd, 1H).

ESI-Mass; 381 [M$^+$+H]

Example 110

3-(2-Cyanophenyl)-5-(2-pyridyl)-1-(2-cyanophenyl)-1,2-dihydropyridin-2-one $^1$H-NMR (400 MHz, CDCl$_3$); δ (ppm) 7.26-7.35 (m, 2H), 7.52-7.58 (m, 2H), 7.64-7.71 (m, 2H), 7.72-7.85 (m, 5H), 8.51 (d, 1H), 8.68-8.72 (m, 1H), 8.77 (d, 1H).

Example 111

3-(2-Cyanophenyl)-5-(2-pyridyl)-1-(pyrimidin-5-yl)-1,2-dihydropyridin-2-one $^1$H-NMR (400 MHz, CDCl$_3$); δ (ppm) 7.24-7.32 (m, 1H), 7.48-7.54 (m, 1H), 7.61-7.72 (m, 2H), 7.73-7.85 (m, 3H), 8.31 (d, 1H), 8.33 (d, 1H), 8.60-8.65 (m, 1H), 9.04 (s, 2H), 9.32 (s, 1H).

Example 112

3-(2-Cyanophenyl)-5-(2-pyridyl)-1-[2-(pyrrolidin-1-yl)-pyridin-5-yl]-1,2-dihydropyridin-2-one $^1$H-NMR (400 MHz, CDCl$_3$); δ (ppm) 2.01-2.07 (m, 4H), 3.49-3.52 (m, 4H), 6.44 (dd, 1H), 7.21 (ddd, 1H), 7.45 (td, 1H), 7.58-7.67 (m, 3H), 7.72 (dd, 1H), 7.76-7.88 (m, 2H), 8.23 (dd, 1H), 8.28 (dd, 2H), 8.59 (ddd, 1H).

ESI-Mass; 420 [M$^+$+H]

Example 113

3-(2-Cyanophenyl)-5-(2-pyridyl)-1-[2-(4-benzylpiperazin-1-yl)-pyridin-5-yl]-1,2-dihydropyridin-2-one $^1$H-NMR (400 MHz, CDCl$_3$); δ (ppm) 2.57 (t, 4H), 3.57 (s, 2H), 3.63(t, 4H), 6.70 (d, 1H), 7.21 (ddd, 1H), 7.25-7.38 (m, 5H), 7.45 (td, 1H), 7.58 (d, 1H), 7.63 (td, 1H), 7.68 (dd, 1H), 7.73 (dd, 1H), 7.75-7.79 (m, 2H), 8.26-8.29 (m, 3H), 8.58-8.60 (m, 1H).

Example 114

3-(2-Cyanophenyl)-5-(2-pyridyl)-1-(2-benzyloxyethoxypyridin-5-yl)-1,2-dihydropyridin-2-one $^1$H-NMR (400 MHz, CDCl$_3$); δ (ppm) 3.84-3.87 (m, 2H), 4.55-4.58 (m, 2H), 4.64 (s, 2H), 6.93 (d, 1H), 7.23 (ddd, 1H), 7.25-7.40 (m, 5H), 7.47 (td, 1H), 7.60 (d, 1H), 7.65 (td, 1H), 7.74-7.82 (m, 4H), 8.27 (d, 1H), 8.28 (d, 1H), 8.30 (d, 1H), 8.59-8.61 (m, 1H).

ESI-Mass; 501 [M$^+$+H]

Example 115

3-(2-Cyanophenyl)-5-(2-pyridyl)-1-(3-benzyloxymethylpyridin-5-yl)-1,2-dihydropyridin-2-one $^1$H-NMR (400 MHz, CDCl$_3$); δ (ppm) 4.64 (s, 2H), 4.66 (s, 2H), 7.23-7.26 (m, 1H), 7.26-7.38 (m, 5H), 7.48 (td, 1H), 7.61 (d, 1H), 7.68(td, 1H), 7.74-7.81 (m, 3H), 7.95-7.98 (m, 1H), 8.29 (d, 1H), 8.32 (d, 1H), 8.61 (d, 1H), 8.69 (d, 1H), 8.72 (d, 1H).

ESI-Mass; 471 [M$^+$+H]

Example 116

3-(2-Cyanophenyl)-5-(2-pyridyl)-1-(2-ethylthiopyridin-5-yl)-1,2-dihydropyridin-2-one $^1$H-NMR (400 MHz, CDCl$_3$); δ (ppm) 1.41 (t, 3H), 3.23 (q, 2H), 7.23 (ddd, 1H), 7.29 (dd, 1H), 7.47 (td, 1H), 7.60 (dt, 1H), 7.65 (td, 1H), 7.72 (dd, 1H), 7.74-7.80 (m, 3H), 8.28 (d, 1H), 8.30 (d, 1H), 8.57 (dd, 1H), 8.60 (ddd, 1H).

Example 117

3-(2-Cyanophenyl)-5-(2-pyridyl)-1-(4-pyridyl)-1,2-dihydropyridin-2-one $^1$H-NMR (400 MHz, CDCl$_3$); δ (ppm) 7.23-7.26 (m, 1H), 7.49 (td, 1H), 7.55-7.57 (m, 2H), 7.61 (d, 1H), 7.67(td, 1H), 7.73-7.81 (m, 3H), 8.29 (d, 1H), 8.30 (d, 1H), 8.61 (ddd, 1H), 8.82 (d, 1H).

ESI-Mass; 351 [M$^+$+H]

Example 118

3-(2-Cyanophenyl)-5-(2-pyridyl)-1-(3-methoxypyridin-5-yl)-1,2-dihydropyridin-2-one $^1$H-NMR (400 MHz, CDCl$_3$); δ (ppm) 3.91 (s, 3H), 7.22-7.27 (m, 1H), 7.46-7.51 (m, 2H), 7.60-7.64 (m, 1H), 7.66 (ddd, 1H), 7.74-7.82 (m, 3H), 8.30 (d, 1H), 8.32 (d, 1H), 8.38 (d, 1H), 8.43 (d, 1H), 8.60-8.63 (m, 1H).

Example 119

3-(2-Cyanophenyl)-5-(2-pyridyl)-1-(2-hydroxyethoxypyridin-5-yl)-1,2-dihydropyridin-2-one $^1$H-NMR (400 MHz, CDCl$_3$); δ (ppm) 3.04 (brs, 1H), 3.97-4.03 (m, 2H), 4.51-4.54 (m, 2H), 6.93 (d, 1H), 7.23 (dd, 1H), 7.47 (td, 1H), 7.61 (dd, 1H), 7.65 (td, 1H), 7.74-7.80 (m, 3H), 7.84 (dd, 1H), 8.27-8.30 (m, 3H), 8.61 (ddd, 1H).

ESI-Mass; 411 [M$^+$+H]

Example 120

3-(2-Cyanophenyl)-5-(2-pyridyl)-1-(2-chloropyridin-5-yl)-1,2-dihydropyridin-2-one $^1$H-NMR (400 MHz, CDCl$_3$); δ (ppm) 7.23-7.28 (m, 1H), 7.47-7.52 (m, 2H), 7.61 (d, 1H), 7.67 (t, 1H), 7.72-7.81 (m, 3H), 7.95 (dd, 1H), 8.28 (d, 1H), 8.30 (d, 1H), 8.59 (d, 1H), 8.61 (dt, 1H).

ESI-Mass; 385 [M$^+$+H]

Example 121

3-(2-Cyanophenyl)-5-(2-pyridyl)-1-[2-(4-methylpiperazin-1-yl)-pyridin-5-yl]-1,2-dihydropyridin-2-one $^1$H-NMR (400 MHz, CDCl$_3$); δ (ppm) 2.37 (s, 3H), 2.54 (t, 4H), 3.66 (t, 4H), 6.73 (d, 1H), 7.21 (ddd, 1H), 7.46 (td, 1H), 7.59 (d, 1H), 7.64(td, 1H), 7.70 (dd, 1H), 7.72-7.79 (m, 3H), 8.27-8.29 (m, 3H), 8.58-8.60 (m, 1H).
ESI-Mass; 449 [M$^+$+H]

Example 122

3-(2-Cyanophenyl)-5-(2-pyridyl)-1-(3-tert-butyldimethylsilyloxymethylpyridin-5-yl)-1,2-dihydropyridin-2-one $^1$H-NMR (400 MHz, CDCl$_3$); δ (ppm) 0.13 (s, 6H), 0.95 (s, 9H), 4.85 (s, 2H), 7.24 (dd, 1H), 7.45-7.81 (m, 7H), 7.88 (s, 1H), 8.29 (d, 1H), 8.32 (d, 1H), 8.61 (dd, 1H), 8.68 (d, 1H).

Example 123

3-(2-Cyanophenyl)-5-(2-pyridyl)-1-(2-fluoropyridin-5-yl)-1,2-dihydropyridin-2-one $^1$H-NMR (400 MHz, CDCl$_3$); δ(ppm) 7.11 (dd, 1H), 7.25 (ddd, 1H), 7.42-7.84 (m, 6H), 8.08 (ddd, 1H), 8.30(t, 2H), 8.41 (dd, 1H), 8.61 (ddd, 1H).
ESI-Mass; 369 [M$^+$+H]

Example 124

3-(2-Cyanophenyl)-5-(2-pyridyl)-1-(2-ethylpyridin-5-yl)-1,2-dihydropyridin-2-one $^1$H-NMR (400 MHz, CDCl$_3$); δ(ppm) 1.36(t, 3H), 2.91(q, 2H), 7.23 (m, 1H), 7.33 (d, 1H), 7.47(td, 1H), 7.60 (d, 1H), 7.65(td, 1H), 7.73-7.80 (m, 3H), 7.86 (dd, 1H), 8.30 (d, 1H), 8.31 (d, 1H), 8.60 (d, 1H), 8.68 (d, 1H).
ESI-Mass; 379 [M$^+$+H]

Example 125

3-Phenyl-5-(2-pyridyl)-1-(2-cyanophenyl)-1,2-dihydropyridin-2-one $^1$H-NMR (DMSO-d$_6$, 400 MHz); δ(ppm) 7.24-7.54(6H, m), 7.62-7.81(4H, m), 7.93(1H, dt), 8.11 (1H, d), 8.57(1H, d), 8.69-8.72(1H, m), 8.89-8.94(1H, m).

Example 126

3-(2-Cyanophenyl)-5-(2-pyridyl)-1-(2-methoxyphenyl)-1,2-dihydropyridin-2-one $^1$H-NMR (DMSO-d$_6$, 400 MHz); δ (ppm) 3.80(3H, s), 7.12(1H, t), 7.24-7.33(2H, m), 7.44(1H, dd), 7.49(1H, dt), 7.59(1H, dt), 7.71(1H, d), 7.75-7.86(2H, m), 7.90-8.00(2H, m), 8.42(1H, d), 8.47(1H, d), 8.56-8.60(1H, m).

The following compounds were synthesized by the same method as mentioned in Example 32.

Example 127

3-Phenyl-5-(2-pyridyl)-1-(3-pyridyl)-1,2-dihydropyridin-2-one $^1$H-NMR (400 MHz, CDCl$_3$); δ (ppm) 7.23 (ddd, 1H), 7.36-7.50 (m, 4H), 7.60(td, 1H), 7.75 (dd, 1H), 7.76-7.80 (m, 2H), 7.94 (ddd, 1H), 8.22 (d, 1H), 8.24 (d, 1H), 8.62 (ddd, 1H), 8.71 (dd, 1H), 8.75-8.79 (m, 1H).
ESI-Mass; 326 [M$^+$+H]

Example 128

3-(2-Chlorophenyl)-5-(2-pyridyl)-1-(3-pyridyl)-1,2-dihydropyridin-2-one $^1$H-NMR (400 MHz, CDCl$_3$); δ (ppm) 7.23 (ddd, 1H), 7.31-7.36 (m, 2H), 7.41-7.51 (m, 3H), 7.56-7.59 (m, 1H), 7.75(td, 1H), 7.95 (ddd, 1H), 8.15 (d, 1H), 8.30 (d, 1H), 8.60-8.62 (m, 1H), 8.69 (dd, 1H), 8.80 (d, 1H).
ESI-Mass; 360 [M$^+$+H]

Example 129

3-(2-Methoxyphenyl)-5-(2-pyridyl)-1-(3-pyridyl)-1,2-dihydropyridin-2-one $^1$H-NMR (400 MHz, CDCl$_3$); δ (ppm) 3.84 (s, 3H), 6.98-7.05 (m, 2H), 7.21 (ddd, 1H), 7.37(td, 1H), 7.41-7.49 (m, 2H), 7.56 (d, 1H), 7.74(td, 1H), 7.94-7.97 (m, 1H), 8.13 (d, 1H), 8.25 (d, 1H), 8.58-8.60 (m, 1H), 8.67 (dd, 1H), 8.79 (d, 1H).
ESI-Mass; 356 [M$^+$+H]

Example 130

3-(2-Formylthiophen-3-yl)-5-(2-pyridyl)-1-(3-pyridyl)-1,2-dihydropyridin-2-one $^1$H-NMR (400 MHz, CDCl$_3$); δ (ppm) 7.24-7.28 (m, 1H), 7.46-7.52 (m, 2H), 7.57 (d, 1H), 7.50-7.79 (m, 2H), 7.92-7.96 (m, 1H), 8.24 (d, 1H), 8.30 (d, 1H), 8.61-8.63 (m, 1H), 8.74 (dd, 1H), 8.79 (d, 1.H), 9.99 (d, 1H).

Example 131

3-(2,4-Dichlorophenyl)-5-(2-pyridyl)-1-(3-pyridyl)-1,2-dihydropyridin-2-one $^1$H-NMR (400 MHz, CDCl$_3$); δ (ppm) 7.22-7.25 (m, 1H), 7.32 (dd, 1H), 7.41-7.61 (m, 4H), 7.74-7.79 (m, 1H), 7.93-7.96 (m, 1H), 8.15 (d, 1H), 8.29 (d, 1H), 8.59-8.63 (m, 1H), 8.69-8.72 (m, 1H), 8.79 (d, 1H).
ESI-Mass; 394 [M$^+$+H]

Example 132

3-(2-Trifluoromethylphenyl)-5-(2-pyridyl)-1-(3-pyridyl)-1,2-dihydropyridin-2-one $^1$H-NMR (400 MHz, CDCl$_3$); δ (ppm) 7.22 (ddd, 1H), 7.44-7.56 (m, 4H), 7.59-7.63 (m, 2H), 7.72-7.78 (m, 1H), 7.94 (ddd, 1H), 8.04 (d, 1H), 8.30 (d, 1H), 8.59-8.61 (m, 1H), 8.69 (dd, 1H), 8.78-8.79 (m, 1H).
ESI-Mass; 394 [M$^+$+H]

Example 133

3-(Thiophen-3-yl)-5-(2-pyridyl)-1-(3-pyridyl)-1,2-dihydropyridin-2-one $^1$H-NMR (400 MHz, CDCl$_3$); δ (ppm) 7.24 (ddd, 1H), 7.39 (dd, 1H), 7.50 (dd, 1H), 7.60-7.63 (m, 1H), 7.65 (dd, 1H), 7.77(td, 1H), 7.93 (ddd, 1H), 8.15 (d, 1H), 8.32 (dd, 1H), 8.44 (d, 1H), 8.62-8.64 (m, 1H), 8.72-8.73 (m, 1H), 8.77 (d, 1H).
ESI-Mass; 332 [M$^+$+H]

Example 134

3-(1-tert-Butoxycarbonylpyrrol-2-yl)-5-(2-pyridyl)-1-(3-pyridyl)-1,2-dihydropyridin-2-one $^1$H-NMR (400 MHz, CDCl$_3$); δ (ppm) 1.47 (s, 9H), 6.25(t, 1H), 6.36-6.34 (m, 1H), 7.21 (dd, 1H), 7.37 (dd, 1H), 7.43-7.48 (m, 1H), 7.57 (d, 1H), 7.72-7.77 (m, 1H), 7.88-7.92 (m, 1H), 8.06 (d, 1H), 8.22 (d, 1H), 8.59-8.61 (m, 1H), 8.68 (dd, 1H), 8.76 (d, 1H).
ESI-Mass; 415 [M$^+$+H]

Example 135

3-(2,6-Dimethylphenyl)-5-(2-pyridyl)-1-(3-pyridyl)-1,2-dihydropyridin-2-one $^1$H-NMR (400 MHz, CDCl$_3$); δ (ppm) 2.23 (s, 6H), 7.11-7.27 (m, 3H), 7.45-7.55 (m, 3H), 7.65-8.02 (m, 2H), 8.20-8.33 (m, 1H), 8.59-8.61 (m, 1H), 8.68-8.81 (m, 3H).
ESI-Mass; 354 [M$^+$+H]

Example 136

3-(3-Acetylaminophenyl)-5-(2-pyridyl)-1-(3-pyridyl)-1,2-dihydropyridin-2-one $^1$H-NMR (400 MHz, CDCl$_3$); δ (ppm) 2.08 (s, 3H), 7.21-7.26 (m, 1H), 7.34 (d, 1H), 7.44-7.49 (m, 2H), 7.58-7.61 (m, 2H), 7.75(td, 1H), 7.82(brs, 1H), 7.84-7.88 (m, 1H), 7.89-7.92 (m, 1H), 8.20-8.23 (m, 2H), 8.59-8.61 (m, 1H), 8.69-8.71 (m, 1H), 8.77-8.78 (m, 1H).
ESI-Mass; 383 [M$^+$+H]

Example 137

3-(2-Cyanothiophen-3-yl)-5-(2-pyridyl)-1-(3-pyridyl)-1,2-dihydropyridin-2-one $^1$H-NMR (400 MHz, CDCl$_3$); δ (ppm) 7.23-7.26 (m, 1H), 7.50 (dd, 1H), 7.61-7.74 (m, 3H), 7.79(td, 1H), 7.91-7.94 (m, 1H), 8.36 (d, 1H), 8.57 (d, 1H), 8.60-8.61 (m, 1H), 8.74 (dd, 1H), 8.79 (d, 1H).
ESI-Mass; 357 [M$^+$+H]

Example 138

3-(2-Cyano-6-methoxyphenyl)-5-(2-pyridyl)-1-(3-pyridyl)-1,2-dihydropyridin-2-one $^1$H-NMR (400 MHz, CDCl$_3$): δ(ppm) 3.82 (s, 3H), 7.18-7.27 (m, 2H), 7.35-7.38 (dd, 1H), 7.43-7.50 (m, 2H), 7.60 (d, 1H), 7.74-7.80 (m, 1H), 7.98-8.02 (m, 1H), 8.16 (d, 1H), 8.35 (d, 1H), 8.59-8.62 (m, 1H), 8.67-8.72 (m, 1H), 8.83 (d, 1H).

Example 139

3-(2-Fluoro-3-pyridyl)-5-(2-pyridyl)-1-(3-pyridyl)-1,2-dihydropyridin-2-one $^1$H-NMR (400 MHz, CDCl$_3$); δ (ppm) 7.21-7.29 (m, 2H), 7.45-7.52 (m, 1H), 7.59 (d, 1H), 7.78 (dt, 1H), 7.91-7.95 (m, 1H), 8.19-8.25 (m, 2H), 8.30 (d, 1H), 8.35(t, 1H), 8.60-8.63 (m, 1H), 8.70-8.73 (m, 1H), 8.79 (d, 1H).

The following compound was synthesized by the same method as mentioned in Example 15.

Example 140

3-(2-Aminocarbonylphenyl)-5-(2-pyridyl)-1-phenyl-1,2-dihydropyridin-2-one $^1$H-NMR (DMSO-d$_6$, 400 MHz); δ (ppm) 7.17(1H, brs), 7.26-7.31(1H, m), 7.40-7.64(10H, m), 7.82(1H, dt), 7.96(1H, d), 8.21(1H, d), 8.36(1H, d), 8.56-8.59(1H, m).

The following compounds were synthesized by the same method as mentioned in Example 18.

Example 141

3-(2-Hydroxyphenyl)-5-(2-pyridyl)-1-phenyl-1,2-dihydropyridin-2-one $^1$H-NMR (DMSO-d$_6$, 400 MHz); δ (ppm) 6.87-6.93(2H, m), 7.22(1H, dt), 7.30(1H, ddd), 7.38(1H, dd), 7.48-7.60(5H, m), 7.82(1H, dt), 7.99(1H, d), 8.41(1H, d), 8.45(1H, d), 8.57-8.60(1H, m), 9.43(1H, s).

Example 142

3-(2-Hydroxyphenyl)-5-(2-pyridyl)-1-(4-fluorophenyl)-1,2-dihydropyridin-2-one $^1$H-NMR (DMSO-d$_6$, 400 MHz); δ (ppm) 6.86-6.93(2H, m), 7.22(1H, dt), 7.30(1H, ddd), 7.36-7.44(3H, m), 7.62-7.68 (2H, m), 7.83(1H, dt), 7.98(1H, d), 8.40(1H, d), 8.45(1H, d), 8.57-8.60(1H, m), 9.40(1H, s).

Example 143

3-(2-Chlorophenyl)-5-(2-pyridyl)-1-(3-hydroxyphenyl)-1,2-dihydropyridin-2-one $^1$H-NMR (400 MHz, CDCl$_3$); δ (ppm) 6.71-6.76 (m, 1H), 6.85-6.91 (m, 2H), 7.19-7.34 (m, 4H), 7.41-7.50 (m, 2H), 7.56 (d, 1H), 7.74 (ddd, 1H), 8.17 (d, 1H), 8.23 (d, 1H), 8.58-8.62 (m, 1H).

The following compounds were synthesized by the same method as mentioned in Example 19.

Example 144

3-(2-Chlorophenyl)-5-(2-pyridyl)-1-(3-dimethylaminoethoxyphenyl)-1,2-dihydropyridin-2-one $^1$H-NMR (400 MHz, CDCl$_3$); δ (ppm) 2.89 (s, 6H), 3.41(t, 2H), 4.54(t, 2H), 6.99-7.04 (m, 1H), 7.13 (dd, 1H), 7.14-7.18 (m, 1H), 7.21 (ddd, 1H), 7.30-7.35 (m, 2H), 7.43-7.51 (m, 3H), 7.58 (d, 1H), 7.74 (ddd, 1H), 8.15 (d, 1H), 8.28 (d, 1H), 8.59-8.62 (m, 1H).

Example 145

3-(2-Chlorophenyl)-5-(2-pyridyl)-1-(4-dimethylaminopropoxyphenyl)-1,2-dihydropyridin-2-one $^1$H-NMR (400 MHz, CDCl$_3$); δ (ppm) 1.98(tt, 2H), 2.26 (s, 6H), 2.46(t, 2H), 4.06(t, 2H), 6.97-7.03 (m, 2H), 7.19 (ddd, 1H), 7.28-7.33 (m, 2H), 7.39-7.44 (m, 2H), 7.46-7.51 (m, 2H), 7.53-7.58 (m, 1H), 7.72 (ddd, 1H), 8.12 (d, 1H), 8.28 (d, 1H), 8.58-8.61 (m, 1H).

Example 146

3-(2-Chlorophenyl)-5-(2-pyridyl)-1-(3-dimethylaminopropoxyphenyl)-1,2-dihydropyridin-2-one $^1$H-NMR (400 MHz, CDCl$_3$); δ (ppm) 1.96(tt, 2H), 2.25 (s, 6H), 2.44(t, 2H), 4.05(t, 2H), 6.95-7.01 (m, 1H), 7.04-7.11 (m, 2H), 7.17-7.24 (m, 1H), 7.28-7.35 (m, 2H), 7.36-7.43 (m, 1H), 7.45-7.53 (m, 2H), 7.56 (d, 1H), 7.73 (ddd, 1H), 8.14 (d, 1H), 8.29 (d, 1H), 8.58-8.63 (m, 1H).

The following compounds were synthesized by the same method as mentioned in Example 21.

Example 147

3-(2-Hydroxymethylphenyl)-5-(2-pyridyl)-1-phenyl-1,2-dihydropyridin-2-one $^1$H-NMR (DMSO-d$_6$; 400 MHz); δ (ppm) 4.46(2H, d), 5.04(1H, t), 7.24-7.60(10H, m), 7.78-7.84(1H, m), 7.96-8.00 (1H, m), 8.25(1H, d), 8.45(1H, d), 8.55-8.59(1H, m).

Example 148

3-(2-Cyanophenyl)-5-(2-pyridyl)-1-(4-hydroxymethylphenyl)-1,2-dihydropyridin-2-one $^1$H-NMR (400 MHz, CDCl$_3$); δ (ppm) 1.81(t, 1H), 4.78 (d, 2H), 7.19-7.24 (m, 1H), 7.46 (ddd, 1H), 7.51-7.55 (m, 4H), 7.59-7.66 (m, 2H), 7.72-7.80 (m, 3H), 8.28-8.32 (m, 2H), 8.58-8.61 (m, 1H).

Example 149

3-(2-Cyanophenyl)-5-(2-pyridyl)-1-(2-hydroxymethylphenyl)-1,2-dihydropyridin-2-one $^1$H-NMR (400 MHz, CDCl$_3$); δ (ppm) 3.35 (dd, 1H), 4.52 (dd, 1H), 4.62 (dd, 1H), 7.21-7.24 (m, 1H), 7.35 (dd, 1H), 7.46-7.57 (m, 3H), 7.60-7.69 (m, 3H), 7.72-7.81 (m, 3H), 8.26 (d, 1H), 8.36 (d, 1H), 8.58-8.62 (m, 1H).

The following compounds were synthesized by the same method as mentioned in Example 22.

Example 150

3-(2-Cyanophenyl)-5-(2-pyridyl)-1-(4-cyanomethylphenyl)-1,2-dihydropyridin-2-one $^1$H-NMR (400 MHz, CDCl$_3$); δ (ppm) 3.84 (s, 2H), 7.23 (ddd, 1H), 7.47 (ddd, 1H), 7.49-7.54 (m, 2H), 7.55-7.63 (m, 3H), 7.65 (ddd, 1H), 7.73-7.81 (m, 3H), 8.28-8.32 (m, 2H), 8.58-8.62 (m, 1H).

Example 151

3-(2-Cyanophenyl)-5-(2-pyridyl)-1-(2-cyanomethylphenyl)-1,2-dihydropyridin-2-one $^1$H-NMR (400 MHz, CDCl$_3$); δ (ppm) 3.81 (d, 1H), 3.91 (d, 1H), 7.24 (ddd, 1H), 7.39-7.44 (m, 1H), 7.46-7.58 (m, 3H), 7.62 (d, 1H), 7.64-7.71 (m, 3H), 7.73-7.81 (m, 2H), 8.22 (d, 1H), 8.34 (d, 1H), 8.59-8.63 (m, 1H).

The following compounds were synthesized by the same method as mentioned in Example 27.

Example 152

3-(2-Cyanophenyl)-5-(2-pyridyl)-1-(2-ethylsulfonylpyridin-5-yl)-1,2-dihydropyridin-2-one $^1$H-NMR (400 MHz, CDCl$_3$); δ (ppm) 1.36(t, 3H), 3.47(q, 2H), 7.26-7.29 (m, 1H), 7.51(td, 1H), 7.63 (d, 1H), 7.68(td, 1H), 7.71-7.82 (m, 3H), 8.23-8.29 (m, 2H), 8.31-8.33 (m, 2H), 8.61-8.63 (m, 1H), 8.97-8.98 (m, 1H).

ESI-Mass; 443 [M$^+$+H]

Example 153

3-(2-Fluoro-3-pyridyl)-5-(2-pyridyl)-1-(4-methylsulfonylphenyl)-1,2-dihydropyridin-2-one $^1$H-NMR (400 MHz, CDCl$_3$); δ (ppm) 3.11 (s, 3H), 7.24-7.30 (m, 2H), 7.60 (d, 1H), 7.75-7.80 (m, 3H), 8.12(t, 1H), 8.14(t, 1H), 8.17-8.24 (m, 2H), 8.30 (d, 1H), 8.35(t, 1H), 8.61-8.63 (m, 1H).

ESI-Mass; 422 [M$^+$+H]

The following compounds were synthesized by the same manner as mentioned in Example 29.

Example 154

3-(2-Dimethylaminomethylphenyl)-5-(2-pyridyl)-1-phenyl-1,2-dihydropyridin-2-one dihydrochloride $^1$H-NMR (DMSO-d$_6$, 400 MHz); δ (ppm) 2.06(6H, s), 3.37(2H, s), 7.25-7.39(4H, m), 7.44-7.61(6H, m), 7.81(1H, dt), 7.96(1H, d), 8.24(1H, d), 8.43(1H, d), 8.55-8.58(1H, m).

Example 155

3-(2-Cyanophenyl)-5-(2-pyridyl)-1-(2-dimethylaminomethylphenyl)-1,2-dihydropyridin-2-one $^1$H-NMR (400 MHz, CDCl$_3$); δ (ppm) 2.16 (s, 6H), 3.30 (d, 1H), 3.46 (d, 1H), 7.18-7.23 (m, 1H), 7.34-7.38 (m, 1H), 7.40-7.49 (m, 3H), 7.55-7.66 (m, 3H), 7.70-7.79 (m, 3H), 8.21 (d, 1H), 8.37 (d, 1H), 8.58-8.61 (m, 1H).

Example 156

3-(2-Cyanophenyl)-5-(2-pyridyl)-1-(4-dimethylaminomethylphenyl)-1,2-dihydropyridin-2-one $^1$H-NMR (400 MHz, CDCl$_3$); δ (ppm) 2.28 (s, 6H), 3.49 (s, 2H), 7.22 (ddd, 1H), 7.43-7.49 (m, 5H), 7.59-7.66 (m, 2H), 7.72-7.81 (m, 3H), 8.30 (d, 1H), 8.33 (d, 1H), 8.58-8.61 (m, 1H).

Example 157

3-(2-Cyanophenyl)-5-(6-diethylaminomethyl-2-pyridyl)-1-phenyl-1,2-dihydropyridin-2-one $^1$H-NMR (400 MHz, CDCl$_3$); δ (ppm) 1.49(6H, t), 3.10-3.33(4H, m), 4.36(2H, brs), 7.46-7.60(7H, m), 7.63-7.68(2H, m), 7.79-7.89(3H, m), 8.28(1H, d), 8.39(1H, d).

The following compound was synthesized by the same method as mentioned in Example 31.

Example 158

3-(2-Cyanophenyl)-5-(2-pyridyl)-1-phenethyl-1,2-dihydropyridin-2-one $^1$H-NMR (400 MHz, CDCl$_3$); δ (ppm) 3.18(t, 2H), 4.33(t, 2H), 7.19 (ddd, 1H), 7.22-7.34 (m, 3H), 7.39 (d, 1H), 7.43-7.50 (m, 3H), 7.62-7.74 (m, 4H), 7.96 (d, 1H), 8.18 (d, 1H), 8.56-8.60 (m, 1H).

Example 159

3-(2-Cyanophenyl)-1-(2-pyridyl)-5-(2-pyridyl)-1,2-dihydropyridin-2-one

A mixture of 0.05 g of 1-(2-pyridyl)-5-(2-pyridyl)-3-bromo-1,2-dihydropyridin-2-one, 0.04 g of 2-(2-cyanophenyl)-1,3,2-dioxaborinate, 0.02 g of tetrakistriphenylphosphine palladium and 0.1 g of cesium carbonate was stirred at 120° C. in a nitrogen atmosphere for 2 hours in dimethylformamide. The mixture was diluted with water, and extracted with ethyl acetate. The organic layer was washed with water and then saturated saline water, and dried by magnesium sulfate anhydride. The solvent was concentrated under a vacuum, and the residue was refined by silica gel chromatography (ethyl acetate/hexane=3:1), to obtain 0.04 g of the white, powdery subject compound.

$^1$H-NMR (400 MHz, DMSO-d$_6$); δ(ppm) 7.33 (dd, 1H), 7.56-7.64 (m, 2H), 7.75 (d, 1H), 7.78-7.83 (m, 1H), 7.84-7.90 (m, 2H), 7.95 (d, 1H), 8.00 (d, 1H), 8.07 (dt, 1H), 8.50 (d, 1H), 8.61 (d, 1H), 8.70 (d, 1H), 8.83 (d, 1H).

Example 160

1-(2-Cyanophenyl)-3-(2-pyridyl)-5-phenyl-1,2-dihydropyridin-2-one 5 ml of a dimethylformamide solution containing 0.26 g of 3-(2-pyridyl)-5-phenyl-2(1H)-pyridone was incorporated with 0.04 g of sodium hydride. After 15 minutes, the solution was further incorporated with 0.15 g of 2-fluorobenzonitrile and 0.10 g of cuprous iodide, and vigorously stirred at 100° C. for 2 hours. The solution was cooled to room temperature, diluted with water, and extracted with ethyl acetate. The organic layer was washed with water and then saturated saline water, and dried by magnesium sulfate anhydride. The solvent was distilled off under a vacuum. The residue was refined by silica gel chromatography (ethyl acetate/hexane=1:2), to obtain 0.03 g of the light yellow, powdery subject compound.

$^1$H-NMR (400 MHz, DMSO-d$_6$); δ(ppm) 7.34-7.42 (m, 2H), 7.45-7.50 (m, 2H), 7.70-7.78 (m, 3H), 7.84-7.90 (m, 2H), 7.96 (dt, 1H), 8.11 (d, 1H), 8.31 (d, 1H), 8.47 (dd, 1H), 8.71-8.74 (m, 1H), 8.88 (d, 1H).

Example 161

1-Phenyl-3-(1-phenylacetylen-2-yl)-5-(2-pyridyl)-1,2-dihydropyridin-2-one 100 mg of 3-bromo-1-phenyl-5-(pyridin-2-yl)-1,2-dihydropyridin-2-one, 55 mg of phenylacetylene, 1 mg of copper (I) iodide and 4 mg of dichlorobis(triphenylphosphine) palladium were added to a mixed solvent of 1.5 ml of triethylamine and 1 ml of dimethylformamide, and stirred at 50° C. in a nitrogen atmosphere for a night. The reaction mixture was distributed into the ethyl acetate and water layers. The organic layer was washed with water, dried and concentrated, and the residue was refined by silica gel chromatography (ethyl acetate/hexane-based solvent), to obtain 7 mg of the subject compound.

$^1$H-NMR (400 MHz, CDCl$_3$); δ(ppm) 7.22 (dd, 1H), 7.33-7.35 (m, 3H), 7.46-7.60 (m, 8H), 7.75 (dt, 1H), 8.26 (d, 1H), 8.34 (d, 1H), 8.60 (ddd, 1H).

Example 162

5-(5-Acetoxypyridin-2-yl)-3-(2-cyanophenyl)-1-phenyl-1,2-dihydropyridin-2-one (162a) 3-(2-Cyanophenyl)-1-phenyl-5-(tri-n-butyl stannyl)-1,2-dihydropyridin-2-one 5.50 g of 5-bromo-3-(2-cyanophenyl)-1-phenyl-1,2-dihydropyridin-2-one, 45.5 g of bistributyl tin and 907 mg of tetrakistriphenylphosphine palladium were added to 60 ml of xylene, and the mixture was stirred at 120° C. in a nitrogen atmosphere for 40 minutes. The reaction mixture was refined by silica gel chromatography (ethyl acetate/hexane-based solvent), to obtain 3.42 g of the subject compound.

$^1$H-NMR (400 MHz, CDCl$_3$); δ(ppm) 0.90(t, 9H), 1.07-1.11 (m, 6H), 1.30-1.39 (m, 6H), 1.52-1.60 (m, 6H), 7.29 (d, 1H), 7.39-7.47 (m, 5H), 7.49-7.52 (m, 2H), 7.60 (d, 1H), 7.71-7.75 (m, 2H).

(162b) 5-(5-acetoxypyridin-2-yl)-3-(2-cyanophenyl)-1-phenyl-1,2-dihydropyridin-2-one 3.42 g of 3-(2-cyanophenyl)-1-phenyl-5-(tri-n-butyl stannyl)-1,2-dihydropyridin-2-one, 1.57 g of 5-acetoxy-2-chloropyridine and 352 mg of tetrakistriphenylphosphine palladium were added to 40 ml of xylene, and the mixture was stirred at 120° C. in a nitrogen atmosphere for 8.5 hours. The reaction mixture was refined by silica gel chromatography (ethyl acetate/hexane-based solvent), to obtain 953 mg of the subject compound.

$^1$H-NMR (400 MHz, CDCl$_3$); δ(ppm) 2.36 (s, 3H), 7.44-7.56 (m, 6H), 7.62-7.68 (m, 3H), 7.77-7.80 (m, 2H), 8.27 (d, 1H), 8.28 (d, 1H), 8.40 (dd, 1H).

Example 163

3-(2-Cyanophenyl)-5-(5-hydroxypyridin-2-yl)-1-phenyl-1,2-dihydropyridin-2-one 953 mg of 5-(5-acetoxypyridin-2-yl)-3-(2-cyanophenyl)-1-phenyl-1,2-dihydropyridin-2-one and 192 mg of potassium carbonate were added to 50 ml of methanol, and the mixture was stirred at room temperature for 30 minutes. The mixture was further incorporated with 50 ml of methanol, and stirred at 40° C. for 15 minutes. The reaction mixture was diluted with ethyl acetate, and filtered by silica gel. The filtrate was concentrated under a vacuum and washed with a diethyl ether/methanol-based solvent, to obtain 786 mg of the subject compound.

$^1$H-NMR (400 MHz, DMSO-d$_6$); δ(ppm) 7.19 (dd, 1H), 7.49-7.52 (m, 1H), 7.55-7.61 (m, 5H), 7.71 (dd, 1H), 7.78 (dt, 1H), 7.82 (d, 1H), 7.93 (dd, 1H), 8.14 (d, 1H), 8.34 (d, 1H), 8.37 (d, 1H).

Example 164

3-(2-Cyanophenyl)-1-phenyl-5-(2-pyrimidinyl)-1,2-dihydropyridin-2-one 63 mg of 2-tributyl tin pyrimidine, prepared in accordance with Tetrahedron 50(1), 275, (1994), 50 mg of 5-bromo-3-(2-cyanophenyl)-1-phenyl-1,2-dihydropyridin-2-one and 5 mg tetrakistriphenylphosphine palladium were added to 2 ml of xylene, and the mixture was stirred at 120° C. in a nitrogen atmosphere for a night. The reaction mixture was refined by silica gel chromatography (ethyl acetate/hexane-based solvent), to obtain 10 mg of the subject compound.

$^1$H-NMR (400 MHz, CDCl$_3$); δ(ppm) 7.15(t, 1H), 7.44-7.54 (m, 6H), 7.64 (dt, 1H), 7.72-7.78 (m, 2H), 8.70 (s, 1H), 8.71 (s, 1H), 8.72 (d, 1H), 8.76 (d, 1H).

Example 165

3-(2-Hydroxypyridin-6-yl)-1-phenyl-5-(2-pyridyl)-1,2-dihydropyridin-2-one 20 mg of 3-(2-methoxypyridin-6-yl)-1-phenyl-5-(pyridin-2-yl)-1,2-dihydropyridin-2-one is added to 3 ml of 5N hydrochloric acid. The mixture was heated under reflux for 3 hours, to which 0.5 ml of concentrated hydrochloric acid was added, and further stirred for 1 hour. The reaction mixture was concentrated under a vacuum and washed with ether, to quantitatively obtain the subject compound.

$^1$H-NMR (400 MHz, DMSO-d$_6$); δ(ppm) 6.44 (d, 1H), 7.08(brs, 1H), 7.47 (dd, 1H), 7.52-7.62 (m, 6H), 8.02-8.06 (m, 1H), 8.18 (d, 1H), 8.62 (d, 1H), 8.68 (dd, 1H), 8.82 (dd, 1H).

Example 166

1-(2-Aminobenzothiazol-6-yl)-3-(2-cyanophenyl)-5-(2-pyridyl)-1,2-dihydropyridin-2-one 150 mg of 1-(3-aminophenyl)-3-(2-cyanophenyl)-5-(2-pyridyl)-1,2-dihydropyridin-2-one and 63 mg of ammonium thiocyanate were added to 2 ml of acetic acid. The mixture was stirred at room temperature for 1 hour, to which 0.022 ml of bromine was added, and further stirred for 1 hour. The reaction mixture was distributed into the ethyl acetate and water layers, and neutralized with 20% aqueous solution of potassium carbonate. The organic layer was washed with water, dried and concentrated, and the residue was refined by silica gel chromatography (ethyl acetate/hexane-based solvent), to obtain 58 mg of the subject compound.

$^1$H-NMR (400 MHz, CDCl$_3$); δ(ppm) 5.37(brs, 1H), 6.76 (d, 1H), 7.20-7.24 (m, 1H), 7.41-7.80 (m, 8H), 8.28-9.40 (m, 2H), 8.59-8.61 (m, 1H).

Example 167

1,3-Diphenyl-4-methyl-5-(2-pyridyl)-1,2-dihydropyridin-2-one

The subject compound was obtained, at a yield of 27%, in accordance with the method for Referential Examples 4, 5 and 6 and Example 32 from 2,5-dibromo-4-methylpyridine.

$^1$H-NMR (400 MHz, CDCl$_3$); δ(ppm) 2.10 (s, 3H), 7.27 (ddd, 1H), 7.30-7.51 (m, 12H), 7.76 (ddd, 1H), 8.66-8.70 (m, 1H).

Example 168

1-Phenyl-3-[N—(N'-phenylureylenyl)]-5-(2-pyridyl)-1,2-dihydropyridin-2-one 50 mg of 3-amino-1-phenyl-5-(2-pyridyl)-1,2-dihydropyridin-2-one and 25 mg of phenyl isocyanate were dissolved in 1 ml of tetrahydrofuran, and the solution was stirred at room temperature for 2 hours and at 60° C. for 2 hours. The reaction solution was left to cool to room temperature, to which diethyl ether was added. The resultant crystal was separated by filtration, to obtain 30 mg of the subject compound.

$^1$H-NMR (400 MHz, CDCl$_3$); δ(ppm) 7.03-7.14 (m, 3H), 7.17-7.33 (m, 4H), 7.38-7.44 (m, 2H), 7.45-7.50 (m, 2H), 7.59(brs, 1H), 7.68-7.76 (m, 2H), 8.02 (d, 1H), 8.54-8.57 (m, 1H), 8.58 (brs, 1H), 9.00 (d, 1H).

Example 169

3-Benzoylamino-1-phenyl-5-(2-pyridyl)-1,2-dihydropyridin-2-one 30 mg of 3-amino-1-phenyl-5-(2-pyridyl)-1,2-dihydropyridin-2-one was dissolved in 1 ml of methylene chloride and 1 ml of pyridine, to which 19 mg of benzoyl chloride was added with cooling with ice, and the mixture was stirred at room temperature for a night. The reaction mixture was concentrated, diluted with ethyl acetate, and washed with a saturated aqueous solution of sodium bicarbonate. The organic layer was dried by magnesium sulfate, and refined by NH silica gel chromatography (ethyl acetate). The solvent was concentrated, and the resultant crude crystal was washed with ethyl acetate/hexane, to obtain 35 mg of the subject compound.

$^1$H-NMR (400 MHz, CDCl$_3$); δ(ppm) 7.23 (ddd, 1H), 7.47-7.60 (m, 8H), 7.70-7.80 (m, 2H), 7.95-8.00 (m, 2H), 8.12 (d, 1H), 8.57-8.61 (m, 1H), 9.28 (d, 1H), 9.35(br s, 1H).

Example 170

3-Benzylamino-1-phenyl-5-(2-pyridyl-1,2-dihydropyridin-2-one 40 mg of 3-amino-1-phenyl-5-(2-pyridyl)-1,2-dihydropyridin-2-one and 10 mg of sodium hydride were added to 1 ml of toluene, to which 30 mg of benzyl chloride was added dropwise at 70° C. The mixture was stirred for 30 minutes, and heated for 1 hour under reflux. The reaction mixture was left to cool to room temperature, diluted with ethyl acetate, and washed with a water and a saturated saline water. The organic layer was dried by magnesium sulfate, and refined by NH silica gel chromatography (ethyl acetate/hexane-based solvent), to obtain 13 mg of the subject compound.

$^1$H-NMR (400 MHz, CDCl$_3$); δ(ppm) 4.48 (d, 2H), 5.60(br t, 1H), 6.86 (d, 1H), 7.15 (ddd, 1H), 7.26-7.32 (m, 1H), 7.34-7.40 (m, 2H), 7.40-7.56 (m, 9H), 7.66 (ddd, 1H), 8.55-8.58 (m, 1H).

Example 171

3-(2-Cyanophenyl)-1-cyclopentyl-5-(2-pyridyl)-1,2-dihydropyridin-2-one 2.00 g of 3-bromo-5-(2-pyridyl)-1,2-dihydropyridin-2-one as the stock material was N-alkylated by the normal method with 5.94 g of bromocyclopentane and 5.50 g of potassium carbonate, to obtain 506 mg of 3-bromo-1-cyclopentyl-5-(2-pyridyl)-1,2-dihydropyridin-2-one, 150 mg of which was treated in accordance with the method for Example 32, to obtain 120 mg of the subject compound.
$^1$H-NMR (400 MHz, CDCl$_3$); δ(ppm) 1.73-2.02 (m, 6H), 2.23-2.35 (m, 2H), 5.37(quintet, 1H), 7.20 (ddd, 1H), 7.45 (ddd, 1H), 7.57 (d, 1H), 7.64 (ddd, 1H), 7.70-7.79 (m, 3H), 8.11 (d, 1H), 8.36 (d, 1H), 8.59-8.63 (m, 1H).

Example 172

1-{3-[1-(Benzyloxycarbonyl)piperidin-4-yl-oxy]phenyl}-3-(2-cyanophenyl)-5-(2-pyridyl)-1,2-dihydropyridin-2-one 0.99 g of 3-bromo-1-(3-hydroxyphenyl)-5-(2-pyridyl)-1,2-dihydropyridin-2-one was obtained in accordance with the method for Example 18 from 1.02 g of 3-bromo-1-(3-methoxyphenyl)-5-(2-pyridyl)-1,2-dihydropyridin-2-one, synthesized in accordance with the method for Referential Example 6. It was dissolved 30 ml of tetrahydrofuran and 10 ml of N,N-dimethylformamide, to which 1.52 g of triphenyl phosphine and 1.36 g of N-benzyloxycarbonyl-4-piperidinol were added, and further 2.52 g of a 40% toluene solution of diethylazodicarboxylate was added dropwise with cooling with ice, and the mixture was stirred at room temperature for a night. The reaction solution was concentrated under a vacuum and refined by silica gel chromatography (ethyl acetate/hexane-based solvent) to obtain 0.98 g of 1-{3-[N-(benzyloxycarbonyl)piperidin-4-yl-oxy]phenyl}-3-bromo-5-(2-pyridyl)-1,2-dihydropyridin-2-one, from which 0.85 g of the subject compound was obtained in accordance with the method for Example 32.
$^1$H-NMR (400 MHz, CDCl$_3$); δ(ppm) 1.73-1.87 (m, 2H), 1.88-2.02 (m, 2H), 3.43-3.52 (m, 2H), 3.70-3.80 (m, 2H), 4.50-4.58 (m, 1H), 5.14 (s, 2H), 6.98-7.02 (m, 1H), 7.06-7.11 (m, 2H), 7.22 (dd, 1H), 7.30-7.38 (m, 5H), 7.40-7.49 (m, 2H), 7.60 (ddd, 1H), 7.64 (ddd, 1H), 7.72-7.80 (m, 3H), 8.29 (d, 1H), 8.31 (d, 1H), 8.58-8.61 (m, 1H).

Example 173

3-(2-Cyanophenyl)-5-(2-pyridyl 1-oxide)-1-phenyl-1,2-dihydropyridin-2-one 1.00 g of 3-(2-cyanophenyl)-5-(2-pyridyl)-1-phenyl-1,2-dihydropyridin-2-one was dissolved in 30 ml of chloroform, to which 0.99 g of 60% m-chloroperbenzoic acid was added, and the mixture was stirred at room temperature for 2 hours. Another 1.00 g of 60% m-chloroperbenzoic acid was added to the mixture, and the mixture was stirred for 3 hours. The reaction solution was incorporated with 50 ml of an aqueous solution of 1N sodium hydroxide, and extracted with ethyl acetate. The organic layer was washed with saturated saline water, dried by magnesium sulfate anhydride, and the solvent was distilled off under a vacuum. The residue was recrystallized from ethyl acetate/diethyl ether, to obtain 0.46 g of the subject compound.
$^1$H-NMR (400 MHz, CDCl$_3$); δ(ppm) 7.21-7.27 (m, 1H), 7.36 (dt, 1H), 7.43-7.48 (m, 2H), 7.50-7.54 (m, 4H), 7.61 (dd, 1H), 7.63 (dt, 1H), 7.78 (dd, 1H), 7.81-7.85 (m, 1H), 8.10 (d, 1H), 8.21 (dd, 1H), 8.83 (d, 1H).

Example 174

3-Phenylamino-5-(2-pyridyl)-1-phenyl-1,2-dihydropyridin-2-one 53 mg of 3-bromo-5-(2-pyridyl)-1-phenyl-1,2-dihydropyridin-2-one and 23 mg of aniline were dissolved in 10 ml of toluene, to which 2 mg of palladium acetate, 7 mg of 1,1'-bis(diphenylphosphino)ferrocene and 23 mg of sodium tert-butoxide were added, and the mixture was stirred at 110° C. for a night. The reaction solution was cooled to room temperature, filtered by silica gel and washed with ether, and the filtrate was distilled under a vacuum to remove the solvent. The residue was refined by silica gel chromatography (NH silica) (hexane/ethyl acetate-based solvent), to obtain 47 mg of the subject compound.
$^1$H-NMR (400 MHz, CDCl$_3$); δ(ppm) 7.06(tt, 1H), 7.15-7.19 (m, 2H), 7.29-7.31 (m, 2H), 7.38(tt, 2H), 7.43-7.56 (m, 5H), 7.67 (d, 1H), 7.69(td, 1H), 7.75 (d, 1H), 8.58 (ddd, 1H).
ESI-Mass; 340 [M$^+$+H]

Example 175

3-Phenoxy-5-(2-pyridyl)-1-phenyl-1,2-dihydropyridin-2-one 100 mg of 3-bromo-5-(2-pyridyl)-1-phenyl-1,2-dihydropyridin-2-one and 58 mg of phenol were dissolved in 10 ml of dimethylformamide, to which 84 mg of potassium carbonate and 6 mg of copper iodide were added, and the mixture was stirred at 150° C. for 5 hours. The reaction solution was cooled to room temperature, to which ammonia water was added, and extracted with ethyl acetate. The organic layer was washed with saturated saline water and dried by magnesium sulfate anhydride, and the solvent was distilled off under a vacuum. The residue was refined by silica gel chromatography (hexane/ethyl acetate-based solvent), to obtain 66 mg of the subject compound.
$^1$H-NMR (400 MHz, CDCl$_3$); δ(ppm) 7.13-7.19 (m, 3H), 7.26-7.27 (m, 2H), 7.36-7.54 (m, 7H), 7.60-7.61 (m, 1H), 7.66-7.71 (m, 1H), 8.03-8.04 (m, 1H), 8.54-8.57 (m, 1H).
ESI-Mass; 341 [M$^+$+H]

Example 176

3-(1-Adamantylamino)-5-(2-pyridyl)-1-phenyl-1,2-dihydropyridin-2-one 27 mg of 3-bromo-5-(2-pyridyl)-1-phenyl-1,2-dihydropyridin-2-one and 130 mg of 1-adamantylamine were dissolved in 10 ml of dimethylformamide. To the mixture was added 20 mg of sodium hydride, followed by stirring at 130° C. in nitrogen atmosphere overnight. After the reaction solution was cooled to room temperature, a saturated aqueous solution of ammonium chloride and water were added thereto, followed by extracting with ethyl acetate. The organic layer was washed with brine and dried over anhydrous magnesium sulfate. The solvent was evaporated, and the residue was purified by silica gel chromatography (hexane/ethyl acetate system), to give 3 mg of the title compound.
$^1$H-NMR (400 MHz, CDCl$_3$); δ(ppm) 1.19-2.29 (m, 16H), 7.06-7.33 (m, 3H), 7.34-7.61 (m, 5H), 7.66-7.69 (m, 1H), 8.08-8.11 (m, 2H).
ESI-Mass; 398 [M$^+$+H]

Example 177

3-[4-(2-Cyanophenyl)piperadin-1-yl]-5-(2-pyridyl)-1-phenyl-1,2-dihydropyridin-2-one 29 mg of 3-bromo-5-(2-pyridyl)-1-phenyl-1,2-dihydropyridin-2-one was dissolved in 200 mg of 1-(2-cyanophenyl)piperazine, followed by heating at 130° C. for 72 hours. After the reaction solution was cooled to room temperature, water was added thereto, followed by extracting with ethyl acetate.

The organic layer was washed with brine and dried over anhydrous magnesium sulfate. The solvent was evaporated, and the residue was purified by silica gel chromatography (hexane/ethyl acetate system), to give 8 mg of the title compound.

$^1$H-NMR (400 MHz, CDCl$_3$); δ(ppm) 3.20-3.22 (m, 4H), 3.50-3.56 (m, 4H), 7.00-7.13 (m, 3H), 7.32-7.61 (m, 10H), 7.79-7.84 (m, 2H).

ESI-Mass; 434 [M$^+$+H]

Example 178

3-(1-Adamantyl)-5-(2-pyridyl)-1-phenyl-1,2-dihydropyridin-2-one 40 mg of 3-bromo-5-(2-pyridyl)-1-phenyl-1,2-dihydropyridin-2-one was dissolved in 10 ml of tetrahydrofuran. To the mixture were added 5 mg of [1,1-bis(diphenylphosphino) ferrocene]dichloropalladium (II) and 1.2 mg of copper (I) iodide. While stirring the mixture at room temperature in nitrogen atmosphere overnight, 0.4 ml of 1-adamantyl zinc bromide (0.5M tetrahydrofuran solution) was added dropwise thereinto. After stirring in nitrogen atmosphere overnight, an aqueous ammonia was added thereto, followed by extracting with ethyl acetate. The organic layer was washed with brine and dried over anhydrous magnesium sulfate. The solvent was evaporated, and the residue was purified by silica gel chromatography (hexane/ethyl acetate system), to give 12 mg of the title compound.

$^1$H-NMR (400 MHz, CDCl$_3$); δ(ppm) 1.44-2.19 (m, 15H), 7.13 (ddd, 1H), 7.31-7.55 (m, 6H), 7.66(td, 1H), 7.93 (d, 1H), 8.05 (d, 1H), 8.55-8.58 (m, 1H).

ESI-Mass; 383 [M$^+$+H]

Example 179

3-(1,1-Dichlorohexyl-1-hydroxymethyl)-5-(2-pyridyl)-1-phenyl-1,2-dihydropyridin-2-one 13 mg of 3-methoxycarbonyl-5-(2-pyridyl)-1-phenyl-1,2-dihydropyridin-2-one was dissolved in 20 ml of tetrahydrofuran, followed by the dropwise addition of 0.05 ml of cyclohexyl magnesiumchloride (2.0M diethyl ether solution) in nitrogen atmosphere, under ice-cooling and stirring. After the mixture was stirred for 3 hours while heating to room temperature, a saturated aqueous solution of ammonium chloride was added thereto, followed by extracting with ethyl acetate. The organic layer was washed with brine and dried over anhydrous magnesium sulfate. The solvent was evaporated, and the residue was purified by silica gel chromatography (hexane/ethyl acetate system), to give 8 mg of the title compound.

$^1$H-NMR (400 MHz, CDCl$_3$); δ(ppm) 0.89-1.84 (m, 20H), 2.72-2.90 (m, 2H), 7.06-7.12 (m, 1H), 7.25-7.49 (m, 8H), 7.59-7.68 (m, 1H), 8.50-8.54 (m, 1H).

ESI-Mass; 443 [M$^+$+H]

Example 180

3-(2-Cyanophenyl)-5-(2-pyridyl)-1-(1-benzyl-1,2,5, 6-tetrahydropyridin-3-yl-1,2-dihydropyridin-2-one 718 mg of 3-bromo-5-(2-pyridyl)-1-(3-pyridyl)-1,2-dihydropyridin-2-one was dissolved in 40 ml of acetonitrile. 383 mg of benzyl bromide was added thereto, followed by stirring at 70° C. overnight. Further, 383 mg of benzyl bromide was added thereto, followed by stirring at 70° C. for 2 nights. After cooling to room temperature, the mixture was evaporated. The residue was dissolved in 30 ml of methanol, followed by cooling to 0° C. under stirring. 265 mg of sodium borohydride was added thereto, followed by stirring overnight under heating from 0° C. to room temperature. Water was added thereto, the solvent was evaporated, and then the residue was extracted with ethyl acetate. The organic layer was washed with brine and dried over anhydrous magnesium sulfate. The solvent was evaporated, and the residue was purified by silica gel chromatography (hexane/ethyl acetate system), to give 550 mg of 3-bromo-5-(2-pyridyl)-1-(1-benzyl-1,2,5,6-tetrahydropyridin-3-yl)-1,2-dihydropyridin-2-one. 270 mg of the product was dissolved in 20 ml of dimethylformamide. 179 mg of 2-(2-cyanophenyl)-1,3,2-dioxaborinate, 313 mg of cesium carbonate and 15 mg of tetrakistriphenylphosphine palladium were added thereto, followed by stirring at 120° C. for 1 hour. After cooling to room temperature, water was added thereto, followed by extracting with ethyl acetate. The organic layer was washed with brine and dried over magnesium sulfate. The solvent was evaporated, and the residue was purified by silica gel chromatography (hexane/ethyl acetate system), to give 174 mg of the title compound.

$^1$H-NMR (400 MHz, CDCl$_3$); δ(ppm) 2.38-2.42 (m, 2H), 2.70(t, 2H), 3.43 (d, 2H), 3.68 (s, 2H), 6.05(t, 1H), 7.21 (dd, 1H), 7.22-7.26 (m, 1H), 7.30(t, 2H), 7.36 (d, 2H), 7.44(t, 1H), 7.54 (d, 1H), 7.63(t, 1H), 7.70-7.77 (m, 3H), 8.19 (d, 1H), 8.23 (d, 1H), 8.60 (dd, 1H).

Example 181

3-(2-Cyanophenyl)-5-phenylaminocarbonyl-1-phenyl-1,2-dihydropyridin-2-one 41 mg of carboxylate obtained by hydrolyzing the ester group of 3-(2-cyanophenyl)-5-(methoxycarbonyl)-1-phenyl-1,2-dihydropyridin-2-one was dissolved in 5 ml of dichloromethane. Under ice-cooling, a solution of 25 mg of oxalyl chloride in dichloromethane was added dropwise thereinto and a catalytic amount of dimethylformamide was added thereto, followed by stirring at room temperature in nitrogen atmosphere for 1 hour. The reaction solution was evaporated, and the residue was dissolved in dichloromethane. The solution was added dropwise into a solution of 13 mg of aniline and 0.03 ml of triethylamine in dichloromethane under ice-cooling. After heating to room temperature, it was stirred in nitrogen atmosphere for 3 hours. Under ice-cooling, the mixture was poured into a saturated aqueous solution of sodium hydrogen carbonate, followed by extracting with ethyl acetate. The organic layer was washed with brine, and then dried over anhydrous magnesium sulfate. The solvent was evaporated, and the residue was purified by silica gel chromatography (hexane/ethyl acetate system), to give 11 mg of the title compound as white crystals.

$^1$H-NMR (400 MHz, CDCl$_3$); δ(ppm) 7.15(tt, 1H), 7.33-7.39 (m, 2H), 7.55-7.42 (m, 6H), 7.56-7.60 (m, 2H), 7.65(td, 1H), 7.73-7.79 (m, 2H), 7.85(brs, 1H), 8.06 (d, 1H), 8.25 (d, 1H).

Example 182

3-(2-Cyanophenyl)-5-(1-phenylbenzimidazol-2-yl)-1-phenyl-1,2-dihydropyridin-2-one 24 mg of carboxylate obtained by hydrolyzing the ester group of 3-(2-cyanophenyl)-5-(methoxycarbonyl)-1-phenyl-1,2-dihydropyridin-2-one was dissolved in 20 ml of dichloromethane. Under ice-cooling, a solution of 16 mg of oxalyl chloride in dichloromethan was added dropwise thereinto. A catalytic amount of dimethylformamide was added thereto, followed by stirring at room temperature in nitrogen atmosphere for 1 hour. The reaction solution was evaporated, and the residue was dissolved in dichloromethane. The solution was added dropwise into a solution of 21 mg of N-phenyl-1,2-phenylenediamine in dichloromethane, under ice-cooling. The mixture was heated to room temperature, followed by stirring in nitrogen atmosphere overnight. Dichloromethane was evaporated, 10 ml of acetic acid was added, and the mixture was stirred at 100° C. for 5 hours. After cooling to room temperature, acetic acid was evaporated. Under ice-cooling, the residue was poured into a saturated aqueous solution of sodium hydrogen carbonate, followed by extracting with ethyl acetate. The organic layer was washed with brine and dried over anhydrous magnesium sulfate. The solvent was evaporated, and the residue was purified by silica gel chromatography (hexane/ethyl acetate system), to give 18 mg of the title compound as white crystals.

$^1$H-NMR (400 MHz, CDCl$_3$); δ(ppm) 7.19-7.30 (m, 4H), 7.33-7.37 (m, 1H), 7.39-7.43 (m, 4H), 7.44-7.45 (m, 1H), 7.46-7.47 (m, 1H), 7.55-7.61 (m, 3H), 7.61-7.66 (m, 2H), 7.68 (d, 1H), 7.71 (dd, 1H), 7.81-7.84 (m, 1H), 7.87 (d, 1H).

ESI-Mass; 465 [M$^+$+H]

Example 183

3-(2-Chlorophenyl)-5-(benzothiazol-2-yl)-1-phenyl-1,2-dihydropyridin-2-one 19 mg of carboxylate obtained by hydrolyzing the ester group of 3-(2-chlorophenyl)-5-(methoxycarbonyl)-1-phenyl-1,2-dihydropyridin-2-one (synthesized from 3-bromo-5-(methoxycarbonyl)-1-phenyl-1,2-dihydropyridin-2-one and 2-chlorophenylboronic acid in accordance with the method for Referential Example 3) was dissolved in 20 ml of dichloromethane. Under ice-cooling, a solution of 11 mg of oxalyl chloride in dichloromethane was added dropwise thereinto and a catalytic amount of dimethylformamide was added thereto, followed by stirring at room temperature in nitrogen atmosphere for 1 hour. The reaction solution was evaporated, and the residue was dissolved in dichloromethane. The solution was added dropwise into a solution of 22 mg of 2-aminobenzothiol in dichloromethane under ice-cooling. After heating to room temperature, dichloromethane was evaporated. To the residue was added 1 ml of polyphosphoric acid, followed by stirring at 180° C. overnight. After cooling to room temperature, the reaction mixture was neutralized with 1N aqueous solution of sodium hydroxide and saturated aqueous solution of sodium hydrogen carbonate under ice-cooling and extracted with ethyl acetate. The organic layer was washed with brine and dried over anhydrous magnesium sulfate. The solvent was evaporated, and the residue was purified by silica gel chromatography (hexane/ethyl acetate system), to give 4 mg of the title compound as white crystals.

$^1$H-NMR (400 MHz, CDCl$_3$); δ(ppm) 7.32-7.35 (m, 2H), 7.37-7.41 (m, 1H), 7.46-7.51 (m, 4H), 7.51-7.55 (m, 4H), 7.87-7.89 (m, 1H), 8.00 (d, 1H), 8.14 (d, 1H), 8.42 (d, 1H).

ESI-Mass; 415 [M$^+$+H]

Example 184

3-(2-Chlorophenyl)-5-(benzoxazol-2-yl)-1-phenyl-1,2-dihydropyridin-2-one 19 mg of carboxylate obtained by hydrolyzing the ester group of 3-(2-chlorophenyl)-5-(methoxycarbonyl)-1-phenyl-1,2-dihydropyridin-2-one (synthesized from 3-bromo-5-(methoxycarbonyl)-1-phenyl-1,2-dihydropyridin-2-one and 2-chlorophenylboronic acid in accordance with the method of Referential Example 3) was dissolved in 20 ml of dichloromethane. Under ice-cooling, a solution of 11 mg of oxalyl chloride in dichloromethane was added dropwise thereinto and a catalytic amount of dimethylformamide was added thereto, followed by stirring at room temperature in nitrogen atmosphere for 1 hour. The reaction solution was evaporated, and the residue was dissolved in dichloromethane. The solution was added dropwise into a solution of 19 mg of 2-aminophenol in dichloromethane under ice-cooling. After heating to room temperature, dichloromethane was evaporated. To the residue was added 1 ml of polyphosphoric acid, followed by stirring at 180° C. overnight. After cooling to room temperature, the reaction mixture was neutralized with 1N aqueous solution of sodium hydroxide and saturated aqueous solution of sodium hydrogen carbonate under ice-cooling. The mixture was extracted with ethyl acetate, and the resulting organic layer was washed with brine and dried over anhydrous magnesium sulfate. The solvent was evaporated, and the residue was purified by silica gel chromatography (hexane/ethyl acetate system), to give 3 mg of the title compound as white crystals.

$^1$H-NMR (400 MHz, CDCl$_3$); δ(ppm) 7.31-7.38 (m, 4H), 7.45-7.57 (m, 8H), 7.69-7.71 (m, 1H), 8.29 (d, 1H), 8.49 (d, 1H).

ESI-Mass; 399 [M$^+$+H]

Example 185

3-(2-Chlorophenyl)-5-phenoxymethyl-1-phenyl-1,2-dihydropyridin-2-one 24 mg of 3-(2-Chlorophenyl)-5-hydroxymethyl-1-phenyl-1,2-dihydropyridin-2-one was dissolved in 10 ml of tetrahydrofuran. 9.4 mg of phenol, 33 mg of triphenylphosphine polymer (3 mmol/g resin) and 17 mg of 1,1'-azobis(N,N-dimethylformamide) were added thereto, followed by stirring at 60° C. overnight. Further, 50 mg of triphenylphosphine polymer (3 mmol/g resin) and 30 mg of 1,1'-azobis(N,N-dimethylformamide) were added, followed by stirring at 60° C. overnight. After cooling to room temperature, ethyl acetate was added thereto and the triphenylphosphine polymer was removed by filtration through Celite. The filtrate was washed with water and 1N aqueous solution of sodium hydroxide. The organic layer was washed with brine and dried over anhydrous magnesium sulfate. The solvent was evaporated, and the residue was purified by silica gel chromatography (hexane/ethyl acetate system), to give 12 mg of the title compound.

$^1$H-NMR (400 MHz, CDCl$_3$); δ(ppm) 4.87 (s, 2H), 6.97 (dd, 2H), 7.01 (dd, 1H), 7.26-7.34 (m, 4H), 7.40-7.51 (m, 7H), 7.54-7.56 (m, 1H), 7.60 (d, 1H).

ESI-Mass; 388 [M$^+$+H]

Example 186

3-(2-Cyanophenyl)-5-(1-methyl-1,2,3,6-tetrahydropyridin-2-yl)-1-phenyl-1,2-dihydropyridin-2-one 99 mg of 3-bromo-5-(2-pyridyl)-1-phenyl-1,2-dihydropyridin-2-one was dissolved in 10 ml of acetonitrile. 2 ml of methyl benzenesulfonate was added thereto, followed by stirring at 100° C. for 2 nights. After cooling to room temperature, the solvent was evaporated. The residue was dissolved in 10 ml of methanol, followed by cooled to 0° C. under stirring.

Sodium borohydride was added 5 times at intervals of 5 hours, 1 g for each time, followed by further stirring at 0° C. overnight. Then the solvent was evaporated and a saturated aqueous solution of ammonium chloride was added to the residue, followed by extracting with ethyl acetate. The organic layer was washed with brine and dried over anhydrous magnesium sulfate. The solvent was evaporated, and the residue was purified by silica gel chromatography (hexane/ethyl acetate system), to give 107 mg of 3-bromo-5-(1-methyl-1,2,3,6-tetrahydropyridin-2-yl)-1-phenyl-1,2-dihydropyridin-2-one. The product was dissolved in 10 ml of dimethylformamide. 81 mg of 2-(2-cyanophenyl)-1,3,2-dioxaborinate, 142 mg of cesium carbonate and 7 mg of tetrakistriphenylphosphine palladium were added thereto, followed by stirring at 140° C. for 2 hours. After cooling to room temperature, water was added thereto, followed by extracting with ethyl acetate. The organic layer was washed with brine and dried over anhydrous magnesium sulfate. The solvent was evaporated, and the residue was purified by silica gel chromatography (hexane/ethyl acetate system), to give 41 mg of the title compound.

$^1$H-NMR (400 MHz, CDCl$_3$); δ(ppm) 2.26 (s, 3H), 2.30-2.50 (m, 1H), 2.90-2.98 (m, 1H), 3.15 (dd, 1H), 3.31-3.40 (m, 1H), 3.85(t, 1H), 5.72-5.78 (m, 1H), 5.79-5.85 (m, 1H), 7.40 (d, 1H), 7.40-7.57 (m, 5H), 7.60(td, 1H), 7.64-7.70 (m, 1H), 7.72-7.73 (m, 1H), 7.74-7.75 (m, 1H), 7.76 (d, 1H).

Example 187

3-(2-Pyridylethenyl)-5-(2-pyridyl)-1-phenyl-1,2-dihydropyridin-2-one 23 mg of 3-bromo-5-(2-pyridyl)-1-phenyl-1,2-dihydropyridin-2-one was dissolved in 20 ml of acetonitrile. To the mixture were added 0.2 mg of palladium acetate, 4.3 mg of tri-o-tolylphosphine and 0.04 ml of triethylamine, followed by stirring at 110° C. in nitrogen atmosphere overnight. To the mixture was added 9.2 mg of 2-vinylpyridine, followed by stirring at 110° C. in nitrogen atmosphere for 5 hours. After cooling to room temperature, the reaction mixture was poured into water, followed by extracting with ethyl acetate. The organic layer was washed with brine and dried over anhydrous magnesium sulfate. The solvent was evaporated, and the residue was purified by silica gel chromatography (hexane/ethyl acetate system), to give 2 mg of the title compound.

$^1$H-NMR (400 MHz, CDCl$_3$); δ(ppm) 7.12-7.16 (m, 1H), 7.18-7.23 (m, 1H), 7.36 (d, 1H), 7.44-7.51 (m, 3H), 7.51-7.55 (m, 2H), 7.57-7.60 (m, 1H), 7.64 (dt, 1H), 7.70-7.79 (m, 1H), 7.78-7.82 (m, 1H), 8.03-8.07 (m, 1H), 8.24 (d, 1H), 8.28 (d, 1H), 8.57-8.63 (m, 2H).

ESI-Mass; 352 [M$^+$+H]

Example 188

3-(4-Chlorophenylthio)-5-(2-pyridyl)-1-phenyl-1,2-dihydropyridin-2-one 25 mg of 3-bromo-5-(2-pyridyl)-1-phenyl-1,2-dihydropyridin-2-one was dissolved in 20 ml of dimethylformamide. To the mixture were added 17 mg of 4-chlorothiophenol, 3 mg of sodium hydroxide and 2 mg of copper iodide, followed by stirring at 150° C. in nitrogen atmosphere overnight. After cooling to room temperature, the reaction mixture was poured into water. An aqueous ammonia was added thereto, followed by extracting with ethyl acetate. The organic layer was washed with brine and dried over anhydrous magnesium sulfate. The solvent was evaporated, and the residue was purified by silica gel chromatography (hexane/ethyl acetate system), to give 8 mg of the title compound.

$^1$H-NMR (400 MHz, CDCl$_3$); δ(ppm) 7.17 (ddd, 1H), 7.30 (d, 1H), 7.39-7.56 (m, 9H), 7.61 (d, 1H), 7.67(td, 1H), 8.08 (d, 1H), 8.52-8.54 (m, 1H).

ESI-Mass; 391 [M$^+$+H]

Example 189

3-(2-Chlorophenyl)-5-cyclohexyl-1-phenyl-1,2-dihydropyridin-2-one 30 mg of 5-bromo-3-(2-chlorophenyl)-1-phenyl-1,2-dihydropyridin-2-one synthesized from 5-bromo-1-phenyl-3-iodo-1,2-dihydropyridin-2-one and 2-chlorophenyl boronic acid in accordance with the method of Referential Example 3 was dissolved in 20 ml of tetrahydrofuran, followed by adding 1 mg of [1,3-bis(diphenylphosphino)propane] nickel (II) chloride. Under stirring in nitrogen atmosphere, 0.1 ml of cyclohexyl magnesium chloride (2.0M ether solution) was added dropwise thereinto. After stirring at room temperature in nitrogen atmosphere overnight, the mixture was heated under reflux for 1 hour. After cooling to room temperature, a saturated aqueous solution of ammonium chloride was added thereto, followed by extracting with ethyl acetate. The organic layer was washed with brine and dried over anhydrous magnesium sulfate. The solvent was evaporated, and the residue was purified by silica gel chromatography (chloroform/methanol system), to give 6 mg of the title compound.

$^1$H-NMR (400 MHz, CDCl$_3$); δ(ppm) 1.15-1.47 (m, 5H), 1.53-1.93 (m, 5H), 2.35 (m, 1H), 6.99-7.34 (m, 3H), 7.36-7.60 (m, 8H).

ESI-Mass; 364 [M$^+$+H]

Example 190

3-(1H-Benzimidazol-2-yl)-5-(2-pyridyl)-1-phenyl-1,2-dihydropyridin-2-one 25 mg of carboxylate obtained by de-protecting the ester group of 3-methoxycarbonyl-5-(2-pyridyl)-1-phenyl-1,2-dihydropyridin-2-one in a convention manner was dissolved in 20 ml of dichloromethane. Under ice-cooling, a solution of 16 mg of oxalyl chloride in dichloromethan was added dropwise thereinto and a catalytic amount of dimethylformamide was added thereto, followed by stirring at room temperature in nitrogen atmosphere for 1 hour. The reaction solution was evaporated, and to the residue was added dichloromethane. The solution was added dropwise into a solution of 17 mg of o-phenylenediamine in dichloromethane under ice-cooling. After heating to room temperature, the mixture was stirred in nitrogen atmosphere overnight. Dichloromethane was evaporated, followed by adding methanol and heating under reflux for 5 hours. After cooling to room temperature, the reaction mixture was poured into an ice-cooled saturated aqueous solution of sodium hydrogen carbonate, followed by extracting with ethyl acetate. The organic layer was washed with brine and dried over anhydrous magnesium sulfate. The solvent was evaporated, and the residue was refined by silica gel chromatography (hexane/ethyl acetate system), to give 1.3 mg of the title compound as white crystals.

$^1$H-NMR (400 MHz, CDCl$_3$); δ(ppm) 7.10-7.94 (m, 13H), 8.57 (d, 1H), 8.58-8.62 (m, 1H), 9.43 (d, 1H).

ESI-Mass; 365 [M$^+$+H]

Example 191

3-(2-Pyridon-1-yl)-5-(2-pyridyl)-1-phenyl-1,2-dihydropyridin-2-one 40 mg of 3-bromo-5-(2-pyridyl)-1-phenyl-1,2-dihydropyridin-2-one and 23 mg of 2-hydroxypyridine were dissolved in 10 ml of dimethylformamide. 34 mg of potassium carbonate and 3 mg of copper iodide were added thereto, followed by stirring at 140° C. overnight. After cooling the reaction mixture to room temperature, an aqueous ammonia was added thereto, followed by extracting with ethyl acetate. The organic layer was washed with brine and dried over magnesium sulfate. The solvent was evaporated, and the residue was purified by silica gel chromatography (NH silica) (chloroform/methanol system), to give 10 mg of the title compound.

$^1$H-NMR (400 MHz, CDCl$_3$); δ(ppm) 6.24(td, 1H), 6.69 (dd, 1H), 7.22 (dd, 1H), 7.37-7.42 (m, 2H), 7.45-7.57 (m, 6H), 7.73(td, 1H), 8.33 (d, 1H), 8.36 (d, 1H), 8.58-8.60 (m, 1H).

Example 192

3-Cyclohexyl-5-(2-pyridyl)-1-phenyl-1,2-dihydropyridin-2-one 34 mg of 3-bromo-5-(2-pyridyl)-1-phenyl-1,2-dihydropyridin-2-one was dissolved in 10 ml of tetrahydrofuran, followed by adding 1 mg of [1,3-bis(diphenylphosphino)propane] nickel (II) chloride. Under stirring in nitrogen atmosphere, 0.1 ml of cyclohexyl magnesium chloride (2.0M ether solution) was added dropwise thereinto. The mixture was stirred at room temperature in nitrogen atmosphere for 1 hour, followed by heating under reflux for 72 hours. After cooling to room temperature, water was added thereto, followed by extracting with ethyl acetate. The organic layer was washed with brine, and then dried over anhydrous magnesium sulfate. The solvent was evaporated, and the residue was purified by silica gel chromatography (chloroform/methanol system), to give 5 mg of the title compound.

$^1$H-NMR (400 MHz, CDCl$_3$); δ(ppm) 1.22-1.52 (m, 5H), 1.73-1.80 (m, 1H), 1.81-1.89 (m, 2H), 1.97-2.04 (m, 2H), 2.90-2.99 (m, 1H), 7.18 (ddd, 1H), 7.53-7.55 (m, 6H), 7.71 (td, 1H), 7.78 (dd, 1H), 8.04 (d, 1H), 8.59 (ddd, 1H).

Example 193

3-[2-(5-Methyl-1,2,4-oxadiazol-3-yl)phenyl]-1-phenyl-5-(2-pyridyl)-1,2-dihydropyridin-2-one 53 mg of 3-(2-cyanophenyl)-5-(2-pyridyl)-1-phenyl-1,2-dihydropyridin-2-one was dissolved in 10 ml of ethanol containing 20% of water. 19 mg of hydroxylamine hydrochloride and 17 mg of sodium acetate were added thereto, followed by heating under reflux for 24 hours. Further, 19 mg of hydroxylamine hydrochloride and 17 mg of sodium acetate were added thereto, followed by heating under reflux for 36 hours. After cooling to room temperature, the mixture was evaporated, and the resulting crystals were washed with water, dried, and 50 mg of amidoxime compound was collected by filtration. 20 mg of the product was dissolved in 4 ml of toluene. 16 mg of acetic anhydride was added thereto, followed by heating under reflux for 96 hours. After cooling to room temperature, the mixture was neutralized with potassium carbonate under ice-cooling. After extracting with ethyl acetate, the extract was successively washed with water and brine, and dried over anhydrous magnesium sulfate. The solvent was evaporated, and the residue was purified by silica gel chromatography (hexane/ethyl acetate system), to give 4 mg of the title compound.

$^1$H-NMR (400 MHz, CDCl$_3$); δ(ppm) 2.56 (s, 3H), 7.18 (ddd, 1H), 7.38-7.59 (m, 8H), 7.72 (ddd, 1H), 7.71 (ddd, 1H), 8.08 (ddd, 1H), 8.11 (d, 1H), 8.27 (d, 1H), 8.58 (ddd, 1H).

ESI-Mass; 410 [M$^+$+H]

The following compounds were synthesized by the methods similar to, or in accordance with, the method for Example 1.

Example 194

3-(2-Cyanophenyl)-5-(1-methylpyrazol-4-yl)-1-phenyl-1,2-dihydropyridin-2-one $^1$H-NMR (400 MHz, CDCl$_3$); δ(ppm) 4.01 (s, 3H), 7.46-7.56 (m, 8H), 7.62-7.68 (m, 3H), 7.78-7.81 (m, 2H).

Example 195

3-(2-Cyanophenyl)-5-(6-methylpyridin-2-yl)-1-phenyl-1,2-dihydropyridin-2-one $^1$H-NMR (400 MHz, CDCl$_3$); δ(ppm) 2.56 (s, 3H), 7.07 (d, 1H), 7.40-7.66 (m, 9H), 7.76-7.80 (m, 2H), 8.28 (d, 1H), 8.30 (d, 1H).

Example 196

3-(2-Cyanophenyl)-5-(5-methylpyridin-2-yl)-1-phenyl-1,2-dihydropyridin-2-one $^1$H-NMR (400 MHz, CDCl$_3$); δ(ppm) 2.36 (s, 3H), 7.42-7.56 (m, 8H), 7.63 (dt, 1H), 7.76-7.80 (m, 2H), 8.26 (d, 1H), 8.28 (d, 1H), 8.41-8.42 (m, 1H).

Example 197

3-(2-Cyanophenyl)-5-(4-methylpyridin-2-yl)-1-phenyl-1,2-dihydropyridin-2-one $^1$H-NMR (400 MHz, CDCl$_3$); δ(ppm) 2.36 (s, 3H), 7.43-7.57 (m, 8H), 7.63 (dt, 1H), 7.77-7.80 (m, 2H), 8.27 (d, 1H), 8.28 (d, 1H), 8.41-8.42 (m, 1H).

Example 198

3-(2-Cyanophenyl)-5-(3-hydroxypyridin-2-yl)-1-phenyl-1,2-dihydropyridin-2-one $^1$H-NMR (400 MHz, CDCl$_3$); δ(ppm) 7.20 (dd, 1H), 7.31 (dd, 1H), 7.51-7.60 (m, 6H), 7.68 (dd, 1H), 7.75 (dt, 1H), 7.83 (dd, 1H), 8.11 (dd, 1H), 8.51 (d, 1H), 8.55 (d, 1H).

Example 199

3-(2-Cyanophenyl)-1-phenyl-5-(2-pyrazinyl)-1,2-dihydropyridin-2-one $^1$H-NMR (400 MHz, CDCl$_3$); δ(ppm) 7.46-7.57 (m, 6H), 7.66 (dt, 1H), 7.75-7.81 (m, 2H), 8.33 (d, 1H), 8.35 (d, 1H), 8.50 (d, 1H), 8.55 (dd, 1H), 8.93 (d, 1H).

Example 200

3-(2-Cyanophenyl)-5-(2-methoxypyridin-5-yl)-phenyl-1,2-dihydropyridin-2-one $^1$H-NMR (400 MHz, CDCl$_3$); δ(ppm) 3.69 (s, 3H), 6.67 (d, 1H), 7.18 (d, 1H), 7.44-7.66 (m, 8H), 7.78-7.81 (m, 2H), 8.27 (d, 1H), 8.34 (d, 1H).

Example 201

3-(2-Cyanophenyl)-1-phenyl-5-(2-thiazolyl)-1,2-dihydropyridin-2-one $^1$H-NMR (400 MHz, CDCl$_3$); δ(ppm) 7.31 (d, 1H), 7.45-7.56 (m, 6H), 7.65 (dt, 1H), 7.72 (dd, 1H), 7.77-7.80 (m, 2H), 8.18 (d, 1H), 8.25 (d, 1H).

Example 202

3-(2-Cyanophenyl)-1-phenyl-5-(4-pyrimidinyl)-1,2-dihydropyridin-2-one $^1$H-NMR (400 MHz, CDCl$_3$); δ(ppm) 7.46-7.59 (m, 7H), 7.66 (dt, 1H), 7.76-7.81 (m, 2H), 8.31 (d, 1H), 8.56 (d, 1H), 8.74 (d, 1H), 9.16 (d, 1H).

Example 203

3-(2-Cyanophenyl)-1-phenyl-5-(5-pyrimidinyl)-1,2-dihydropyridin-2-one $^1$H-NMR (400 MHz, CDCl$_3$); δ(ppm) 7.47-7.58 (m, 6H), 7.66 (dt, 1H), 7.75 (d, 1H), 7.78-7.81 (m, 2H), 7.92 (d, 1H), 8.92 (s, 2H), 9.22 (s, 1H).

Example 204

3-(2-Cyanophenyl)-1-phenyl-5-(3-pyridazinyl)-1,2-dihydropyridin-2-one $^1$H-NMR (400 MHz, CDCl$_3$); δ(ppm) 7.46-7.56 (m, 7H), 7.66 (dt, 1H), 7.77-7.83 (m, 3H), 8.32 (d, 1H), 8.54 (d, 1H), 9.15 (dd, 1H).

Example 205

3-(2-Cyanophenyl)-1-phenyl-5-(4-pyridazinyl)-1,2-dihydropyridin-2-one $^1$H-NMR (400 MHz, CDCl$_3$); δ(ppm) 7.48-7.61 (m, 7H), 7.67 (dt, 1H), 7.79-7.83 (m, 2H), 7.92 (d, 1H), 8.00 (d, 1H), 9.23 (dd, 1H), 9.40 (dd, 1H).

Example 206

3-(2-Cyanophenyl)-5-(6-methoxypyridin-2-yl)-1-phenyl-1,2-dihydropyridin-2-one $^1$H-NMR (400 MHz, CDCl$_3$); δ(ppm) 3.96 (s, 3H), 6.67 (dd, 1H), 7.18 (dd, 1H), 7.44-7.66 (m, 8H), 7.77-7.81 (m, 2H), 8.27 (d, 1H), 8.33 (d, 1H).

Example 207

3-(2-Cyanophenyl)-1-phenyl-5-(thiazol-4-yl)-1,2-dihydropyridin-2-one $^1$H-NMR (400 MHz, CDCl$_3$); δ(ppm) 7.46-7.57 (m, 6H), 7.66 (ddd, 1H), 7.72-7.81 (m, 3H), 7.87 (d, 1H), 7.97 (s, 1H), 8.76 (s, 1H).

Example 208

3-(2-Cyanophenyl)-5-(3-oxo-1-cyclohexen-1-yl)-1-phenyl-1,2-dihydropyridin-2-one $^1$H-NMR (400 MHz, CDCl$_3$); δ(ppm) 2.12-2.19 (m, 2H), 2.46-2.50 (m, 2H), 2.65-2.69 (m, 2H), 6.36 (s, 1H), 7.45-7.57 (m, 6H), 7.62-7.70 (m, 2H), 7.76-7.79 (m, 2H), 7.88 (d, 1H).

Example 209

3-(2-Cyanophenyl)-5-(5,6-dihydro-1,4-dioxin-2-yl)-1-phenyl-1,2-dihydropyridin-2-one $^1$H-NMR (400 MHz, CDCl$_3$); δ(ppm) 4.12-4.14 (m, 2H), 4.21-4.23 (m, 2H), 7.42-7.78 (m, 12H).

Example 210

3-(2-Cyanophenyl)-5-(1-naphthyl)-1-(3-pyridyl)-1,2-dihydropyridin-2-one $^1$H-NMR (400 MHz, CDCl$_3$); δ(ppm) 7.41-7.67 (m, 9H), 7.55-7.83 (m, 2H), 7.88-7.94 (m, 2H), 8.02 (ddd, 1H), 8.11 (d, 1H), 8.70 (d, 1H), 8.83 (d, 1H).

ESI-Mass; 400 [M$^+$+H]

Example 211

3-(2-Cyanophenyl)-5-(2-naphthyl)-1-(3-pyridyl)-1,2-dihydropyridin-2-one $^1$H-NMR (400 MHz, CDCl$_3$); δ(ppm) 7.44-7.58 (m, 4H), 7.61-7.70 (m, 3H), 7.78-7.82 (m, 2H), 7.83-7.90 (m, 2H), 7.92 (d, 1H), 7.95-7.96 (m, 1H), 8.00 (ddd, 1H), 8.12 (d, 1H), 8.72 (dd, 1H), 8.83 (d, 1H).

ESI-Mass; 400 [M$^+$+H]

Example 212

3-(2-Cyanophenyl)-5-(8-quinolinyl)-1-(3-pyridyl)-1,2-dihydropyridin-2-one $^1$H-NMR (400 MHz, CDCl$_3$); δ(ppm) 7.43-7.50 (m, 3H), 7.60-7.69 (m, 2H), 7.75-7.79 (m, 1H), 7.81-7.87 (m, 2H), 8.03-8.10 (m, 2H), 8.18 (d, 1H), 8.23 (dd, 1H), 8.68-8.72 (m, 2H), 8.87 (d, 1H), 8.98 (dd, 1H).

ESI-Mass; 401 [M$^+$+H]

Example 213

3-(2-Cyanophenyl)-5-(3-pyridyl)-1-(3-pyridyl)-1,2-dihydropyridin-2-one $^1$H-NMR (400 MHz, DMSO-d$_6$); δ(ppm) 7.45-7.51 (m, 1H), 7.59 (ddd, 1H), 7.64 (dd, 1H), 7.75-7.82 (m, 2H), 7.94 (d, 1H), 8.10 (ddd, 1H), 8.15-8.20 (m, 1H), 8.28 (d, 1H), 8.39-8.41 (m, 1H), 8.53-8.56 (m, 1H), 8.69 (dd, 1H), 8.84 (d, 1H), 8.98-8.90 (m, 1H).

ESI-Mass; 351 [M$^+$+H]

Example 214

5-[(1-Benzenesulfonyl)indol-2-yl]-3-(2-cyanophenyl)-1-(3-pyridyl)-1,2-dihydropyridin-2-one $^1$H-NMR (400 MHz, CDCl$_3$); δ(ppm) 6.70 (d, 1H), 7.23-7.43 (m, 4H), 7.45-7.56 (m, 5H), 7.65 (d, 1H), 7.68(td, 2H), 7.78(td, 2H), 7.83 (d, 1H), 8.02 (ddd, 1H), 8.30 (dd, 1H), 8.72 (dd, 1H), 8.79 (d, 1H).
ESI-Mass; 529 [M$^+$+H]

The following compounds were synthesized by the methods similar to, or in accordance with, the method for Example 2.

Example 215

1-(4-Aminophenyl)-3-(2-cyanophenyl)-5-(2-pyridyl)-1,2-dihydropyridin-2-one $^1$H-NMR (400 MHz, CDCl$_3$); δ(ppm) 3.86(brs, 2H), 6.76 (td, 2H), 7.20 (ddd, 1H), 7.28(td, 2H), 7.44 (dt, 1H), 7.60(td, 1H), 7.64 (dd, 1H), 7.71-7.80 (m, 3H), 8.28 (d, 1H), 8.29 (d, 1H), 8.60 (ddd, 1H).

Example 216

5-(3-Aminopyridin-2-yl)-3-(2-cyanophenyl)-1-phenyl-1,2-dihydropyridin-2-one $^1$H-NMR (400 MHz, CDCl$_3$); δ(ppm) 4.05(br s, 2H), 7.07-7.08 (m, 2H), 7.42-7.47 (m, 2H), 7.51-7.53 (m, 4H), 7.62 (ddd, 1H), 7.75-7.78 (m, 1H), 7.79-7.82 (m, 1H), 7.99 (dd, 1H), 8.06 (dd, 1H), 8.15 (dd, 1H).

Example 217

5-(5-Aminopyridin-2-yl)-3-(2-cyanophenyl)-1-phenyl-1,2-dihydropyridin-2-one $^1$H-NMR (400 MHz, CDCl$_3$); δ(ppm) 3.77(brs, 2H), 7.04 (dd, 1H), 7.39-7.52 (m, 7H), 7.60-7.64 (m, 1H), 7.76-7.80 (m, 2H), 8.08 (dd, 1H), 8.13 (d, 1H), 8.22 (d, 1H).

Example 218

1-(3-Aminophenyl)-3-(2-cyanophenyl)-5-(2-pyrimidinyl)-1,2-dihydropyridin-2-one $^1$H-NMR (400 MHz, CDCl$_3$); δ(ppm) 3.85(brs, 2H), 6.76 (ddd, 1H), 6.84(t, 1H), 6.86 (ddd, 1H), 7.14(t, 1H), 7.27-7.31 (m, 1H), 7.45 (dt, 1H), 7.63 (dt, 1H), 7.71-7.78 (m, 2H), 8.69-8.71 (m, 3H), 8.75 (d, 1H).

Example 219

3-(2-Aminophenyl)-1-phenyl-5-(2-pyridyl)-1,2-dihydropyridin-2-one $^1$H-NMR (400 MHz, DMSO-d$_6$); δ(ppm) 7.23-7.37 (m, 3H), 7.40-7.47 (m, 1H), 7.47-7.56 (m, 2H), 7.56-7.66 (m, 5H), 7.88 (ddd, 1H), 8.08 (d, 1H), 8.46 (d, 1H), 8.58 (d, 1H), 8.59-8.64 (m, 1H).

Example 220

3-(3-Aminophenyl)-1-phenyl-5-(2-pyridyl)-1,2-dihydropyridin-2-one $^1$H-NMR (400 MHz, CDCl$_3$); δ(ppm) 3.70(br s, 2H), 6.68-6.72 (m, 1H), 7.13-7.26 (m, 3H), 7.42-7.56 (m, 5H), 7.56-7.60 (m, 1H), 7.64-7.76 (m, 2H), 8.22 (s, 2H), 8.58-8.61 (m, 1H).

Example 221

3-(4-Aminophenyl)-1-phenyl-5-(2-pyridyl)-1,2-dihydropyridin-2-one $^1$H-NMR (400 MHz, CDCl$_3$); δ(ppm) 3.77(br s, 2H), 6.70-6.76 (m, 2H), 7.17-7.21 (m, 1H), 7.42-7.60 (m, 6H), 7.64-7.75 (m, 3H), 8.15 (s, 2H), 8.58-8.61 (m, 1H).

Example 222

3-(2-Cyanophenyl)-5-(2-pyridyl)-1-(3-amino-4-methylphenyl)-1,2-dihydropyridin-2-one $^1$H-NMR (400 MHz, CDCl$_3$); δ(ppm) 2.21 (s, 3H), 3.76 (s, 2H), 6.78-6.83 (m, 2H), 7.17 (d, 1H), 7.20 (ddd, 1H), 7.44(td, 1H), 7.58 (d, 1H), 7.63(td, 1H), 7.73(td, 1H), 7.78(td, 2H), 8.29 (s, 2H), 8.59 (ddd, 1H).
ESI-Mass; 379 [M$^+$+H]

The following compounds were synthesized by the methods similar to, or in accordance with, the method for Example 3.

Example 223

3-Benzenesulfonylamino-1-phenyl-5-(2-pyridyl)-1,2-dihydropyridin-2-one $^1$H-NMR (400 MHz, CDCl$_3$); δ(ppm) 7.22 (ddd, 1H), 7.31-7.33 (m, 2H), 7.44-7.60 (m, 7H), 7.76 (dt, 1H), 7.92-7.95 (m, 2H), 7.97 (d, 1H), 8.21 (d, 1H), 8.56-8.58 (m, 1H).

Example 224

3-(2-Cyanophenyl)-5-benzenesulfonylamino-1-phenyl-1,2-dihydropyridin-2-one $^1$H-NMR (400 MHz, CDCl$_3$); δ(ppm) 7.26-7.27 (m, 1H), 7.30-7.33 (m, 2H), 7.41-7.65 (m, 10H), 7.70-7.73 (m, 1H), 7.83-7.86 (m, 2H).

Example 225

3-(2-Cyanophenyl)-5-(3-methylsulfonylaminopyridin-2-yl)-1-phenyl-1,2-dihydropyridin-2-one $^1$H-NMR (400 MHz, CDCl$_3$); δ(ppm) 3.40 (s, 3H), 7.43-7.48 (m, 4H), 7.50-7.54 (m, 4H), 7.64-7.66 (m, 2H), 7.74 (dd, 1H), 7.95 (d, 1H), 8.20 (d, 1H), 8.77 (dd, 1H).

Example 226

3-(2-Methylsulfonylaminophenyl)-1-phenyl-5-(2-pyridyl)-1,2-dihydropyridin-2-one $^1$H-NMR (400 MHz, CDCl$_3$); δ(ppm) 2.96 (s, 3H), 7.25 (ddd, 1H), 7.30-7.35 (m, 1H), 7.43-7.63 (m, 9H), 7.76 (ddd, 1H), 8.30(br s, 1H), 8.33 (d, 1H), 8.39 (d, 1H), 8.60-8.64 (m, 1H).

Example 227

3-(4-Methylsulfonylaminophenyl)-1-phenyl-5-(2-pyridyl)-1,2-dihydropyridin-2-one

¹H-NMR (400 MHz, CDCl₃); δ(ppm) 3.01 (s, 3H), 6.57(br s, 1H), 7.20-7.28 (m, 3H), 7.45-7.61 (m, 6H), 7.77 (ddd, 1H), 7.79-7.85 (m, 2H), 8.22 (d, 1H), 8.24 (d, 1H), 8.60-8.64 (m, 1H).

Example 228

3-(3-Methylsulfonylaminophenyl)-1-phenyl-5-(2-pyridyl)-1,2-dihydropyridin-2-one

¹H-NMR (400 MHz, CDCl₃); δ(ppm) 2.92 (s, 3H), 6.98(br s, 1H), 7.20-7.32 (m, 2H), 7.36-7.61 (m, 8H), 7.69-7.78 (m, 2H), 8.22 (d, 1H), 8.26 (d, 1H), 8.59-8.63 (m, 1H).

The following compounds were synthesized by the methods similar to, or in accordance with, the method for Example 10.

Example 229

5-(6-Acetylaminopyridin-2-yl)-3-(2-cyanophenyl)-1-phenyl-1,2-dihydropyridin-2-one ¹H-NMR (400 MHz, CDCl₃); δ(ppm) 2.22 (s, 3H), 7.33 (dd, 1H), 7.44-7.80 (m, 10H), 7.85 (d, 1H), 8.08-8.12 (m, 1H), 8.24 (d, 1H), 8.28 (d, 1H).

Example 230

3-(2-Acetylaminophenyl)-1-phenyl-5-(2-pyridyl)-1,2-dihydropyridin-2-one

¹H-NMR (400 MHz, DMSO-d₆); δ(ppm) 1.96 (s, 3H), 7.19-7.26 (m, 1H), 7.30 (ddd, 1H), 7.34-7.40 (m, 1H), 7.40-7.46 (m, 1H), 7.48-7.56 (m, 1H), 7.56-7.64 (m, 4H), 7.72 (d, 1H), 7.83 (ddd, 1H), 8.01 (d, 1H), 8.32 (d, 1H), 8.50 (d, 1H), 8.57-8.61 (m, 1H), 9.16(br s, 1H).

Example 231

3-(2-Diacetylaminophenyl)-1-phenyl-5-(2-pyridyl)-1,2-dihydropyridin-2-one

¹H-NMR (400 MHz, CDCl₃); δ(ppm) 2.28 (s, 6H), 7.18 (ddd, 1H), 7.23-7.27 (m, 1H), 7.42-7.60 (m, 9H), 7.71 (ddd, 1H), 7.95 (d, 1H), 8.35 (d, 1H), 8.54-8.58 (m, 1H).

Example 232

3-(3-Acetylaminophenyl)-1-phenyl-5-(2-pyridyl)-1,2-dihydropyridin-2-one

¹H-NMR (400 MHz, CDCl₃); δ(ppm) 2.11 (s, 3H), 7.19-7.23 (m, 1H), 7.34-7.40 (m, 1H), 7.42-7.56 (m, 6H), 7.60 (d, 1H), 7.64-7.77 (m, 3H), 7.83-7.87 (m, 1H), 8.24 (d, 1H), 8.26 (d, 1H), 8.58-8.62 (m, 1H).

Example 233

3-(4-Acetylaminophenyl)-1-phenyl-5-(2-pyridyl)-1,2-dihydropyridin-2-one

¹H-NMR (400 MHz, CDCl₃); δ(ppm) 2.15 (s, 3H), 7.21 (ddd, 1H), 7.34(br s, 1H), 7.44-7.57 (m, 8H), 7.59 (ddd, 1H), 7.74 (ddd, 1H), 7.80 (d, 1H), 8.21 (s, 2H), 8.59-8.62 (m, 1H).

The following compound was synthesized by the method similar to, or in accordance with, the method for Example 12.

Example 234

3-(4-Dimethylaminophenyl)-1-phenyl-5-(2-pyridyl)-1,2-dihydropyridin-2-one

¹H-NMR (400 MHz, CDCl₃); δ(ppm) 3.00 (s, 6H), 6.75-6.80 (m, 2H), 7.19 (ddd, 1H), 7.41-7.54 (m, 5H), 7.57-7.60 (m, 1H), 7.73 (ddd, 1H), 7.76-7.81 (m, 2H), 8.14-8.17 (m, 2H), 8.58-8.61 (m, 1H).

The following compound was synthesized by the method similar to, or in accordance with, the method for Example 15.

Example 235

5-(6-Aminocarbonylpyridin-2-yl)-3-(2-cyanophenyl)-1-phenyl-1,2-dihydropyridin-2-one ¹H-NMR (400 MHz, CDCl₃); δ(ppm) 7.46-7.60 (m, 6H), 7.64 (dt, 1H), 7.74 (dd, 1H), 7.80-7.83 (m, 1H), 7.91-7.95 (m, 2H), 8.14-8.17 (m, 2H), 8.52 (d, 1H).

The following compound was synthesized by the methods similar to, or in accordance with, the method of Example 16, Route 1.

Example 236

3-(2-Cyanophenyl)-5-(2-cyanopyridin-6-yl)-1-phenyl-1,2-dihydropyridin-2-one

¹H-NMR (400 MHz, CDCl₃); δ(ppm) 7.46-7.57 (m, 6H), 7.60 (dd, 1H), 7.66 (dt, 1H), 7.79-7.83 (m, 3H), 7.89 (dd, 1H), 8.29 (d, 1H), 8.41 (d, 1H).

The following compounds were synthesized by the methods similar to, or in accordance with, the method of Example 18.

Example 237

3-(3-Hydroxyphenyl)-1-phenyl-5-(2-pyridyl)-1,2-dihydropyridin-2-one

¹H-NMR (400 MHz, DMSO-d₆); δ(ppm) 6.74-6.78 (m, 1H), 7.15-7.26 (m, 3H), 7.27-7.32 (m, 1H), 7.47-7.61 (m, 5H), 7.83 (ddd, 1H), 8.02 (d, 1H), 8.41 (s, 2H), 8.57-8.62 (m, 1H), 9.43(br s, 1H).

Example 238

3-(4-Hydroxyphenyl)-1-phenyl-5-(2-pyridyl)-1,2-dihydropyridin-2-one

¹H-NMR (400 MHz, DMSO-d₆); δ(ppm) 6.79-6.84 (m, 2H), 7.28 (ddd, 1H), 7.47-7.59 (m, 5H), 7.61-7.66 (m, 2H), 7.82 (ddd, 1H), 8.00 (d, 1H), 8.33 (d, 1H), 8.35 (d, 1H), 8.57-8.61 (m, 1H), 9.57(br s, 1H).

The following compounds were synthesized by the same methods as in Example 19.

Example 239

3-(2-Cyanophenyl)-1-(3-dimethylaminoethoxyphenyl)-5-(2-pyridyl)-1,2-dihydropyridin-2-one $^1$H-NMR (400 MHz, CDCl$_3$); δ(ppm) 2.34 (s, 6H), 2.74(t, 2H), 4.10(t, 2H), 7.01-7.05 (m, 1H), 7.07-7.11 (m, 2H), 7.21 (ddd, 1H), 7.42 (dd, 1H), 7.45 (ddd, 1H), 7.59-7.66 (m, 2H), 7.72-7.81 (m, 3H), 8.30 (s, 2H), 8.58-8.61 (m, 1H).

Example 240

3-(2-Cyanophenyl)-1-(3-piperidinoethoxyphenyl)-5-(2-pyridyl)-1,2-dihydropyridin-2-one $^1$H-NMR (400 MHz, CDCl$_3$); δ(ppm) 1.39-1.48 (m, 2H), 1.56-1.64 (m, 4H), 2.46-2.56 (m, 4H), 2.78(t, 2H), 4.14(t, 2H), 6.99-7.03 (m, 1H), 7.06-7.11 (m, 2H), 7.21 (ddd, 1H), 7.41 (dd, 1H), 7.45 (ddd, 1H), 7.59-7.66 (m, 2H), 7.72-7.81 (m, 3H), 8.30 (s, 2H), 8.58-8.61 (m, 1H).

Example 241

3-(2-Cyanophenyl)-1-(3-(pyrrolidinoethoxyphenyl)-5-(2-pyridyl)-1,2-dihydropyridin-2-one $^1$H-NMR (400 MHz, CDCl$_3$); δ(ppm) 1.76-1.86 (m, 4H), 2.57-2.70 (m, 4H), 2.92(t, 2H), 4.16(t, 2H), 7.03 (ddd, 1H), 7.06-7.11 (m, 2H), 7.21 (ddd, 1H), 7.41 (dd, 1H), 7.45 (ddd, 1H), 7.59-7.66 (m, 2H), 7.72-7.81 (m, 3H), 8.30 (s, 2H), 8.58-8.61 (m, 1H).

Example 242

3-(2-Cyanophenyl)-1-(3-diisopropylaminoethoxyphenyl)-5-(2-pyridyl)-1,2-dihydropyridin-2-one $^1$H-NMR (400 MHz, CDCl$_3$); δ(ppm) 1.03 (d, 12H), 2.83 (t, 2H), 3.04(heptet, 2H), 3.92(t, 2H), 6.97-7.01 (m, 1H), 7.04 (dd, 1H), 7.07 (ddd, 1H), 7.21 (ddd, 1H), 7.41 (dd, 1H), 7.45 (ddd, 1H), 7.59-7.66 (m, 2H), 7.72-7.82 (m, 3H), 8.29-8.32 (m, 2H), 8.58-8.61 (m, 1H).

Example 243

3-(2-Cyanophenyl)-1-(3-dimethylaminopropoxyphenyl)-5-(2-pyridyl)-1,2-dihydropyridin-2-one $^1$H-NMR (400 MHz, CDCl$_3$); δ(ppm) 1.96(tt, 2H), 2.24 (s, 6H), 2.44(t, 2H), 4.05(t, 2H), 7.00 (ddd, 1H), 7.05-7.09 (m, 2H), 7.21 (ddd, 1H), 7.41 (dd, 1H), 7.45 (ddd, 1H), 7.59-7.66 (m, 2H), 7.72-7.81 (m, 3H), 8.30 (s, 2H), 8.58-8.61 (m, 1H).

Example 244

3-(2-Cyanophenyl)-1-(3-piperidinopropoxyphenyl)-5-(2-pyridyl)-1,2-dihydropyridin-2-one $^1$H-NMR (400 MHz, CDCl$_3$); δ(ppm) 1.37-1.50 (m, 2H), 1.53-1.64 (m, 4H), 1,97(tt, 2H), 2.30-2.45 (m, 4H), 2.47(t, 2H), 4.04(t, 2H), 6.97-7.02 (m, 1H), 7.04-7.09 (m, 2H), 7.21 (ddd, 1H), 7.41 (dd, 1H), 7.45 (ddd, 1H), 7.59-7.66 (m, 2H), 7.70-7.82 (m, 3H), 8.31 (s, 2H), 8.58-8.62 (m, 1H).

Example 245

3-(2-Cyanophenyl)-1-(3-morpholinoethoxyphenyl)-5-(2-pyridyl)-1,2-dihydropyridin-2-one $^1$H-NMR (400 MHz, CDCl$_3$); δ(ppm) 2.48-2.65 (m, 4H), 2.81(t, 2H), 3.68-3.80 (m, 4H), 4.15(t, 2H), 6.99-7.04 (m, 1H), 7.06-7.13 (m, 2H), 7.22 (ddd, 1H), 7.42 (dd, 1H), 7.46 (ddd, 1H), 7.61 (dd, 1H), 7.64 (ddd, 1H), 7.74 (ddd, 1H), 7.78 (dd, 2H), 8.28-8.33 (m, 2H), 8.58-8.62 (m, 1H).

Example 246

3-(2-Cyanophenyl)-1-(3-diethylaminoethoxyphenyl)-5-(2-pyridyl)-1,2-dihydropyrdin-2-one $^1$H-NMR (400 MHz, CDCl$_3$); δ(ppm) 1.07(t, 6H), 2.64(q, 4H), 2.89(t, 2H), 4.08(t, 2H), 7.01 (ddd, 1H), 7.05-7.10 (m, 2H), 7.21 (ddd, 1H), 7.41 (dd, 1H), 7.45 (ddd, 1H), 7.59-7.66 (m, 2H), 7.72-7.81 (m, 3H), 8.31 (s, 2H), 8.58-8.61 (m, 1H).

Example 247

3-(3-Dimethylaminoethoxyphenyl)-1-phenyl-5-(2-pyridyl)-1,2-dihydropyridin-2-one $^1$H-NMR (400 MHz, CDCl$_3$); δ(ppm) 2.34 (s, 6H), 2.74(t, 2H), 4.13(t, 2H), 6.92-6.98 (m, 1H), 7.19-7.24 (m, 1H), 7.33 (dd, 1H), 7.37-7.42 (m, 1H), 7.44-7.56 (m, 6H), 7.57-7.62 (m, 1H), 7.75 (ddd, 1H), 8.25 (s, 2H), 8.59-8.63 (m, 1H).

Example 248

3-(4-Dimethylaminoethoxyphenyl)-1-phenyl-5-(2-pyridyl)-1,2-dihydropyridin-2-one $^1$H-NMR (400 MHz, CDCl$_3$); δ(ppm) 2.35 (s, 6H), 2.76(t, 2H), 4.12(t, 2H), 6.95-7.00 (m, 2H), 7.20 (ddd, 1H), 7.43-7.54 (m, 5H), 7.59 (ddd, 1H), 7.73 (ddd, 1H), 7.76-7.81 (m, 2H), 8.17-8.20 (m, 2H), 8.59-8.62 (m, 1H).

Example 249

3-(2-Cyanophenyl)-1-[3-(4-piperidinobutoxy)phenyl]-5-(2-pyridyl)-1,2-dihydropyridin-2-one $^1$H-NMR (400 MHz, CDCl$_3$); δ(ppm) 1.38-1.46 (m, 2H), 1.54-1.61 (m, 4H), 1.62-1.71 (m, 2H), 1.75-1.83 (m, 2H), 2.30-2.43 (m, 6H), 4.01(t, 2H), 6.97-7.01 (m, 1H), 7.03-7.08 (m, 2H), 7.21 (ddd, 1H), 7.40 (dd, 1H), 7.45 (ddd, 1H), 7.59-7.66 (m, 2H), 7.72-7.82 (m, 3H), 8.30 (s, 2H), 8.58-8.61 (m, 1H).

The following compounds were synthesized by the methods similar to, or in accordance with, the method for Example 29.

Example 250

3-(2-Cyanophenyl)-1-(3-pyrrolidinomethylphenyl)-5-(2-pyridyl)-1,2-dihydropyridin-2-one $^1$H-NMR (400 MHz, CDCl$_3$); δ(ppm) 1.74-1.84 (m, 4H), 2.48-2.58 (m, 4H), 3.69 (s, 2H), 7.14-7.25 (m, 2H), 7.38-7.51 (m, 4H), 7.61 (d, 1H), 7.63 (ddd, 1H), 7.72-7.82 (m, 3H), 8.30 (d, 1H), 8.32 (d, 1H), 8.58-8.62 (m, 1H).

Example 251

1-(3-[(4-Acetylpiperazinomethyl)phenyl]-3-(2-cyanophenyl)-5-(2-pyridyl)-1,2-dihydropyridin-2-one $^1$H-NMR (400 MHz, CDCl$_3$); δ(ppm) 2.07 (s, 3H), 2.45 (dd, 4H), 3.45 (dd, 2H), 3.58 (s, 2H), 3.63 (dd, 2H), 7.22 (ddd, 1H), 7.40-7.54 (m, 5H), 7.60-7.67 (m, 2H), 7.73-7.80 (m, 3H), 8.29 (d, 1H), 8.33 (d, 1H), 8.58-8.62 (m, 1H).

The following compounds were synthesized by the methods similar to, or in accordance with, the method for Example 32.

Example 252

3-(2-Cyanophenyl)-1-(4-nitrophenyl)-5-(2-pyridyl)-1,2-dihydropyridin-2-one $^1$H-NMR (400 MHz, CDCl$_3$); δ(ppm) 7.24-7.30 (m, 1H), 7.47-7.52 (m, 1H), 7.61-7.82 (m, 7H), 8.31 (dd, 2H), 8.42 (d, 2H), 8.60-8.63 (m, 1H).

Example 253

1-Phenyl-3-(2-pyrazinyl)-5-(2-pyridyl)-1,2-dihydropyridin-2-one $^1$H-NMR (400 MHz, CDCl$_3$); δ(ppm) 7.21-7.25 (m, 1H), 7.49-7.59 (m, 5H), 7.72-7.79 (m, 2H), 8.46 (d, 1H), 8.54 (d, 1H), 8.61 (ddd, 1H), 8.65 (dd, 1H), 9.14 (d, 1H), 9.87 (d, 1H).

Example 254

1-Phenyl-3-(2-pyrimidinyl)-5-(2-pyridyl)-1,2-dihydropyridin-2-one $^1$H-NMR (400 MHz, CDCl$_3$); δ(ppm) 7.20 (ddd, 1H), 7.25 (t, 1H), 7.44-7.54 (m, 5H), 7.66 (d, 1H), 7.75 (dt, 1H), 8.45 (d, 1H), 8.58-8.60 (m, 1H), 8.82 (d, 1H), 8.88 (s, 1H), 8.89 (s, 1H).

Example 255

1-Phenyl-5-(2-pyridyl)-3-(2-thiazolyl)-1,2-dihydropyridin-2-one $^1$H-NMR (400 MHz, CDCl$_3$); δ(ppm) 7.22-7.26 (m, 1H), 7.48-7.57 (m, 6H), 7.78-7.80 (m, 2H), 8.00 (dd, 1H), 8.52 (dd, 1H), 8.59-8.61 (m, 1H), 9.29 (d, 1H).

Example 256

1-Phenyl-3-(4-pyrimidinyl)-5-(2-pyridyl)-1,2-dihydropyridin-2-one $^1$H-NMR (400 MHz, CDCl$_3$); δ(ppm) 7.22-7.26 (m, 1H), 7.48-7.59 (m, 5H), 7.77-7.82 (m, 2H), 8.53 (d, 1H), 8.60-8.62 (m, 1H), 8.73-8.77 (m, 2H), 9.27 (dd, 1H), 9.40 (d, 1H).

Example 257

1-Phenyl-3-(5-pyrimidinyl)-5-(2-pyridyl)-1,2-dihydropyridin-2-one $^1$H-NMR (400 MHz, CDCl$_3$); δ(ppm) 7.24-7.27 (m, 1H), 7.48-7.61 (m, 7H), 7.77 (dt, 1H), 8.28 (d, 1H), 8.37 (d, 1H), 8.63 (ddd, 1H), 9.21 (d, 1H), 9.22 (s, 1H).

Example 258

1-Phenyl-3-(3-pyridazinyl)-5-(2-pyridyl)-1,2-dihydropyridin-2-one $^1$H-NMR (400 MHz, CDCl$_3$); δ(ppm) 7.22-7.25 (m, 1H), 7.48-7.58 (m, 6H), 8.55 (d, 1H), 8.60 (m, 1H), 8.78 (dd, 1H), 9.14 (dd, 1H), 9.34 (d, 1H).

Example 259

1-Phenyl-3-(4-pyridazinyl)-5-(2-pyridyl)-1,2-dihydropyridin-2-one $^1$H-NMR (400 MHz, CDCl$_3$); δ(ppm) 7.24-7.28 (m, 1H), 7.47-7.62 (m, 6H), 7.78 (dt, 1H), 8.16 (dd, 1H), 8.33 (d, 1H), 8.53 (d, 1H), 8.63-8.65 (m, 1H), 9.23 (dd, 1H), 9.62 (dd, 1H).

Example 260

3-(6-Methoxypyridin-2-yl)-1-phenyl-5-(2-pyridyl)-1,2-dihydropyridin-2-one $^1$H-NMR (400 MHz, CDCl$_3$); δ(ppm) 4.07 (s, 3H), 6.73 (dd, 1H), 7.22 (ddd, 1H), 7.46-7.56 (m, 5H), 7.62-7.70 (m, 2H), 7.78 (ddd, 1H), 8.35 (dd, 1H), 8.39 (d, 1H), 8.66 (ddd, 1H), 9.21 (d, 1H).

Example 261

3-(2-Cyanophenyl)-1-(3-pyridyl)-5-(2-pyrimidinyl)-1,2-dihydropyridin-2-one $^1$H-NMR (400 MHz, CDCl$_3$); δ(ppm) 7.18(t, 1H), 7.46-7.52 (m, 2H), 7.65 (dt, 1H), 7.71 (dd, 1H), 7.74-7.80 (m, 1H), 7.99 (ddd, 1H), 8.72-8.75 (m, 5H), 8.82 (dd, 1H).

Example 262

3-(2-Fluoropyridin-3-yl)-1-phenyl-5-(2-pyrimidinyl)-1,2-dihydropyridin-2-one $^1$H-NMR (400 MHz, CDCl$_3$); δ(ppm) 7.16(t, 1H), 7.24-7.27 (m, 2H), 7.48-7.57 (m, 5H), 8.19-8.23 (m, 2H), 8.69-8.76 (m, 3H).

Example 263

3-(2-Fluoropyridin-3-yl)-1-(3-pyridyl)-5-(2-pyrimidinyl)-1,2-dihydropyridin-2-one $^1$H-NMR (400 MHz, CDCl$_3$); δ(ppm) 7.19(t, 1H), 7.26-7.30 (m, 1H), 7.47-7.52 (m, 1H), 7.94 (ddd, 1H), 8.17 (ddd, 1H), 8.70-8.80 (m, 7H).

Example 264

3-(2-Cyanopyridin-3-yl)-1-phenyl-5-(2-pyrimidyl)-1,2-dihydropyridin-2-one $^1$H-NMR (400 MHz, CDCl$_3$); δ(ppm) 7.17(t, 1H), 7.47-7.56 (m, 6H), 8.14 (dd, 1H), 8.70 (dd, 1H), 8.72 (d, 2H), 8.80 (d, 1H), 8.85 (d, 1H).

Example 265

3-(2-Cyanopyridin-3-yl)-1-(3-pyridyl)-5-(2-pyrimidinyl)-1,2-dihydropyridin-2-one ¹H-NMR (400 MHz, CDCl₃); δ(ppm) 7.20(t, 1H), 7.52 (ddd, 1H), 7.58 (dd, 1H), 7.97 (ddd, 1H), 8.11 (dd, 1H), 8.71-8.76 (m, 4H), 8.78 (d, 1H), 8.81 (dd, 1H), 8.66 (d, 1H).

Example 266

3-(2-Cyanophenyl)-1-(3-nitrophenyl)-5-(2-pyrimidinyl)-1,2-dihydropyridin-2-one

¹H-NMR (400 MHz, CDCl₃); δ(ppm) 7.20(t, 1H), 7.49 (ddd, 1H), 7.65-7.80 (m, 5H), 7.98 (ddd, 1H), 8.36 (ddd, 1H), 8.46(t, 1H), 8.73-8.77 (m, 3H).

Example 267

1-Phenyl-5-(2-pyridyl)-3-(thiazol-4-yl)-1,2-dihydropyridin-2-one

¹H-NMR (400 MHz, CDCl₃); δ(ppm) 7.24-7.28 (m, 1H), 7.48-7.58 (m, 5H), 7.64(td, 1H), 7.79 (dt, 1H), 8.23 (d, 1H), 8.58 (d, 1H), 8.64-8.66 (m, 2H), 8.85 (d, 1H).

Example 268

3-(3-Oxo-1-cyclohexen-1-yl)-1-phenyl-5-(2-pyridyl)-1,2-dihydropyridin-2-one

¹H-NMR (400 MHz, CDCl₃); δ(ppm) 2.09-2.16 (m, 2H), 2.48-2.51 (m, 2H), 2.87-2.91 (m, 2H), 6.53(t, 1H), 7.22 (ddd, 1H), 7.43-7.57 (m, 6H), 7.75 (dt, 1H), 8.17 (d, 1H), 8.25 (d, 1H), 8.60 (ddd, 1H).

Example 269

3-(5,6-Dihydro-1,4-dioxin-2-yl)-1-phenyl-5-(2-pyridyl)-1,2-dihydropyridin-2-one

¹H-NMR (400 MHz, CDCl₃); δ(ppm) 4.18-4.20 (m, 2H), 4.30-4.32 (m, 2H), 7.19 (ddd, 1H), 7.41-7.54 (m, 5H), 7.63 (td, 1H), 7.73 (dt, 1H), 8.02 (s, 1H), 8.10 (d, 1H), 8.28 (d, 1H), 8.58 (ddd, 1H).

Example 270

3-(2-Nitrophenyl)-1-phenyl-5-(2-pyridyl)-1,2-dihydropyridin-2-one

¹H-NMR (400 MHz, CDCl₃); δ(ppm) 7.22 (ddd, 1H), 7.40-7.61 (m, 8H), 7.68 (ddd, 1H), 7.74 (ddd, 1H), 8.06 (dd, 1H), 8.22-8.25 (m, 2H), 8.60-8.63 (m, 1H).

Example 271

3-(4-Biphenyl)-1-phenyl-5-(2-pyridyl)-1,2-dihydropyridin-2-one

¹H-NMR (400 MHz, CDCl₃); δ(ppm) 7.20-7.25 (m, 1H), 7.33-7.40 (m, 1H), 7.42-7.57 (m, 6H), 7.60-7.79 (m, 7H), 7.90-7.95 (m, 2H), 8.25 (d, 1H), 8.30 (d, 1H), 8.60-8.64 (m, 1H).

Example 272

3-(2-Acetylphenyl)-5-(2-pyridyl)-1-phenyl-1,2-dihydropyridin-2-one

¹H-NMR (400 MHz, CDCl₃); δ(ppm) 2.59 (s, 3H), 7.16-7.21 (m, 1H), 7.40-7.60 (m, 9H), 7.63-7.67 (m, 1H), 7.68-7.75 (m, 1H), 8.16 (d, 1H), 8.22 (d, 1H), 8.57-8.61 (m, 1H).

Example 273

3-(3-Nitrophenyl)-1-phenyl-5-(2-pyridyl)-1,2-dihydropyridin-2-one

¹H-NMR (400 MHz, CDCl₃); δ(ppm) 7.24 (ddd, 1H), 7.46-7.64 (m, 7H), 7.76 (ddd, 1H), 8.20-8.26 (m, 2H), 8.27 (d, 1H), 8.37 (d, 1H), 8.61-8.65 (m, 1H), 8.69 (dd, 1H).

Example 274

1-Phenyl-3-(4-pyridyl)-5-(2-pyridyl)-1,2-dihydropyridin-2-one

¹H-NMR (400 MHz, CDCl₃); δ(ppm) 7.24 (ddd, 1H), 7.46-7.62 (m, 6H), 7.73-7.81 (m, 3H), 8.28 (d, 1H), 8.39 (d, 1H), 8.61-8.64 (m, 1H), 8.66 (dd, 2H).

Example 275

3-(4-Nitrophenyl)-1-phenyl-5-(2-pyridyl)-1,2-dihydropyridin-2-one

¹H-NMR (400 MHz, CDCl₃); δ(ppm) 7.22-7.26 (m, 1H), 7.47-7.58 (m, 5H), 7.60 (ddd, 1H), 7.76 (ddd, 1H), 8.01-8.06 (m, 2H), 8.26-8.31 (m, 3H), 8.38 (d, 1H), 8.61-8.65 (m, 1H).

Example 276

1-(3-(Benzyloxyphenyl)-3-(2-cyanophenyl)-5-(2-pyridyl)-1,2-dihydropyridin-2-one

¹H-NMR (400 MHz, CDCl₃); δ(ppm) 5.10 (s, 2H), 7.05-7.14 (m, 2H), 7.17 (dd, 1H), 7.21 (ddd, 1H), 7.30-7.48 (m, 7H), 7.60 (ddd, 1H), 7.64 (ddd, 1H), 7.71-7.81 (m, 3H), 8.29-8.32 (m, 2H), 8.58-8.61 (m, 1H).

Example 277

1-(3-Acetylphenyl)-3-(2-cyanophenyl)-5-(2-pyridyl)-1,2-dihydropyridin-2-one

¹H-NMR (400 MHz, CDCl₃); δ(ppm) 2.66 (s, 3H), 7.24 (ddd, 1H), 7.48 (ddd, 1H), 7.61-7.69 (m, 3H), 7.74-7.81 (m, 4H), 8.07 (ddd, 1H), 8.11 (ddd, 1H), 8.32 (d, 1H), 8.34 (d, 1H), 8.59-8.62 (m, 1H).

Example 278

3-[4-(tert-Butylaminosulfonyl)-phenyl]-1-phenyl-5-(2-pyridyl)-1,2-dihydropyridin-2-one ¹H-NMR (400 MHz, CDCl₃); δ(ppm) 1.26 (s, 9H), 4.46 (s, 1H), 7.24 (ddd, 1H), 7.46-7.58 (m, 5H), 7.58-7.61 (m, 1H), 7.76 (ddd, 1H), 7.90-7.99 (m, 4H), 8.26 (d, 1H), 8.33 (d, 1H), 8.61-8.64 (m, 1H).

Example 279

3-(1-Naphthyl)-5-(2-pyridyl)-1-(3-pyridyl)-1,2-dihydropyridin-2-one $^1$H-NMR (400 MHz, CDCl$_3$); δ(ppm) 7.21 (dd, 1H), 7.42-7.50 (m, 3H), 7.51-7.61 (m, 3H), 7.71(td, 1H), 7.81-7.85 (m, 1H), 7.87-7.90 (m, 2H), 7.96-7.99 (m, 1H), 8.20 (d, 1H), 8.37 (d, 1H), 8.60 (d, 1H), 8.67 (d, 1H), 8.84 (d, 1H).

ESI-Mass; 376 [M$^+$+H]

Example 280

3-(1-Naphthyl)-5-(2-pyridyl)-1-phenyl-1,2-dihydropyridin-2-one $^1$H-NMR (400 MHz, CDCl$_3$); δ(ppm) 7.19 (ddd, 1H), 7.38-7.59 (m, 9H), 7.71(td, 2H), 7.84-7.89 (m, 3H), 8.18 (d, 1H), 8.39 (d, 1H), 8.59 (ddd, 1H).

ESI-Mass; 375 [M$^+$+H]

Example 281

3-(8-Quinolinyl)-5-(2-pyridyl)-1-(3-pyridyl)-1,2-dihydropyridin-2-one $^1$H-NMR (400 MHz, CDCl$_3$); δ(ppm) 7.18-7.23 (m, 1H), 7.38-7.56 (m, 3H), 7.84-7.58 (m, 3H), 7.86-8.01 (m, 3H), 8.19-8.23 (m, 1H), 8.30-8.36 (m, 2H), 8.56-8.62 (m, 1H), 8.66-8.70 (m, 1H), 8.91-8.97 (m, 1H).

ESI-Mass; 377 [M$^+$+H]

Example 282

3-(8-Quinolinyl)-5-(2-pyridyl)-1-phenyl-1,2-dihydropyridin-2-one $^1$H-NMR (400 MHz, CDCl$_3$); δ(ppm) 7.18 (dd, 1H), 7.39-7.54 (m, 4H), 7.55-7.65 (m, 3H), 7.66-7.73 (m, 2H), 7.85 (dd, 1H), 7.98 (dd, 1H), 8.2 (dd, 1H), 8.34 (d, 1H), 8.36 (d, 1H), 8.58 (d, 1H), 8.94 (dd, 1H).

ESI-Mass; 376 [M$^+$+H]

Example 283

3-(2-Naphthyl)-5-(2-pyridyl)-1-(3-pyridyl)-1,2-dihydropyridin-2-one $^1$H-NMR (400 MHz, CDCl$_3$); δ(ppm) 7.23-7.28 (m, 1H), 7.48-7.53 (m, 3H), 7.64 (dt, 1H), 7.78(td, 1H), 7.85-7.91 (m, 4H), 7.97 (ddd, 1H), 8.25 (d, 1H), 8.35 (s, 1H), 8.38 (d, 1H), 8.64 (ddd, 1H), 8.72 (d, 1H), 8.81 (d, 1H).

ESI-Mass; 376 [M$^+$+H]

Example 284

3-(2-Naphthyl)-5-(2-pyridyl)-1-phenyl-1,2-dihydropyridin-2-one $^1$H-NMR (400 MHz, CDCl$_3$); δ(ppm) 7.21 (dd, 1H), 7.44-7.50 (m, 4H), 7.53-7.56 (m, 3H), 7.62 (dd, 1H), 7.72-7.77 (m, 1H), 7.83-7.91 (m, 2H), 7.92(td, 2H), 8.25 (d, 1H), 8.37 (d, 1H), 8.39(brs, 1H), 8.61-8.64 (m, 1H).

Example 285

3-(2-Pyrrolidinopyridin-5-yl)-5-(2-pyridyl)-1-phenyl-1,2-dihydropyridin-2-one $^1$H-NMR (400 MHz, CDCl$_3$); δ(ppm) 2.00-2.04 (m, 4H), 3.50(t, 4H), 7.74-7.78 (m, 9H), 8.03 (d, 1H), 8.06 (d, 1H), 8.21 (d, 1H), 8.57-8.60 (m, 2H).

ESI-Mass; 396 [M$^+$+H]

Example 286

3-(2-Formylthiophen-3-yl)-5-(2-pyridyl)-1-phenyl-1,2-dihydropyridin-2-one $^1$H-NMR (400 MHz, CDCl$_3$); δ(ppm) 7.21-7.29 (m, 2H), 7.46-7.57 (m, 6H), 7.73 (d, 1H), 7.75(td, 1H), 8.22 (d, 1H), 8.31 (d, 1H), 8.60-8.62 (m, 1H), 10.00 (s, 1H).

ESI-Mass; 359 [M$^+$+H]

Example 287

3-(2-Chloropyridin-5-yl)-5-(2-pyridyl)-1-phenyl-1,2-dihydropyridin-2-one $^1$H-NMR (400 MHz, CDCl$_3$); δ(ppm) 7.24 (ddd, 1H), 7.37 (d, 1H), 7.44-7.51 (m, 3H), 7.53-7.60 (m, 2H), 7.64-7.70 (m, 1H), 7.76(td, 1H), 8.24 (d, 1H), 8.26(t, 1H), 8.31 (d, 1H), 8.62 (ddd, 1H), 8.75 (d, 1H).

ESI-Mass; 360 [M$^+$+H]

Example 288

3-(2-Fluoropyridin-5-yl)-5-(2-pyridyl)-1-phenyl-1,2-dihydropyridin-2-one $^1$H-NMR (400 MHz, CDCl$_3$); δ(ppm) 6.99 (dd, 1H), 7.24 (dd, 1H), 7.47-7.57 (m, 5H), 7.59 (dd, 1H), 7.76(tdd, 1H), 8.25 (dd, 1H), 8.30 (dd, 1H), 8.37(td, 1H), 8.57-8.58 (m, 1H), 8.63 (dt, 1H).

Example 289

3-(2-Ethylthiopyridin-5-yl)-5-(2-pyridyl)-1-phenyl-1,2-dihydropyridin-2-one $^1$H-NMR (400 MHz, CDCl$_3$); δ(ppm) 1.39(t, 3H), 3.20(q, 2H), 7.20-7.24 (m, 2H), 7.44-7.59 (m, 6H), 7.75(td, 1H), 8.08 (dd, 1H), 8.23 (d, 1H), 8.26 (d, 1H), 8.61 (ddd, 1H), 8.78 (d, 1H).

ESI-Mass; 386 [M$^+$+H]

Example 290

3-(2-Cyanophenyl)-5-(2-pyridyl)-1-(2-naphthyl)-1,2-dihydropyridin-2-one $^1$H-NMR (400 MHz, CDCl$_3$); δ(ppm) 7.22 (ddd, 1H), 7.47 (td, 1H), 7.53-7.60 (m, 2H), 7.62-7.67 (m, 3H), 7.76(td, 1H), 7.81(td, 2H), 7.88-7.94 (m, 2H), 7.98 (d, 1H), 7.99 (s, 1H), 8.34 (d, 1H), 8.43 (d, 1H), 8.60 (ddd, 1H).

ESI-Mass; 400 [M$^+$+H]

Example 291

3-(2-Cyanophenyl)-5-(2-pyridyl)-1-(1-naphthyl)-1,2-dihydropyridin-2-one $^1$H-NMR (400 MHz, CDCl$_3$); δ(ppm) 7.21 (ddd, 1H), 7.45 (td, 1H), 7.54-7.65 (m, 6H), 7.65-7.83 (m, 4H), 7.93-8.02 (m, 2H), 8.30 (d, 1H), 8.46 (d, 1H), 8.57 (ddd, 1H).
ESI-Mass; 400 [M$^+$+H]

Example 292

3-(2-Cyanophenyl)-5-(2-pyridyl)-1-(8-quinolinyl)-1,2-dihydropyridin-2-one $^1$H-NMR (400 MHz, CDCl$_3$); δ(ppm) 7.18 (ddd, 1H), 7.43 (td, 1H), 7.48 (dd, 1H), 7.61(td, 1H), 7.63 (d, 1H), 7.69 (dd, 1H), 7.72(td, 1H), 7.78 (dd, 1H), 7.86 (dd, 1H), 7.92 (dd, 1H), 7.98 (dd, 1H), 8.26 (dd, 1H), 8.36 (d, 1H), 8.43 (d, 1H), 8.55-8.57 (m, 1H), 8.95 (dd, 1H).

Example 293

3-(1-Benzenesulfonylindol-2-yl)-1-phenyl-5-(2-pyridyl)-1,2-dihydropyridin-2-one $^1$H-NMR (400 MHz, CDCl$_3$); δ(ppm) 6.95 (d, 1H), 7.21 (ddd, 1H), 7.22 (ddd, 1H), 7.26-7.33 (m, 3H), 7.42 (dt, 1H), 7.44-7.49 (m, 2H), 7.50-7.56 (m, 4H), 7.60 (dt, 1H), 7.71-7.77 (m, 3H), 8.07 (dd, 1H), 8.20 (d, 1H), 8.34 (d, 1H), 8.60 (ddd, 1H).

Example 294

3-(2-Cyanopyridin-3-yl)-5-(2-pyridyl)-1-(3-pyridyl)-1,2-dihydropyridin-2-one $^1$H-NMR (400 MHz, CDCl$_3$); δ(ppm) 7.20-7.28 (m, 1H), 7.51 (dd, 1H), 7.58 (dd, 1H), 7.64 (d, 1H), 7.79(td, 1H), 7.94-7.97 (m, 1H), 8.18 (dd, 1H), 8.35 (d, 1H), 8.44 (d, 1H), 8.60-8.63 (m, 1H), 8.72 (dd, 1H), 8.74 (dd, 1H), 8.81 (d, 1H).
ESI-Mass; 352 [M$^+$+H]

Example 295

3-(2-Cyanophenyl)-5-(2-pyridyl)-1-(pyrrol-3-yl)-1,2-dihydropyridin-2-one $^1$H-NMR (400 MHz, CDCl$_3$); δ(ppm) 6.46-6.50 (m, 1H), 6.79 (dd, 1H), 7.21 (dd, 1H), 7.29-7.32 (m, 1H), 7.45(t, 1H), 7.60-7.66 (m, 2H), 7.72-7.80 (m, 3H), 8.23 (d, 1H), 8.47 (d, 1H), 8.61 (d, 1H), 8.72(brs, 1H).

The following compounds were synthesized by the methods similar to, or in accordance with, the method for Example 162.

Example 296

3-(2-Cyanophenyl)-5-(3-nitropyridin-2-yl)-1-phenyl-1,2-dihydropyridin-2-one $^1$H-NMR (400 MHz, CDCl$_3$); δ(ppm) 7.43-7.54 (m, 7H), 7.62-7.67 (m, 2H), 7.73-7.76 (m, 2H), 8.03 (d, 1H), 8.24 (dd, 1H), 8.82 (dd, 1H).

Example 297

3-(2-Cyanophenyl)-5-[2-(2,6-dimethylpyrrol-1-yl)pyridin-6-yl]-1-phenyl-1,2-dihydropyridin-2-one $^1$H-NMR (400 MHz, CDCl$_3$); δ(ppm) 2.17 (s, 6H), 5.91 (s, 2H), 7.12 (dd, 1H), 7.45-7.56 (m, 6H), 7.61 (dd, 1H), 7.65 (dd, 1H), 7.78-7.80 (m, 2H), 7.88(t, 1H), 8.35 (d, 1H), 8.40 (d, 1H).

Example 298

5-(2-Aminopyridin-6-yl)-3-(2-cyanophenyl)-1-phenyl-1,2-dihydropyridin-2-one $^1$H-NMR (400 MHz, CDCl$_3$); δ(ppm) 4.44(brs, 2H), 6.43 (dd, 1H), 6.96 (d, 1H), 7.42-7.54 (m, 7H), 7.63 (dt, 1H), 7.76-7.78 (m, 2H), 8.24 (d, 1H), 8.26 (d, 1H).

Example 299

3-(2-Cyanophenyl)-5-(5-nitropyridin-2-yl)-1-phenyl-1,2-dihydropyridin-2-one $^1$H-NMR (400 MHz, CDCl$_3$); δ(ppm) 7.47-7.59 (m, 6H), 7.67 (dt, 1H), 7.75-7.82 (m, 3H), 8.35 (d, 1H), 8.52 (dd, 1H), 8.55 (d, 1H), 9.39 (dd, 1H).

Example 300

5-(6-Bromopyridin-2-yl)-3-(2-cyanophenyl)-1-phenyl-1,2-dihydropyridin-2-one $^1$H-NMR (400 MHz, CDCl$_3$); δ(ppm) 7.39 (dd, 1H), 7.45-7.67 (m, 9H), 7.78-7.80 (m, 2H), 8.23 (d, 1H), 8.34 (d, 1H).

Example 301

3-(2-Cyanophenyl)-1-phenyl-5-(5-trifluoromethylpyridin-2-yl)-1,2-dihydropyridin-2-one $^1$H-NMR (400 MHz, CDCl$_3$); δ(ppm) 7.46-7.58 (m, 6H), 7.63-7.68 (m, 1H), 7.72 (d, 1H), 7.78-7.81 (m, 2H), 7.97 (ddd, 1H), 8.33 (d, 1H), 8.44 (d, 1H), 8.83-8.84 (m, 1H).

Example 302

3-(2-Cyanophenyl)-5-(2-morpholinopyridin-6-yl)-1-phenyl-1,2-dihydropyridin-2-one $^1$H-NMR (400 MHz, CDCl$_3$); δ(ppm) 3.55(t, 4H), 3.83(t, 4H), 6.57 (d, 1H), 6.97 (d, 1H), 7.43-7.66 (m, 8H), 7.77-7.80 (m, 2H), 8.18 (d, 1H), 8.31 (d, 1H).

Example 303

3-(2-Cyanophenyl)-5-(2-methoxycarbonylpyridin-6-yl)-1-phenyl-1,2-dihydropyridin-2-one $^1$H-NMR (400 MHz, CDCl$_3$); δ(ppm) 3.99 (s, 3H), 7.44-7.57 (m, 6H), 7.65 (dt, 1H), 7.78-7.81 (m, 3H), 7.91(t, 1H), 8.04 (dd, 1H), 8.30 (d, 1H), 8.37 (d, 1H).

The following compound was synthesized by the method similar to, or in accordance with, the method for Example 164.

Example 304

5-[4-(tert-Butylaminosulfonyl)phenyl]-3-(2-cyanophenyl)-1-(3-pyridyl)-1,2-dihydropyridin-2-one ¹H-NMR (400 MHz, CDCl₃); δ(ppm) 1.25 (s, 9H), 4.72(br s, 1H), 7.47-7.54 (m, 2H), 7.60-7.71 (m, 4H), 7.73-7.83 (m, 2H), 7.93-8.02 (m, 4H), 8.73 (dd, 1H), 8.79 (d, 1H).

The following compound was synthesized by the method similar to, or in accordance with, the method for Example 167.

Example 305

3-(2-Cyanophenyl)-4-methyl-1-phenyl-5-(2-pyridyl)-1,2-dihydropyridin-2-one

¹H-NMR (400 MHz, CDCl₃); δ(ppm) 2.12 (s, 3H), 7.28 (ddd, 1H), 7.38-7.52 (m, 8H), 7.59 (s, 1H), 7.66 (ddd, 1H), 7.75-7.80 (m, 2H), 8.66-8.70 (m, 1H).

The following compounds were synthesized by the methods similar to, or in accordance with, the method for Example 168.

Example 306

1-Phenyl-3-[N—(N'-phenylthioureylenyl)]-5-(2-pyridyl)-1,2-dihydropyridin-2-one

¹H-NMR (400 MHz, CDCl₃); δ(ppm) 7.19-7.24 (m, 1H), 7.26-7.36 (m, 3H), 7.37-7.54 (m, 7H), 7.70 (d, 1H), 7.78 (ddd, 1H), 7.92(br s, 1H), 8.09 (d, 1H), 8.55-8.59 (m, 1H), 9.33(br s, 1H), 10.03 (d, 1H).

Example 307

3-(2-Cyanophenyl)-1-phenyl-5-[N—(N'-phenylureylenyl)]-1,2-dihydropyridin-2-one

¹H-NMR (400 MHz, DMSO-d₆); δ(ppm) 6.95 (dd, 1H), 7.25 (dd, 1H), 7.41-7.61 (m, 8H), 7.65 (d, 1H), 7.71 (d, 1H), 7.77 (dd, 1H), 7.92 (d, 1H), 8.03 (d, 1H), 8.56-8.66 (m, 1H), 9.02-9.10 (m, 1H).

Example 308

3-{4[N—(N'-butylureylenyl)phenyl]}-1-phenyl-5-(2-pyridyl)-1,2-dihydropyridin-2-one ¹H-NMR (400 MHz, DMSO-d₆); δ(ppm) 0.90(t, 3H), 1.32 (tt, 2H), 1.42(tt, 2H), 3.09 (dt, 2H), 6.16(br t, 1H), 7.29 (dd, 1H), 7.44 (d, 2H), 7.47-7.54 (m, 1H), 7.54-7.60 (m, 4H), 7.69 (d, 2H), 7.82 (ddd, 1H), 8.02 (d, 1H), 8.35 (d, 1H), 8.39 (d, 1H), 8.53(br s, 1H), 8.58-8.61 (m, 1H).

The following compounds were synthesized by the methods similar to, or in accordance with, the method for Example 169.

Example 309

3-(2-Cyanophenyl)-1-phenyl-5-(2-pyridincarbonyl)amino-1,2-dihydropyridin-2-one

¹H-NMR (400 MHz, CDCl₃); δ(ppm) 7.42-7.54 (m, 7H), 7.63 (ddd, 1H), 7.74-7.79 (m, 3H), 7.92 (ddd, 1H), 8.20 (d, 1H), 8.58 (d, 1H), 8.59-8.62 (m, 1H), 9.80(br s, 1H).

Example 310

1-Phenyl-3-[2-(1-pyrrolidino)acetylamino]-5-(2-pyridyl)-1,2-dihydropyridin-2-one ¹H-NMR (400 MHz, CDCl₃); δ(ppm) 1.78-1.86 (m, 4H), 2.66-2.74 (m, 4H), 3.36 (s, 2H), 7.20 (ddd, 1H), 7.44-7.56 (m, 5H), 7.66 (d, 1H), 7.75 (ddd, 1H), 8.07 (d, 1H), 8.54-8.58 (m, 1H), 9.12 (d, 1H), 10.15(br s, 1H).

Example 311

1-Phenyl-3-{3-[1-(4-phenylpiperadino)]propionylamino}-5-(2-pyridyl)-1,2-dihydropyridin-2-one ¹H-NMR (400 MHz, CDCl₃); δ(ppm) 2.66(t, 2H), 2.69-2.76 (m, 4H), 2.80(t, 2H), 3.30-3.36 (m, 4H), 6.81-6.86 (m, 1H), 6.90-6.97 (m, 2H), 7.18 (ddd, 1H), 7.22-7.29 (m, 2H), 7.40-7.53 (m, 5H), 7.62-7.67 (m, 1H), 7.73 (ddd, 1H), 8.03 (d, 1H), 8.53-8.57 (m, 1H), 9.11 (d, 1H), 10.56(br s, 1H).

Example 312

3-(3-pyrrolidinopropionyl)amino-1-phenyl-5-(2-pyridyl)-1,2-dihydropyridin-2-one

¹H-NMR (400 MHz, CDCl₃); δ(ppm) 1.80-1.88 (m, 4H), 2.58-2.67 (m, 6H), 2.86(t, 2H), 7.17 (ddd, 1H), 7.42-7.54 (m, 5H), 7.65 (d, 1H), 7.73 (ddd, 1H), 8.03 (d, 1H), 8.53-8.57 (m, 1H), 9.11 (d, 1H), 10.91(br s, 1H).

The following compounds were synthesized by the methods similar to, or in accordance with, the method for Example 170.

Example 313

5-Benzylamino-3-(2-cyanophenyl)-1-phenyl-1,2-dihydropyridin-2-one

¹H-NMR (400 MHz, CDCl₃); δ(ppm) 4.15 (s, 2H), 6.70 (d, 1H), 7.30-7.36 (m, 1H), 7.36-7.43 (m, 8H), 7.43-7.49 (m, 3H), 7.59 (ddd, 1H), 7.72-7.77 (m, 2H).

Example 314

3-Dibenzylamino-1-phenyl-5-(2-pyridyl)-1,2-dihydropyridin-2-one

¹H-NMR (400 MHz, CDCl₃); δ(ppm) 4.52 (s, 4H), 7.12 (ddd, 1H), 7.16-7.33 (m, 10H), 7.37-7.54 (m, 7H), 7.63 (ddd, 1H), 7.80 (d, 1H), 8.50-8.54 (m, 1H).

Example 315

3-(2-Cyanophenyl)-1-(3-hydroxyphenyl)-5-(2-pyridyl)-1,2-dihydropyridin-2-one 52 mg of 1-(3-benzyloxyphenyl)-3-(2-cyanophenyl)-5-(2-pyridyl)-1,2-dihydropyridin-2-one and 20 mg of 5% palladium-carbon were added to 3 ml of methanol, followed by stirring at room temperature in hydrogen atmosphere overnight. After the resulting insoluble matters were filtered off, the filtrate was evaporated. The residue was purified by silica gel chromatography (ethyl acetate/hexane system), to give 26 mg the title compound.

¹H-NMR (400 MHz, CDCl₃); δ(ppm) 6.76 (dd, 1H), 6.87-6.92 (m, 1H), 6.93 (dd, 1H), 7.22-7.30 (m, 2H), 7.44 (ddd, 1H), 7.60-7.67 (m, 2H), 7.73-7.80 (m, 3H), 8.25 (d, 1H), 8.32 (d, 1H), 8.33(br s, 1H), 8.59-8.63 (m, 1H).

The following compounds were synthesized by the methods similar to, or in accordance with, the method for Example 171.

Example 316

1-Benzyloxymethyl-3-(2-cyanophenyl)-5-(2-pyridyl)-1,2-dihydropyridin-2-one $^1$H-NMR (400 MHz, CDCl$_3$); δ(ppm) 4.76 (s, 2H), 5.63 (s, 2H), 7.22 (ddd, 1H), 7.26-7.42 (m, 5H), 7.47 (ddd, 1H), 7.57 (d, 1H), 7.64-7.80 (m, 4H), 8.23 (d, 1H), 8.34 (d, 1H), 8.60-8.64 (m, 1H).

Example 317

3-(2-Cyanophenyl)-1-cyclopentylmethyl-5-(2-pyridyl)-1,2-dihydropyridin-2-one $^1$H-NMR (400 MHz, CDCl$_3$); δ(ppm) 1.32-1.42 (m, 2H), 1.55-1.64 (m, 2H), 1.65-1.75 (m, 2H), 1.76-1.86 (m, 2H), 2.53 (ddd, 1H), 4.10 (d, 2H), 7.21 (ddd, 1H), 7.45 (ddd, 1H), 7.58 (d, 1H), 7.64 (ddd, 1H), 7.71-7.79 (m, 3H), 8.16 (d, 1H), 8.28 (d, 1H), 8.59-8.63 (m, 1H).

Example 318

1-[1-(tert-butoxycarbonyl)piperidin-4-yl]methyl-3-(2-cyanophenyl)-5-(2-pyridyl)-1,2-dihydropyridin-2-one $^1$H-NMR (400 MHz, CDCl$_3$); δ(ppm) 1.22-1.35 (m, 2H), 1.45 (s, 9H), 1.68-1.78 (m, 2H), 2.14-2.27 (m, 1H), 2.61-2.76 (m, 2H), 3.90-4.25 (m, 4H), 7.22 (ddd, 1H), 7.46 (ddd, 1H), 7.58 (ddd, 1H), 7.65 (ddd, 1H), 7.73 (ddd, 2H), 7.78 (dd, 1H), 8.17 (d, 1H), 8.21 (d, 1H), 8.59-8.63 (m, 1H).

Example 319

1-(1-Benzyloxycarbonylpiperidin-4-yl)methyl-3-(2-cyanophenyl)-5-(2-pyridyl)-1,2dihydropyridin-2-one $^1$H-NMR (400 MHz, CDCl$_3$); δ(ppm) 1.25-1.38 (m, 2H), 1.68-1.81 (m, 2H), 2.17-2.30 (m, 1H), 2.70-2.86 (m, 2H), 3.92-4.08 (m, 2H), 4.15-4.32 (m, 2H), 5.12 (s, 2H), 7.22 (ddd, 1H), 7.28-7.38 (m, 5H), 7.46 (ddd, 1H), 7.57 (d, 1H), 7.65 (ddd, 1H), 7.69-7.79 (m, 3H), 8.17 (d, 1H), 8.20 (d, 1H), 8.59-8.62 (m, 1H).

The following compounds were synthesized by the methods similar to, or in accordance with, the method for Example 174.

Example 320

3-(Pyrrol-1-yl)-5-(2-pyridyl)-1-phenyl-1,2-dihydropyridin-2-one $^1$H-NMR (400 MHz, CDCl$_3$); δ(ppm) 6.33(t, 2H), 7.22 (ddd, 1H), 7.36(t, 2H), 7.45-7.57 (m, 6H), 7.74(td, 1H), 8.10 (d, 1H), 8.12 (d, 1H), 8.61 (ddd, 1H).

ESI-Mass; 314 [M$^+$+H]

Example 321

3-(2-Cyanophenylamino)-5-(2-pyridyl)-1-phenyl-1,2-dihydropyridin-2-one $^1$H-NMR (400 MHz, CDCl$_3$); δ(ppm) 7.06 (ddd, 1H), 7.21 (ddd, 1H), 7.41-7.65 (m, 9H), 7.71(td, 1H), 7.76 (d, 1H), 7.88 (d, 1H), 8.60 (ddd, 1H).

ESI-Mass; 365 [M$^+$+H]

Example 322

3-(2-Pyridylamino)-5-(2-pyridyl)-1-phenyl-1,2-dihydropyridin-2-one $^1$H-NMR (400 MHz, CDCl$_3$); δ(ppm) 6.80-6.86 (m, 2H), 7.20 (dd, 1H), 7.44-7.58 (m, 6H), 7.70 (d, 1H), 7.77(td, 1H), 7.87 (d, 1H), 7.96 (s, 1H), 8.37 (d, 1H), 8.59 (d, 1H), 9.29 (d, 1H).

ESI-Mass; 341 [M$^+$+H]

Example 323

3-(1-Isoquinolylamino)-5-(2-pyridyl)-1-phenyl-1,2-dihydropyridin-2-one $^1$H-NMR (400 MHz, CDCl$_3$); δ(ppm) 7.15-7.24 (m, 3H), 7.46-7.59 (m, 5H), 7.66(t, 1H), 7.77 (d, 2H), 7.80(td, 1H), 7.97 (d, 1H), 8.10 (d, 1H), 8.25 (d, 1H), 8.61 (d, 1H), 9.11 (s, 1H), 9.60 (d, 1H).

ESI-Mass; 391 [M$^+$+H]

Example 324

3-(1-Indazolyl)-5-(2-pyridyl)-1-phenyl-1,2-dihydropyridin-2-one $^1$H-NMR (400 MHz, CDCl$_3$); δ(ppm) 6.52 (dt, 1H), 7.06 (ddd, 1H), 7.22 (ddd, 1H), 7.31(td, 1H), 7.36 (ddd, 1H), 7.43-7.57 (m, 7H), 7.75 (dt, 1H), 8.03 (s, 1H), 8.09 (d, 1H), 8.50 (dd, 1H).

ESI-Mass; 365 [M$^+$+H]

Example 325

3-(9-Carbazolyl)-5-(2-pyridyl)-1-phenyl-1,2-dihydropyridin-2-one $^1$H-NMR (400 MHz, CDCl$_3$); δ(ppm) 7.22-7.29 (m, 4H), 7.35-7.63 (m, 9H), 7.52-7.57 (m, 1H), 8.12 (dd, 2H), 8.43 (dd, 1H), 8.46 (dd, 1H), 8.61 (ddd, 1H).

Example 326

3-(Indol-1-yl)-5-(2-pyridyl)-1-phenyl-1,2-dihydropyridin-2-one $^1$H-NMR (400 MHz, CDCl$_3$); δ(ppm) 6.68 (d, 1H), 7.17 (td, 1H), 7.20-7.26 (m, 2H), 7.47-7.55 (m, 7H), 7.62 (d, 1H), 7.66 (d, 1H), 7.74(td, 1H), 8.27 (d, 1H), 8.34 (d, 1H), 8.61 (ddd, 1H).

ESI-Mass; 364 [M$^+$+H]

Example 327

3-(2-Methyl-5-phenylpyrrol-1-yl)-5-(2-pyridyl)-1-phenyl-1,2-dihydropyridin-2-one 25 mg of 3-amino-1-phenyl-5-(2-pyridyl)-1,2-dihydropyridin-2-one was dissolved in 10 ml of toluene. To the mixture were added 20 mg of 1-phenyl-1,4-pentandione and 0.2 mg of p-toluenesulfonate (hydrate), followed by heating under reflux for 1 hour. After cooling to room temperature, the reaction mixture was poured into a saturated aqueous solution of sodium hydrogen carbonate, followed by extracting with ethyl acetate. The organic layer was washed with brine and dried over anhydrous magnesium sulfate. The solvent was evaporated, and the residue was purified by silica gel chromatography (hexane/ethyl acetate system), to give 12 mg of the title compound.

$^1$H-NMR (400 MHz, CDCl$_3$); δ(ppm) 2.26 (s, 3H), 6.10 (d, 1H), 6.34 (d, 1H), 7.21(tt, 1H), 7.17 (ddd, 1H), 7.21-7.27 (m, 2H), 7.28-7.32 (m, 3H), 7.39-7.54 (m, 5H), 7.66(td, 1H), 7.83 (d, 1H), 8.31 (d, 1H), 8.53 (ddd, 1H).

The following compounds were synthesized by the method similar to, or in accordance with, the method for Example 327.

Example 328

3-(2,5-Dimethylpyrrol-1-yl)-5-(2-pyridyl)-1-phenyl-1,2-dihydropyridin-2-one $^1$H-NMR (400 MHz, CDCl$_3$); δ(ppm) 2.16 (s, 6H), 5.92 (s, 2H), 7.22 (ddd, 1H), 7.56-7.43 (m, 6H), 7.75(td, 1H), 8.07 (d, 1H), 8.37 (d, 1H), 8.60 (ddd, 1H).

Example 329

3-(2-Cyanophenyl)-1-(piperidin-4-yl)methyl-5-(2-pyridyl)-1,2-dihydropyridin-2-one The titled compound (382 mg) was obtained by catalytically hydrogenating 590 mg of 1-[1-(benzyloxycarbonyl)piperidin-4-yl]methyl-3-(2-cyanophenyl)-5-(2-pyridyl)-1,2-dihydropyridin-2-one using in a conventional manner using 10% palladium-carbon.

$^1$H-NMR (400 MHz, CDCl$_3$); δ(ppm) 1.22-1.34 (m, 2H), 1.62-1.77 (m, 2H), 2.08-2.20 (m, 1H), 2.55-2.63 (m, 2H), 3.05-3.13 (m, 2H), 4.00 (d, 2H), 7.21 (ddd, 1H), 7.45 (ddd, 1H), 7.58 (ddd, 1H), 7.64 (ddd, 1H), 7.70-7.79 (m, 3H), 8.17 (d, 1H), 8.21 (d, 1H), 8.59-8.63 (m, 1H).

The following compound was synthesized by the method similar to, or in accordance with, the method for Example 329.

Example 330

3-(2-Cyanophenyl)-1-[3-(4-piperidyloxy)]phenyl-5-(2-pyridyl)-1,2-dihydropyridin-2-one $^1$H-NMR (400 MHz, CDCl$_3$); δ(ppm) 1.60-1.73 (m, 2H), 1.98-2.07 (m, 2H), 2.69-2.77 (m, 2H), 3.08-3.17 (m, 2H), 4.39-4.46 (m, 1H), 6.98-7.02 (m, 1H), 7.04-7.09 (m, 2H), 7.21 (ddd, 1H), 7.38-7.48 (m, 2H), 7.58-7.67 (m, 2H), 7.72-7.81 (m, 3H), 8.29-8.32 (m, 2H), 8.58-8.61 (m, 1H).

Example 331

1-(1-Benzoylpiperidin-4-yl)methyl-3-(2-cyanophenyl)-5-(2-pyridyl)-1,2-dihydropyridin-2-one 30 mg of 3-(2-cyanophenyl)-1-(piperidin-4-yl)methyl-5-(2-pyridyl)-1,2-dihydropyridin-2-one was dissolved in 2 ml of chloroform. Under ice-cooling, 0.04 ml of triethylamine and 19 mg of benzoyl chloride were added thereto, followed by stirring at room temperature for 2 hours. The reaction solution was diluted with chloroform, and washed with a saturated aqueous solution of sodium hydrogen carbonate and brine. The organic layer was dried over magnesium sulfate, and then evaporated and the residue was purified by silica gel chromatography (ethyl acetate/hexane), to give 25 mg of the title compound.

$^1$H-NMR (400 MHz, CDCl$_3$); δ(ppm) 1.22-1.52 (m, 2H), 1.65-1.78 (m, 1H), 1.80-1.98 (m, 1H), 2.28-2.41 (m, 1H), 2.70-2.86 (m, 1H), 2.88-3.06 (m, 1H), 3.70-3.88 (m, 1H), 3.90-4.23 (m, 2H), 4.65-4.87 (m, 1H), 7.22 (dd, 1H), 7.36-7.42 (m, 5H), 7.46 (dd, 1H), 7.55-7.60 (m, 1H), 7.62-7.72 (m, 2H), 7.72-7.79 (m, 2H), 8.16 (d, 1H), 8.22 (d, 1H), 8.59-8.63 (m, 1H).

The following compounds were synthesized by the methods similar to, or in accordance with, the method for Example 331.

Example 332

1-(1-Acetylpiperidin-4-yl)methyl-3-(2-cyanophenyl)-5-(2-pyridyl)-1,2-dihydropyridin-2-one $^1$H-NMR (400 MHz, CDCl$_3$); δ(ppm) 1.22-1.38 (m, 2H), 1.75-1.86 (m, 2H), 2.08 (s, 3H), 2.20-2.35 (m, 1H), 2.50-2.60 (m, 1H), 2.98-3.08 (m, 1H), 3.79-3.87 (m, 1H), 3.95 (dd, 1H), 4.05-4.15 (m, 1H), 4.61-4.70 (m, 1H), 7.23 (ddd, 1H), 7.47 (ddd, 1H), 7.58 (d, 1H), 7.63-7.71 (m, 2H), 7.72-7.80 (m, 2H), 8.17 (d, 1H), 8.21 (d, 1H), 8.59-8.63 (m, 1H).

Example 333

1-[3-(N-acetylpiperidin-4-yl-oxy)phenyl]-3-(2-cyanophenyl)-5-(2-pyridyl)-1,2-dihydropyridin-2-one $^1$H-NMR (400 MHz, CDCl$_3$); δ(ppm) 1.77-2.02 (m, 4H), 2.12 (s, 3H), 3.37-3.45 (m, 1H), 3.59-3.72 (m, 2H), 3.75-3.83 (m, 1H), 4.57-4.62 (m, 1H), 7.01 (ddd, 1H), 7.07-7.12 (m, 2H), 7.22 (ddd, 1H), 7.43 (dd, 1H), 7.46 (ddd, 1H), 7.61 (ddd, 1H), 7.64 (ddd, 1H), 7.72-7.80 (m, 3H), 8.29 (d, 1H), 8.31 (d, 1H), 8.58-8.62 (m, 1H).

Example 334

1-[3-(N-benzoylpiperidin-4-yl-oxy)phenyl]-3-(2-cyanophenyl)-5-(2-pyridyl)-1,2-dihydropyridin-2-one $^1$H-NMR (400 MHz, CDCl$_3$); δ(ppm) 1.75-2.13 (m, 4H), 3.30-3.47 (m, 1H), 3.58-3.72 (m, 1H), 3.75-3.87 (m, 1H), 3.88-4.03 (m, 1H), 4.56-4.68 (m, 1H), 6.99-7.03 (m, 1H), 7.07-7.13 (m, 2H), 7.20-7.25 (m, 1H), 7.38-7.49 (m, 7H), 7.59-7.67 (m, 2H), 7.72-7.80 (m, 3H), 8.28 (d, 1H), 8.31 (d, 1H), 8.58-8.62 (m, 1H).

Example 335

1-(1-Benzenesulfonylpiperidin-4-yl)methyl-3-(2-cyanophenyl)-5-(2-pyridyl)-1,2-dihydropyridin-2-one 30 mg of 3-(2-cyanophenyl)-1-(piperidin-4-yl)methyl-5-(2-pyridyl)-1,2-dihydropyridin-2-one was dissolved in 2 ml of chloroform. Under ice-cooling, 0.04 ml of triethylamine and 23 mg of benzenesulfonyl chloride were added thereto, followed by stirring at room temperature for 2 hours. The reaction solution was diluted with chloroform, and washed with a saturated aqueous solution of sodium hydrogen carbonate and brine. The organic layer was dried over magnesium sulfate, and then evaporated and the residue was purified by silica gel chromatography (ethyl acetate/hexane), to give 30 mg of the title compound.

$^1$H-NMR (400 MHz, CDCl$_3$); δ(ppm) 1.41-1.60 (m, 2H), 1.77-1.85 (m, 2H), 1.95-2.06 (m, 1H), 2.20-2.31 (m, 2H), 3.80-3.88 (m, 2H), 3.98 (d, 2H), 7.22 (dd, 1H), 7.45 (ddd, 1H), 7.48-7.68 (m, 6H), 7.70-7.79 (m, 4H), 8.15 (d, 1H), 8.17 (d, 1H), 8.59-8.63 (m, 1H).

The following compounds were synthesized by the methods similar to, or in accordance with, the method for Example 335.

Example 336

3-(2-Cyanophenyl)-1-(1-methylsulfonylpiperidin-4-yl)methyl-5-(2-pyridyl)-1,2-dihydropyridin-2-one $^1$H-NMR (400 MHz, CDCl$_3$); δ(ppm) 1.43-1.56 (m, 2H), 1.83-1.92 (m, 2H), 2.17-2.30 (m, 1H), 2.63-2.72 (m, 2H), 2.77 (s, 3H), 3.80-3.88 (m, 2H), 4.03 (d, 2H), 7.20-7.26 (m, 1H), 7.44-7.51 (m, 1H), 7.55-7.61 (m, 1H), 7.63-7.72 (m, 2H), 7.73-7.82 (m, 2H), 8.17 (d, 1H), 8.21 (d, 1H), 8.59-8.64 (m, 1H).

Example 337

1-[3-(1-Benzenesulfonylpiperidin-4-yl-oxy)phenyl]-3-(2-cyanophenyl)-5-(2-pyridyl)-1,2-dihydropyridin-2-one $^1$H-NMR (400 MHz, CDCl$_3$); δ((ppm) 1.90-2.10 (m, 4H), 3.10-3.23 (m, 4H), 4.38-4.45 (m, 1H), 6.87-6.92 (m, 1H), 6.98 (dd, 1H), 7.05 (ddd, 1H), 7.22 (ddd, 1H), 7.38 (dd, 1H), 7.46 (ddd, 1H), 7.52-7.66 (m, 5H), 7.72-7.80 (m, 5H), 8.25-8.28 (m, 2H), 8.57-8.60 (m, 1H).

Example 338

3-(2-Cyanophenyl)-1-[3-(1-(methylsulfonylpiperidin-4-yl-oxy)phenyl]-5-(2-pyridyl)-1,2-dihydropyridin-2-one $^1$H-NMR (400 MHz, CDCl$_3$); δ(ppm) 1.98-2.10 (m, 4H), 2.81 (s, 3H), 3.30-3.41 (m, 4H), 4.56-4.62 (m, 1H), 6.98-7.02 (m, 1H), 7.08-7.13 (m, 2H), 7.23 (ddd, 1H), 7.44 (dd, 1H), 7.47 (ddd, 1H), 7.61 (ddd, 1H), 7.65 (ddd, 1H), 7.73-7.80 (m, 3H), 8.28 (d, 1H), 8.32 (d, 1H), 8.59-8.62 (m, 1H).

Example 339

3-(2-Cyanophenyl)-1-(1-benzylpiperidin-4-yl)methyl-5-(2-pyridyl)-1,2-dihydropyridin-2-one 80 mg of 3-(2-cyanophenyl)-1-(piperidin-4-yl)methyl-5-(2-pyridyl)-1,2-dihydropyridin-2-one was dissolved in 2 ml of chloroform. To the mixture were added 73 mg of benzaldehyde, 97 mg of triacetoxy sodium borohydride and 41 mg of acetic acid, followed by stirring at room temperature for 4 hours. The reaction solution was diluted with chloroform, and washed with a saturated aqueous solution of sodium hydrogen carbonate and brine. The organic layer was dried over magnesium sulfate. Then the mixture was evaporated, and the residue was purified by NH silica gel chromatography (hexane/ethyl acetate system), to give 80 mg of the title compound.

$^1$H-NMR (400 MHz, CDCl$_3$); δ((ppm) 1.44 (ddd, 2H), 1.68-1.76 (m, 2H), 1.92-2.06 (m, 3H), 2.37-2.93 (m, 2H), 3.48 (s, 2H), 4.01 (d, 2H), 7.18-7.25 (m, 2H), 7.27-7.32 (m, 4H), 7.45 (ddd, 1H), 7.56 (d, 1H), 7.64 (ddd, 1H), 7.70-7.78 (m, 3H), 8.16 (d, 1H), 8.19 (d, 1H), 8.58-8.61 (m, 1H).

The following compounds were synthesized by the methods similar to, or in accordance with, the method for Example 339.

Example 340

3-(2-Cyanophenyl)-1-(1-methylpiperidin-4-yl)methyl-5-(2-pyridyl)-1,2-dihydropyridin-2-one $^1$H-NMR (400 MHz, CDCl$_3$); δ(ppm) 1.38-1.50 (m, 2H), 1.65-1.80 (m, 2H), 1.88-2.05 (m, 3H), 2.25 (s, 3H), 2.82-2.92 (m, 2H), 4.01 (d, 2H), 7.19-7.24 (m, 1H), 7.43-7.49 (m, 1H), 7.56-7.60 (m, 1H), 7.62-7.68 (m, 1H), 7.70-7.80 (m, 3H), 8.17 (d, 1H), 8.20 (d, 1H), 8.59-8.63 (m, 1H).

Example 341

1-[3-(N-methylpiperidin-4-yl-oxy)phenyl]-3-(2-cyanophenyl)-5-(2-pyridyl)-1,2-dihydropyridin-2-one $^1$H-NMR (400 MHz, CDCl$_3$); δ(ppm) 1.80-1.93 (m, 2H), 1.97-2.08 (m, 2H), 2.23-2.37 (m, 5H), 2.60-2.73 (m, 2H), 4.33-4.42 (m, 1H), 6.97-7.02 (m, 1H), 7.04-7.10 (m, 2H), 7.19-7.24 (m, 1H), 7.38-7.49 (m, 2H), 7.58-7.68 (m, 2H), 7.72-7.82 (m, 3H), 8.28-8.33 (m, 2H), 8.58-8.62 (m, 1H).

Example 342

1-[3-(N-benzylpiperidin-4-yl-oxy)phenyl]-3-(2-cyanophenyl)-5-(2-pyridyl)-1,2-dihydropyridin-2-one $^1$H-NMR (400 MHz, CDCl$_3$); δ(ppm) 1.78-1.88 (m, 2H), 1.97-2.06 (m, 2H), 2.26-2.35 (m, 2H), 2.58-2.76 (m, 2H), 3.52 (s, 2H), 4.33-4.41 (m, 1H), 6.97-7.01 (m, 1H), 7.04-7.08 (m, 2H), 7.21 (ddd, 1H), 7.24-7.28 (m, 1H), 7.30-7.34 (m, 4H), 7.40 (dd, 1H), 7.46 (ddd, 1H), 7.60 (ddd, 1H), 7.64 (ddd, 1H), 7.72-7.80 (m, 3H), 8.30 (s, 2H), 8.58-8.61 (m, 1H).

Example 343

3-(4-Sulfamoylphenyl)-1-phenyl-5-(2-pyridyl)-1,2-dihydropyridin-2-one 80 mg of 3-[4-(tert-butylaminosulfonyl)phenyl]-1-phenyl-5-(2-pyridyl)-1,2-dihydropyridin-2-one was dissolved in 3 ml of trifluoroacetic acid, followed by heating under reflux for 1 hour. It was left to cool to room temperature, and then the reaction mixture was diluted with ethyl acetate/tetrahydrofuran, and washed with a saturated aqueous solution of sodium hydrogen carbonate and brine. The organic layer was dried over magnesium sulfate, and then evaporated. The resulting crude crystals were washed with ethyl acetate, to give 60 mg of the title compound.

$^1$H-NMR (400 MHz, DMSO-d$_6$); δ(ppm) 7.31 (ddd, 1H), 7.49-7.61 (m, 5H), 7.82-7.90 (m, 3H), 7.97-8.02 (m, 2H), 8.03-8.07 (m, 1H), 8.48 (d, 1H), 8.54 (d, 1H), 8.59-8.62 (m, 1H).

The following compounds were synthesized by the methods similar to, or in accordance with, the method for Example 181.

Example 344

3-Cyclohexylaminocarbonyl-5-(2-pyridyl)-1-phenyl-1,2-dihydropyridin-2-one $^1$H-NMR (400 MHz, CDCl$_3$); δ(ppm) 1.12-2.10 (m, 10H), 3.97-4.04 (m, 1H), 7.23 (ddd, 1H), 7.43-7.58 (m, 1H), 7.49-7.59 (m, 4H), 7.74-7.77 (m, 1H), 7.79(td, 1H), 8.55-8.56 (m, 1H), 8.57 (d, 1H), 9.18 (d, 1H), 9.64 (d, 1H).

ESI-Mass; 374 [M$^+$+H]

Example 345

3-(2-Cyanophenyl)-5-(1-adamantylaminocarbonyl)-1-phenyl-1,2-dihydropyridin-2-one $^1$H-NMR (400 MHz, CDCl$_3$); δ(ppm) 1.77-1.56 (m, 7H), 1.97-2.15 (m, 8H), 5.63 (s, 1H), 7.42-7.54 (m, 6H), 7.63(td, 1H), 7.74-7.78 (m, 2H), 7.88 (d, 1H), 8.12 (d, 1H).

Example 346

3-(1-Adamantylaminocarbonyl)-5-(2-pyridyl)-1-phenyl-1,2-dihydropyridin-2-one $^1$H-NMR (400 MHz, CDCl$_3$); δ(ppm) 1.50-1.72 (m, 12H), 1.99-2.15 (m, 3H), 7.21-7.29 (m, 1H), 7.43-7.49 (m, 2H), 7.48-7.60 (m, 4H), 7.75-7.80 (m, 1H), 8.47 (d, 1H), 8.55 (d, 1H), 8.60 (ddd, 1H).

Example 347

3-{1-[4-(2-Cyanophenyl)piperadino]carbonyl}-5-(2-pyridyl)-1-phenyl-1,2-dihydropyridin-2-one $^1$H-NMR (400 MHz, CDCl$_3$); δ(ppm) 3.12-3.31 (m, 4H), 3.59-3.79 (m, 4H), 6.99-7.06 (m, 2H), 7.22 (dd, 1H), 7.27-7.62 (m, 8H), 7.75(td, 1H), 8.29 (d, 1H), 8.37 (d, 1H), 8.58 (ddd, 1H).

ESI-Mass; 462 [M$^+$+H]

Example 348

3-[(2-Phenylhydrazino)carbonyl]-5-(2-pyridyl)-1-phenyl-1,2-dihydropyridin-2-one $^1$H-NMR (400 MHz, CDCl$_3$); δ(ppm) 6.53 (d, 1H), 6.89(t, 1H), 6.94 (d, 2H), 7.20-7.30 (m, 3H), 7.62-7.47 (m, 5H), 7.71-7.77 (m, 1H), 7.80 (dd, 1H), 8.56-8.57 (m, 1H), 8.64 (d, 1H), 9.16 (d, 1H), 11.23 (d, 1H).

ESI-Mass; 383 [M$^+$+H]

Example 349

3-Phenylaminocarbonyl-5-(2-pyridyl)-1-phenyl-1,2-dihydropyridin-2-one $^1$H-NMR (400 MHz, CDCl$_3$); δ(ppm) 7.06-7.17 (m, 1H), 7.23-7.28 (m, 1H), 7.31-7.37 (m, 2H), 7.46-7.62 (m, 5H), 7.73-7.83 (m, 4H), 8.58 (ddd, 1H), 8.63 (d, 1H), 9.29 (d, 1H), 11.86(brs, 1H).

Example 350

350A 3-(2-Chlorophenyl)-5-(4-chlorobenzenesulfinyl)-1-(3-pyridyl)-1,2-dihydropyridin-2-one

350B 3-(2-Chlorophenyl)-5-(4-chlorobenzenesulfonyl)-1-(3-pyridyl)-1,2-dihydropyridin-2-one 3 8 mg of 3-(2-chlorophenyl)-5-(4-chlorophenylthio)-1-(3-pyridyl)-1,2-dihydropyridin-2-one was dissolved in 10 ml of dichloromethane. Under ice-cooling, 15.4 mg of m-chloroperbenzoic acid was added thereto, followed by stirring at the same temperature for 1 hour. Further, 10 mg of m-chloroperbenzoic acid was added thereto, followed by stirring for 2 hours under ice-cooling. Then, the mixture was diluted with 30 ml of ethyl acetate, and washed with an aqueous solution of 1 N sodium hydroxide. The organic layer was washed with brine, and then dried over anhydrous magnesium sulfate. The solvent was evaporated, and the residue was purified by silica gel chromatography (hexane/ethyl acetate system), to give 9 mg of 3-(2-chlorophenyl)-5-(4-chlorobenzenesulfinyl)-1-(3-pyridyl)-1,2-dihydropyridin-2-one and 6 mg of 3-(2-chlorophenyl)-5-(4-chlorobenzenesulfonyl)-1-(3-pyridyl)-1,2-dihydropyridin-2-one as the title compounds.

(350A)
$^1$H-NMR (400 MHz, CDCl$_3$); δ(ppm) 7.27-7.33 (m, 3H), 7.36 (d, 1H), 7.40-7.44 (m, 1H), 7.48-7.57 (m, 3H), 7.63-7.67 (m, 2H), 7.87-7.92 (m, 1H), 7.97 (d, 1H), 8.70-8.76 (m, 2H).

ESI-Mass; 441 [M$^+$+H]

(350B)
$^1$H-NMR (400 MHz, CDCl$_3$); δ(ppm) 7.30-7.37 (m, 2H), 7.44-7.52 (m, 3H), 7.56(t, 1H), 7.58(t, 1H), 7.34 (d, 1H), 7.84-7.88 (m, 1H), 7.89(t, 1H), 7.92(t, 1H), 8.24 (d, 1H), 8.71 (dd, 1H), 8.75 (dd, 1H).

ESI-Mass; 457 [M$^+$+H]

The following compounds were synthesized by the methods similar to, or in accordance with, the method for Example 182.

Example 351

3-(2-Cyanophenyl)-5-(5-methyl-1H-benzimidazol-2-yl)-1-phenyl-1,2-dihydropyridin-2-one $^1$H-NMR (400 MHz, CDCl$_3$); δ(ppm) 2.45 (s, 3H), 7.05 (d, 1H), 7.34-7.43 (m, 7H), 7.57(td, 2H), 7.62 (ddd, 1H), 7.68 (ddd, 1H), 8.18 (d, 1H), 8.27 (d, 1H).

ESI-Mass; 403 [M$^+$+H]

Example 352

3-(2-Cyanophenyl)-5-(4-methyl-1H-benzimidazol-2-yl)-1-phenyl-1,2-dihydropyridin-2-one $^1$H-NMR (400 MHz, CDCl$_3$); δ(ppm) 2.50(brs, 1.5H), 2.63(brs, 1.5H), 7.02 (d, 1H), 7.14(t, 1H), 7.30-7.40 (m, 7H), 7.52-7.58 (m, 2H), 7.65 (d, 1H), 8.18-8.23 (m, 1H), 8.24 (d, 1H).

ESI-Mass; 403 [M$^+$+H]

Example 353

3-(2-Cyanophenyl)-5-(5,6-dichloro-1H-benzimidazol-2-yl)-1-phenyl-1,2-dihydropyridin-2-one $^1$H-NMR (400 MHz, CDCl$_3$); δ(ppm) 7.39-7.49 (m, 6H), 7.52-7.54 (m, 1H), 7.60-7.66 (m, 2H), 7.70-7.72 (m, 1H), 7.72-7.74 (m, 1H), 8.21 (d, 1H), 8.37 (d, 1H).
ESI-Mass; 457 [M$^+$+H]

Example 354

3-(5,6-Dichloro-1H-benzimidazol-2-yl)-5-(2-pyridyl)-1-phenyl-1,2-dihydropyridin-2-one $^1$H-NMR (400 MHz, CDCl$_3$); δ(ppm) 7.27 (ddd, 1H), 7.48-7.63 (m, 6H), 7.82(td, 1H), 7.83-7.89 (m, 2H), 8.59 (d, 1H), 8.60 (dt, 1H), 9.38 (d, 1H), 12.15 (s, 1H).
ESI-Mass; 433 [M$^+$+H]

Example 355

3-(6-Chloro-1H-benzimidazol-2-yl)-5-(2-pyridyl)-1-phenyl-1,2-dihydropyridin-2-one $^1$H-NMR (400 MHz, CDCl$_3$); δ(ppm) 7.22-7.28 (m, 2H), 7.50-7.63 (m, 6H), 7.78-7.88 (m, 3H), 8.58 (dd, 1H), 8.61 (ddd, 1H), 9.40 (d, 1H).
ESI-Mass; 399 [M$^+$+H]

Example 356

3-[1-(Pyridin-4-yl)benzimidazol-2-yl]-5-(2-pyridyl)-1-phenyl-1,2-dihydropyridin-2-one $^1$H-NMR (400 MHz, CDCl$_3$); δ(ppm) 7.10-7.13 (m, 2H), 7.22-7.28 (m, 2H), 7.31-7.46 (m, 8H), 7.69 (dt, 1H), 7.77(td, 1H), 7.91 (dt, 1H), 8.43 (d, 1H), 8.59 (ddd, 1H), 8.73-8.75 (m, 2H).
ESI-Mass; 442 [M$^+$+H]

Example 357

3-[1-(1-Benzylpiperidin-4-yl)benzimidazol-2-yl]-5-(2-pyridyl)-1-phenyl-1,2-dihydropyridin-2-one $^1$H-NMR (400 MHz, CDCl$_3$); δ(ppm) 2.01-2.20 (m, 4H), 2.56-2.66 (m, 2H), 3.02-3.07 (m, 2H), 3.58 (s, 2H), 4.09-4.18 (m, 1H), 7.21 (ddd, 1H), 7.24-7.30 (m, 3H), 7.31-7.36 (m, 2H), 7.45-7.50 (m, 4H), 7.52-7.60 (m, 3H), 7.64 (d, 1H), 7.74(td, 1H), 7.77-7.84 (m, 2H), 8.48 (d, 1H), 8.49 (d, 1H), 8.58 (ddd, 1H).
ESI-Mass; 538 [M$^+$+H]

Example 358

3-(2-Cyanophenyl)-5-(5,6-dihydro-4H-imidazo[4,5,1-i,j]quinolin-2-yl)-1-phenyl-1,2-dihydropyridin-2-one $^1$H-NMR (400 MHz, CDCl$_3$); δ(ppm) 2.30(qu, 2H), 3.02(t, 2H), 4.47(t, 2H), 7.04 (dd, 1H), 7.20 (dd, 1H), 7.45-7.57 (m, 7H), 7.65(td, 1H), 7.79 (dd, 1H), 7.81 (dd, 1H), 8.10 (d, 1H), 8.22 (d, 1H).
ESI-Mass; 429 [M$^+$+H]

Example 359

3-(5,6-Dihydro-4H-imidazo[4,5,1-i,j]quinolin-2-yl)-5-(2-pyridyl)-1-phenyl-1,2-dihydropyridin-2-one $^1$H-NMR (400 MHz, CDCl$_3$); δ(ppm) 2.20(qu, 2H), 2.98(t, 2H), 4.35(t, 2H), 7.03 (d, 1H), 7.18-7.23 (m, 2H), 7.44-7.58 (m, 5H), 7.62 (d, 1H), 7.70 (d, 1H), 7.75 (dt, 1H), 8.52 (d, 1H), 8.57 (ddd, 1H), 8.70 (d, 1H).
ESI-Mass; 405 [M$^+$+H]

Example 360

3-(1-Phenylbenzimidazol-2-yl)-5-(2-pyridyl)-1-phenyl-1,2-dihydropyridin-2-one $^1$H-NMR (400 MHz, CDCl$_3$); δ(ppm) 7.05-7.21 (m, 3H), 7.25-7.45 (m, 6H), 7.47-7.65 (m, 7H), 8.10 (d, 1H), 8.54-8.59 (m, 1H), 8.85-8.95 (m, 1H), 9.22 (d, 1H).
ESI-Mass; 441 [M$^+$+H]

Example 361

3-(2-Chlorophenyl)-5-(6-chloro-1H-benzimidazol-2-yl)-1-phenyl-1,2-dihydropyridin-2-one $^1$H-NMR (400 MHz, CDCl$_3$); δ(ppm) 6.92(td, 1H), 6.97-7.07 (m, 4H), 7.11-7.14 (m, 2H), 7.18-7.24 (m, 3H), 7.25-7.29 (m, 2H), 7.94 (d, 1H), 8.24 (d, 1H).
ESI-Mass; 432 [M$^+$+H]

Example 362

3-(2-Cyanophenyl)-5-(1H-imidazo[4,5-c]pyridin-2-yl)-1-phenyl-1,2-dihydropyridin-2-one $^1$H-NMR (400 MHz, CDCl$_3$); δ(ppm) 7.04-7.09 (m, 1H), 7.28-7.31 (m, 1H), 7.44-7.60 (m, 5H), 7.66-7.70 (m, 2H), 7.74-7.78 (m, 1H), 7.80 (d, 1H), 7.93-7.96 (m, 1H), 8.01 (d, 1H), 8.40 (d, 1H), 8.51 (d, 1H).
ESI-Mass; 390 [M$^+$+H]

Example 363

3-(6-Methyl-1H-benzimidazol-2-yl)-5-(2-pyridyl)-1-phenyl-1,2-dihydropyridin-2-one $^1$H-NMR (400 MHz, CDCl$_3$); δ(ppm) 2.50 (s, 3H), 7.08-7.15 (m, 1H), 7.23-7.26 (m, 1H), 7.45-7.69 (m, 7H), 7.81(td, 1H), 7.88 (d, 1H), 8.56 (d, 1H), 8.59 (ddd, 1H), 9.40 (d, 1H), 11.95-12.07 (m, 1H).
ESI-Mass; 379 [M$^+$+H]

Example 364

3-(5-Methyl-1H-benzimidazol-2-yl)-5-(2-pyridyl)-1-phenyl-1,2-dihydropyridin-2-one $^1$H-NMR (400 MHz, CDCl$_3$); δ(ppm) 2.49 (s, 3H), 7.12(t, 1H), 7.24-7.27 (m, 1H), 7.31-7.72 (m, 7H), 7.80(td, 1H), 7.87 (d, 1H), 8.56 (d, 1H), 8.59 (ddd, 1H), 9.40 (d, 1H), 11.94-12.07 (m, 1H).
ESI-Mass; 379 [M$^+$+H]

Example 365

3-(2-Cyanophenyl)-5-[1-(1-benzylpiperidin-4-yl)benzimidazol-2-yl]-1-phenyl-1,2-dihydropyridin-2-one ¹H-NMR (400 MHz, CDCl₃); δ(ppm) 1.92 (dd, 2H), 2.36 (t, 2H), 2.75 (ddd, 2H), 3.05 (d, 2H), 3.62 (s, 2H), 4.58(tt, 1H), 7.26-7.41 (m, 7H), 7.44-7.51 (m, 2H), 7.52-7.56 (m, 4H), 7.65(td, 1H), 7.70 (dd, 1H), 7.72 (d, 1H), 7.73-7.81 (m, 3H), 8.01 (d, 1H).
ESI-Mass; 562 [M⁺+H]

Example 366

3-(2-Cyanophenyl)-5-(5-methoxy-1H-benzimidazol-2-yl)-1-phenyl-1,2-dihydropyridin-2-one ¹H-NMR (400 MHz, CDCl₃); δ(ppm) 3.83 (s, 3H), 6.85 (dd, 1H), 7.24-7.47 (m, 8H), 7.50 (d, 2H), 7.60 (dt, 1H), 8.15 (s, 1H), 8.16 (s, 1H).
ESI-Mass; 419 [M⁺+H]

Example 367

3-(1H-Imidazo[4,5-c]pyridin-2-yl)-5-(2-pyridyl)-1-phenyl-1,2-dihydropyridin-2-one ¹H-NMR (400 MHz, CDCl₃); δ(ppm) 7.19-7.28 (m, 1H), 7.48-7.63 (m, 4H), 7.69-7.90 (m, 2H), 8.08 (d, 1H), 8.12 (d, 1H), 8.16-8.22 (m, 1H), 8.34 (d, 1H), 8.59 (d, 1H), 8.58-8.62 (m, 1H), 9.44 (d, 1H), 12.20(brs, 1H).
ESI-Mass; 366 [M⁺+H]

Example 368

3-(2-Cyanophenyl)-5-[1-(pyridin-4-yl)benzimidazol-2-yl]-1-phenyl-1,2-dihydropyridin-2-one ¹H-NMR (400 MHz, CDCl₃); δ(ppm) 7.29-7.34 (m, 4H), 7.35-7.51 (m, 8H), 7.59(td, 1H), 7.69 (d, 1H), 7.73 (dd, 1H), 7.82 (d, 1H), 7.84 (dt, 1H), 8.91 (dd, 2H).
ESI-Mass; 466 [M⁺+H]

The following compounds were synthesized by the methods similar to, or in accordance with, the method for Example 183.

Example 369

3-(2-Chlorophenyl)-5-(5-trifluoromethylbenzothiazol-2-yl)-1-phenyl-1,2-dihydropyridin-2-one ¹H-NMR (400 MHz, CDCl₃); δ(ppm) 7.32-7.37 (m, 2H), 7.47-7.58 (m, 7H), 7.61 (ddd, 1H), 7.99 (d, 1H), 8.14 (d, 1H), 8.21-8.23 (m, 1H), 8.39 (d, 1H).
ESI-Mass; 483 [M⁺+H]

Example 370

3-(5-Trifluoromethylbenzothiazol-2-yl)-5-(2-pyridyl)-1-phenyl-1,2-dihydropyridin-2-one ¹H-NMR (400 MHz, CDCl₃); δ(ppm) 7.26-7.30 (m, 1H), 7.51-7.64 (m, 6H), 7.81-7.87 (m, 2H), 8.08 (d, 1H), 8.39 (s, 1H), 8.63 (d, 1H), 8.64(t, 1H), 9.50 (d, 1H).
ESI-Mass; 450 [M⁺+H]

Example 371

3-(2-Benzothiazolyl)-5-(2-pyridyl)-1-phenyl-1,2-dihydropyridin-2-one

¹H-NMR (400 MHz, CDCl₃); δ(ppm) 7.26-7.30 (m, 1H), 7.41(t, 1H), 7.50-7.60 (m, 6H), 7.84(t, 1H), 7.88-7.94 (m, 1H), 7.98 (d, 1H), 8.12 (d, 1H), 8.60-8.63 (m, 2H), 9.48-9.52 (m, 1H).
ESI-Mass; 382 [M⁺+H]

Example 372

5-(2-Benzothiazolyl)-3-[2-(2-benzothiazolyl)phenyl]-1-phenyl-1,2-dihydropyridin-2-one ¹H-NMR (400 MHz, CDCl₃); δ(ppm) 7.09-7.14 (m, 2H), 7.25-7.33 (m, 4H), 7.37(td, 1H), 7.42(td, 1H), 7.46-7.52 (m, 4H), 7.80 (ddt, 2H), 7.90 (ddt, 2H), 7.95 (d, 1H), 8.12 (d, 1H), 8.30 (d, 1H).
ESI-Mass; 514 [M⁺+H]

The following compounds were synthesized by the methods similar to, or in accordance with, the method for Example 184.

Example 373

5-(2-Benzoxazolyl)-3-[2-(2-benzoxazolyl)phenyl]-1-phenyl-1,2-dihydropyridin-2-one ¹H-NMR (400 MHz, CDCl₃); δ(ppm) 7.22-7.42 (m, 7H), 7.44-7.73 (m, 9H), 8.26 (d, 1H), 8.34 (d, 1H), 8.48 (d, 1H).
ESI-Mass; 482 [M⁺+H]

Example 374

3-(2-Benzoxazolyl)-5-(2-pyridyl)-1-phenyl-1,2-dihydropyridin-2-one

¹H-NMR (400 MHz, CDCl₃); δ(ppm) 7.22-7.28 (m, 1H), 7.29-7.32 (m, 2H), 7.42-7.46 (m, 2H), 7.48-7.50 (m, 3H), 7.54-7.58 (m, 1H), 7.70-7.80 (m, 3H), 8.55-8.60 (m, 2H), 9.03 (d, 1H).
ESI-Mass; 366 [M⁺+H]

Example 375

3-(2-Chlorophenyl)-5-(5-chlorobenzoxazol-2-yl)-1-phenyl-1,2-dihydropyridin-2-one ¹H-NMR (400 MHz, CDCl₃); δ(ppm) 7.27-7.35 (m, 3H), 7.41-7.51 (m, 4H), 7.52-7.57 (m, 4H), 7.67 (d, 1H), 8.25 (d, 1H), 8.49 (d, 1H).
ESI-Mass; 433 [M⁺+H]

Example 376

3-(5-Chlorobenzoxazol-2-yl)-5-(2-pyridyl)-1-phenyl-1,2-dihydropyridin-2-one

¹H-NMR (400 MHz, CDCl₃); δ(ppm) 7.26 (ddd, 1H), 7.33 (dd, 1H), 7.47-7.58 (m, 6H), 7.72 (dt, 1H), 7.79 (d, 1H), 7.79(td, 1H), 8.55 (d, 1H), 8.62 (ddd, 1H), 9.12 (d, 1H).
ESI-Mass; 340 [M⁺+H]

The following compounds were synthesized by the methods similar to, or in accordance with, the method for Example 315.

Example 377

3-[1-(Piperidin-4-yl)benzimidazol-2-yl]-5-(2-pyridyl)-1-phenyl-1,2-dihydropyridin-2-one $^1$H-NMR (400 MHz, CDCl$_3$); δ(ppm) 2.01-2.15 (m, 2H), 2.42-2.52 (m, 2H), 2.66-2.84 (m, 2H), 3.20-3.30 (m, 2H), 4.21-4.40 (m, 1H), 7.19-7.83 (m, 12H), 8.49 (d, 1H), 8.52 (d, 1H), 8.56-8.59 (m, 1H).

ESI-Mass; 448 [M$^+$+H]

Example 378

(378A) 3-(2-Cyanophenyl)-5-[1-(piperidin-4-yl) benzimidazol-2-yl-1-phenyl-1,2-dihydropyridin-2-one (378B) 3-(2-Cyanophenyl)-5-[1-(1-methylpiperidin-4-yl]benzimidazol-2-yl]-1-phenyl-1,2-dihydropyridin-2-one (378A)
$^1$H-NMR (400 MHz, CDCl$_3$); δ(ppm) 1.90-2.02 (m, 2H), 2.65 (ddd, 2H), 3.01(t, 2H), 3.28 (d, 2H), 4.69(tt, 1H), 7.27-7.29 (m, 2H), 7.47-7.55 (m, 6H), 7.67(td, 1H), 7.71 (d, 1H), 7.67-7.83 (m, 4H), 8.05 (d, 1H).

ESI-Mass; 472 [M$^+$+H]

(378B)
$^1$H-NMR (400 MHz, CDCl$_3$); δ(ppm) 1.90-2.00 (m, 2H), 2.35-2.40 (m, 2H), 2.41 (s, 3H), 2.73-2.87 (m, 2H), 3.00-3.10 (m, 2H), 4.51-4.62 (m, 1H), 7.26-7.30 (m, 2H), 7.44-7.54 (m, 6H), 7.65(td, 1H), 7.70-7.83 (m, 5H), 8.03 (d, 1H).

ESI-Mass; 486 [M$^+$+H]

Example 379

(379A) 3-(2-Cyanophenyl)-5-(2-pyridyl)-1-(piperidin-3-yl)-1,2-dihydropyridin-2-one (379B) 3-(2-Cyanophenyl)-5-(2-pyridyl)-1-(N-benzylpiperidin-3-yl)-1,2-dihydropyridin-2-one (379A)
$^1$H-NMR (400 MHz, CDCl$_3$); δ(ppm) 1.90-2.05 (m, 2H), 2.13-2.22 (m, 1H), 2.35-2.44 (m, 1H), 2.70(td, 1H), 3.05-3.12 (m, 1H), 3.37 (d, 1H), 3.60-3.72 (m, 1H), 4.97-5.05 (m, 1H), 7.21 (ddd, 1H), 7.45(td, 1H), 7.57 (d, 1H), 7.64(td, 1H), 7.68-7.78 (m, 3H), 8.13 (d, 1H), 8.48 (d, 1H), 8.62 (ddd, 1H).

ESI-Mass; 357 [M$^+$+H]

(379B)
$^1$H-NMR (400 MHz, CDCl$_3$); δ(ppm) 1.65-1.75 (m, 2H), 1.92-2.05 (m, 2H), 2.45-2.60 (m, 2H), 2.70-2.80 (m, 1H), 2.97 (dd, 1H), 3.55 (s, 2H), 5.15-5.20 (m, 1H), 7.22 (ddd, 1H), 7.27-7.32 (m, 1H), 7.40-7.49 (m, 4H), 7.52-7.58 (m, 2H), 7.61-7.77 (m, 5H), 8.15 (d, 1H), 8.65 (ddd, 1H).

ESI-Mass; 447 [M$^+$+H]

Example 380

3-(2-Cyanophenyl)-5-(N-methylpiperidin-2-yl)-1-phenyl-1,2-dihydropyridin-2-one $^1$H-NMR (400 MHz, CDCl$_3$); δ(ppm) 1.24-1.39 (m, 2H), 1.73-1.85 (m, 2H), 2.04-2.14 (m, 3H), 2.16 (s, 3H), 2.63 (dd, 1H), 3.00 (d, 1H), 7.37-7.56 (m, 5H), 7.59(td, 1H), 7.64-7.70 (m, 2H), 7.72-7.74 (m, 1H), 7.74-7.76 (m, 2H).

ESI-Mass; 370 [M$^+$+H]

The following compound was synthesized by the method similar to the method for Example 7.

Example 381

3-(2-Cyanophenyl)-5-(2-pyridyl)-1-(3-nitro-4-methylphenyl)-1,2-dihydropyridin-2-one $^1$H-NMR (400 MHz, CDCl$_3$); δ(ppm) 2.69 (s, 3H), 7.23-7.28 (m, 1H), 7.48(td, 1H), 7.51-7.56 (m, 1H), 7.62 (d, 1H), 7.66(t, 1H), 7.74-7.81 (m, 4H), 8.21 (d, 1H), 8.30 (d, 1H), 8.32 (d, 1H), 8.61 (d, 1H).

Example 382

(382A) 3-(4-Chlorobenzenesulfinyl)-5-(2-pyridyl)-1-phenyl-1,2-dihydropyridin-2-one (382B) 3-(4-Chlorobenzenesulfonyl)-5-(2-pyridyl)-1-phenyl-1,2-dihydropyridin-2-one 6 mg of 3-(4-chlorophenylthio)-5-(2-pyridyl)-1-phenyl-1,2-dihydropyridin-2-one was dissolved in 3 ml of dichloromethane. Under ice-cooling, 3 mg of m-chloroperbenzoic acid was added thereto, followed by stirring at the same temperature for 30 minutes. After stirring at room temperature for 5 hours, the mixture was diluted with 10 ml of ethyl acetate, and washed with a 1N aqueous solution of sodium hydroxide. The organic layer was washed with brine, and then dried over anhydrous magnesium sulfate. The solvent was evaporated, and the residue was purified by silica gel chromatography (hexane/ethyl acetate system), to give 1.2 mg of 3-(4-chlorobenzenesulfinyl)-5-(2-pyridyl)-1-phenyl-1,2-dihydropyridin-2-one and 1.5 mg of 3-(4-chlorobenzenesulfonyl)-5-(2-pyridyl)-1-phenyl-1,2-dihydropyridin-2-one as the title compounds.

(382A)
$^1$H-NMR (400 MHz, CDCl$_3$); δ(ppm) 7.23-7.29 (m, 2H), 7.37-7.54 (m, 6H), 7.72 (dt, 1H), 7.79(td, 1H), 7.87(t, 1H), 7.89(t, 1H), 8.44 (d, 1H), 8.57-8.60 (m, 1H), 8.69 (d, 1H).

ESI-Mass; 407 [M$^+$+H]

(382B)
$^1$H-NMR (400 MHz, CDCl$_3$); δ(ppm) 7.22-7.30 (m, 2H), 7.37-7.40 (m, 2H), 7.42-7.52 (m, 4H), 7.67 (dt, 1H), 7.80(td, 1H), 8.09(t, 1H), 8.11(t, 1H), 8.58 (d, 1H), 8.60 (ddd, 1H), 9.06 (d, 1H).

ESI-Mass; 423 [M$^+$+H]

The following compounds were synthesized by the methods similar to, or in accordance with, the method for Example 382.

Example 383

(383A) 3-(2-Ethylsulfinylpyridin-5-yl)-5-(2-pyridyl)-1-phenyl-1,2-dihydropyridin-2-one (383B) 3-(2-Ethylsulfonylpyridin-5-yl)-5-(2-pyridyl)-1-phenyl-1,2-dihydropyridin-2-one (383A)
$^1$H-NMR (400 MHz, CDCl$_3$); δ(ppm) 1.24(t, 3H), 2.96 (dt, 1H), 3.21 (dt, 1H), 7.23-7.27 (m, 1H), 7.48-7.58 (m, 5H), 7.60 (d, 1H), 7.77(td, 1H), 8.03 (d, 1H), 8.28 (d, 1H), 8.38 (d, 1H), 8.44 (dd, 1H), 8.64 (ddd, 1H), 9.04 (d, 1H).
ESI-Mass; 402 [M$^+$+H]

(383B)
$^1$H-NMR (400 MHz, CDCl$_3$); δ(ppm) 1.33(t, 3H), 3.44(q, 2H), 7.25-7.28 (m, 1H), 7.49-7.62 (m, 6H), 7.78 (dd, 1H), 8.14 (d, 1H), 8.31 (d, 1H), 8.41 (d, 1H), 8.51 (dd, 1H), 8.64 (ddd, 1H), 9.13 (d, 1H).
ESI-Mass; 418 [M$^+$+H]

Example 384

3-(2-Ethylpyridin-5-yl)-5-(2-pyridyl)-1,2-phenyl-1,2-dihydropyridin-2-one 13 mg of 3-(2-chloropyridin-5-yl)-5-(2-pyridyl)-1-phenyl-1,2-dihydropyridin-2-one was dissolved in 20 ml of dimethylformamide, followed by the addition of 10 mg of potassium carbonate and 2 mg of tetrakistriphenylphosphine palladium. Under stirring at room temperature in nitrogen atmosphere, triethylborane (1.0M tetrahydrofuran solution) was added dropwise thereinto, followed by heating under stirring at 100° C. for 1 hour in nitrogen atmosphere. After the reaction mixture was cooled to room temperature, water was added thereto, and extracted with ethyl acetate. The organic layer was washed with brine, and then dried over anhydrous magnesium sulfate. The solvent was evaporated, and the residue was purified by silica gel chromatography (hexane/ethyl acetate system), to give 4 mg of the title compound.
$^1$H-NMR (400 MHz, CDCl$_3$); δ(ppm) 1.33(t, 3H), 2.87(q, 2H), 7.20-7.24 (m, 2H), 7.44-7.60 (m, 5H), 7.64-7.70 (m, 1H), 7.75(td, 1H), 8.18 (dd, 1H), 8.25 (d, 1H), 8.26 (d, 1H), 8.60-8.62 (m, 1H), 8.84 (d, 1H).

Example 385

3-(2-Chlorophenyl)-5-(4-chlorophenylthio)-1-(3-pyridyl)-1,2-dihydropyridin-2-one The title compound was synthesized by the method similar to the method for Example 188.
$^1$H-NMR (400 MHz, CDCl$_3$); δ(ppm) 7.23-7.50 (m, 8H), 7.52 (d, 1H), 7.55-7.58 (m, 1H), 7.72 (d, 1H), 7.86-7.93 (m, 1H), 8.66-8.76 (m, 2H).

Example 386

3-(2-Cyanophenyl)-5-(1H-benzimidazol-2-yl)-1-phenyl-1,2-dihydropyridin-2-one

The above compound was synthesized by the method similar to the method for Example 190.
$^1$H-NMR (400 MHz, CDCl$_3$); δ(ppm) 7.22-7.28 (m, 2H), 7.32-7.50 (m, 7H), 7.54-7.76 (m, 4H), 8.20-8.21 (m, 1H), 8.28-8.34 (m, 1H).
ESI-Mass; 389 [M$^+$+H]

Example 387

3-(2-Adamantyl)-5-(2-pyridyl)-1-phenyl-1,2-dihydropyridin-2-one

The above compound was synthesized by the method similar to the method for Example 178.
$^1$H-NMR (400 MHz, CDCl$_3$); δ(ppm) 1.21-2.06 (m, 12H), 2.48 (s, 2H), 3.25 (s, 1H), 7.18 (ddd, 1H), 7.33-7.52 (m, 5H), 7.54 (d, 1H), 7.72(td, 1H), 8.09 (d, 1H), 8.11-8.13 (m, 1H), 8.60 (ddd, 1H).

Example 388

3-(2-Cyanophenyl)-5-(4-methyl-imidazo[4,5-b]pyridin-2-yl)-1-phenyl-1,2-dihydropyridin-2-one 3 mg of 3-(2-cyanophenyl)-5-(1H-imidazo[4,5-c]pyridin-2-yl)-1-phenyl-1,2-dihydropyridin-2-one was dissolved in 3 ml of acetone. To the mixture was added 2 ml of methyl iodide, followed by stirring at room temperature overnight. The mixture was evaporated, and the residue was diluted with 1 ml of water. To the mixture was added 20 mg of sodium hydroxide, followed by stirring at room temperature for 4 hours. The reaction solution was extracted with ethyl acetate. The organic layer was washed with water and brine, dried over anhydrous magnesium sulfate, and filtered. The filtrate was evaporated, and the residue was purified by silica gel chromatography (NH silica) (hexane/ethyl acetate system), to give 2 mg of the title compound.
$^1$H-NMR (400 MHz, CDCl$_3$); δ(ppm) 4.31 (s, 3H), 7.07 (dd, 1H), 7.43-7.61 (m, 7H), 7.64(td, 1H), 7.72 (dd, 1H), 7.76 (dd, 1H), 8.09 (d, 1H), 8.71 (d, 1H), 8.73 (d, 1H).
ESI-Mass; 404 [M$^+$+H]

Example 389

3-(2-Cyanophenyl)-1-phenyl-5-(3-phenyl-1,2,4-oxadiazol-5-yl)-1,2-dihydropyridin-2-one 31 mg of carboxylic acid, obtained by hydrolyzing 3-(2-cyanophenyl)-5-(methoxycarbonyl)-1-phenyl-1,2-dihydropyridin-2-one was dissolved in 20 ml of dichloromethane, followed by the dropwise addition of a solution of 20 mg of oxalyl chloride in dichloromethane under ice-cooling. A catalytic amount of dimethylformamide was added thereto, followed by stirring at room temperature for 1 hour in nitrogen atmosphere. The reaction solution was evaporated, and the residue was dissolved in dichloromethane. The mixture was added dropwise into a solution of 16 mg of benzamidoxime and 0.05 ml of triethylamine in toluene, under ice-cooling. After heating to room temperature, it was stirred in nitrogen atmosphere overnight. It was heated to 100° C. for 1 hour, cooled to room temperature, and then washed with water. The organic layer was washed with brine, and then dried over anhydrous magnesium sulfate. The solvent was evaporated, and 28 mg of the residue was dissolved in 10 ml of toluene, followed by heating under reflux for 5 hours. After cooling to room temperature, the solvent was evaporated, to give 24 mg of the title compound as white crystals.

¹H-NMR (400 MHz, CDCl₃); δ(ppm) 7.40-7.66 (m, 9H), 7.68 (dd, 2H), 7.80 (dd, 1H), 8.12 (dd, 2H), 8.32 (dd, 1H), 8.52 (dd, 1H).

Example 390

3-(3-Phenyl-1,2,4-oxadiazol-5-yl)-1-phenyl-5-(2-pyridyl)-1,2-dihydropyridin-2-one The above compound was synthesized by the method similar to the method for Example 389.

¹H-NMR (400 MHz, CDCl₃); δ(ppm) 7.25-7.29 (m, 2H), 7.46-7.59 (m, 7H), 7.70 (d, 1H), 7.81(td, 1H), 8.20-8.23 (m, 2H), 8.59 (d, 1H), 8.63 (ddd, 1H), 9.14 (d, 1H).

Example 391

3-(2-Cyanothiophen-3-yl)-5-(2-pyridyl)-1-phenyl-1,2-dihydropyridin-2-one 22 mg of 3-(2-formylthiophen-3-yl)-5-(2-pyridyl)-1-phenyl-1,2-dihydropyridin-2-one was dissolved in 20 ml of ethanol. To the mixture were added 6.4 mg of hydroxylamine hydrochloride and 10.1 mg of sodium acetate, followed by heating at 80° C. for 3 hours. After cooling the reaction mixture to room temperature, it was poured into a saturated aqueous solution of sodium hydrogen carbonate, followed by extracting with ethyl acetate. The organic layer was washed with brine, and then dried over anhydrous magnesium sulfate. The solvent was evaporated, and the resulting residue (25 mg) obtained as an oxime compound was dissolved in 10 ml of dimethylformamide, followed by adding 0.02 ml of triethylamine. Under ice-cooling, 43 mg of 1,1'-carbonyldiimidazole was added thereto, followed by stirring at 60° C. for 1 hour. Then, it was cooled to room temperature, water was added thereto, and the mixture was extracted with ethyl acetate. The organic layer was washed with brine, and then dried over anhydrous magnesium sulfate. The solvent was evaporated, and the residue was purified by silica gel chromatography (hexane/ethyl acetate system), to give 15 mg of the title compound as white crystals.

¹H-NMR (400 MHz, CDCl₃); δ(ppm) 7.23 (ddd, 1H), 7.46-7.58 (m, 5H), 7.59 (d, 1H), 7.65 (d, 1H), 7.77(td, 1H), 7.78 (d, 1H), 8.38 (d, 1H), 8.57 (d, 1H), 8.59 (ddd, 1H).

ESI-Mass; 356 [M⁺+H]

Example 392

3-[2-(5-Oxazolyl)phenyl]-1-phenyl-5-(2-pyridyl)-1,2-dihydropyridin-2-one 13 mg of 3-(2-formylphenyl)-5-(2-pyridyl)-1-phenyl-1,2-dihydropyridin-2-one was dissolved in 10 ml of methanol. To the mixture were added 11 mg of tosylmethylisocyanide and 8 mg of potassium carbonate, followed by heating under reflux overnight. After the reaction solution was cooled to room temperature, water was added, and the mixture was extracted with ethyl acetate. The organic layer was washed with water and brine, and then dried over anhydrous magnesium sulfate. It was filtered through NH silica gel and silica gel, and the filtrate was evaporated. The resulting precipitates were washed with ether and dried, to give 9 mg of the title compound.

¹H-NMR (400 MHz, CDCl₃); δ(ppm) 6.98 (s, 1H), 7.20 (ddd, 1H), 7.36-7.51 (m, 7H), 7.54 (dt, 2H), 7.72 (ddd, 2H), 7.84 (s, 1H), 8.11 (d, 1H), 8.30 (d, 1H), 8.59 (ddd, 1H).

Example 393

3-[2-(5-Oxazolyl)thiophen-3-yl]-1-phenyl-5-(2-pyridyl)-1,2-dihydropyridin-2-one

The title compound was synthesized by the method similar to the method for Example 392.

¹H-NMR (400 MHz, CDCl₃); δ(ppm) 7.14 (s, 1H), 7.16-7.76 (m, 10H), 7.82 (s, 1H), 8.16 (d, 1H), 8.29 (d, 1H), 8.58 (d, 1H).

Example 394

3-(2-Cyanophenyl)-5-(2-pyridinecarbonyl)-1-phenyl-1,2-dihydropyridin-2-one (394a) α-(2-Methoxypyridin-5-yl)-2-pyridinemethanol 50 ml of a tetrahydrofuran solution containing 3.00 g of 2-methoxy-5-bromopyridine was cooled to −78° C., followed by the dropwise addition of 10 ml of n-butyl lithium (1.6M hexane solution). After the completion of the dropwise addition, 1.70 g of picoline aldehyde was immediately added thereto, followed by stirring at −78° C. for 1 hour, to return the mixture slowly to room temperature. To the mixture was added a saturated aqueous solution of ammonium chloride, and then it was extracted with ethyl acetate. The ethyl acetate layer was washed with water and brine, and then dried over magnesium sulfate. The solvent was evaporated, and the resulting residue was purified by silica gel chromatography (ethyl acetate), to give 1.53 g of the title compound as a pale yellow solid.

¹H-NMR (400 MHz, CDCl₃); δ(ppm) 3.93 (s, 3H), 5.87 (brs, 1H), 6.72 (d, 1H), 7.24 (d, 1H), 7.31-7.36 (m, 1H), 7.55-7.59 (m, 1H), 7.74-7.80 (m, 1H), 8.21 (d, 1H), 8.62 (d, 1H).

(394b) 5-(2-Pyridinecarbonyl)-2-methoxypyridine

To a solution of 0.83 g of α-(2-methoxypyridin-5-yl)-2-pyridinemethanol in 20 ml of an acetone was added 1.70 g of activated manganese dioxide, followed by vigorously stirring at room temperature for 30 minutes. The resulting precipitates were filtered off and washed with acetone. Then, the filtrate was concentrated, to give 0.80 g of the title compound as a white solid.

¹H-NMR (400 MHz, CDCl₃); δ(ppm) 4.04 (s, 3H), 6.84 (dd, 1H), 7.48-7.54 (m, 1H), 7.89-7.95 (m, 1H), 8.09 (d, 1H), 8.36-8.40 (m, 1H), 8.70-8.74 (m, 1H), 9.09 (d, 1H).

(394c) 5-(2-Pyridinecarbonyl)-1,2-dihydropyridin-2(1H)-one 0.79 g of 5-(2-pyridinecarbonyl)-2-methoxypyridine was dissolved in 5.0 ml of 48% hydrobromic acid, and the mixture was stirred at 70° C. for 30 minutes. It was ice-cooled, diluted with water and neutralized with potassium carbonate. The resulting precipitates were collected by filtration, washed with water and hexane, and dried, to give 0.51 g of the title compound as a white powder.

¹H-NMR (400 MHz, DMSO-d₆); δ(ppm) 6.45 (d, 1H), 7.65-7.70 (m, 1H), 7.95-8.00 (m, 1H), 8.05-8.20 (m, 2H), 8.68-8.75 (m, 2H), 12.17(brs, 1H).

(394d) 5-(2-Pyridinecarbonyl)-3-bromo-1,2-dihydropyridin-2(1H)-one

To a solution of 0.23 g of 5-(2-pyridinecarbonyl)-1,2-dihydropyridin-2(1H)-one in 2.0 ml of dimethylformamide was added 0.21 g of N-bromosuccinimide at room temperature, followed by stirring for 1 hour. The mixture was diluted with water, and the resulting precipitates were collected by filtration, washed with water and dried, to give 0.26 g of the title compound as a pale yellow powder.

$^1$H-NMR (400 MHz, DMSO-d$_6$); δ(ppm) 7.67-7.71 (m, 1H), 7.99-8.03 (m, 1H), 8.04-8.08 (m, 1H), 8.47 (d, 1H), 8.73-8.75 (m, 1H), 8.79(brs, 1H), 12.72(brs, 1H).

(394e) 5-(2-Pyridinecarbonyl)-1-phenyl-3-bromo-1,2-dihydropyridin-2-one

A suspension of 0.24 g of 5-(2-pyridinecarbonyl)-3-bromo-1,2-dihydropyridin-2(1H)-one, 0.23 g of phenylboronic acid, 0.30 g of copper acetate and 1 ml of triethylamine in 10 ml of tetrahydrofuran was stirred at room temperature overnight. To the mixture were added concentrated aqueous ammonium (3 ml), water (30 ml) and ethyl acetate (100 ml), to separate the organic layer. It was washed with water and brine, and then dried over magnesium sulfate. The solvent was evaporated, and the residue was purified by silica gel chromatography (ethyl acetate/hexane), to give 0.21 g of the title compound as a white powder.

$^1$H-NMR (400 MHz, DMSO-d$_6$); δ(ppm) 7.50-7.60 (m, 5H), 7.64-7.68 (m, 1H), 8.02-8.09 (m, 1H), 8.57 (d, 1H), 8.66-8.70 (m, 1H), 9.00 (d, 1H).

(394f) 3-(2-Cyanophenyl)-5-(2-pyridinecarbonyl)-1-phenyl-1,2-dihydropyridin-2-one To a mixed liquid of 200 mg of 5-(2-pyridinecarbonyl)-1-phenyl-3-bromo-1,2-dihydropyridin-2-one, 130 mg of 2-(2-cyanophenyl)-1,3,2-dioxaborinate, 400 mg of cesium carbonate and 6 ml of dimethylformamide was added 60 mg of tetrakistriphenylphosphine palladium, followed by stirring at 130° C. for 5 hours in nitrogen atmosphere. After cooling to room temperature, ethyl acetate was added thereto. The extract was washed with water and brine, and dried over magnesium sulfate. The solvent was evaporated, and the residue was purified by silica gel chromatography (ethyl acetate/hexane), to give 45 mg of the title compound as a pale yellow powder.

$^1$H-NMR (400 MHz, CDCl$_3$); δ(ppm) 7.40-7.58 (m, 8H), 7.62-7.68 (m, 1H), 7.75-7.78 (m, 1H), 7.89-7.94 (m, 1H), 8.11-8.15 (m, 1H), 8.47 (d, 1H), 8.65-8.68 (m, 1H), 9.16 (d, 1H).

Example 395

5-(2-Pyridinecarbonyl)-1-phenyl-3-phenyl-1,2-dihydropyridin-2-one

A mixed liquid of 10 mg of 5-(2-pyridinecarbonyl)-1-phenyl-3-bromo-1,2-dihydropyridin-2-one, 10 mg of phenylboronic acid, 40 mg of cesium carbonate, 6 mg of tetrakistriphenylphosphine palladium and 1 ml of dimethylformamide was stirred at 130° C. for 2 hours in nitrogen atmosphere. After cooling to room temperature, ethyl acetate was added thereto. The extract was washed with water and brine, and dried over magnesium sulfate. The solvent was evaporated, and the residue was purified by silica gel chromatography (ethyl acetate/hexane), to give 6 mg of the title compound as a pale yellow powder.

$^1$H-NMR (400 MHz, CDCl$_3$); δ(ppm) 7.32-7.58 (m, 8H), 7.75-7.79 (m, 2H), 7.88-7.94 (m, 1H), 8.09-8.13 (m, 1H), 8.42 (d, 1H), 8.63-8.66 (m, 1H), 9.01 (d, 1H).

Example 396

3-(2-Cyanophenyl)-5-(α-hydroxy-2-picolyl)-1-phenyl-1,2-dihydropyridin-2-one To a solution of 25 mg of 3-(2-cyanophenyl)-5-(2-pyridinecarbonyl)-1-phenyl-1,2-dihydropyridin-2-one in 5 ml of methanol was added 2 mg of sodium borohydride under ice-cooling. After 30 minutes, the mixture was diluted with a saturated aqueous solution of sodium hydrogen carbonate, followed by extraction with ethyl acetate. The ethyl acetate layer was washed with water and brine, and dried over magnesium sulfate. The solvent was evaporated, and the residue was purified by silica gel chromatography (ethyl acetate), to give 15 mg of the title compound as a pale yellow powder.

$^1$H-NMR (400 MHz, CDCl$_3$); δ(ppm) 5.72 (brs, 1H), 7.32-7.72 (m, 13H), 7.80-7.92 (m, 1H), 8.57-8.65 (m, 1H).

Example 397

3-(2-Cyanophenyl)-5-(2-pyridin-2-yl-vinyl)-1-phenyl-1,2-dihydropyridin-2-one A mixed liquid of 100 mg of 3-(2-cyanophenyl)-1-phenyl-5-bromo-1,2-dihydropyridin-2-one, 100 mg of 2-vinylpyridine, 6 mg of palladium acetate, 17 mg of tri-(o-tolyl)phosphine and 3 ml of triethylamine was stirred at 130° C. for 2 hours in nitrogen atmosphere. After cooling to room temperature, ethyl acetate was added thereto. The extract was washed with water and brine, and dried over magnesium sulfate. The solvent was evaporated, and the residue was purified by silica gel chromatography (ethyl acetate/hexane), to give 16 mg of the title compound as a white powder.

$^1$H-NMR (400 MHz, CDCl$_3$); δ(ppm) 6.95-7.00 (m, 1H), 7.16-7.21 (m, 1H), 7.26-7.35 (m, 1H), 7.44-7.60 (m, 7H), 7.62-7.81 (m, 5H), 8.03 (d, 1H), 8.57-8.61 (m, 1H).

Example 398

3-(2-Ethoxycarbonylvinylthiophen-3-yl)-5-(2-pyridyl)-1-phenyl-1,2-dihydropyridin-2-one To a solution of 7.5 mg of ethyl diethylphosphonoacetate in tetrahydrofuran was added 1.3 mg of sodium hydride in nitrogen atmosphere under ice-cooling, followed by the dropwise addition of a solution of 10 mg of 3-(2-formylthiophen-3-yl)-5-(2-pyridyl)-1-phenyl-1,2-dihydropyridin-2-one in tetrahydrofuran. After stirring the mixture at room temperature for 1 hour in nitrogen atmosphere, water was added thereto. Then, it was extracted with ethyl acetate. The organic layer was washed with brine, and then dried over anhydrous magnesium sulfate. The solvent was evaporated, and the residue was purified by silica gel chromatography (hexane/ethyl acetate system), to give 4 mg of the title compound.

$^1$H-NMR (400 MHz, CDCl$_3$); δ(ppm) 1.28(t, 3H), 4.21(q, 2H), 6.34 (d, 1H), 7.19-7.23 (m, 2H), 7.34-7.41 (m, 2H), 7.43-7.56 (m, 5H), 7.74(td, 1H), 7.88 (d, 1H), 8.00 (d, 1H), 8.30 (d, 1H), 8.58-8.60 (m, 1H).

ESI-Mass; 429 [M$^+$+H]

Example 399

5-Bromo-2-methoxypyridine

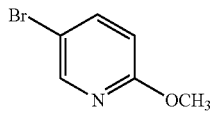

2,5-Dibromopyridine (200 g) and 28% sodium methoxide methanol solution (1535 g) were heated under reflux for 30 minutes, followed by cooling to room temperature. The mixture was partitioned between water (1.6 L) and tert-butylmethyl ether (1.6 L). The resulting organic layer was washed with brine (1 L) for 3 times, and then dried over anhydrous magnesium sulfate overnight. The dried organic layer was evaporated at 65° C., to give 160 g (96%) of the title compound as a brown oil.

$^1$H-NMR (400 MHz, CDCl$_3$); δ(ppm) 3.91 (3H, s), 6.66 (1H, d), 7.64 (1H, dd), 8.20 (1H, d). MS: MH$^+$ 188, 190

Example 400

6-Methoxy-3-pyridylboronic acid

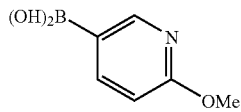

5-Bromo-2-methoxypyridine (152 g) was dissolved in tetrahydrofuran anhydride (1520 mL) under stirring in nitrogen atmosphere, followed by cooling to −75.1° C. as bulk temperature. Under cooling and stirring, 380 mL of a 2.46 mol/L butyl lithium solution was added dropwise thereinto, followed by the dropwise addition of 192 mL of trimethoxyborane. The cooling bath was removed 30 minutes after completion of the dropwise addition, and the mixture was stirred at room temperature overnight. On the next day, 1.5 L of a 2 mol/L aqueous solution of hydrochloric acid, was added thereto, followed by stirring for 1.5 hours. Then, it was neutralized with 460 mL of a 5 mol/L aqueous solution of sodium hydroxide. It was then extracted with 1 L of ethyl acetate, and the resulting aqueous layer was extracted again with 1 L of ethyl acetate. The combined organic layer was washed twice with 1 L of 10% saline water, dried over anhydrous magnesium sulfate, and then evaporated, to give 105 g (88%) of the title compound as a slightly yellowish white solid.

$^1$H-NMR (CDCl$_3$, 400 MHz): 3.83(3H, s), 6.74(1H, d), 7.98 (1H, dd), 8.10 (2H, s), 8.50 (1H, s).

Example 401

2-Methoxy-5-(pyridin-2-yl)-pyridine

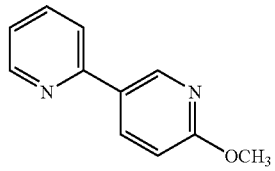

6-Methoxy-3-pyridylboronic acid (105 g), 2-bromopyridine (90 g), palladium acetate (3.21 g), triphenylphosphine (15 g), potassium carbonate (237 g), 1,2-dimethoxyethane (900 mL) and water (900 mL) were heated under reflux for 5 hours and 40 minutes under stirring. After cooling the reaction solution, ethyl acetate (1 L) was added thereto to extract. The organic layer was washed with 1 L of 10% aqueous solution of ammonium chloride, 1 L of 10% aqueous ammonia and 1 L of 10% saline, and then evaporated, to give 126 g (87%) of the title compound.

$^1$H-NMR (CDCl$_3$, 400 MHz): 4.00(3H, s), 6.85(1H, d), 7.21-7.26(1H, m), 7.67(1H, d), 7.75(1H, dt), 8.25(1H, dd), 8.66-8.70(1H, m), 8.74(1H, d). MS: MH$^+$ 187

Example 402

5-(Pyridin-2-yl)-2(1H)-pyridone

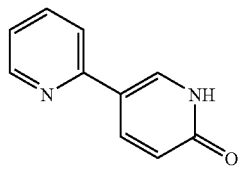

A mixture of 2-methoxy-5-(pyridin-2-yl)-pyridine (550 g) and a 4 mol/L aqueous solution of hydrochloric acid (2.4 L) was heated under reflux for 3 hours. After cooling the reaction solution, and washed with tert-butylmethyl ether (2.2 L). To the aqueous layer was added 8 mol/L aqueous solution of sodium hydroxide (1.1 L) under cooling with ice-water, and then the mixture was washed twice with tert-butylmethyl ether (2.2 L). Then, it was adjusted to pH 8 with concentrated hydrochloric acid (310 ml) and 8 mol/L aqueous solution of sodium hydroxide (100 ml), followed by partitioning between 1-butanol (4.5 L) and brine (1.8 L). The aqueous layer was extracted again with 1-butanol (4.5 L), and the combined organic layer was evaporated at 45-50° C. To the resulting residue was added tert-butylmethyl ether (2.2 L), to give crystals. The resulting crystals were collected by filtration under reduced pressure and air-dried at 60° C. Then, water (1.6 L) was added thereto to dissolve under heating. Then the mixture was water-cooled, and recrystallized. The resulting crystals were collected by filtration under reduced pressure and air-dried at 60° C., to give 188 g (66%) of the title compound as grayish white crystals.

¹H-NMR (DMSO-d₆, 400 MHz): 6.42 (1H, d), 7.19-7.26 (1H, m), 7.74-7.81 (2H, m), 8.11 (1H, d), 8.17 (1H, dd), 8.52-8.55 (1H, m). MS: MH⁺ 173

Example 403

1-Phenyl-5-(pyridin-2-yl)-2(1H)-pyridone

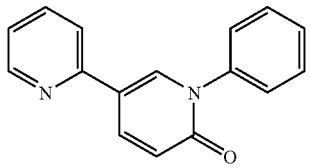

While stirring 5-(pyridin-2-yl)-2(1H)-pyridone (185 g), phenylboronic acid (261 g), copper acetate (19.4 g), pyridine (173 ml) and dimethylformamide (1480 ml) at room temperature, air was blown at 2.0 L/minute therein, to initiate the reactions. Since 26% of the reactant remained unreacted 7 hours after the initiation of the reaction, flow of air was stopped to suspend the reactions. On the next day, air was blown into the solution to restart the reactions, and the reactant was consumed to 0.57% of the initial weight in 5.5 hours. The reaction solution was poured into ice-cooled 10% aqueous ammonia (7.5 L), to give precipitates. The resulting precipitates were collected by filtration under reduced pressure, and washed with water (3 L). The resulting crystals were suspended into 10% aqueous ammonia (3.6 L) under stirring at room temperature for 1 hour. Then the crystals were collected by filtration under reduced pressure, and washed with water (2 L). The resulting crystals were air-dried overnight, to give 187 g (68%) of the title compound as brown crystals.

¹H-NMR (CDCl₃, 400 MHz): 6.77(1H, d), 7.19(1H, dd), 7.42-7.48(3H, m), 7.49-7.55 (3H, m), 7.72 (1H, dt), 8.04 (1H, dd), 8.21 (1H, d), 8.57-8.59 (1H, m). MS: MH⁺ 249

Example 404

3-Bromo-1-phenyl-5-(pyridin-2-yl)-2(1H)-pyridone

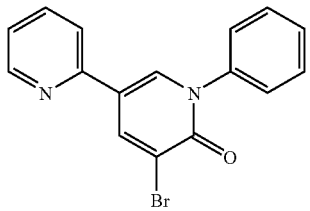

1-Phenyl-5-(pyridin-2-yl)-2(1H)-pyridone (186 g), N-bromosuccinimide (141.7 g) and N,N-dimethylformamide (900 ml) were stirred at room temperature. After 2.5 hr, 6.45 g of N-bromosuccinimide was added thereto. After depletion of the reactant was confirmed, the reaction solution was poured into water (4.5 L) under ice-cooling, followed by stirring in a cold-room (approximately 4° C.) overnight. The resulting crystals were collected by filtration under reduced pressure, followed by dissolving in isopropanol (3.25 L) and water (650 ml) under heating. After the complete dissolution was confirmed, the solution was left to cool gradually, and then ice-cooled. Then, the mixture was stirred in a cold-room overnight. The resulting crystals were collected by filtration under reduced pressure and air-dried at 60° C., to give 191 g (81%) of the title compound.

¹H-NMR (CDCl₃, 400 MHz): 7.19-7.24 (1H, m), 7.42-5.56 (6H, m), 7.74 (1H, dt), 8.19 (1H, d), 8.51 (1H, d), 8.58-8.61 (1H, m). MS: MH⁺ 327, 329

Among the above Examples, the particularly preferable compounds include 3-(2-cyanophenyl)-5-(2-methylsulfonylaminophenyl)-1-phenyl-1,2-dihydropyridin-2-one; 3-(2-chloro-3-pyridyl)-5-(2-pyridyl)-1-phenyl-1,2-dihydropyridin-2-one; 3-(2-cyanophenyl)-5-(2-pyridyl)-1-phenyl-1,2-dihydropyridin-2-one; 3-(2-cyanophenyl)-5-(2-pyridyl)-1-(3-nitrophenyl)-1,2-dihydropyridin-2-one; 3-(2-cyanophenyl)-5-(2-pyridyl)-1-(3-aminophenyl)-1,2-dihydropyridin-2-one; 3-(2-cyanophenyl)-5-(2-pyridyl)-1-(3-methylsulfonylaminophenyl)-1,2-dihydropyridin-2-one; 3-(2-cyanophenyl)-5-(2-pyridyl)-1-(3-methylaminophenyl)-1,2-dihydropyridin-2-one; 3-(2-cyanophenyl)-5-(2-pyridyl)-1-(3-dimethylaminophenyl)-1,2-dihydropyridin-2-one; 3-(2-cyanophenyl)-5-(2-pyridyl)-1-[3-(5-methoxymethyl-2-oxazolidinon-3-yl)-phenyl]-1,2-dihydropyridin-2-one; 3-(2-cyanophenyl)-5-(2-pyridyl)-1-(3-methoxycarbonylphenyl)-1,2-dihydropyridin-2-one; 3-(2-cyanophenyl)-5-(2-pyridyl)-1-(3-methylaminocarbonylphenyl)-1,2-dihydropyridin-2-one; 3-(2-cyano-3-pyridyl)-5-(2-pyridyl)-1-phenyl-1,2-dihydropyridin-2-one; 3-(2-chlorophenyl)-5-(2-pyridyl)-1-(4-hydroxyphenyl)-1,2-dihydropyridin-2-one; 3-(2-chlorophenyl)-5-(2-pyridyl)-1-(4-dimethylaminoethoxyphenyl)-1,2-dihydropyridin-2-one; 3-(2-cyanophenyl)-5-(2-pyridyl)-1-(3-formylphenyl)-1,2-dihydropyridin-2-one; 3-(2-cyanophenyl)-5-(2-pyridyl)-1-(3-hydroxymethylphenyl)-1,2-dihydropyridin-2-one; 3-(2-cyanophenyl)-5-(2-pyridyl)-1-(3-cyanomethylphenyl)-1,2-dihydropyridine-2-one; 3-(2-cyanophenyl)-5-(2-pyridyl)-1-(3-acetylaminomethylphenyl)-1,2-dihydropyridin-2-one; 3-(2-cyanophenyl)-5-(2-pyridyl)-1-(3-methylsulfonylaminomethylphenyl)-1,2-dihydropyridin-2-one; 3-(2-cyanophenyl)-5-(2-pyridyl)-1-(3-acetoxymethylphenyl)-1,2-dihydropyridin-2-one; 3-(2-cyanophenyl)-5-(2-pyridyl)-1-(4-methylthiophenyl)-1,2-dihydropyridin-2-one; 3-(2-cyanophenyl)-5-(2-pyridyl)-1-(4-methylsulfonylphenyl)-1,2-dihydropyridin-2-one; 3-(2-cyanophenyl)-5-(2-formylthiophen-3-yl)-1-phenyl-1,2-dihydropyridin-2-one; 3-(2-cyanophenyl)-5-(2-diethylaminomethylthiophen-3-yl)-1-phenyl-1,2-dihydropyridin-2-cyanophenyl)-5-(2-hydroxymethylthiophen-3-yl)-1-phenyl-1,2-dihydropyridine-2-one; 3-(2-cyanophenyl)-5-(2-pyridyl)-1-benzyl-1,2-dihydropyridin-2-one; 3-(2-cyanophenyl)-5-(2-pyridyl)-1-(3-pyridyl)-1,2-dihydropyridin-2-one; 3-(2-cyanophenyl)-5-phenyl-(2-pyridyl)-1,2-dihydropyridin-2-one; 3-(2-cyanophenyl)-1,5-diphenyl-1,2-dihydropyridin-2-one; 3-(2-cyanophenyl)-5-(2-methoxyphenyl)-1-phenyl-1,2-dihydropyridin-2-one; 3-(2-cyanophenyl)-5-(3,4-dimethoxyphenyl)-1-phenyl-1,2-dihydropyridin-2-one; 3-(2-cyanophenyl)-5-(thiophen-3-yl)-1-phenyl-1,2-dihydropyridin-2-one; 3-(2-cyanophenyl)-5-(2-fluorophenyl)-1-phenyl-1,2-dihydropyridin-2-one; 3-(2-cyanophenyl)-5-(thiophen-2-yl)-1-phenyl-1,2-dihydropyridin-2-one; 3-(2-cyanophenyl)-5-(3-furyl)-1-phenyl-1,2-dihydropyridin-2-one; 3-(2-cyanophenyl)-5-(2-furyl)-1-phenyl-1,2-dihydropyridin-2-one; 3-(2-chlorophenyl)-5-(2-pyridyl)-1-phenyl-1,2-dihydropyridin-2-one, 3(2-methoxycarbonylphenyl)-5-(2-pyridyl)-1-phenyl-1,2-dihydropyridin-2-one; 3-phenyl-5-(2-pyridyl)-1-phenyl-1,2-dihydropyridin-2-one; 3-(2-fluorophenyl)-5-(2-pyridyl)-1-phenyl-1,2-dihydropyridin-2-one; 3-(2-chlorophenyl)-5-(2- pyridyl)-1-(3-methoxyphenyl)-1,2-dihydropyridin-2-one; 1-(2-fluoro-3-pyridyl)-5-(2-pyridyl)-1-phenyl-1,2-dihydropyridin-2-one; 3-(2-methoxy-5-pyridyl)-5-(2-pyridyl)-1-phenyl-1,2-dihydropyridin-2-one; 3-(2-fluoro-3-pyridyl)-5-(2-pyridyl)-1-(3-methoxyphenyl)-1,2-dihydropyridin-2-one; 3-(2-fluoro-3-pyridyl)-5-(2-pyridyl)-1-(3-fluorophenyl)-1,2-dihydropyridin-2-one; 3-(2-cyanophenyl)-5-(2-pyridyl)-1-(4-fluorophenyl)-1,2-dihydropyridin-2-one; 3-(2-cyanophenyl)-5-(2-pyridyl)-1-(3-fluorophenyl)-1,2-dihydropyridin-2-one; 3-(2-cyanophenyl)-5-(2-pyridyl)-1-(4-methoxyphenyl)-1,2-dihydropyridin-2-one; 3-(2-cyanophenyl)-5-(2-pyridyl)-1-(3-methoxyphenyl)-1,2-dihydropyridin-2-one; 3-phenyl-5-(2-pyridyl)-1-(3-fluorophenyl)-1,2-dihydropyridin-2-one; 3-(2-chlorophenyl)-5-(2-pyridyl)-1-(4-fluorophenyl)-1,2-dihydropyridin-one; 3-(2-cyanophenyl)-5-(2-pyridyl)-1-(4-formylphenyl)-1,2-dihydropyridin-2-one; 3-(2-cyanophenyl)-5-(2-pyridyl)-1-(2-formylphenyl)-1,2-dihydropyridin-2-one; 3-(2-cyanophenyl)-5-(2-pyridyl)-1-(3-chlorophenyl)-1,2-dihydropyridin-2-one; 3-(2-cyanophenyl)-5-(2-pyridyl)-1-(3-tolyl)-1,2-dihydropyridin-2-one; 3-(2-cyanophenyl)-5-(2-pyridyl)-1-(3-trifluoromethylphenyl)-1,2-dihydropyridin-2-one; 3-(2-cyanophenyl)-5-(2-pyridyl)-1-(thiophen-3-yl)-1,2-dihydropyridin-2-one; 3-(2-cyanophenyl)-5-(2-pyridyl)-1-(3-furyl)-1,2-dihydropyridin-2-one; 3-(2-cyanophenyl)-5-(2-pyridyl-1-(4-toly)-1,2-dihydropyridin-2-one; 3-(2-cyanophenyl)-5-(2-pyridyl)-1-(4-trifluoromethylphenyl)-1,2-dihydropyridin-2-one; 3-(2-cyanophenyl)-5-(2-pyridyl)-1-(2-methoxypyridin-5-yl)-1,2-dihydropyridin-2-one; 3-(2-cyanophenyl)-5-(2-pyridyl)-1-(pyrimidin-5-yl)-1,2-dihydropyridin-2-one; 3-(2-cyanophenyl)-5-(2-pyridyl)-1-(3-benzyloxymethylpyridin-5-yl)-1,2-dihydropyridin-2-one; 3-(2-cyanophenyl)-5-(2-pyridyl)-1-(2-ethylthiopyridin-5-yl)-1,2-dihydropyridin-2-one; 3-(2-cyanophenyl)-5-(2-pyridyl)-1-(4-pyridyl)-1,2-dihydropyridin-2-one; 3-(2-cyanophenyl)-5-(2-pyridyl)-1-(3-methoxypyridin-5-yl)-1,2-dihydropyridin-2-one; 3-(2-cyanophenyl)-5-(2-pyridyl)-1-(2-chloropyridin-5-yl)-1,2-dihydropyridin-2-one; 3-(2-cyanophenyl)-5-(2-pyridyl)-1-(2-fluoropyridin-5-yl)-1,2-dihydropyridin-2-one; 3-(2-cyanophenyl)-5-(2-pyridyl)-1-(2-methoxyphenyl)-1,2-dihydropyridin-2-one; 3-phenyl-5-(2-pyridyl)-1-(3-pyridyl)-1,2-dihydropyridin-2-one; 3-(2-chlorophenyl)-5-(2-pyridyl)-1-(3-pyridyl)-1,2-dihydropyridin-2-one; 3-(thiophen-3-yl)-5-(2-pyridyl)-1-(3-pyridyl)-1,2-dihydropyridin-2-one; 3-(2,6-dimethylphenyl)-5-(2-pyridyl)-1-(3-pyridyl)-1,2-dihydropyridin-2-one; 3-(2-cyanothiophen-3-yl)-5-(2-pyridyl)-1-(3-pyridyl)-1,2-dihydropyridin-2-one; 3-(2-fluoro-3-pyridyl)-5-(2-pyridyl)-1-(3-pyridyl)-1,2-dihydropyridin-2-one; 3-(2-chlorophenyl)-5-(2-pyridyl)-1-(3-hydroxyphenyl)-1,2-dihydropyridin-2-one; 3-(2-chlorophenyl)-5-(2-pyridyl)-1-(3-dimethylaminoethoxyphenyl)-1,2-dihydropyridin-2-one; 3-(2-chlorophenyl)-5-(2-pyridyl)-1-(3-dimethylaminopropoxyphenyl)-1,2-dihydropyridin-2-one; 3-(2-cyanophenyl)-5-(2-pyridyl)-1-(2-hydroxymethylphenyl)-1,2-dihydropyridin-2-one; 3-(2-cyanophenyl)-5-(2-pyridyl)-1-(4-cyanomethylphenyl)-1,2-dihydropyridin-2-one; 3-(2-cyanophenyl)-5-(2-pyridyl)-1-(2-cyanomethylphenyl)-1,2-dihydropyridin-2-one; 3-(2-cyanophenyl)-5-(6-diethylaminomethyl-2-pyridyl)-1-phenyl-1,2-dihydropyridin-2-one; 3-(2-cyanophenyl)-1-phenyl-5-(2-pyrimidinyl)-1,2-dihydropyridin-2-one; 3-(2-hydroxypyridin-6-yl)-1-phenyl-5-(2-pyridyl)-1,2-dihydropyridin-2-one; 1-(2-aminobenzothiazol-6-yl)-3-(2-cyanophenyl)-5-(2-pyridyl)-1,2-dihydropyridin-2-one; 3-(2-cyanophenyl)-5-(2-pyridyl)-1-(1-benzyl-1,2,5,6-tetrahydropyridin-3-yl)-1,2-dihydropyridin-2-one; 3-[2-(5-methyl-1,2,4-oxadiazol-3-yl)phenyl]-1-phenyl-5-(2-pyridyl)-1,2-dihydropyridin-2-one; 3-(2-cyanophenyl)-5-(6-methylpyridin-2-yl)-1-phenyl-1,2-dihydropyridin-2-one; 3-(2-cyanophenyl)-5-(5-methylpyridin-2-yl)-1-phenyl-1,2-dihydropyridin-2-one; 3-(2-cyanophenyl)-5-(3-hydroxypyridin-2-yl)-1-phenyl-1,2-dihydropyridin-2-one; 3-(2-cyanophenyl)-1-phenyl-5-(2-thiazolyl)-1,2-dihydropyridin-2-one; 3-(2-cyanophenyl)-5-(6-methoxypyridin-2-yl)-1-phenyl-1,2-dihydropyridin-2-one; 1-(4-aminophenyl)-3-(2-cyanophenyl)-5-(2-pyridyl)-1,2-dihydropyridin-2-one; 1-(3-aminophenyl)-3-(2-cyanophenyl)-5-(2-pyrimidinyl)-1,2-dihydropyridin-2-one; 3-(2-cyanophenyl)-5-(2-pyridyl)-1-(3-amino-4-methylphenyl)-1,2-dihydropyridin-2-one; 3-(2-cyanophenyl)-1-(3-dimethylaminoethoxyphenyl)-5-(2-pyridyl)-1,2-dihydropyridin-2-one; 3-(2-cyanophenyl)-1-(3-piperidinoethoxyphenyl)-5-(2-pyridyl)-1,2-dihydropyridin-2-one; 3-(2-cyanophenyl)-1-(3-pyrrolidinoethoxyphenyl)-5-(2-pyridyl)-1,2-dihydropyridin-2-one; 3-(2-cyanophenyl)-1-(3-diisopropylaminoethoxyphenyl)-5-(2-pyridyl)-1,2-dihydropyridin-2-one; 3-(2-cyanophenyl)-1-[3-(4-piperidinobutoxy)phenyl]-5-(2-pyridyl)-1,2-dihydropyridin-2-one; 3-(2-cyanophenyl)-1-(4-nitrophenyl)-5-(2-pyridyl)-1,2-dihydropyridin-2-one; 1-phenyl-5-(2-pyridyl)-3-(2-thiazolyl)-1,2-dihydropyridin-2-one; 3-(2-cyanophenyl)-1-(3-pyridyl)-5-(2-pyrimidinyl)-1,2-dihydropyridin-2-one; 3-(2-fluoropyridin-3-yl)-1-phenyl-5-(2-pyrimidinyl)-1,2-dihydropyridin-2-one; 3-(2-cyanopyridin-3-yl)-1-phenyl-5-(2-pyrimidinyl)-1,2-dihydropyridin-2-one; 3-(2-cyanophenyl)-1-(3-nitrophenyl)-5-(2-pyrimidinyl)-1,2-dihydropyridin-2-one; 3-(2-nitrophenyl)-1-phenyl-5-(2-pyridyl)-1,2-dihydropyridin-2-one; 3-(2-formylthiophen-3-yl)-5-(2-pyridyl)-1-phenyl-1,2-dihydropyridin-2-one; 3-(2-cyanophenyl)-5-(2-pyridyl)-1-(2-naphthyl)-1,2-dihydropyridin-2-one; 3-(2-cyanophenyl)-5-(2-pyridyl)-1-(1-naphthyl)-1,2-dihydropyridin-2-one; 5-(2-aminopyridin-6-yl)-3-(2-cyanophenyl)-1-phenyl-1,2-dihydropyridin-2-one; 5-(6-bromopyridin-2-yl)-3-(2-cyanophenyl)-1-phenyl-1,2-dihydropyridin-2-one; 3-(2-cyanophenyl)-5-(2-morphorinopyridin-6-yl)-1-phenyl-1,2-dihydropyridin-2-one; 3-(2-cyanophenyl)-1-(3-hydroxyphenyl)-5-(2-pyridyl)-1,2-dihydropyridin-2-one; 3-(2-cyanophenyl)-1-[3-(4-piperidyloxy)]phenyl-5-(2-pyridyl)-1,2-dihydropyridin-2-one; 1-[3-(N-acetylpiperidin-4-yl-oxy)phenyl]-3-(2-cyanophenyl)-5-(2-pyridyl)-1,2-dihydropyridin-2-one; 3-(2-cyanophenyl)-1-[3-(1-methylsulfonylpiperidin-4-yl-oxy)phenyl]-5-(2-pyridyl)-1,2-dihydropyridin-2-one; 1-[3-(N-methylpiperidin-4-yl-oxy)phenyl]-3-(2-cyanophenyl)-5-(2-pyridyl)-1,2-dihydropyridin-2-one; 3-(6-chloro-1H-benzimidazol-2-yl)-5-(2-pyridyl)-1-phenyl-1,2-dihydropyridin-2-one; 3-(2-cyanophenyl)-5-(2-pyridyl)-1-(3-nitro-4-methylphenyl)-1,2-dihydropyridin-2-one; 3-(2-cyanothiophen-3-yl)-5-(2-pyridyl)-1-phenyl-1,2-dihydropyridin-2-one; 3-[2-(5-oxazolyl)phenyl]-1-phenyl-5-(2-pyridyl)-1,2-dihydropyridin-2-one; 3-[2-(5-oxazolyl)thiophen-3-yl]-1-phenyl-5-(2-pyridyl)-1,2-dihydropyridin-2-one; and 3-(2-ethoxycarbonylvinylthiophen-3-yl)-5-(2-pyridyl)-1-phenyl-1,2-dihydropyridin-2-one.

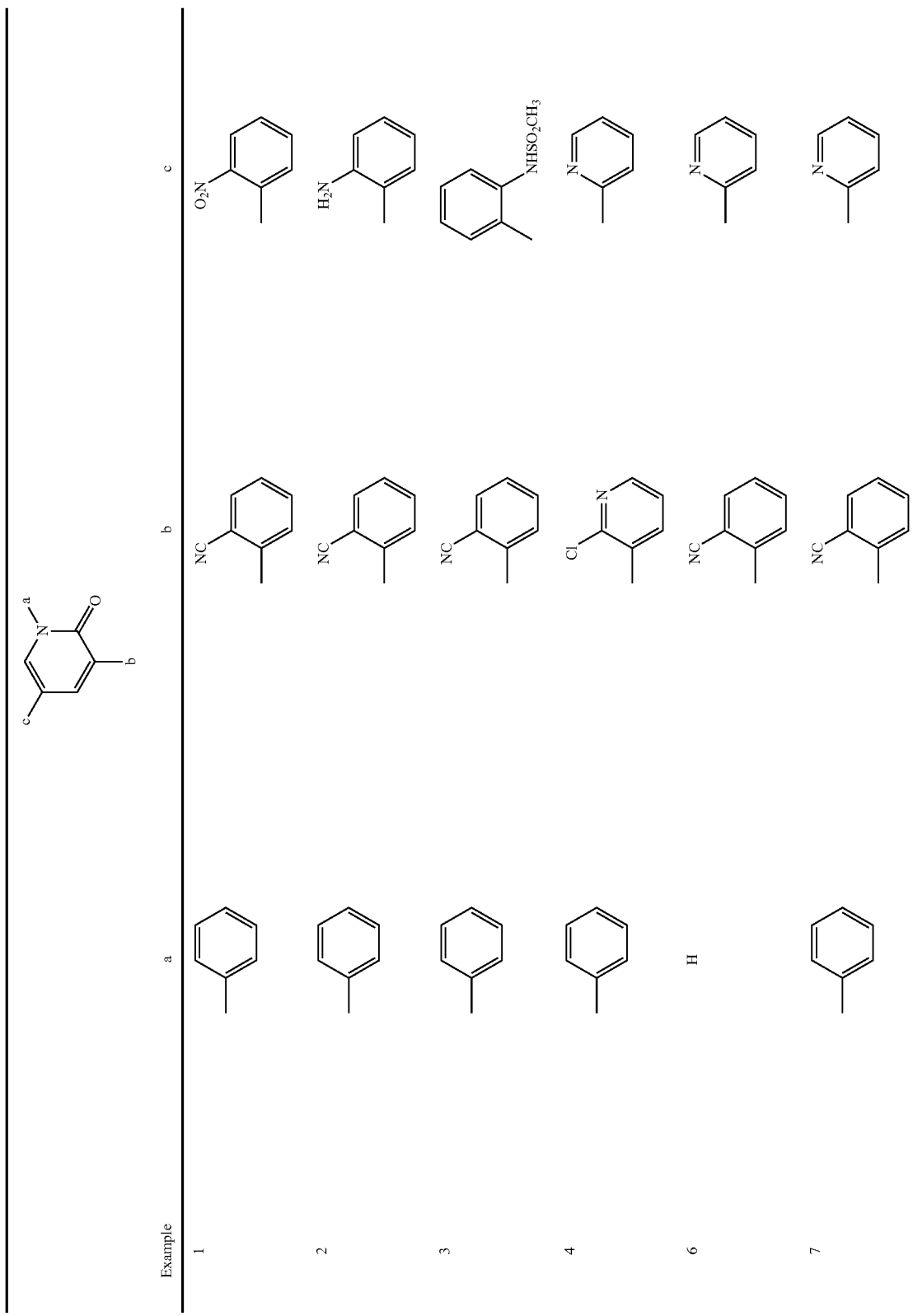

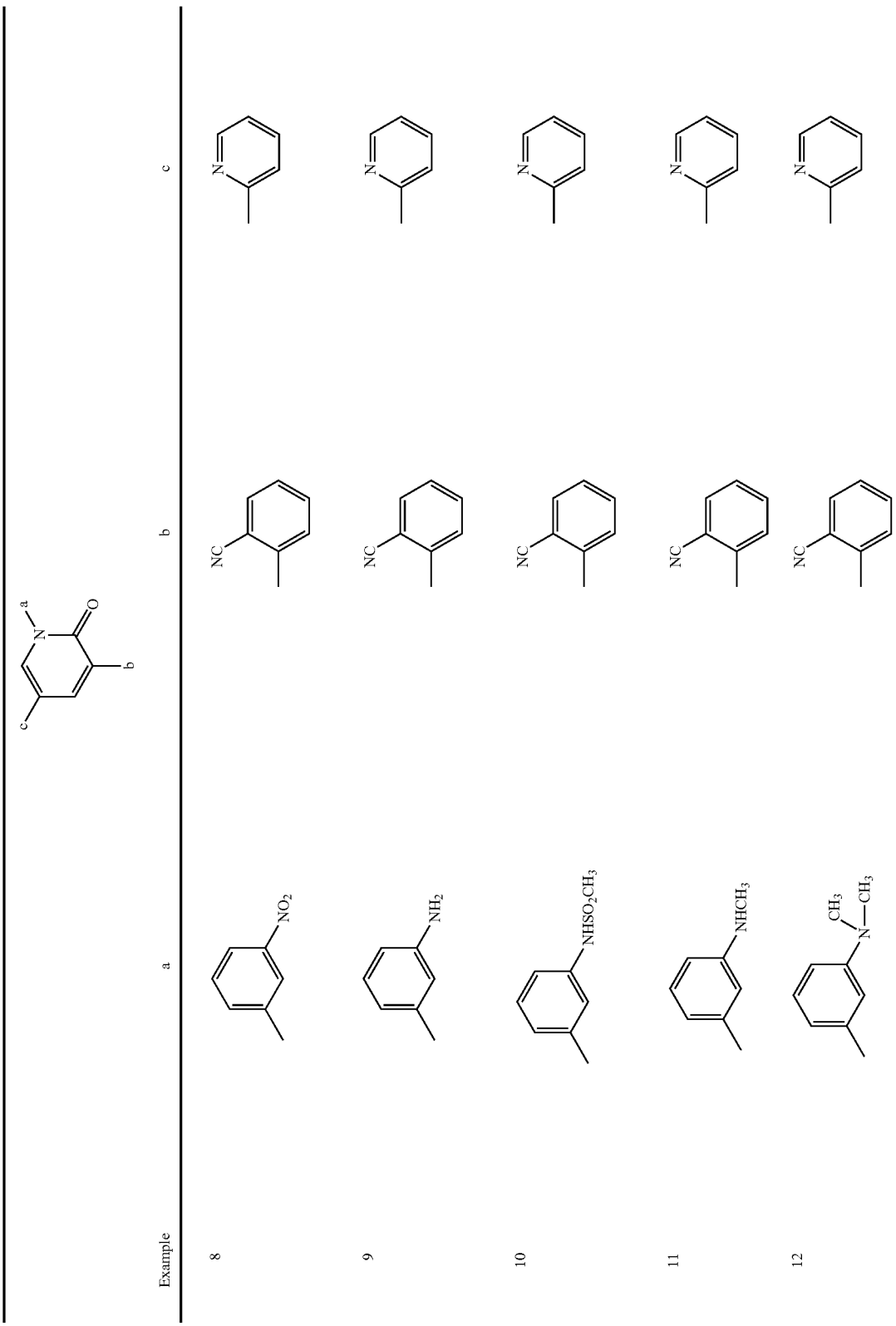

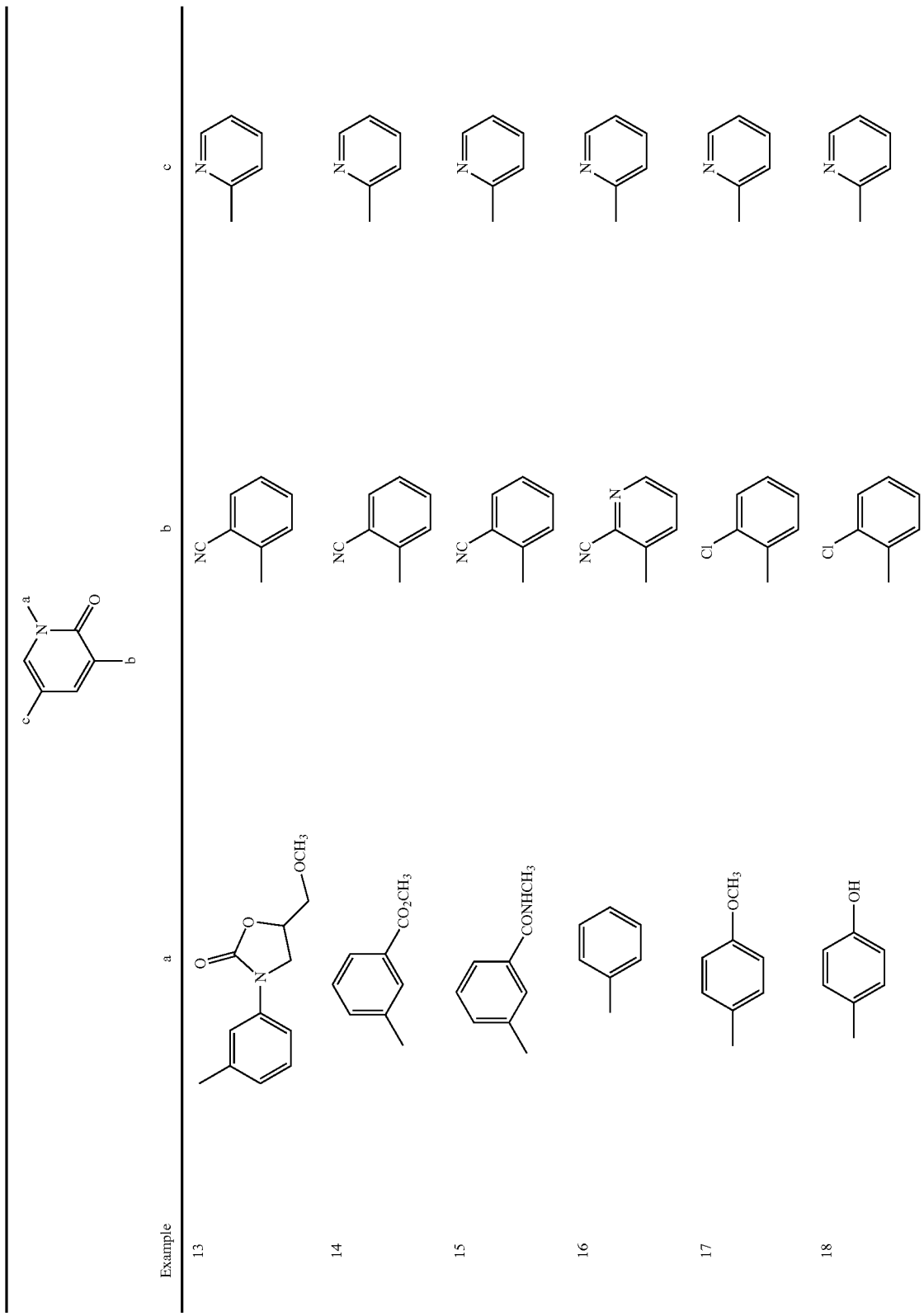

-continued

| Example | a | b | c |
|---|---|---|---|
| 19 | 4-methylphenyl-O-CH₂CH₂-N(CH₃)₂ | 2-Cl-phenyl | 2-methylpyridyl |
| 20 | 3-methylphenyl-CHO | 2-CN-phenyl | 2-methylpyridyl |
| 21 | 3-methylphenyl-CH₂OH | 2-CN-phenyl | 2-methylpyridyl |
| 22 | 3-methylphenyl-CH₂CN | 2-CN-phenyl | 2-methylpyridyl |
| 23 | 3-methylphenyl-NHCOCH₃ | 2-CN-phenyl | 2-methylpyridyl |
| 24 | 3-methylphenyl-NHSO₂CH₃ | 2-CN-phenyl | 2-methylpyridyl |

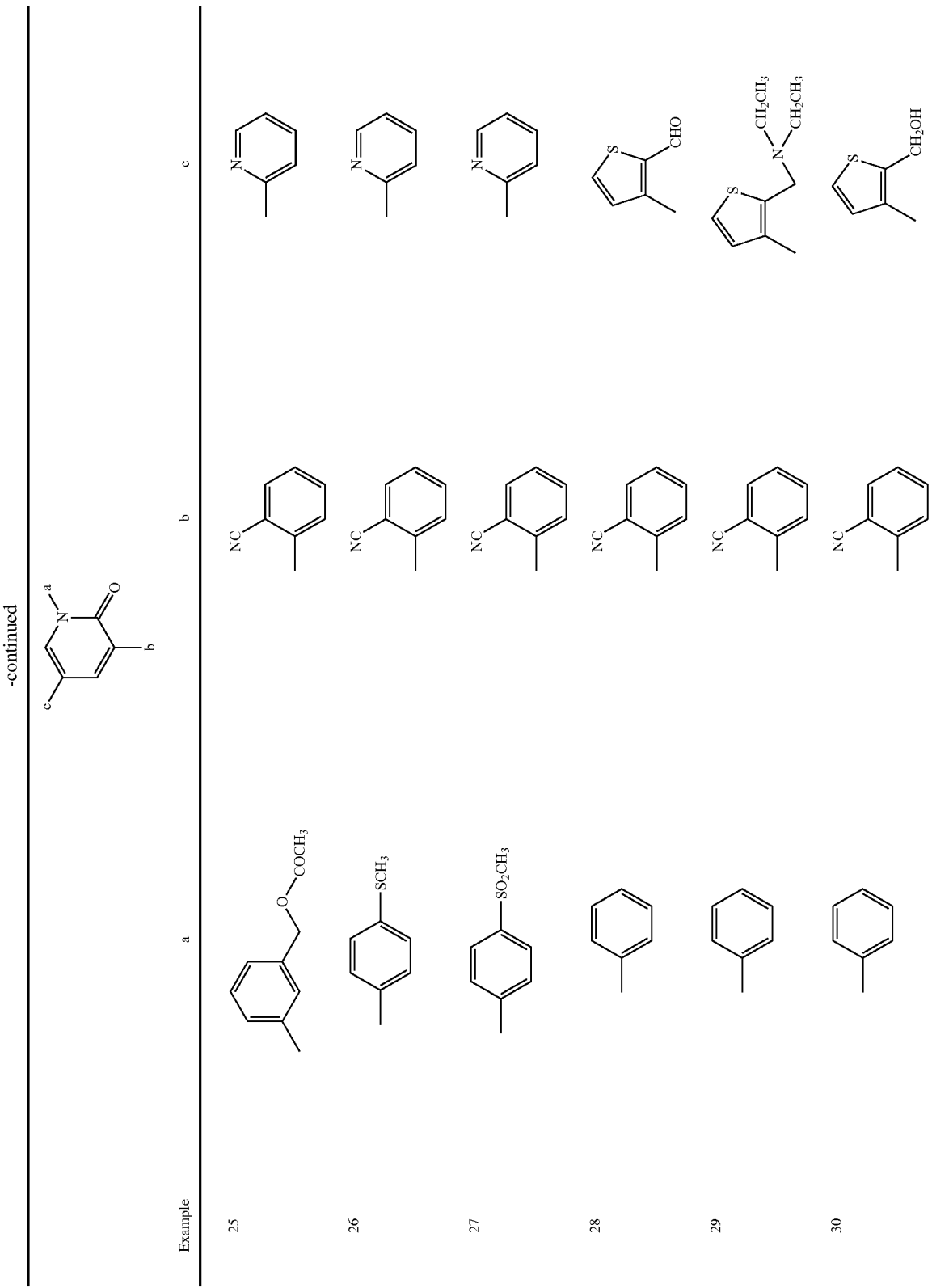

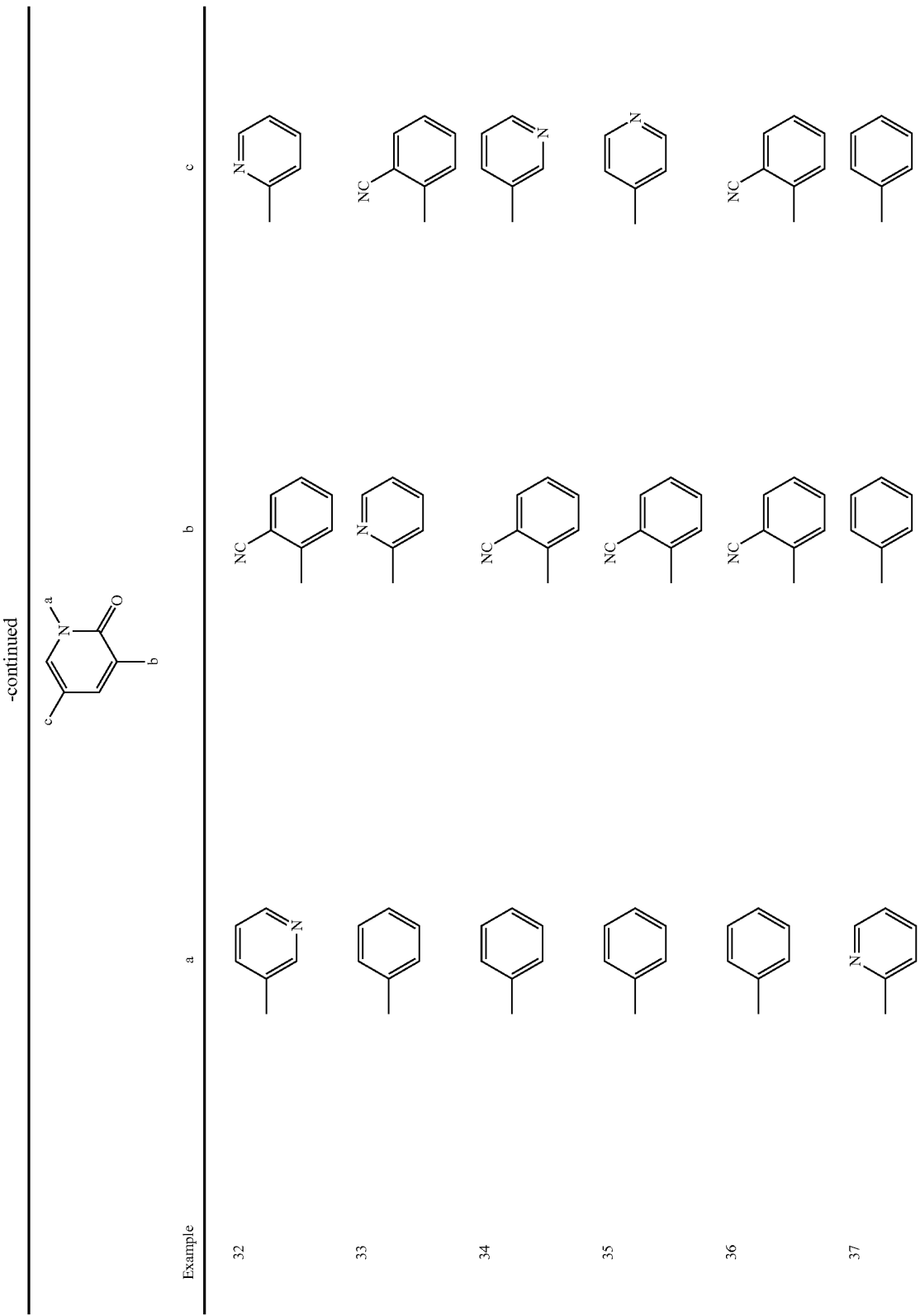

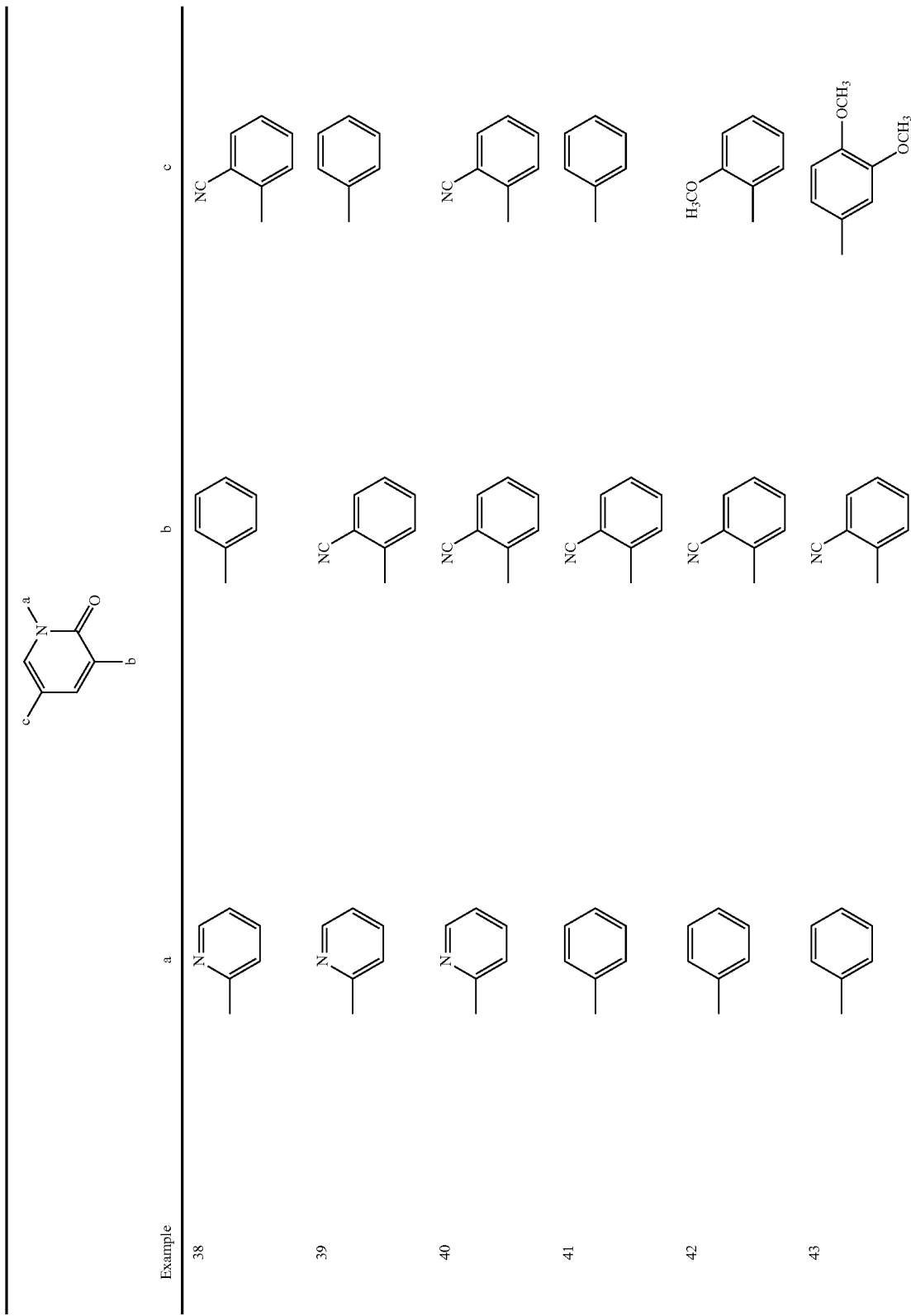

-continued
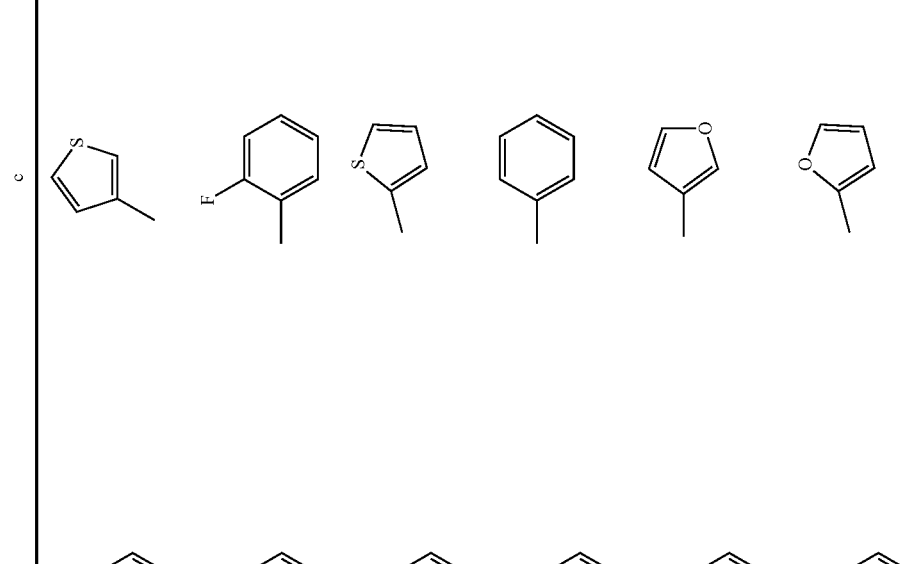
| Example | a | b | c |
|---|---|---|---|
| 44 | phenyl | 2-methyl-6-cyanophenyl | 3-methylthiophene |
| 45 | phenyl | 2-methyl-6-cyanophenyl | 2-fluoro-6-methylphenyl |
| 46 | phenyl | 2-methyl-6-cyanophenyl | 2-methylthiophene |
| 47 | 3-methylpyridyl | 2-methyl-6-cyanophenyl | phenyl |
| 48 | phenyl | 2-methyl-6-cyanophenyl | 3-methylfuran |
| 49 | phenyl | 2-methyl-6-cyanophenyl | 2-methylfuran |

-continued
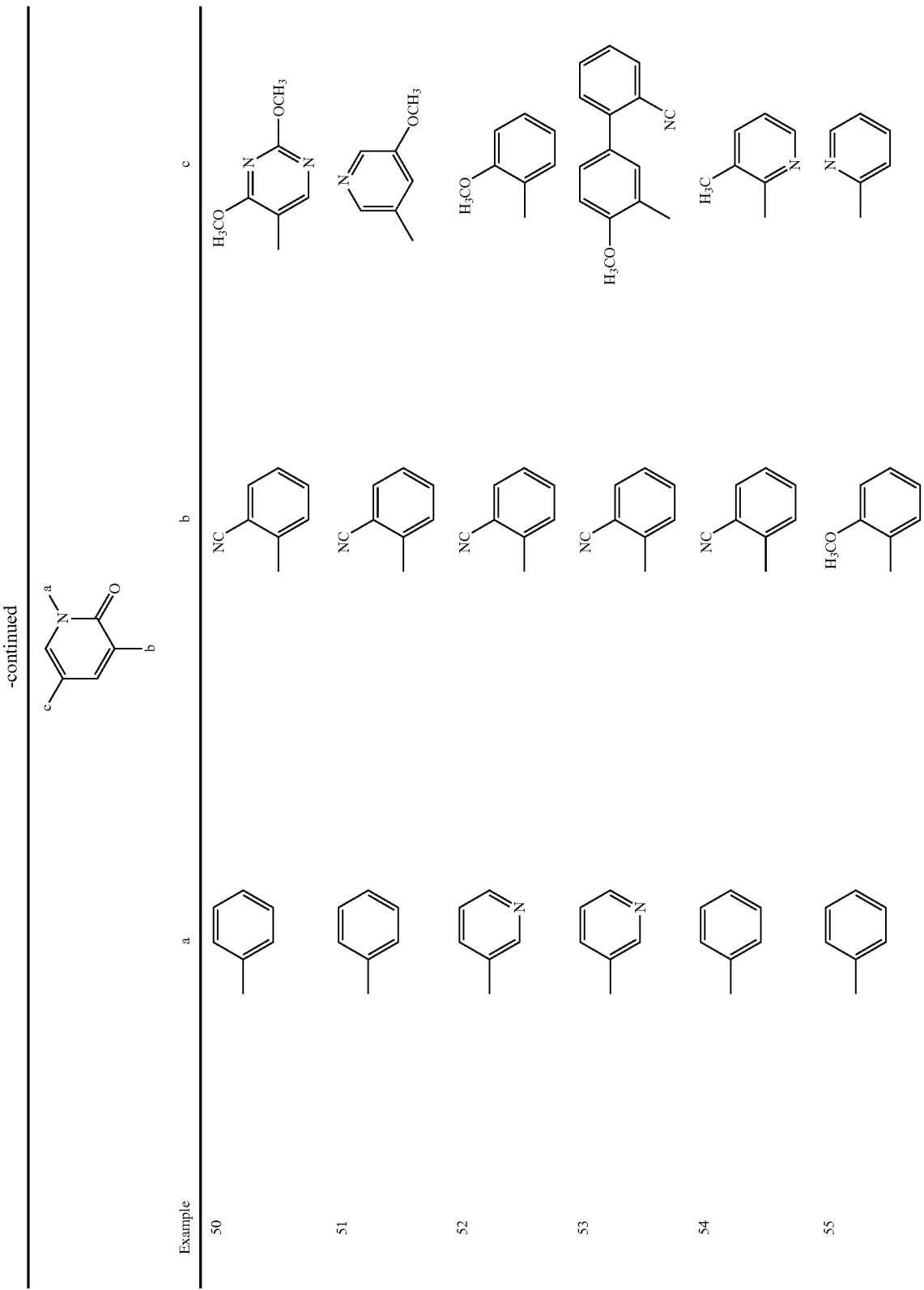

-continued

| Example | a | b | c |
|---|---|---|---|
| 56 | 4-F-phenyl | 2-MeO,6-Me-phenyl | 6-Me-pyridin-2-yl |
| 57 | phenyl | 2-Cl,6-Me-phenyl | 6-Me-pyridin-2-yl |
| 58 | phenyl | 3-CO₂CH₃-phenyl | 6-Me-pyridin-2-yl |
| 59 | phenyl | 3-CONHCH₃-phenyl | 6-Me-pyridin-2-yl |
| 60 | phenyl | 2-Me,6-Me-phenyl | 6-Me-pyridin-2-yl |
| 61 | phenyl | 2-Me-phenyl | 6-Me-pyridin-2-yl |
| 62 | phenyl | 6-Me-pyridin-2-yl | 6-Me-pyridin-2-yl |

-continued
| Example | a | b | c |
|---|---|---|---|
| 63 | 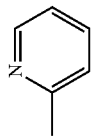 | 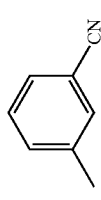 CN | 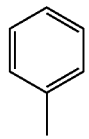 |
| 64 | 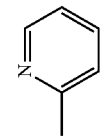 | 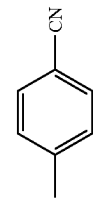 CN | 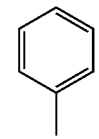 |
| 65 | 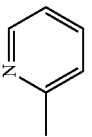 | 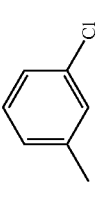 Cl | 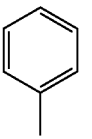 |
| 66 | 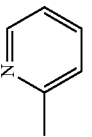 | 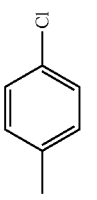 Cl | 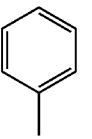 |
| 67 | 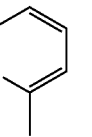 | 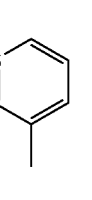 | 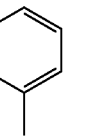 |
| 68 | | 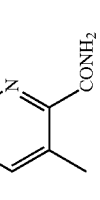 CONH$_2$ | 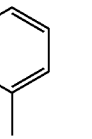 |
| 69 | 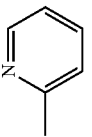 | 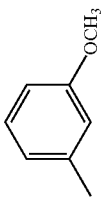 OCH$_3$ | 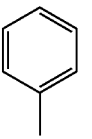 |
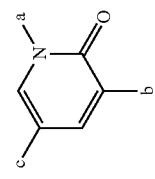

-continued
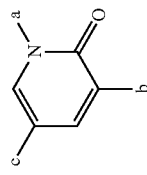
| Example | a | b | c |
|---|---|---|---|
| 70 | 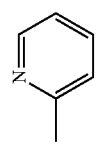 | 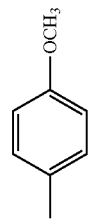 | 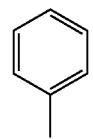 |
| 71 | 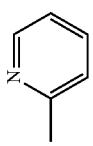 | 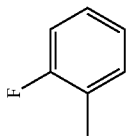 | 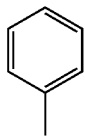 |
| 72 | 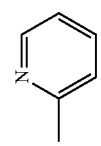 | 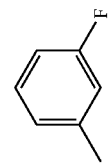 | 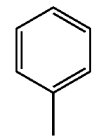 |
| 73 | 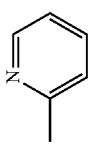 | 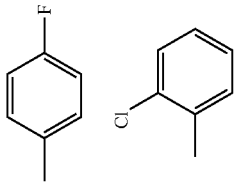 |  |
| 74 | 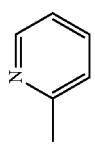 | 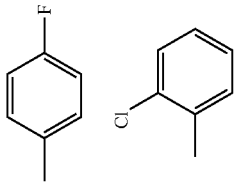 |  |
| 75 | 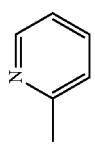 | 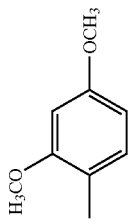 | 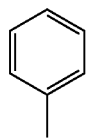 |

-continued
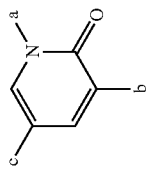
| Example | a | b | c |
|---|---|---|---|
| 76 | 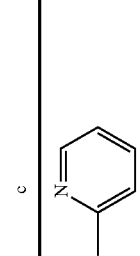 | 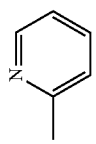 | 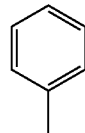 |
| 77 | | 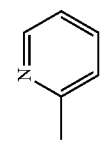 | 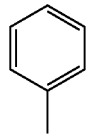 |
| 78 | | 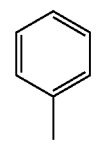 | 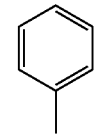 |
| 79 | | 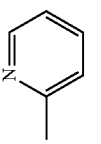 | 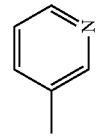 |
| 80 | 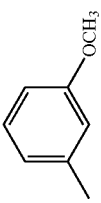 | 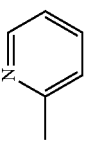 | |
| 81 | | | 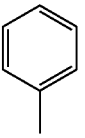 |

-continued
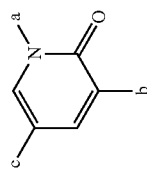
| Example | a | b | c |
|---|---|---|---|
| 82 | 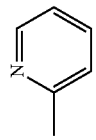 | 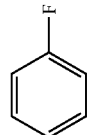 | 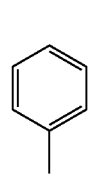 |
| 83 | 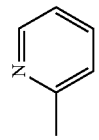 | 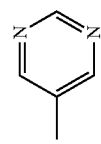 | 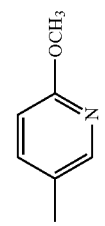 |
| 84 | 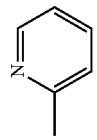 | 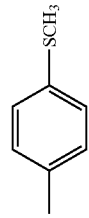 | 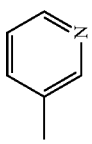 |
| 85 | 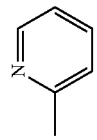 | 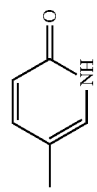 | 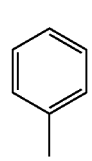 |
| 86 | 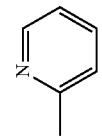 | 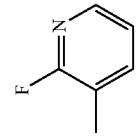 | 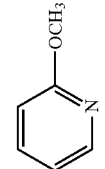 |
| 87 | 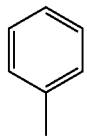 | 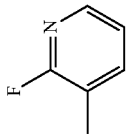 | 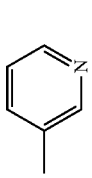 |

-continued
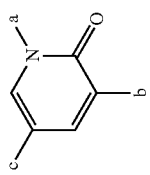
| Example | a | b | c |
|---|---|---|---|
| 88 | 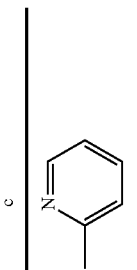 | 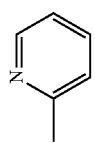 | 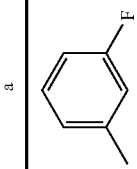 |
| 89 | 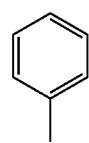 | 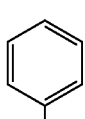 | 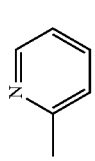 |
| 90 | 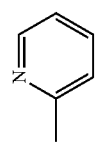 | 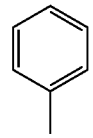 | 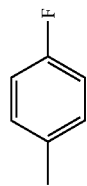 |
| 91 | 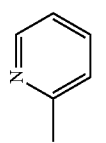 | 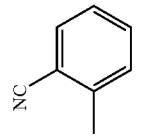 | 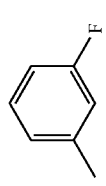 |
| 92 | 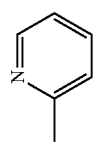 | 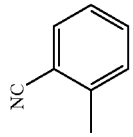 | 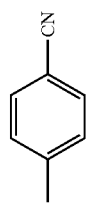 |
| 93 | 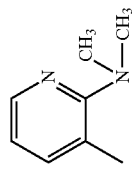 | 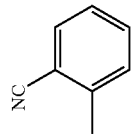 | |

-continued
| Example | a | b | c |
|---|---|---|---|
| 94 | 3-CN-phenyl | 2-methyl-6-CN-phenyl | 2-methylpyridin-yl |
| 95 | 4-OCH₃-phenyl | 2-methyl-6-CN-phenyl | 2-methylpyridin-yl |
| 96 | 3-OCH₃-phenyl | 2-methyl-6-CN-phenyl | 2-methylpyridin-yl |
| 97 | 3-F-phenyl | 2-methyl-phenyl | 2-methylpyridin-yl |
| 98 | 4-F-phenyl | 2-methyl-phenyl | 2-methylpyridin-yl |
| 99 | 4-F-phenyl | 2-methyl-6-Cl-phenyl | 2-methylpyridin-yl |
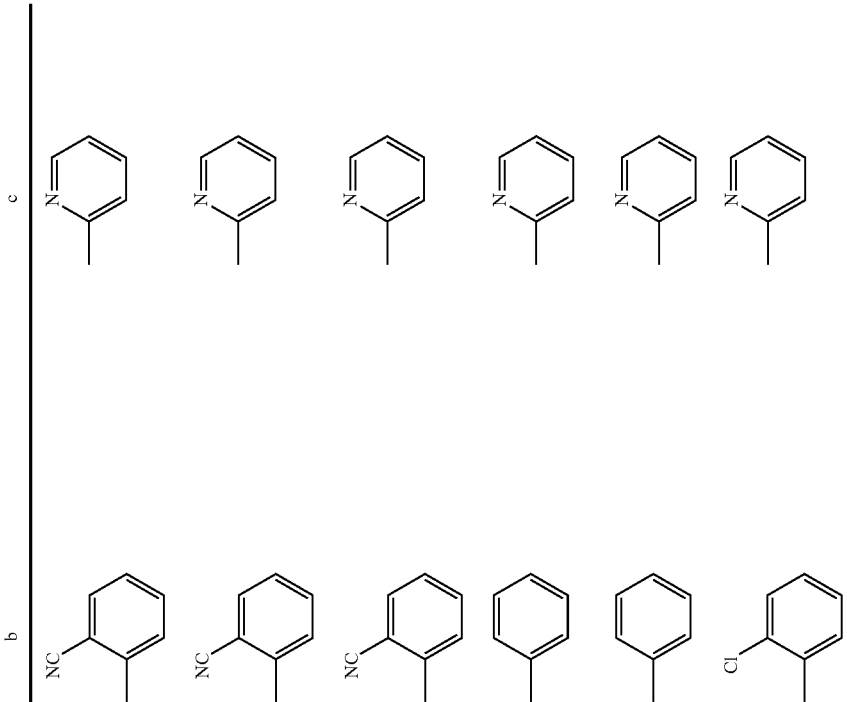

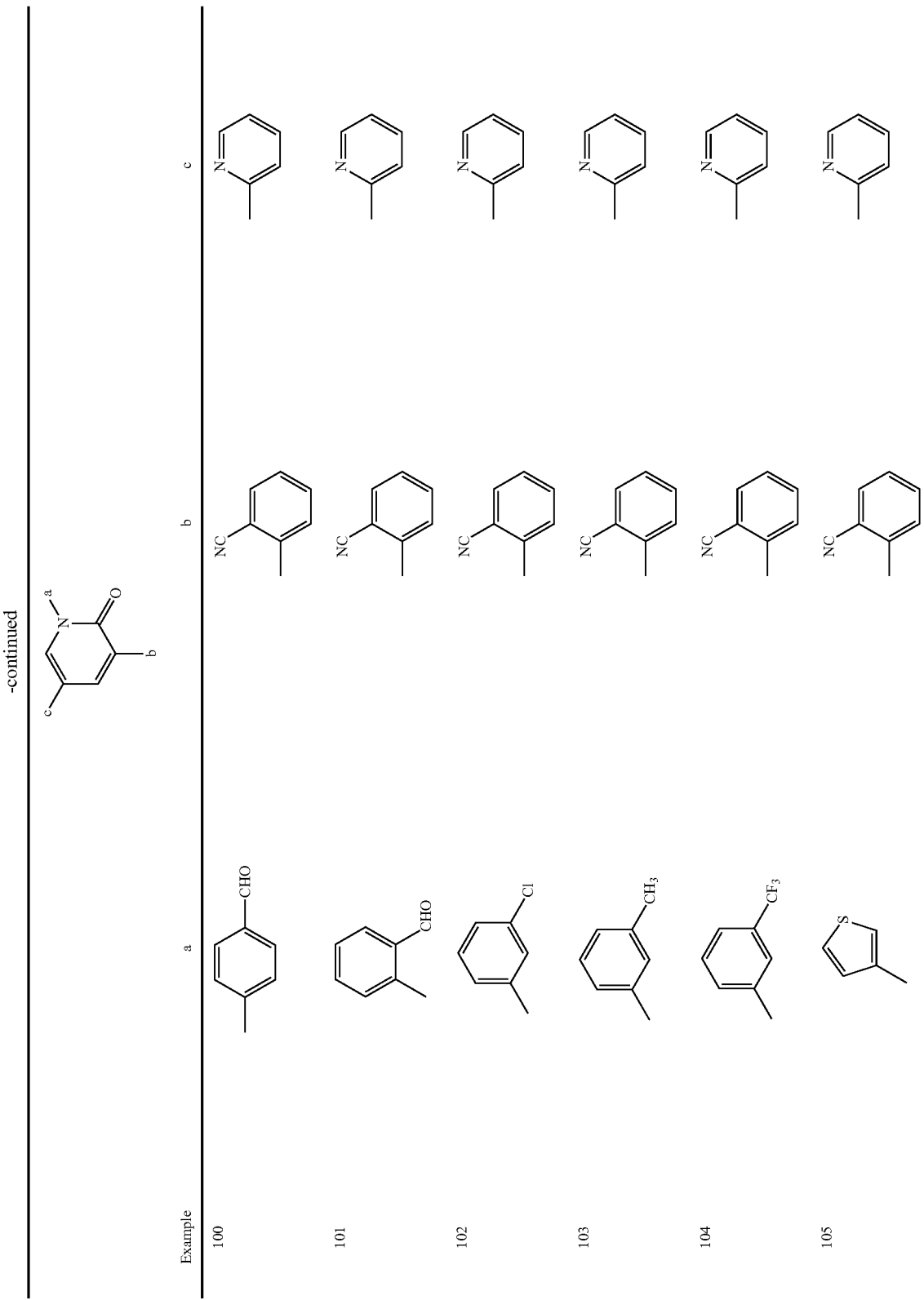

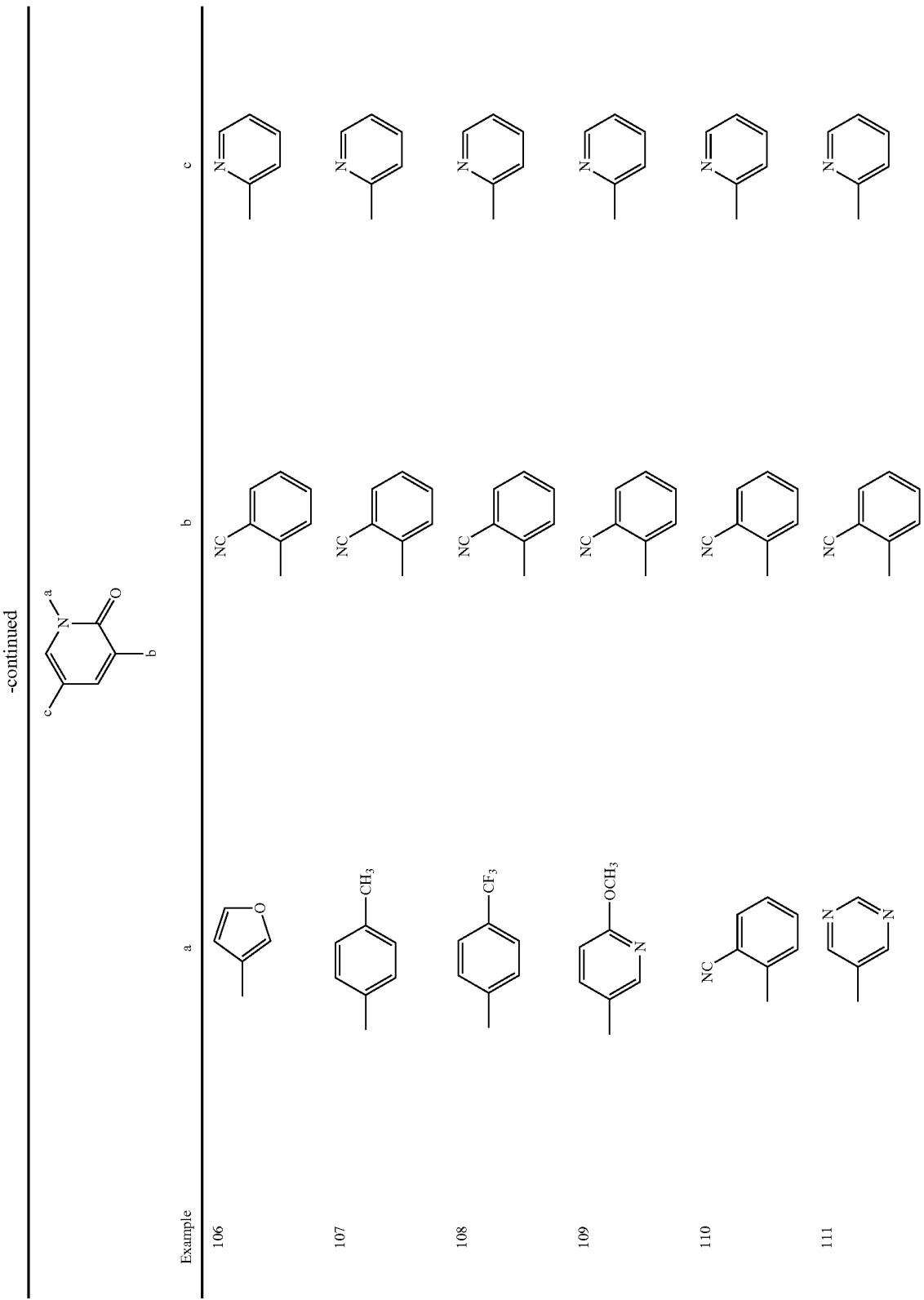

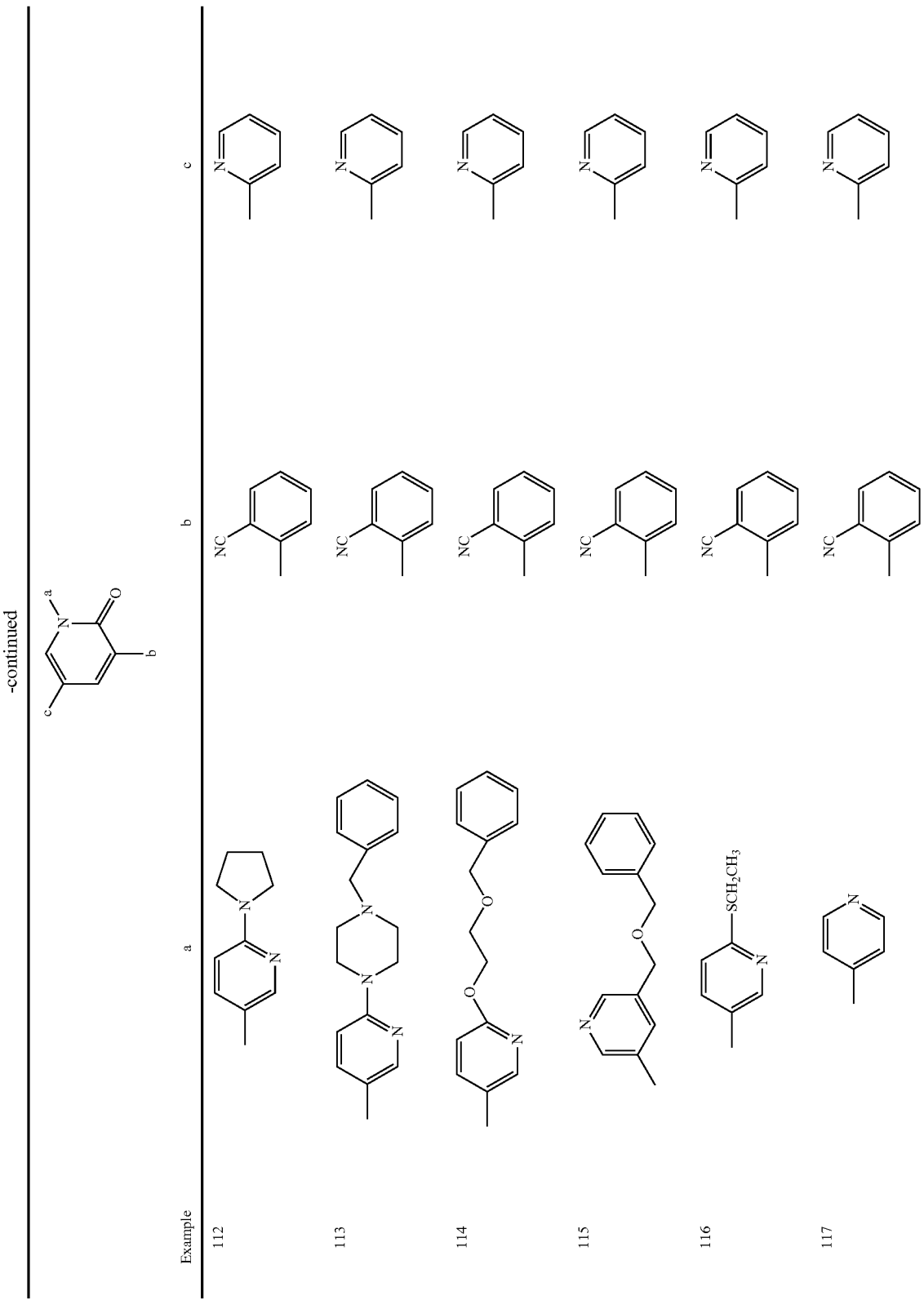

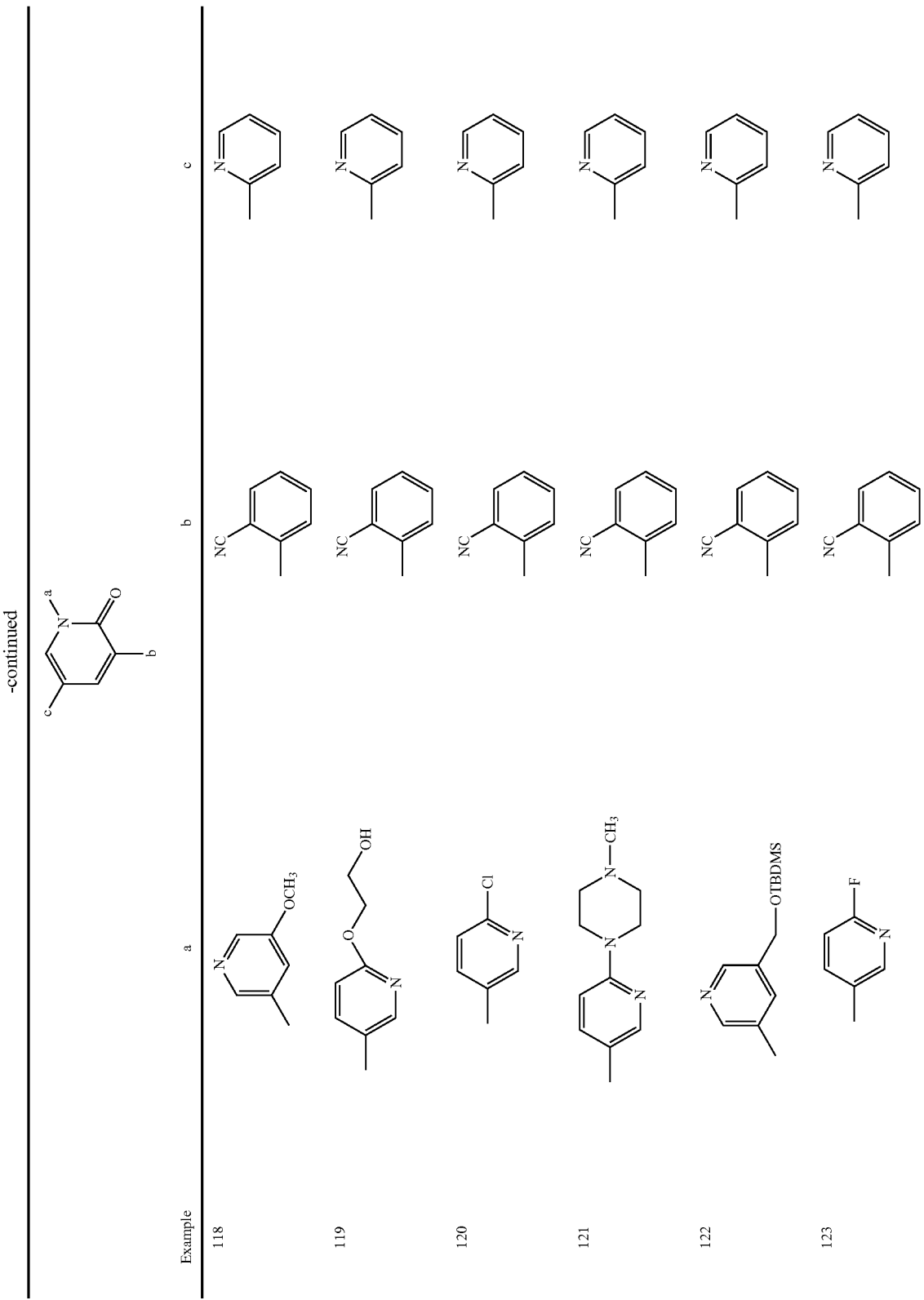

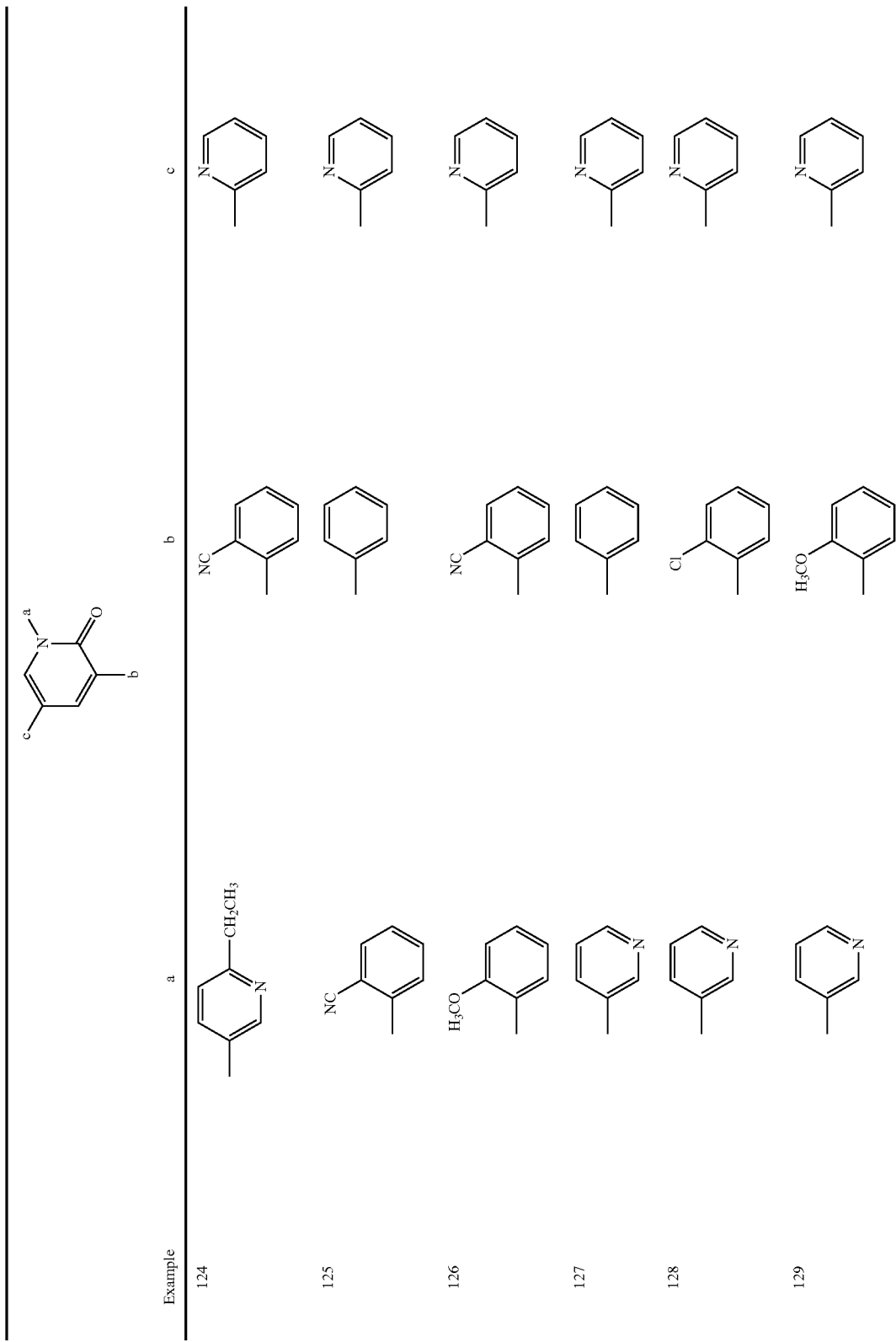

-continued
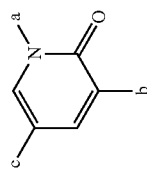
| Example | a | b | c |
|---|---|---|---|
| 130 | 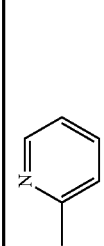 | 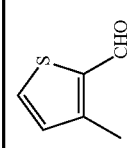 | 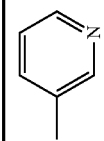 |
| 131 | 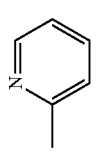 | 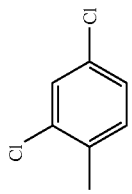 | 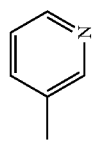 |
| 132 | 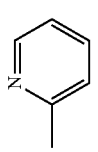 | 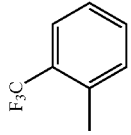 | 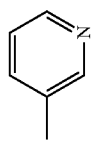 |
| 133 | 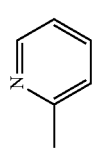 | 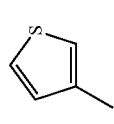 | 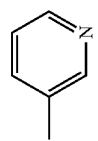 |
| 134 | 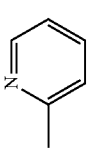 | 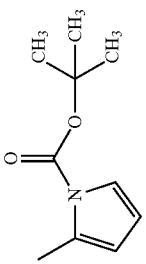 | 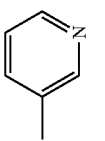 |

-continued

| Example | a | b | c |
|---|---|---|---|
| 135 | 3-methylpyridin-3-yl | 2,6-dimethylphenyl | 2-methylpyridin-2-yl |
| 136 | 3-methylpyridin-3-yl | 3-(acetylamino)-methylphenyl | 2-methylpyridin-2-yl |
| 137 | 3-methylpyridin-3-yl | 2-cyano-3-methylthiophen-2-yl | 2-methylpyridin-2-yl |
| 138 | 3-methylpyridin-3-yl | 3-methoxy-2-methyl-3-cyanophenyl | 2-methylpyridin-2-yl |
| 139 | 3-methylpyridin-3-yl | 2-fluoro-3-methylpyridin-2-yl | 2-methylpyridin-2-yl |

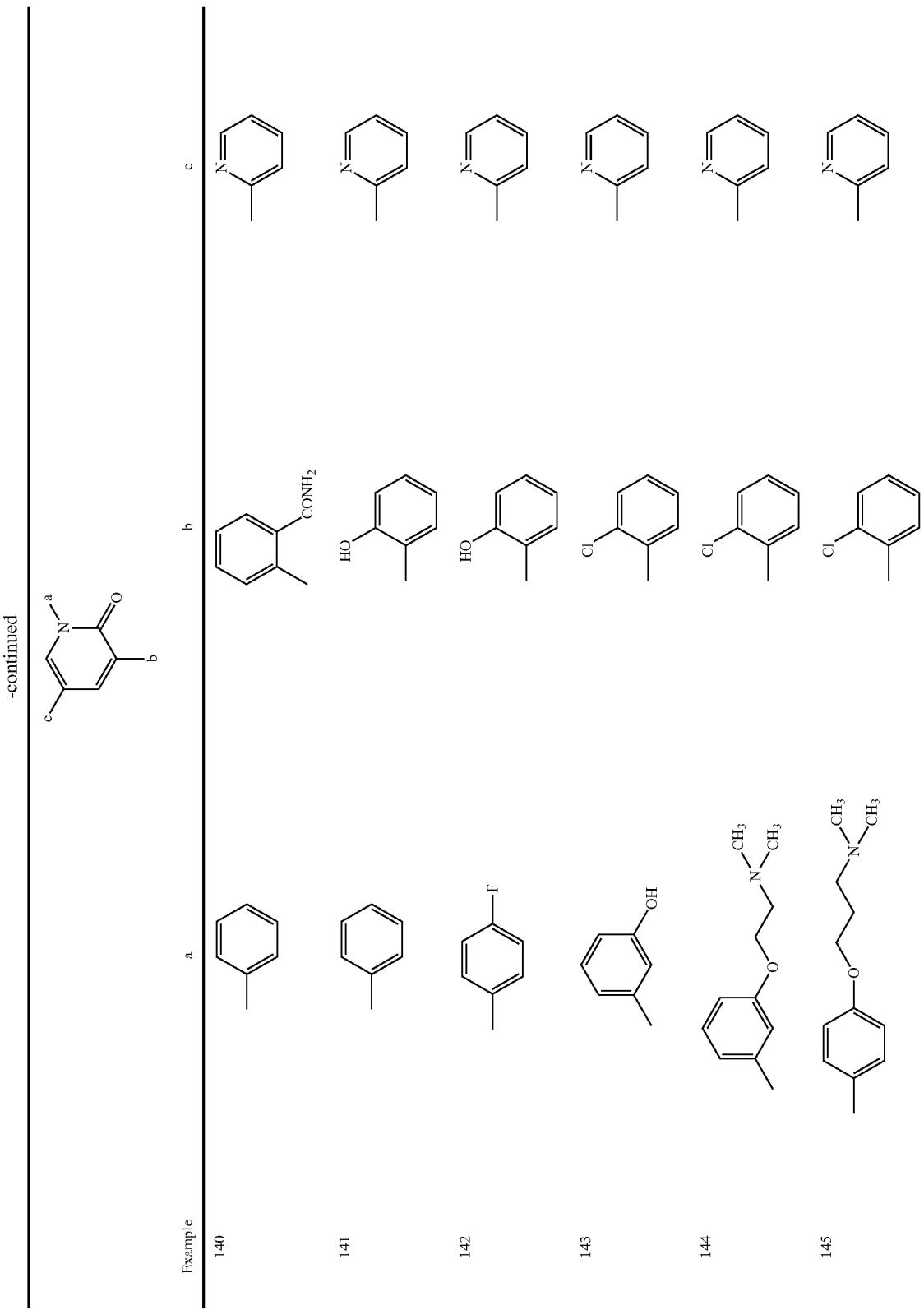

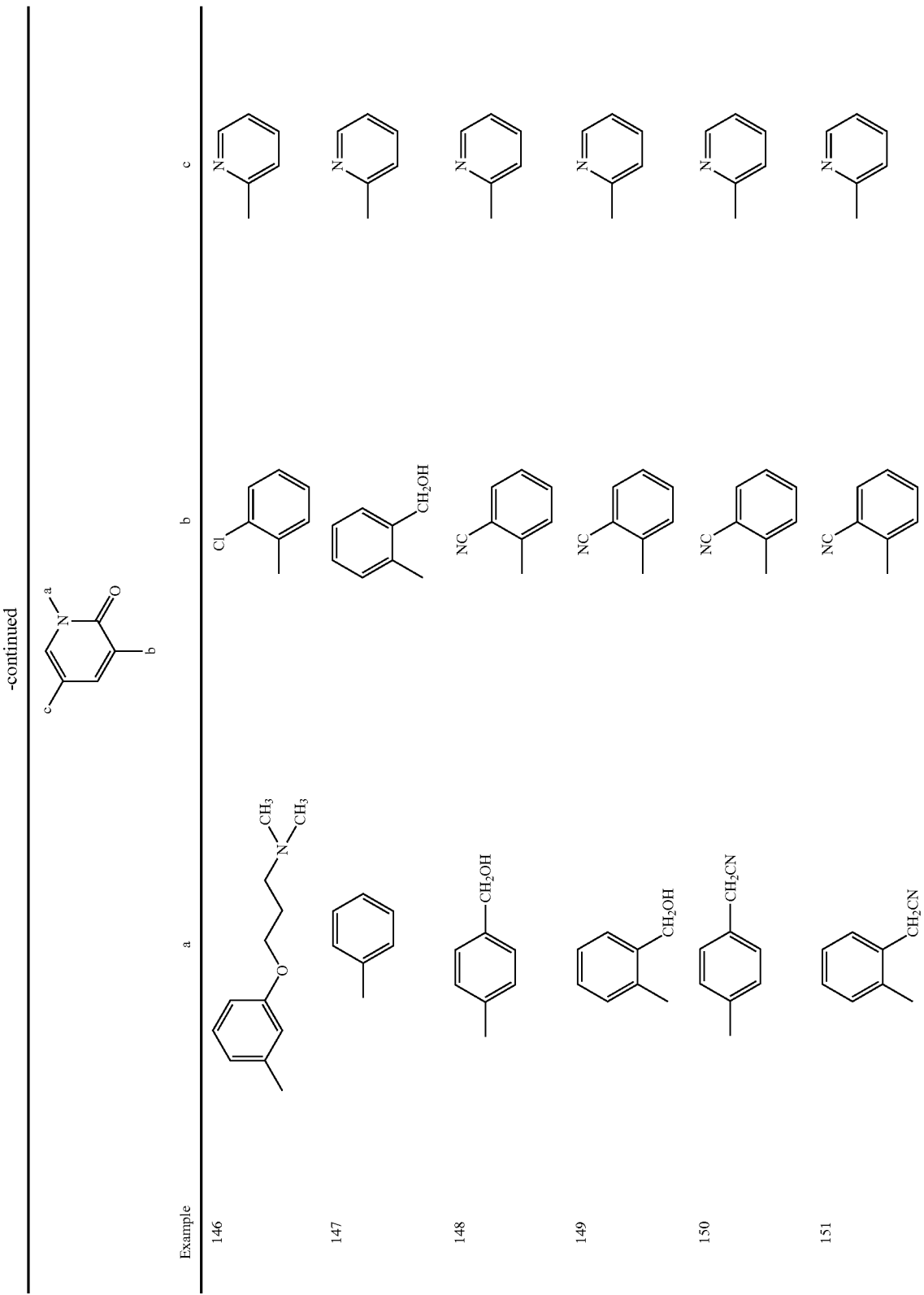

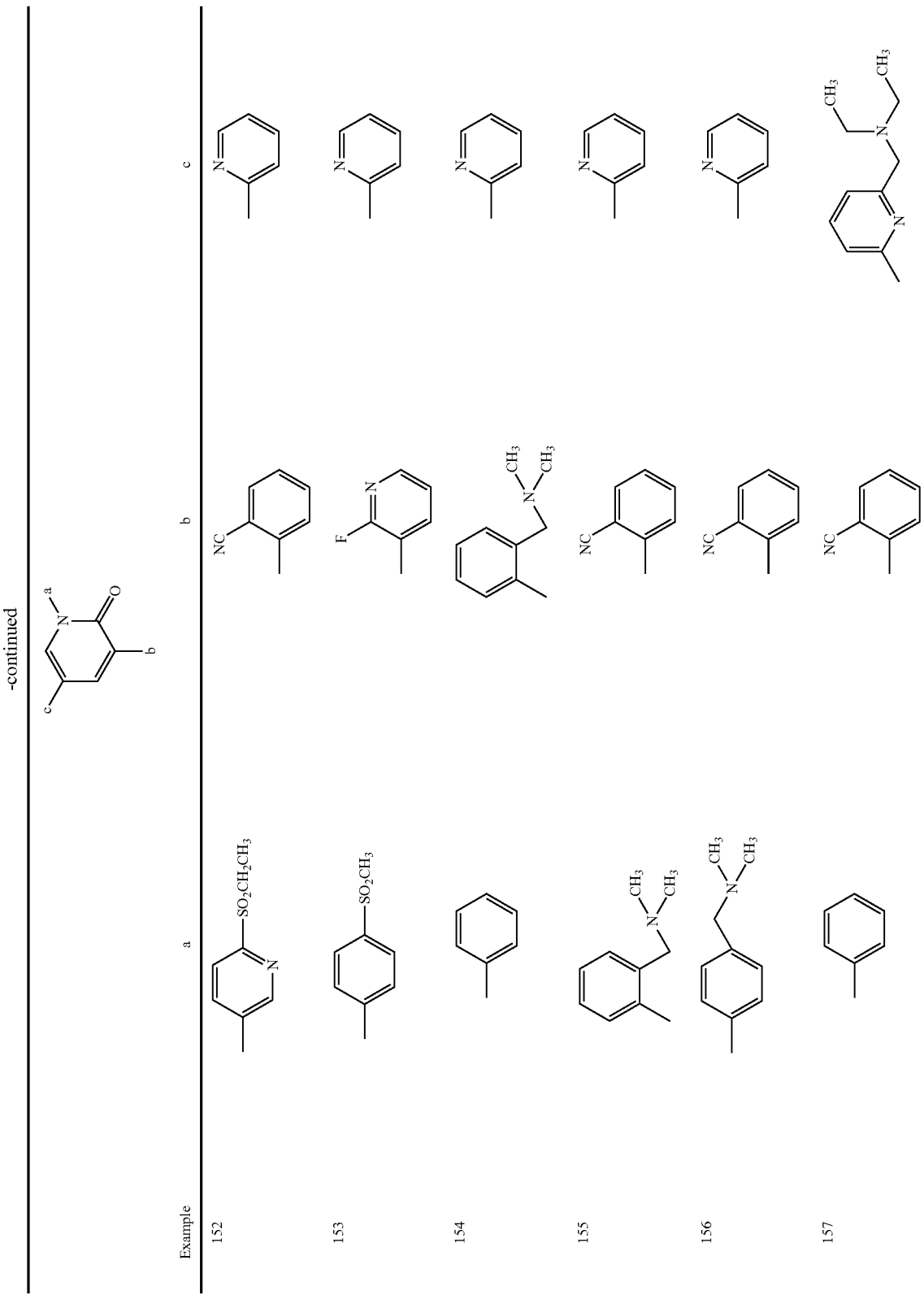

-continued

| Example | a | b | c |
|---|---|---|---|
| 159 | 2-pyridyl | 2-cyano-6-methylphenyl | 2-pyridyl |
| 160 | 2-cyano-6-methylphenyl | 2-pyridyl | phenyl |
| 162 | phenyl | 2-cyano-6-methylphenyl | 5-acetoxy-2-methylpyridin-... |
| 163 | phenyl | 2-cyano-6-methylphenyl | 5-hydroxy-6-methylpyridin-2-yl |
| 164 | phenyl | 2-cyano-6-methylphenyl | 2-methylpyrimidinyl |
| 165 | phenyl | 6-hydroxy-2-methylpyridin-... | 2-methylpyridinyl |

-continued

| Example | a | b | c |
|---|---|---|---|
| 166 | 2-amino-6-methylbenzothiazole | 2-methylbenzonitrile | 2-methylpyridine |
| 171 | methylcyclopentane | 2-methylbenzonitrile | 2-methylpyridine |
| 172 | benzyl 4-piperidinecarboxylate | 2-methylbenzonitrile | 2-methylpyridine |
| 173 | toluene | 2-methylbenzonitrile | 2-methylpyridine N-oxide |
| 177 | toluene | 1-(2-cyanophenyl)-4-methylpiperazine | 2-methylpyridine |
| 178 | toluene | 1-methyladamantane | 2-methylpyridine |

-continued
| Example | a | b | c |
|---|---|---|---|
| 180 | 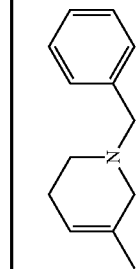 | | 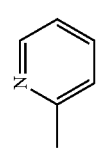 |
| 182 | | 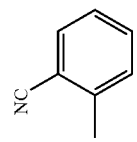 | 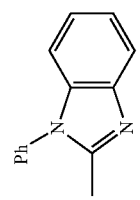 |
| 183 | | 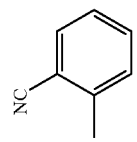 | 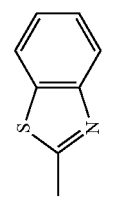 |
| 184 | | 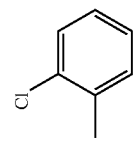 | 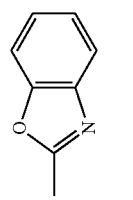 |
| 186 | | 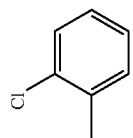 | 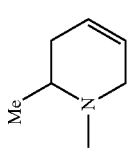 |
| 189 | | 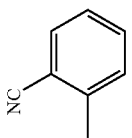 | 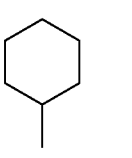 |

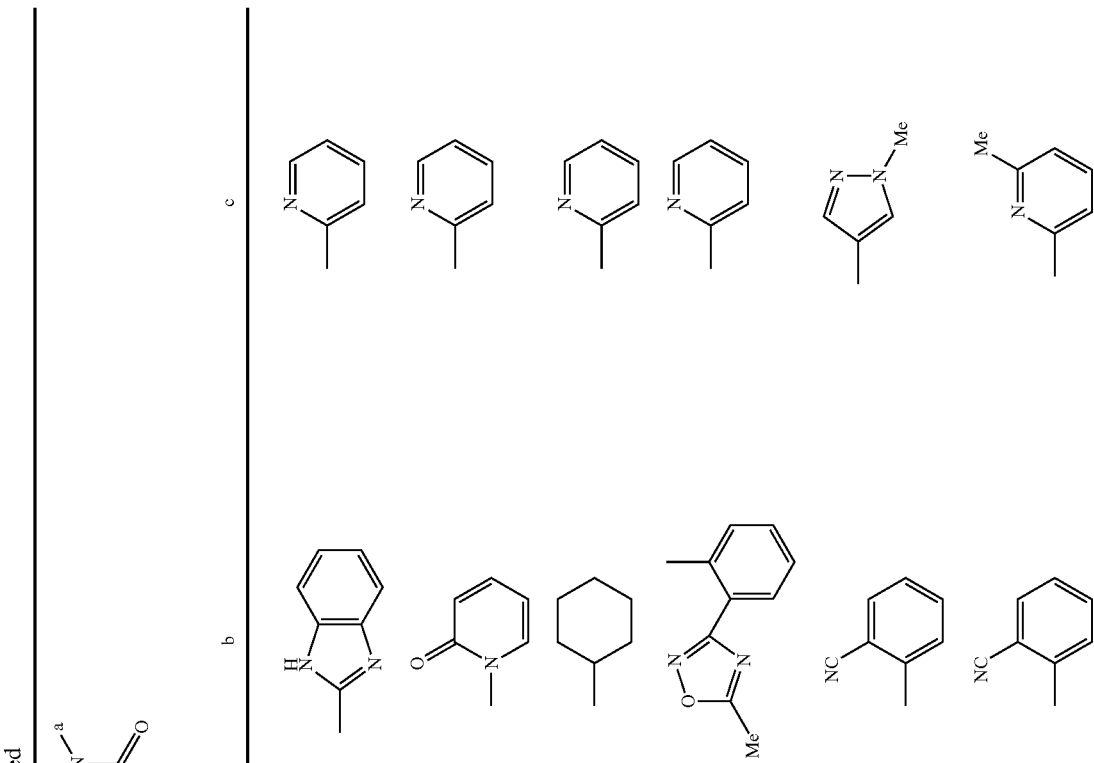

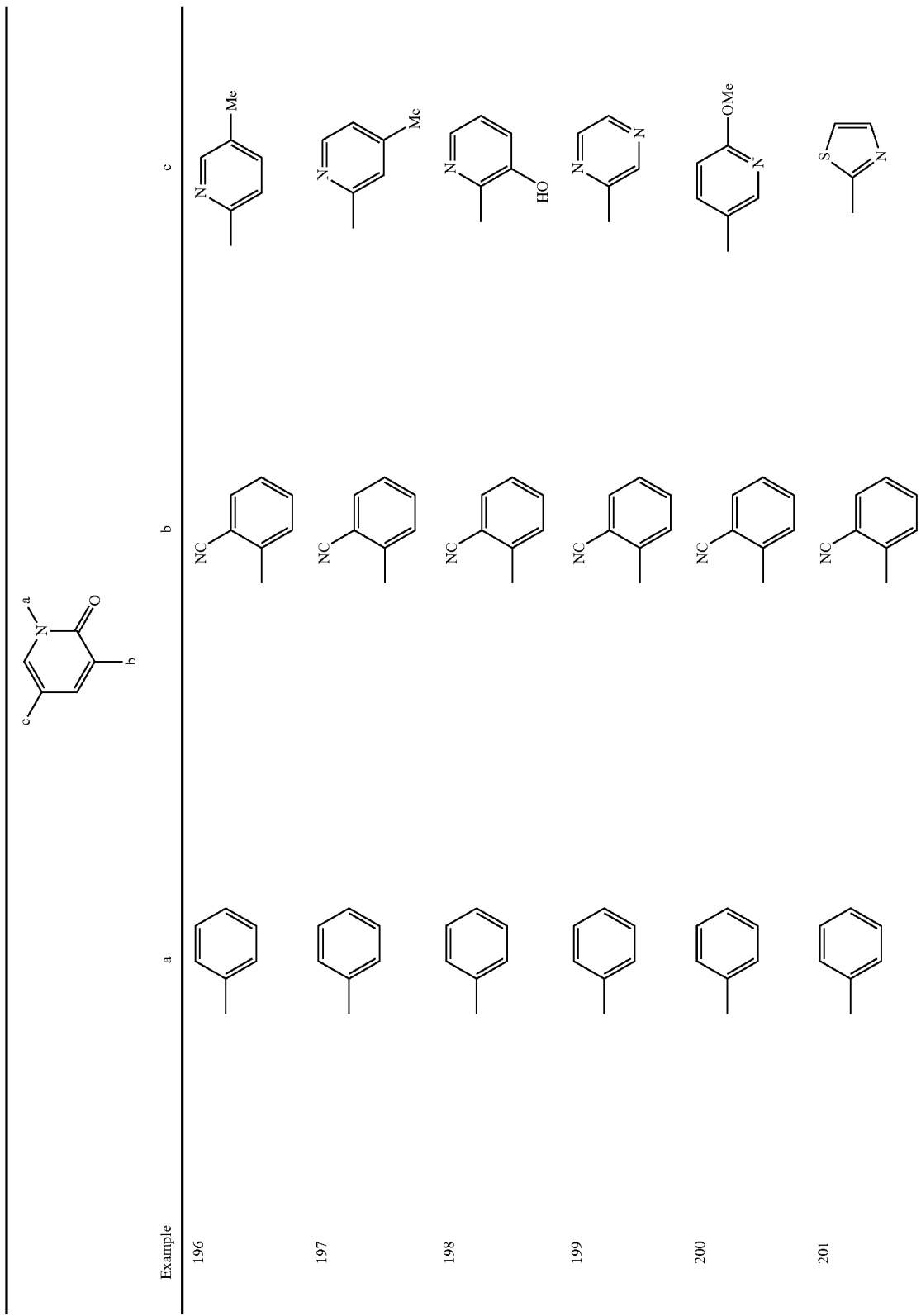

-continued
| Example | a | b | c |
|---|---|---|---|
| | 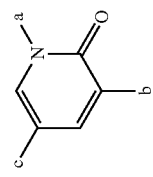 | | |
| 202 | 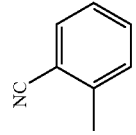 | 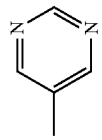 | |
| 203 | 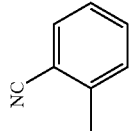 | 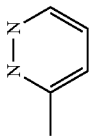 | |
| 204 | 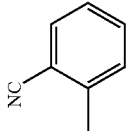 | 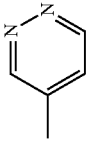 | |
| 205 | 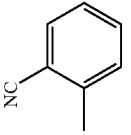 | 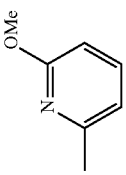 | |
| 206 | 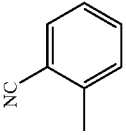 | 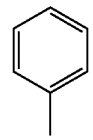 | |
| 207 | 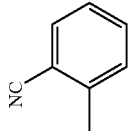 | 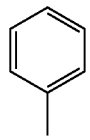 | 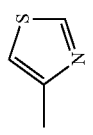 |

-continued
| Example | a | b | c |
|---|---|---|---|
| 208 | 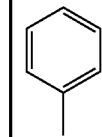 | 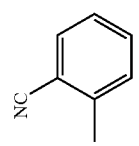 | 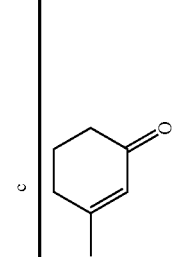 |
| 209 | 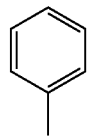 | 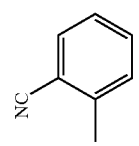 | 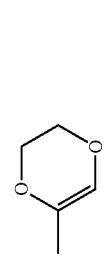 |
| 210 | 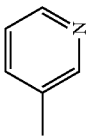 | 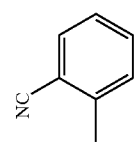 | 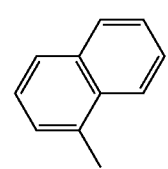 |
| 211 | 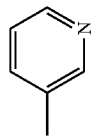 | 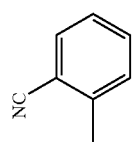 | 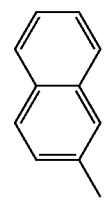 |
| 212 | 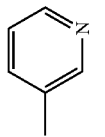 | 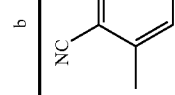 | 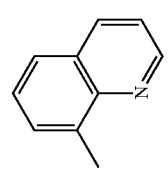 |
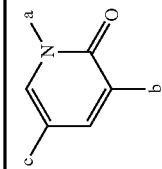

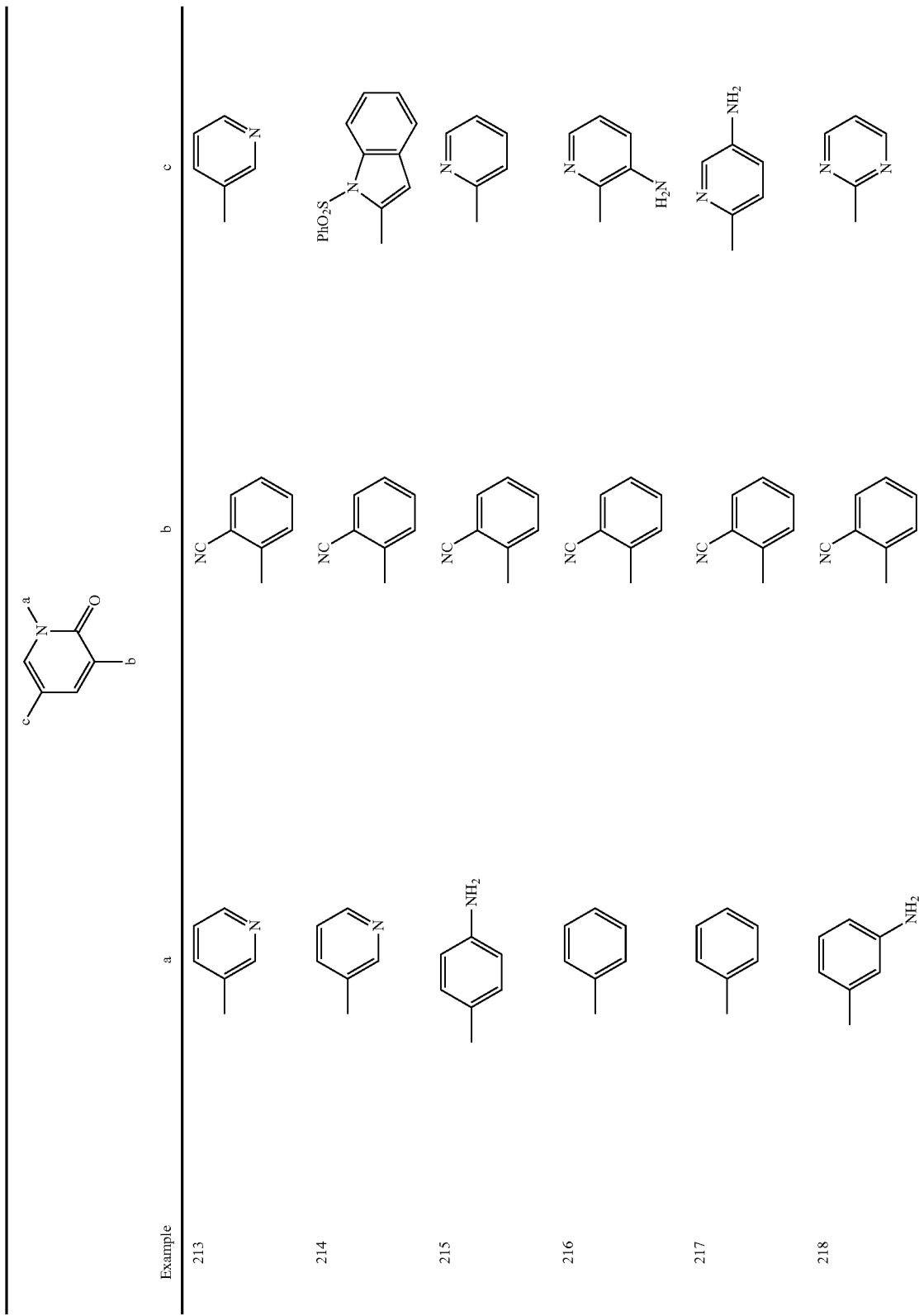

-continued

| Example | a | b | c |
|---|---|---|---|
| 219 | phenyl | 2-methylaniline (H₂N on ortho) | 2-methylpyridine |
| 220 | phenyl | 3-methylaniline (NH₂ on meta) | 2-methylpyridine |
| 221 | phenyl | 4-methylaniline (NH₂ on para) | 2-methylpyridine |
| 222 | 2-Me-5-methyl-3-aminophenyl (Me, NH₂) | 2-methyl-NC (ortho-CN) | 2-methylpyridine |
| 225 | phenyl | 2-methyl-NC (ortho-CN) | 2-methyl-3-(MeSO₂NH)pyridine |
| 226 | phenyl | 2-methyl-(MeSO₂NH) aniline | 2-methylpyridine |

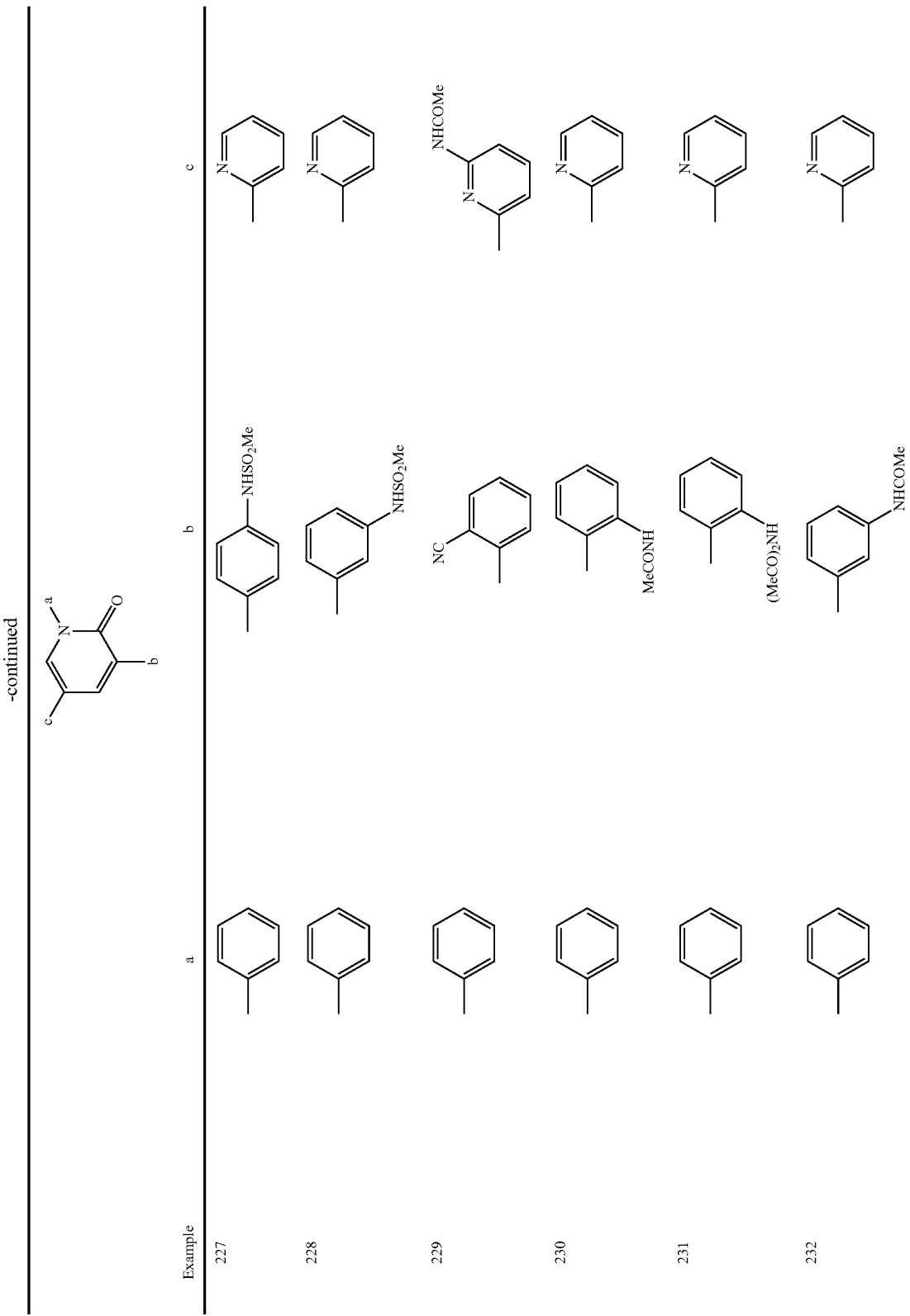

-continued

| Example | a | b | c |
|---|---|---|---|
| 233 | phenyl | 4-(NHCOMe)-phenyl | 2-pyridyl (6-Me) |
| 234 | phenyl | 4-(NMe₂)-phenyl | 2-pyridyl (6-Me) |
| 235 | phenyl | 2-CN-6-Me-phenyl | 2-pyridyl (6-CONH₂) |
| 236 | phenyl | 2-CN-6-Me-phenyl | 2-pyridyl (6-CN) |
| 237 | phenyl | 3-OH-4-Me-phenyl | 2-pyridyl (6-Me) |
| 238 | phenyl | 4-OH-3-Me-phenyl | 2-pyridyl (6-Me) |

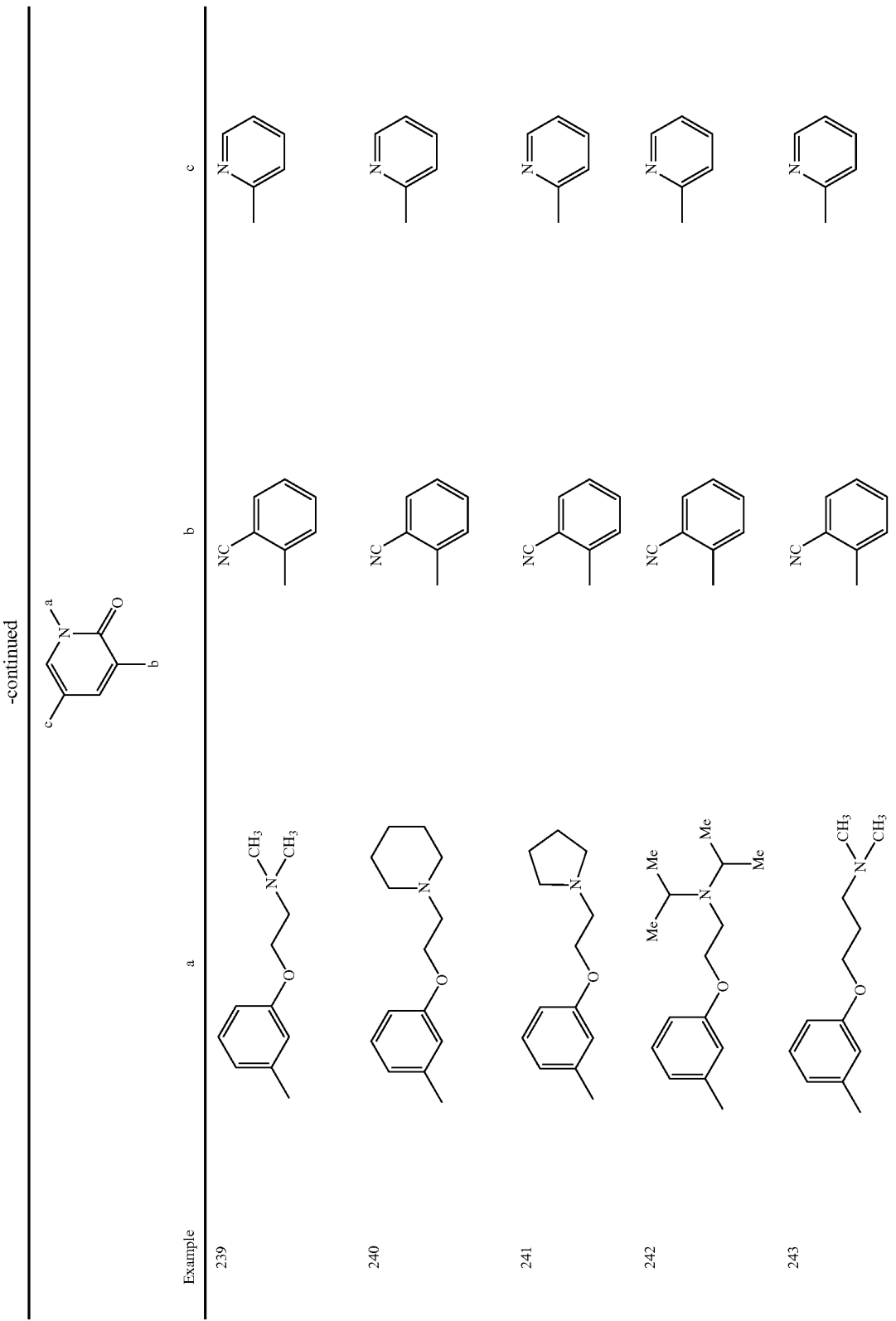

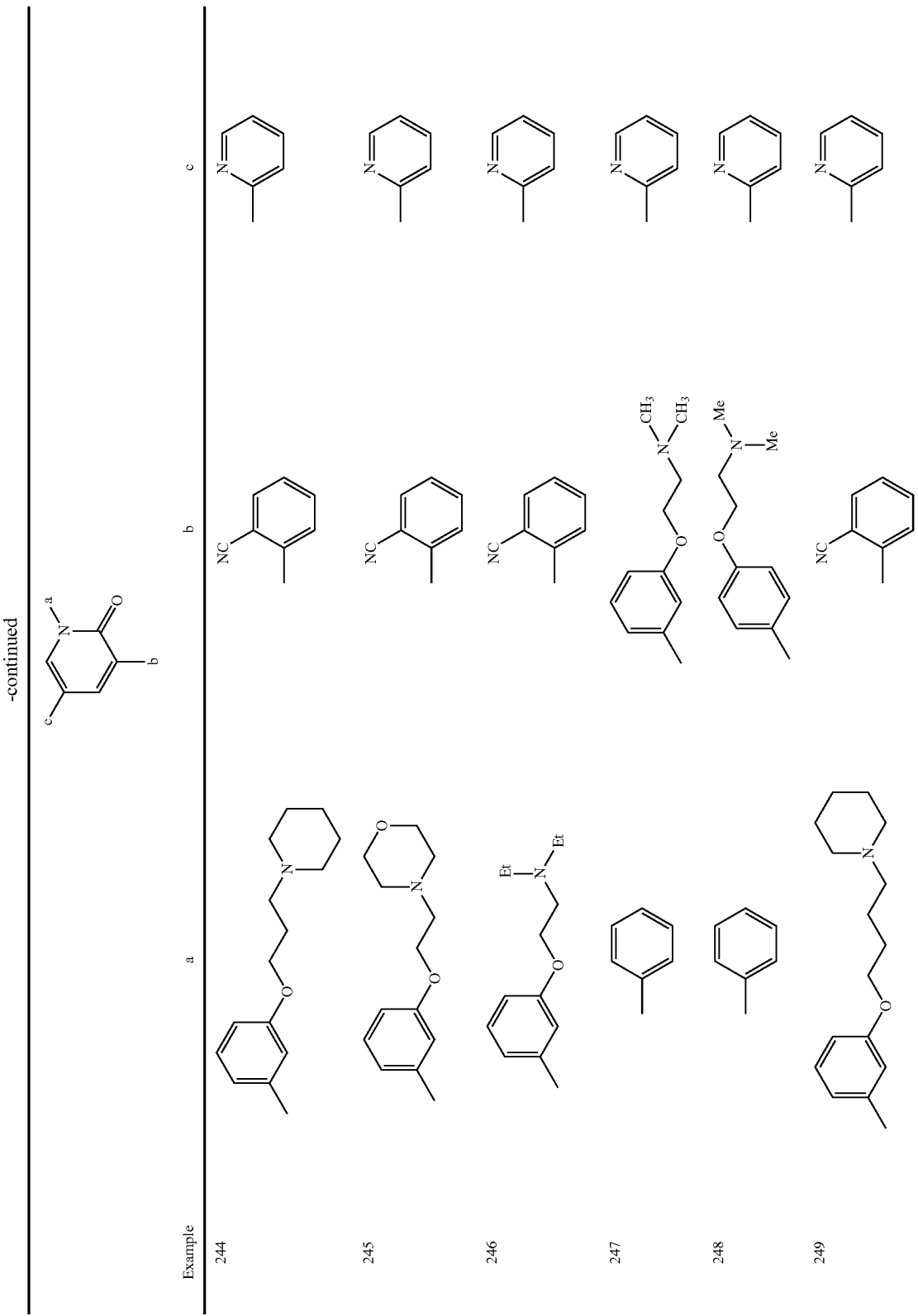

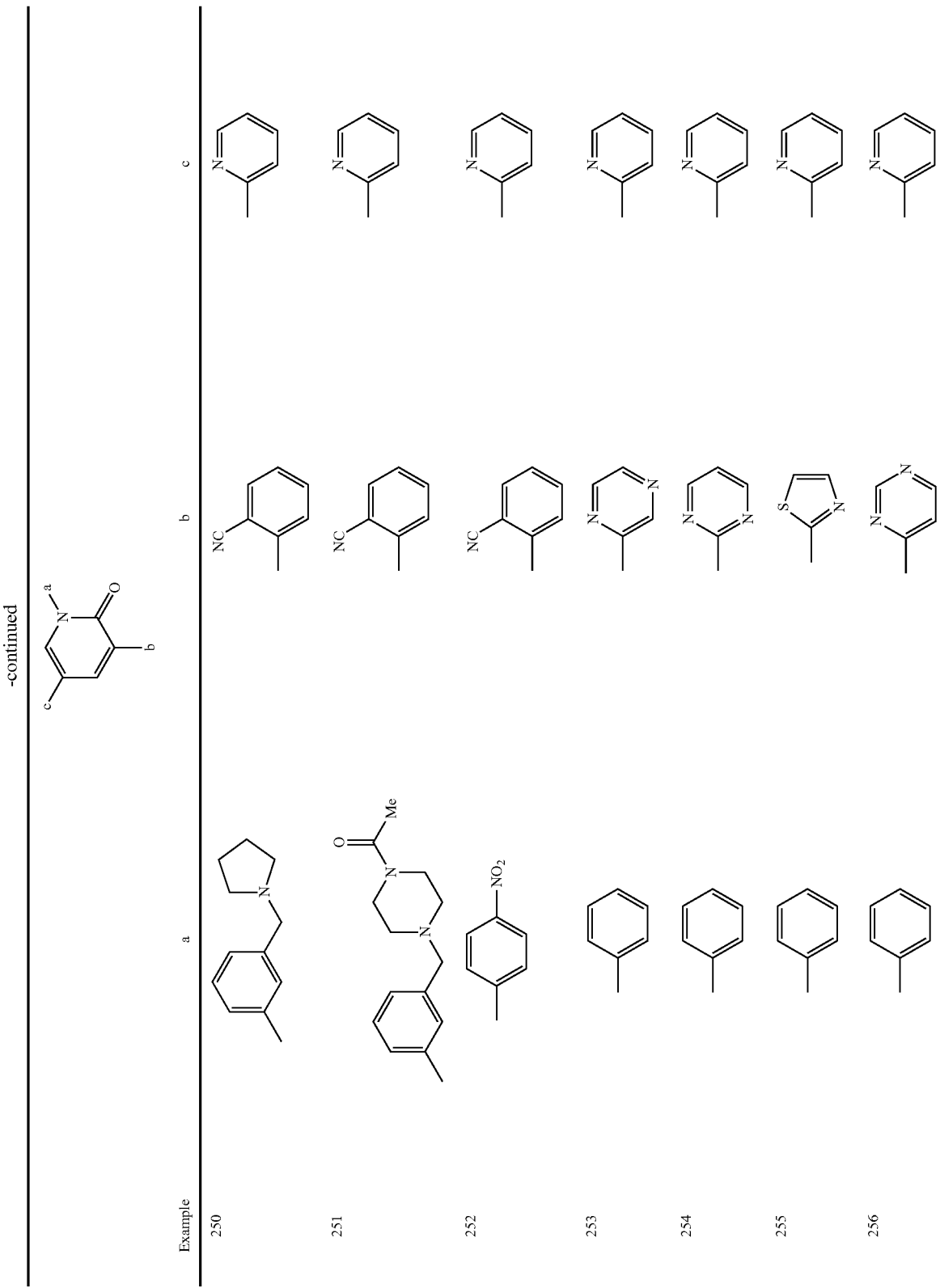

-continued

| Example | a | b | c |
|---|---|---|---|
| 257 | phenyl | 5-methylpyrimidin-4-yl | pyridin-2-yl |
| 258 | phenyl | 3-methylpyridazin-6-yl | pyridin-2-yl |
| 259 | phenyl | 4-methylpyridazin-3-yl | pyridin-2-yl |
| 260 | phenyl | 6-methoxy-2-methylpyridin-... | pyridin-2-yl |
| 261 | pyridin-3-yl | 2-cyano-6-methylphenyl | pyrimidin-2-yl |
| 262 | phenyl | 2-fluoro-3-methylpyridin-... | pyrimidin-2-yl |

-continued
| Example | a | b | c |
|---|---|---|---|
| 263 |  | | |
| 264 | | | |
| 265 | | | |
| 266 | |  | |
| 267 | | | |
| 268 | | 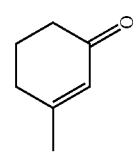 | |

-continued

| Example | a | b | c |
|---|---|---|---|
| 269 | phenyl (methyl-substituted) | 2,3-dihydro-1,4-dioxine-2-yl | 2-methylpyridine |
| 270 | phenyl (methyl-substituted) | 2-nitro-6-methylphenyl | 2-methylpyridine |
| 271 | phenyl (methyl-substituted) | 4-phenylphenyl (methyl-substituted) | 2-methylpyridine |
| 272 | phenyl (methyl-substituted) | 2-methoxy-6-methylphenyl | 2-methylpyridine |
| 273 | phenyl (methyl-substituted) | 3-nitrophenyl | 2-methylpyridine |
| 274 | phenyl (methyl-substituted) | 4-methylpyridine | 2-methylpyridine |
| 275 | phenyl (methyl-substituted) | 4-nitrophenyl (methyl-substituted) | 2-methylpyridine |

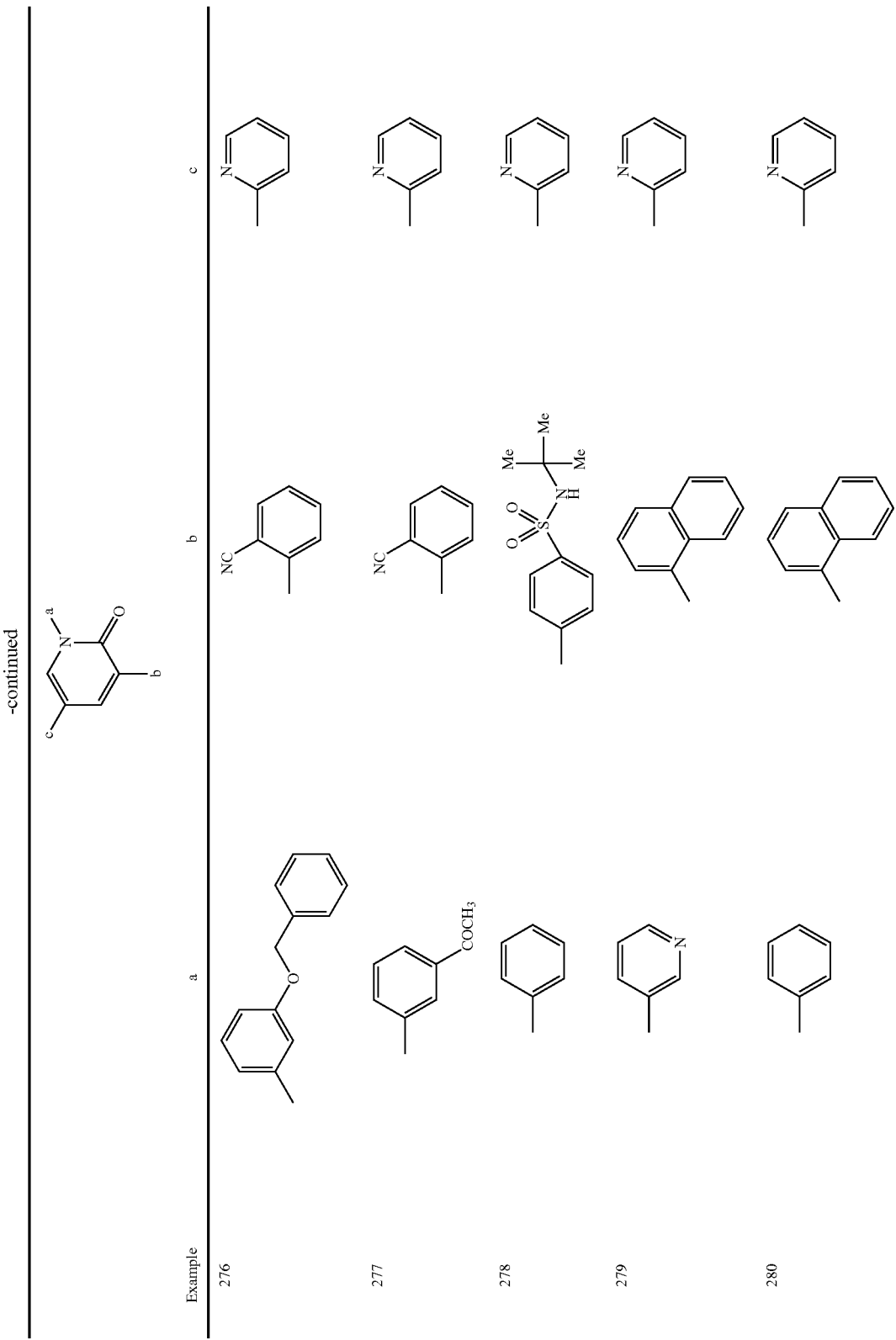

-continued
| Example | a | b | c |
|---|---|---|---|
| 281 | 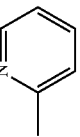 | 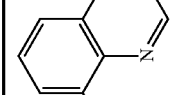 | 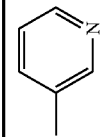 |
| 282 | 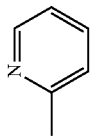 | 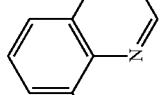 | 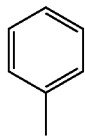 |
| 283 | 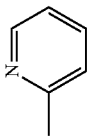 | 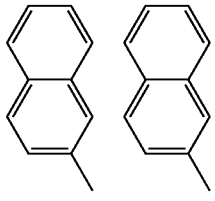 | 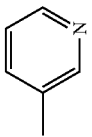 |
| 284 | 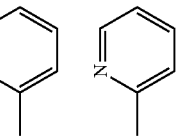 | 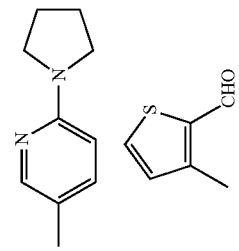 | 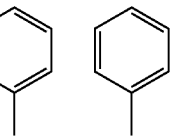 |
| 285 | 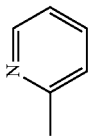 | 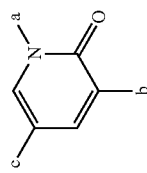 | 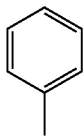 |
| 286 | | | |

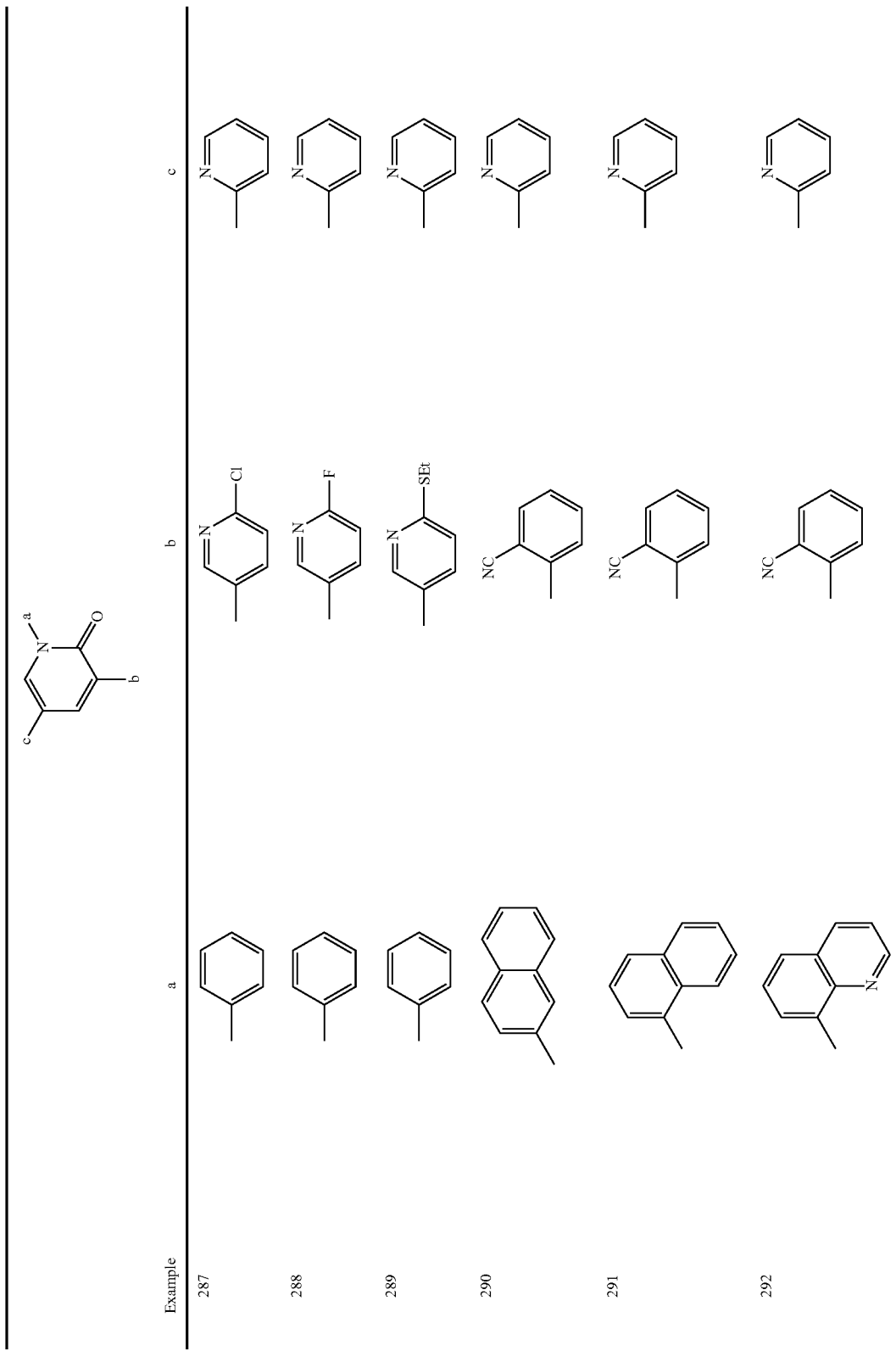

-continued
| Example | a | b | c |
|---|---|---|---|
| 293 | 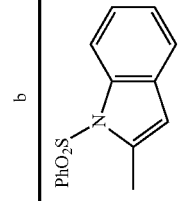 | 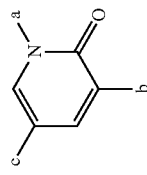 | 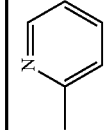 |
| 294 | 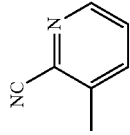 | 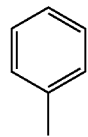 | 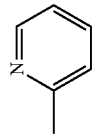 |
| 295 | 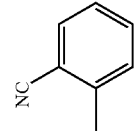 | 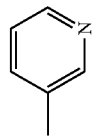 | 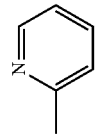 |
| 296 | 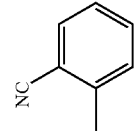 | 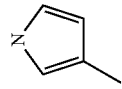 | 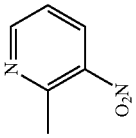 |
| 297 | 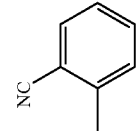 | 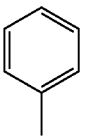 | 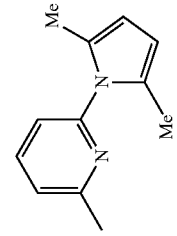 |

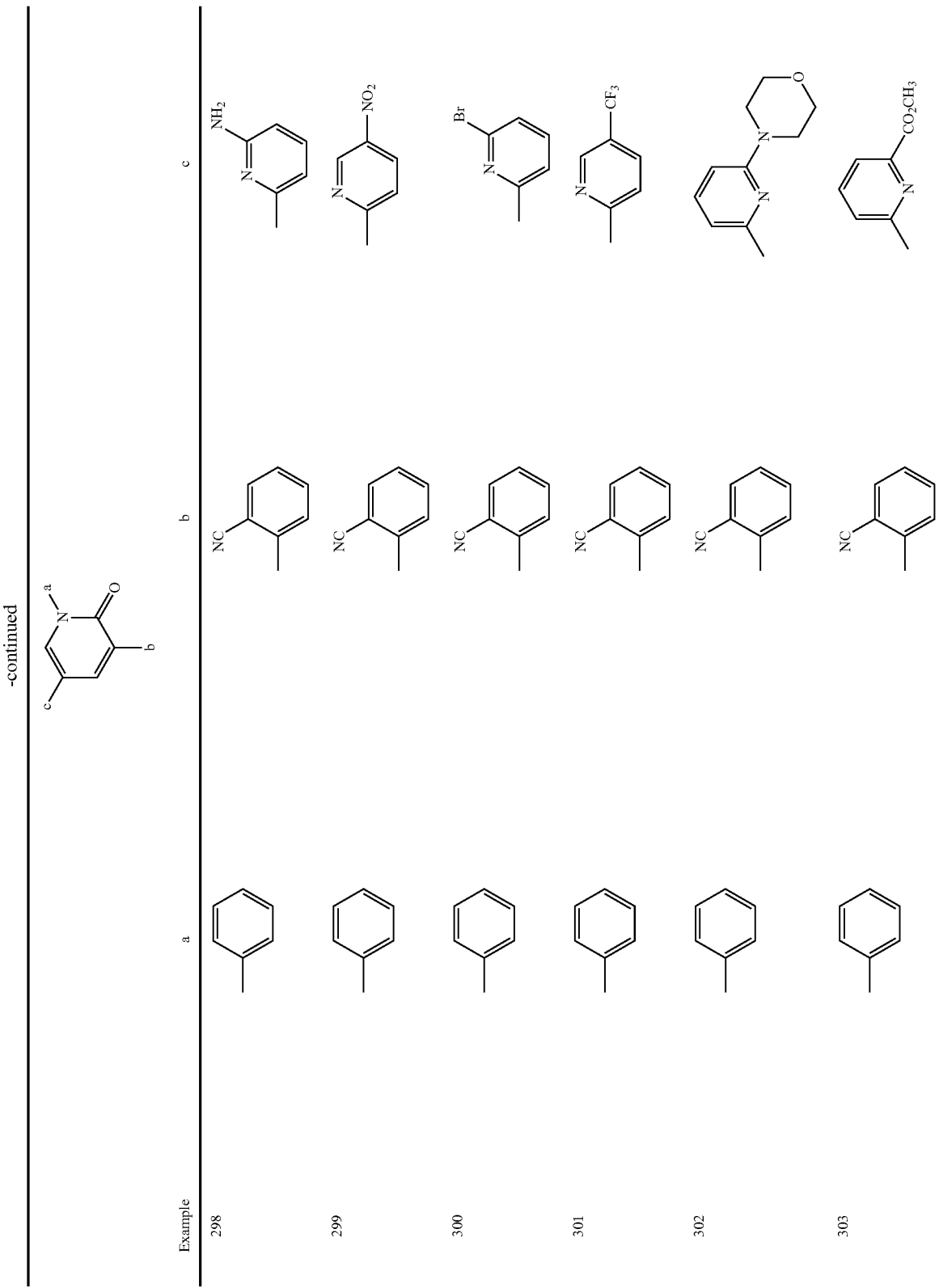

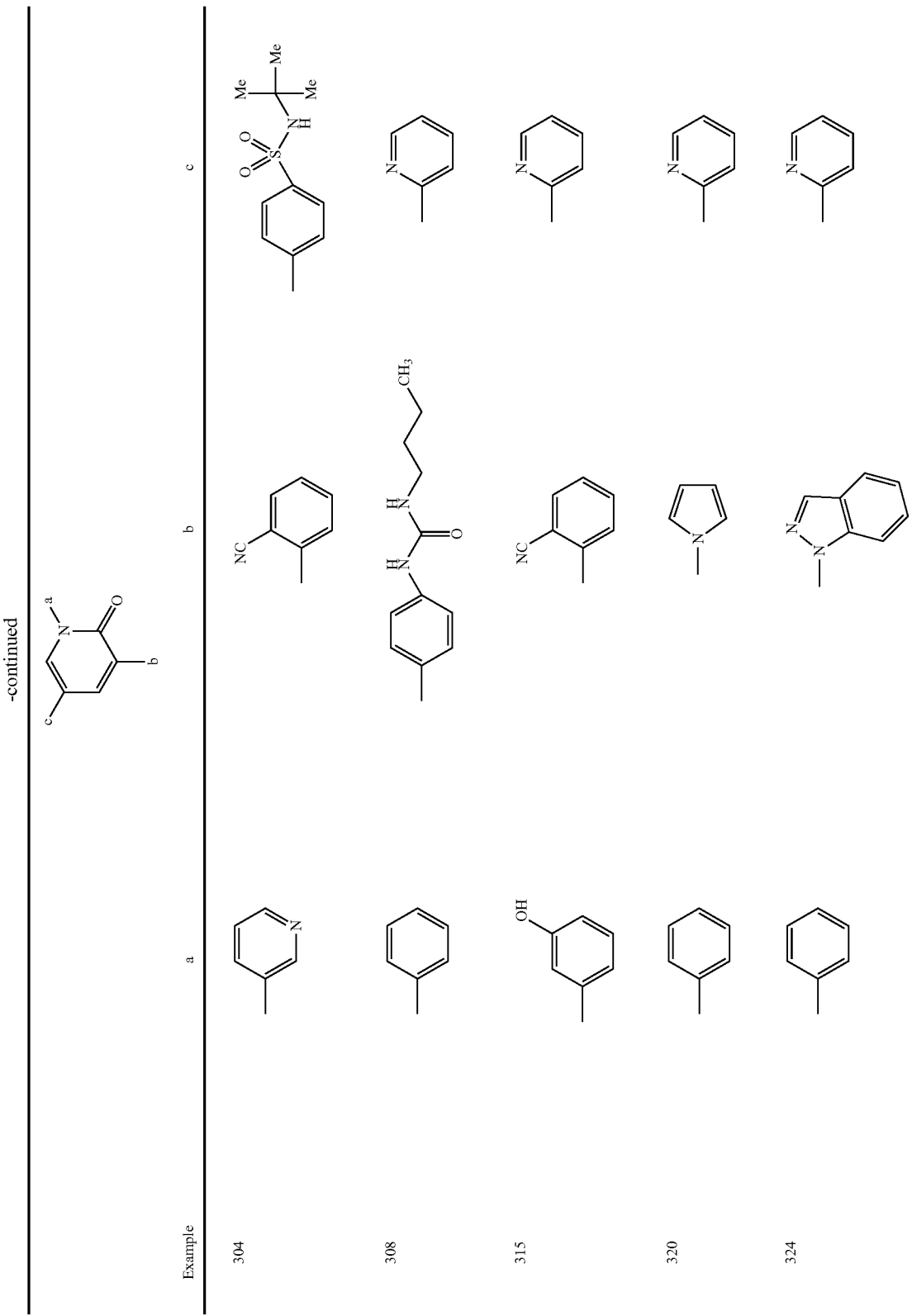

-continued
| Example | a | 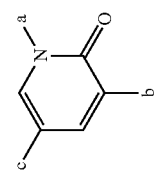 | b | c |
|---|---|---|---|---|
| 325 | 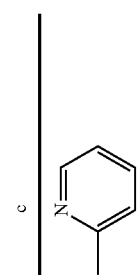 | 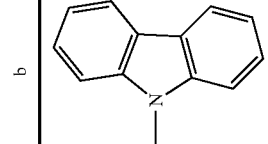 | | 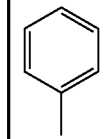 |
| 326 | 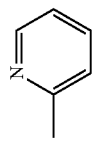 | 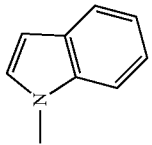 | | 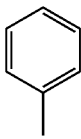 |
| 327 | 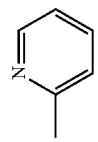 | 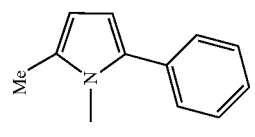 | | 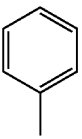 |
| 328 | 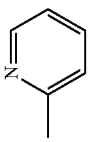 | 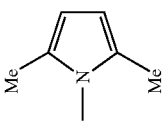 | | 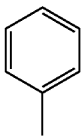 |

-continued
| Example | a | b | c |
|---|---|---|---|
| 330 | 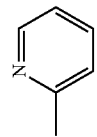 | | |
| 333 | 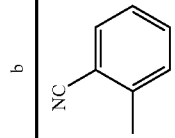 | 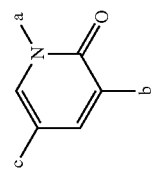 | 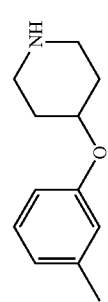 |
| 334 | | | 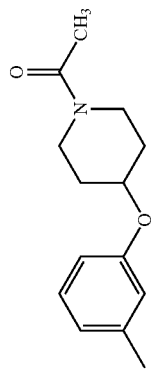 |
| 337 |  | | 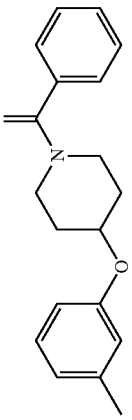 |
| 338 | | | 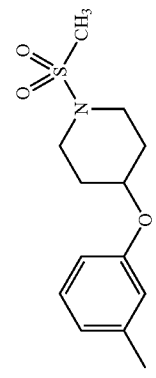 |

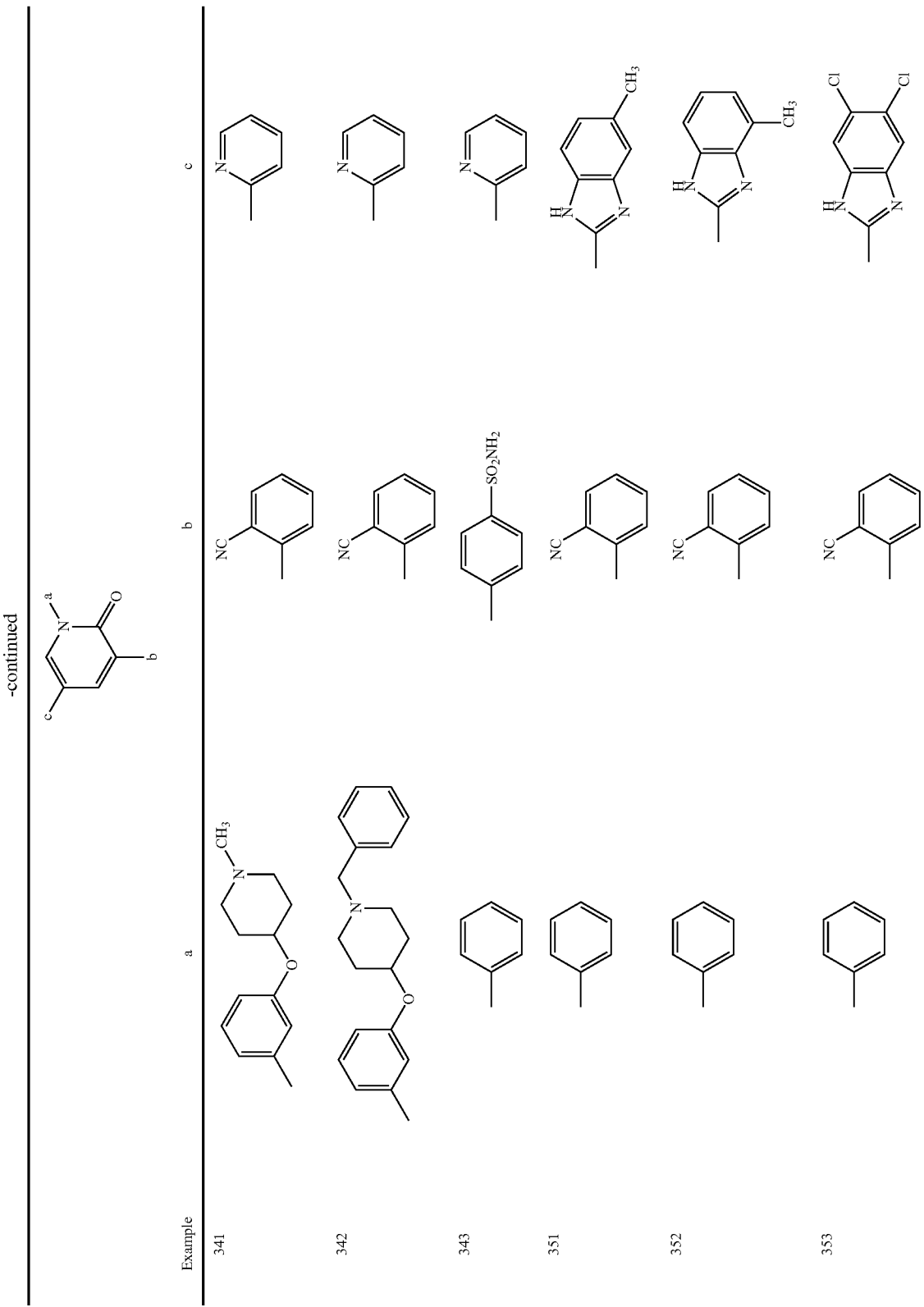

-continued
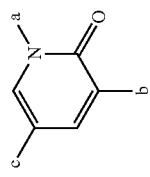
| Example | a | b | c |
|---|---|---|---|
| 354 | 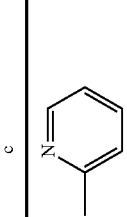 | 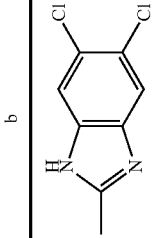 | 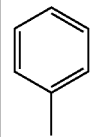 |
| 355 | 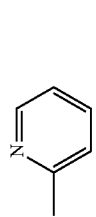 | 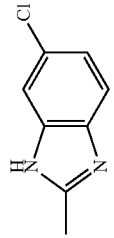 | 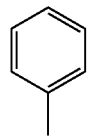 |
| 356 | 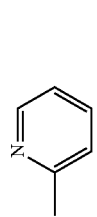 | 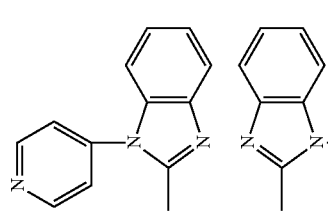 | 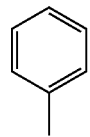 |
| 357 | 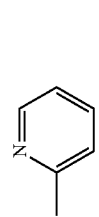 | 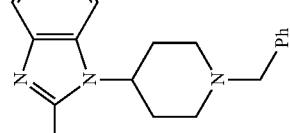 | 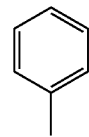 |

-continued
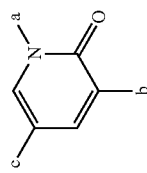
| Example | a | b | c |
|---|---|---|---|
| 358 | 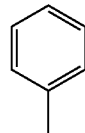 | 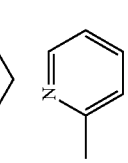 | 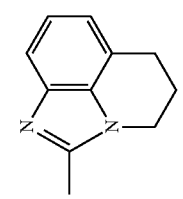 |
| 359 | 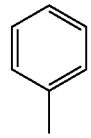 | 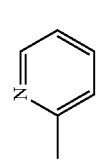 | 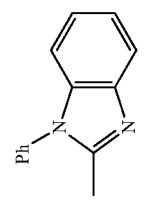 |
| 360 | 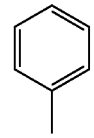 | 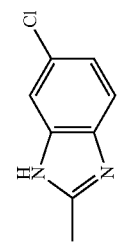 | 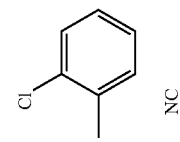 |
| 361 | 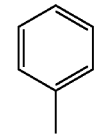 | 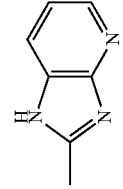 | 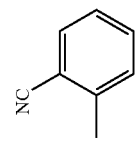 |
| 362 | 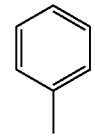 | | |

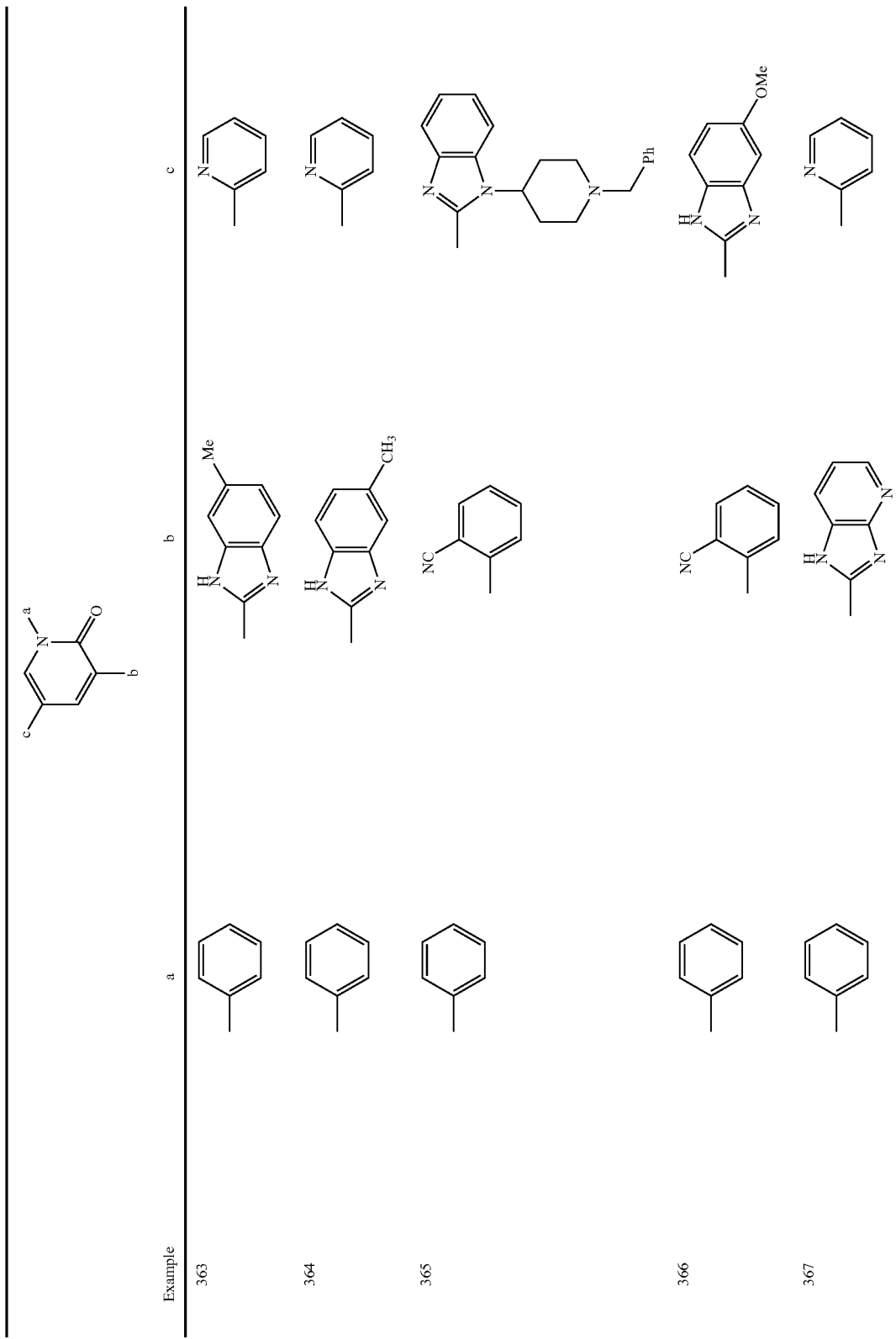

-continued
| Example | a | b | c |
|---|---|---|---|
| 368 | 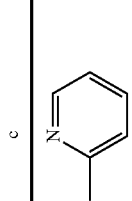 | 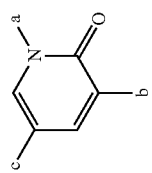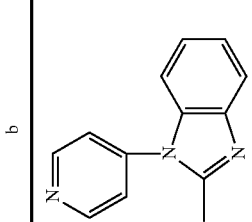 | 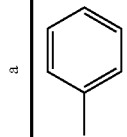 |
| 369 | 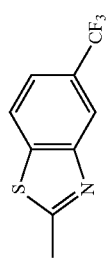 | 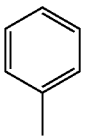 | |
| 370 | 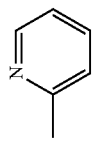 | 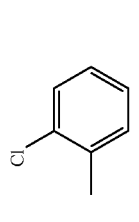 | 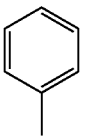 |
| 371 | 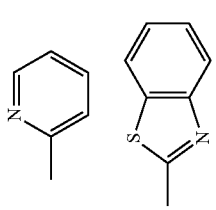 | 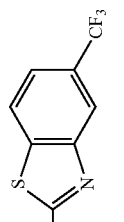 | 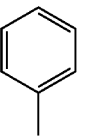 |
| 372 | 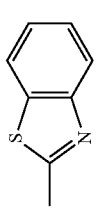 | 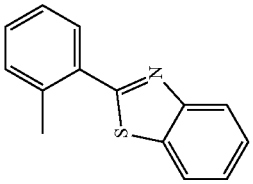 | 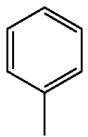 |

-continued
| Example | a | b | c |
|---|---|---|---|
| 373 | 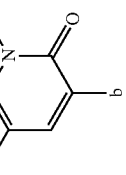 | 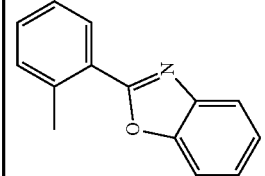 | 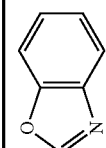 |
| 374 | | 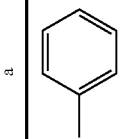 | 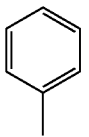 |
| 375 | | 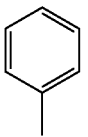 | |
| 376 | | 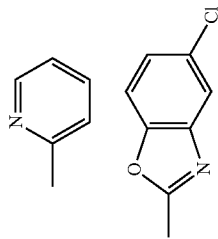 | 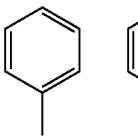 |
| 377 | | 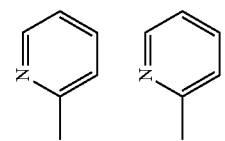 | 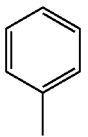 |

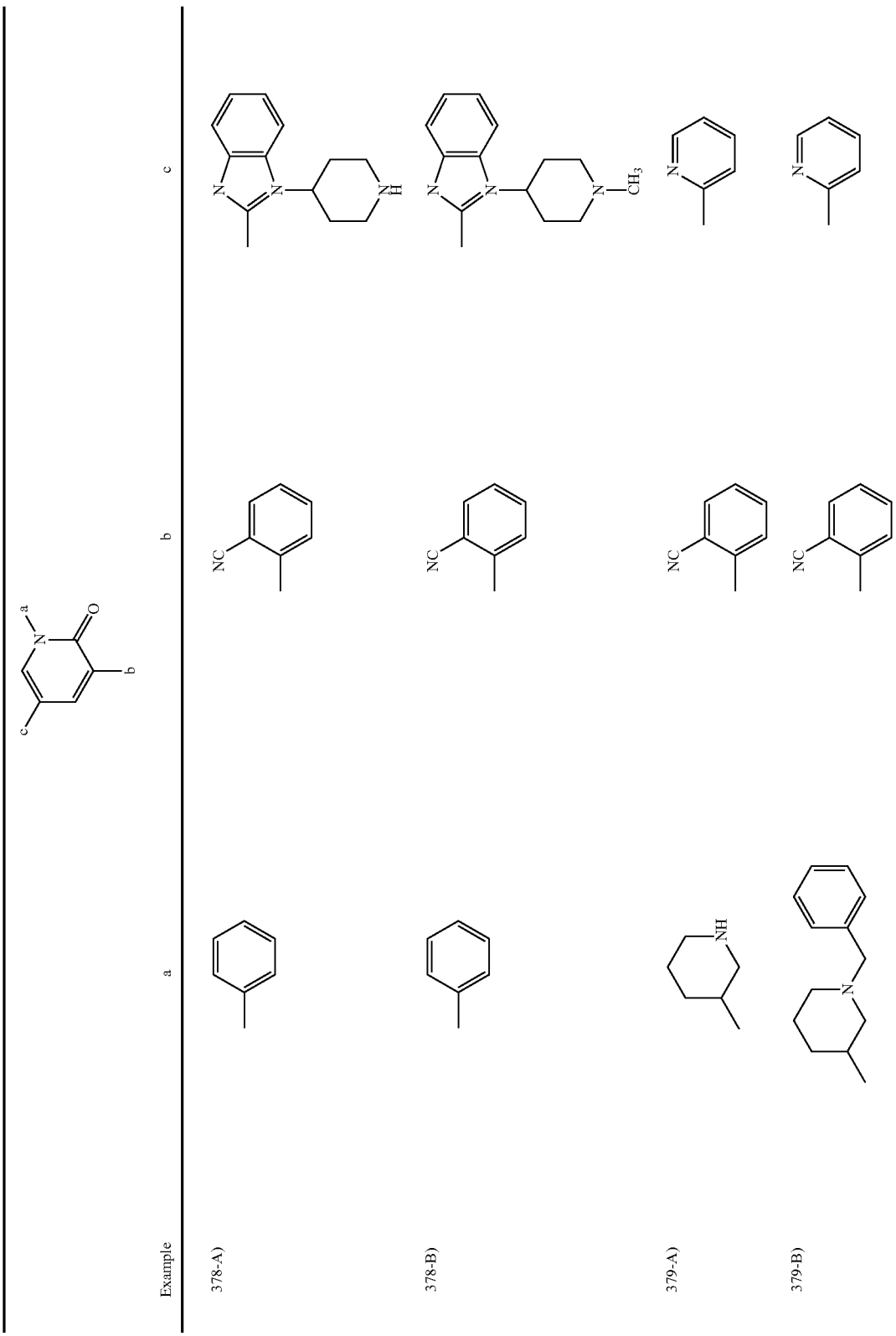

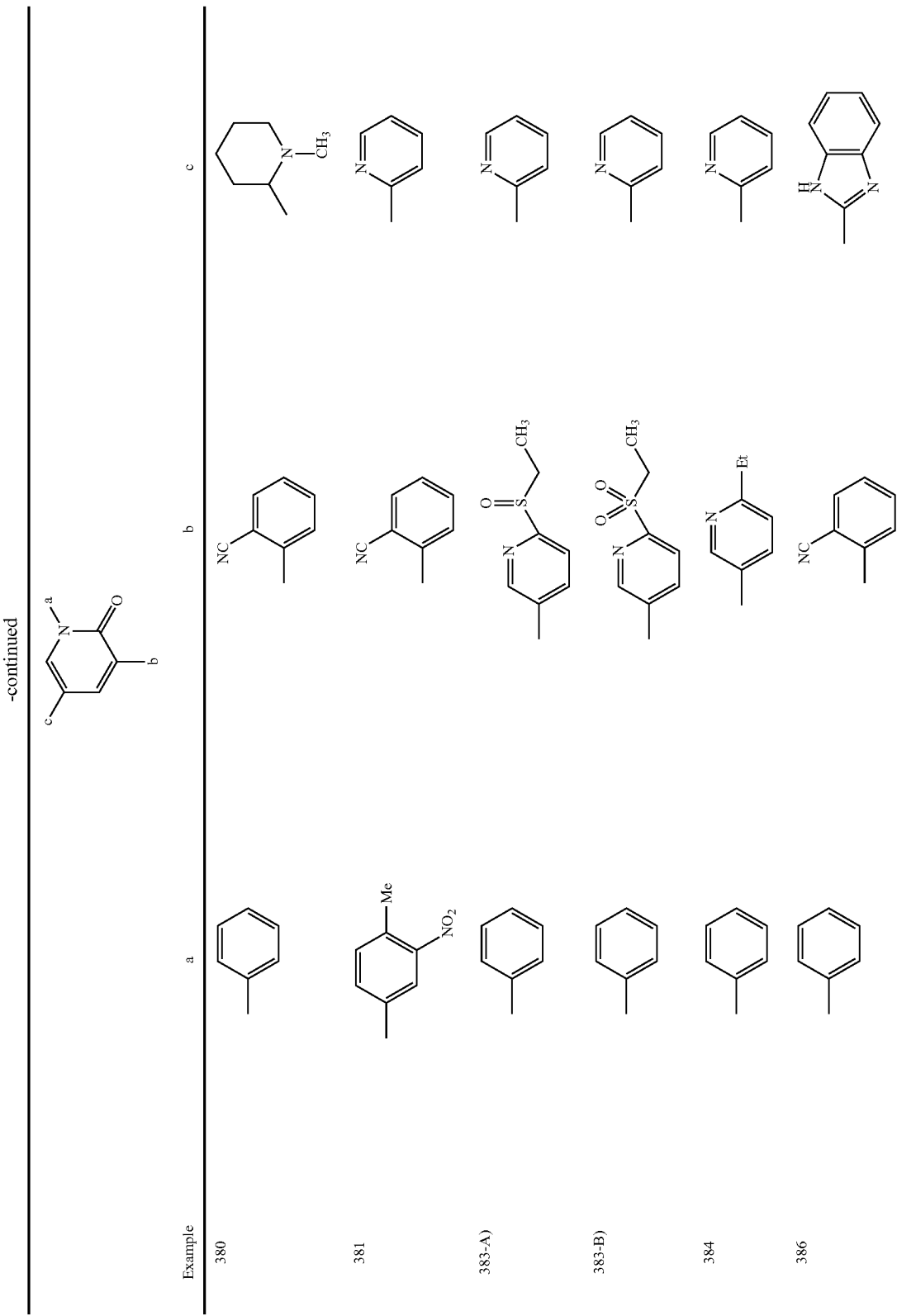

-continued
| Example | a | b | c |
|---|---|---|---|
| 387 | 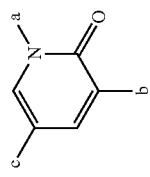 | 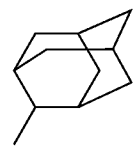 | 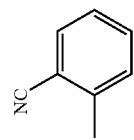 |
| 388 | 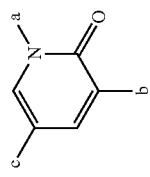 | 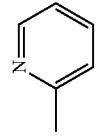 | 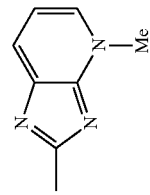 |
| 389 | 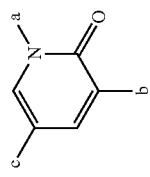 | 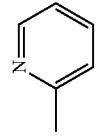 | 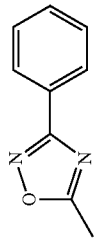 |
| 390 | 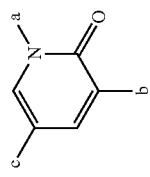 | 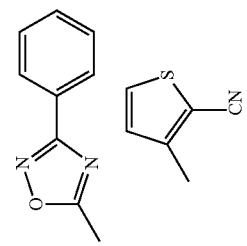 | 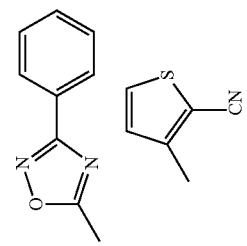 |
| 391 | 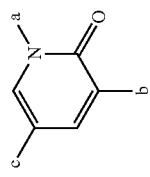 | 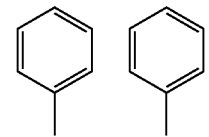 | 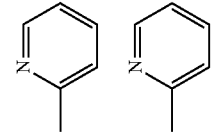 |

-continued
| Example | a | b | c |
|---|---|---|---|
| 392 | 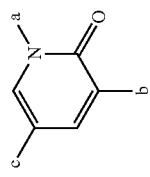 | 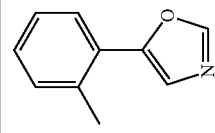 | 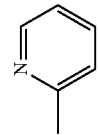 |
| 393 | 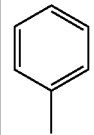 | 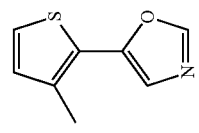 | 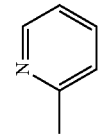 |
| 398 | 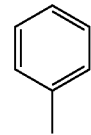 | 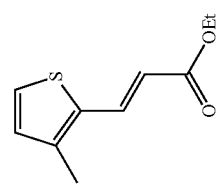 | 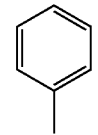 |

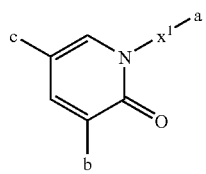

| Example | a | b | c | x¹ |
|---|---|---|---|---|
| 31 | pyridinyl | 2-cyanophenyl | pyridin-2-yl | —CH₂— |
| 158 | pyridinyl | 2-cyanophenyl | pyridin-2-yl | —CH₂CH₂— |
| 316 | phenyl | 2-cyanophenyl | pyridin-2-yl | —CH(OEt)— |
| 317 | cyclopentyl | 2-cyanophenyl | pyridin-2-yl | —CH₂— |
| 318 | 1-Boc-piperidin-4-yl | 2-cyanophenyl | pyridin-2-yl | —CH₂— |
| 319 | 1-Cbz-piperidin-4-yl | 2-cyanophenyl | pyridin-2-yl | —CH₂— |
| 329 | piperidin-4-yl | 2-cyanophenyl | pyridin-2-yl | —CH₂— |
| 331 | 1-benzoyl-piperidin-4-yl | 2-cyanophenyl | pyridin-2-yl | —CH₂— |
| 332 | 1-acetyl-piperidin-4-yl | 2-cyanophenyl | pyridin-2-yl | —CH₂— |

-continued

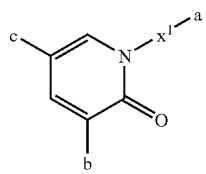

| Example | a | b | c | $x^1$ |
|---|---|---|---|---|
| 335 | 4-(N-phenylsulfonyl)piperidinyl | 2-cyanophenyl | 2-pyridyl | —CH$_2$— |
| 336 | 4-(N-methylsulfonyl)piperidinyl | 2-cyanophenyl | 2-pyridyl | —CH$_2$— |
| 339 | 4-(N-benzyl)piperidinyl | 2-cyanophenyl | 2-pyridyl | —CH$_2$— |
| 340 | 4-(N-methyl)piperidinyl | 2-cyanophenyl | 2-pyridyl | —CH$_2$— |

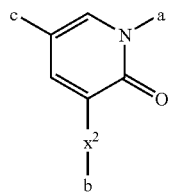

| Example | a | b | c | x2 |
|---|---|---|---|---|
| 161 | phenyl | phenyl | 2-pyridyl | —C≡C— |
| 162 | phenyl | phenyl | 2-pyridyl | —NH—C(O)—NH— |
| 169 | phenyl | phenyl | 2-pyridyl | —NH—C(O)—CH$_3$ |
| 170 | phenyl | phenyl | 2-pyridyl | —NH—CH$_2$CH$_3$ |

-continued

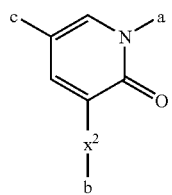

| Example | a | b | c | x2 |
|---|---|---|---|---|
| 174 | phenyl | phenyl | 2-pyridyl | -NHCH3 |
| 175 | phenyl | phenyl | 2-pyridyl | -OCH3 |
| 176 | phenyl | 1-adamantyl | 2-pyridyl | -NHCH3 |
| 179 | phenyl | cyclohexyl | 2-pyridyl | -C(OH)(CH3)(cyclohexyl) |
| 187 | phenyl | 2-pyridyl | 2-pyridyl | -CH=CH-CH3 |
| 188 | phenyl | 4-chlorophenyl | 2-pyridyl | -S- |
| 223 | phenyl | phenyl | 2-pyridyl | -NHS(O)2CH3 |
| 306 | phenyl | phenyl | 2-pyridyl | -NHC(S)NH- |
| 310 | phenyl | 1-pyrrolidinyl | 2-pyridyl | -NHC(O)CH2CH3 |
| 311 | phenyl | 4-phenylpiperazin-1-yl | 2-pyridyl | -NHC(O)CH2CH2CH3 |
| 312 | phenyl | 1-pyrrolidinyl | 2-pyridyl | -NHC(O)CH2CH2CH3 |

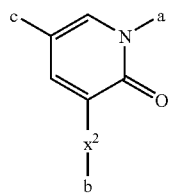

-continued
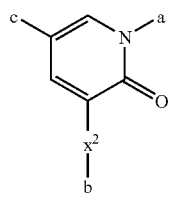
| Example | a | b | c | x2 |
|---|---|---|---|---|
| 382-B | —⌬ | —⌬—Cl | —⌬(pyridyl) | —S(=O)(=O)CH₃ |
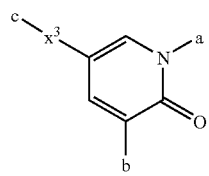
| Example | a | b | c | x3 |
|---|---|---|---|---|
| 181 | —Ph | 2-CN-Ph | —Ph | —C(=O)NHCH₃ |
| 185 | —Ph | 2-Cl-Ph | —Ph | —OCH₂CH₃ |
| 224 | —Ph | 2-CN-Ph | —Ph | —NHS(=O)(=O)CH₃ |
| 307 | —Ph | 2-CN-Ph | —Ph | —NHC(=O)NHCH₃ |
| 309 | —Ph | 2-CN-Ph | 2-pyridyl | —NHC(=O)CH₃ |
| 313 | —Ph | 2-CN-Ph | —Ph | —NHCH₂CH₃ |

-continued

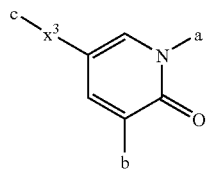

| Example | a | b | c | x3 |
|---|---|---|---|---|
| 345 | phenyl | 2-methyl-6-cyanophenyl | 1-adamantyl | N-methylacetamide |
| 350-A | pyridin-3-yl | 2-chloro-6-methylphenyl | 4-chlorophenyl | S(=O)(CH3) (methylsulfinyl) |
| 350-B | pyridin-3-yl | 2-chloro-6-methylphenyl | 4-chlorophenyl | methylsulfonyl |
| 385 | pyridin-3-yl | 2-chloro-6-methylphenyl | 4-chlorophenyl | —S— |
| 394 | phenyl | 2-methyl-6-cyanophenyl | pyridin-2-yl | acetyl |
| 395 | phenyl | phenyl | pyridin-2-yl | acetyl |
| 396 | phenyl | 2-methyl-6-cyanophenyl | pyridin-2-yl | 2-hydroxypropyl |
| 397 | phenyl | 2-methyl-6-cyanophenyl | pyridin-2-yl | propenyl |

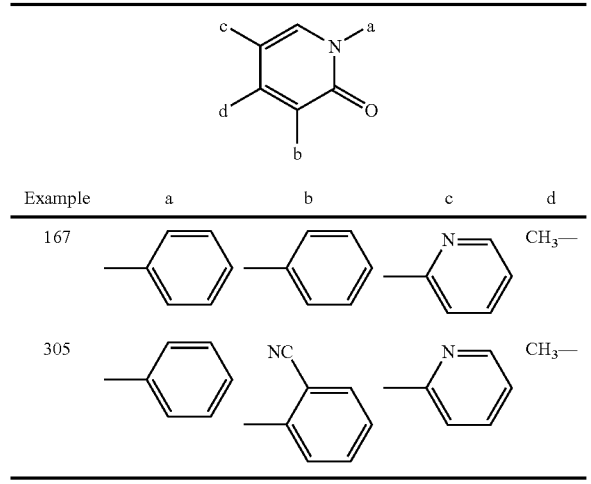

IN VIVO EXAMPLES

The present invention will now be described by way of in vivo examples, with reference to the accompanying drawings, wherein:

FIG. 1 shows that the AMPA receptor antagonist (2-cyanophenyl)-1-(phenyl-5-(2-pyridyl)-1,2-dihydropyridin-2-one (example 7) in combination with interferon-β reduces severity of paralysis during EAE in rats. The compound of example 7 (10 mg/kg p.o. once daily; 7-16 dpi) combined with interferon-β (1×10⁶ Units/rat s.c.) significantly reduces the peak disease score compared to vehicle and either the compound of example 7 or interferon-β treatment alone. Data represent the mean±SEM of disease score (n=8/group).

Figure 2:
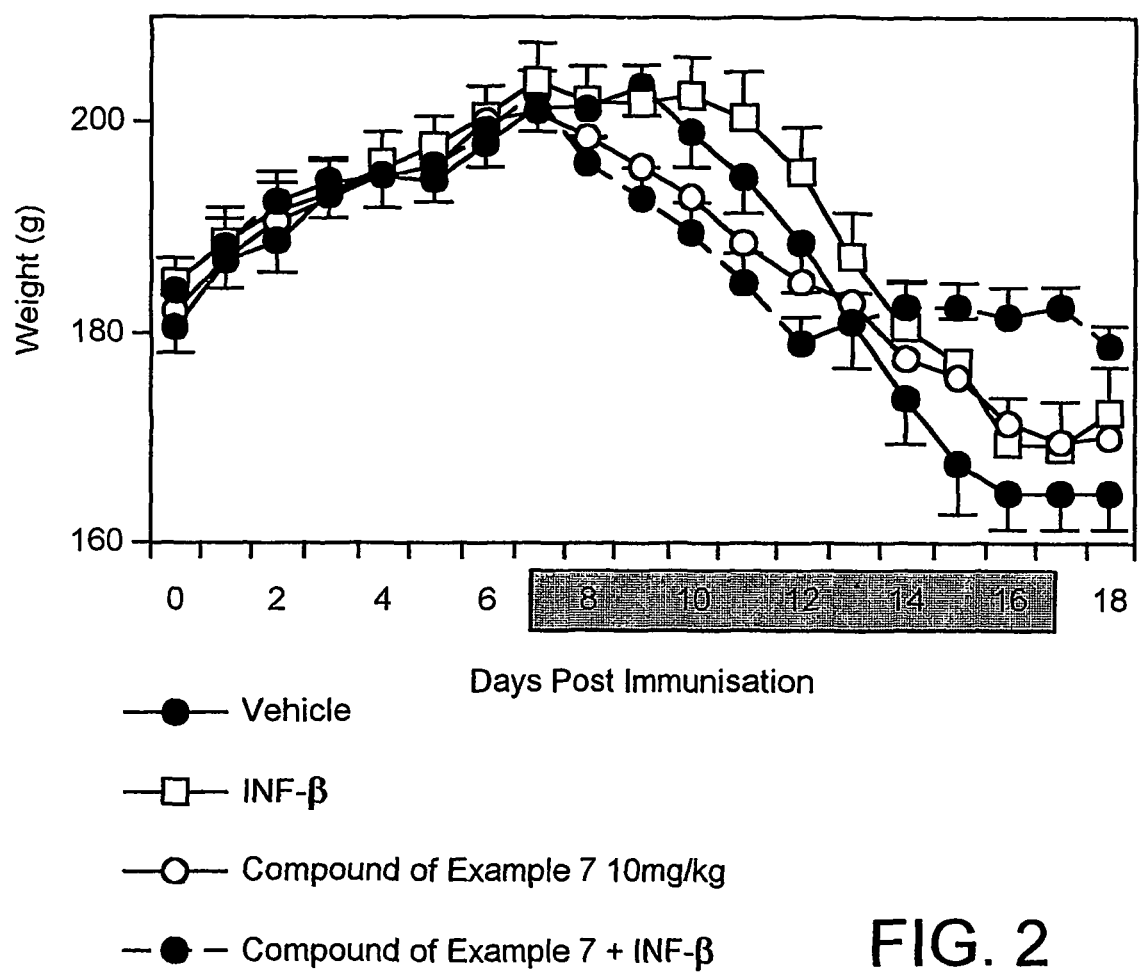

FIG. 2 shows that the AMPA receptor antagonist (2-cyanophenyl)-1-(phenyl-5-(2-pyridyl)-1,2-dihydropyridin-2-one (example 7) (10 mg/kg p.o. once daily; 7-16 dpi) in combination with interferon-β (1×10⁶ Units/rat s.c.) reduces weight (g) loss during the course of EAE in rats. Data represent the mean±SEM of disease score (n=8/group).

In Vivo Example 1

Experimental allergic encephalomyelitis (EAE), an inducible autoimmune disease, represents the best characterized animal model of a demyelinating disorder and drugs active in this model proved to be active in humans (Pender M P (1996). Experimental autoimmune encephalomyelitis, In Autoimmune Neurological Disease, Editors Pender M P and McCombe P A, Cambridge University Press. pp 26-88).

Here we describe a surprising observation on the pronounced reduction in neurological deficits during acute EAE in rats following treatment with a non-immunomodulatory and non-anti inflammatory agent, the AMPA receptor antagonist of example 7, in combination with interferon-β.

Animals

Female Lewis rats (200+10 g) obtained from Charles River, Kent, UK, were housed in pairs under environmentally controlled conditions (6:00 a.m.-6:00 p.m. light/dark cycle; 22-24° C.; 45-55% humidity) and allowed free access to food and water. Experimental groups consisted of 8 animals.

Induction of Acute-Active EAE in Lewis Rats

Rats were immunised in each hind foot with 15 μl of inoculum containing 15 μg guinea pig myelin basic protein (MBP, prepared by the method of Dunkley and Carnegie (1974); final concentration 2 mg/ml), emulsified in Freund's complete adjuvant (CFA; Sigma, UK) containing Mycobacterium tuberculosis H37Ra (final concentration 5.5 mg/ml; Difco Laboratories, UK).

Assessment of Clinical EAE in Lewis Rats

Animals were weighed and monitored daily and clinical disease scored as (0) no clinical signs; (1) flaccid tail and weight loss; (2) hind limb hypotonia with further weight loss; (3) complete hind limb paralysis; (4) paraplegia and (5) death. In addition, intermediate scores were assigned to animals which showed a loss of tonicity in the distal half of the tail (score=0.5), paralysis of one hind limb (score=2.5) or complete hind limb paralysis with forelimb weakness (score=3.5). During the period of compound administration (7-16 days post immunisation; dpi) animals were scored 15 h after injection of vehicle, compound of example 7 or interferon-β to avoid any acute effect of treatment on disease score.

Administration Regime 3-(2-Cyanophenyl)-1-phenyl-5-(2-pyridyl)-1,2-dihydropyridin-2-one; (example 7) was suspended in 0.5% methyl cellulose (MC) solution to obtain a compound concentration of 4 mg/ml. Interferon-β was dissolved in PBS to obtain a compound concentration of 5×10⁶ Units/ml. Rats were dosed once daily (9 a.m.) on days 7 to 16 post immunisation with either vehicle (methyl cellulose p.o. and PBS s.c.), the compound alone in the dose of 10 mg/kg (p.o. plus vehicle PBS s.c), interferon-β alone in the dose of 1×10⁶ Units/rat (s.c. plus methyl cellulose p.o.) or example 7 in the dose of 10 mg/kg (p.o) combined with interferon-β in the dose of 1×10⁶ Units/rat (s.c.).

Results

Effect of the Compound of Example 7 and Interferon-β on Disease Progression During EAE in Tile Lewis Rat Following immunisation with MBP, neurological deficit developed in 8/8 vehicle treated animals, all of which displayed paralysis of both hind limbs; the mean disease onset and duration were 11.8 dpi and 4.3 days respectively (FIG. 1 and Table 1). Similarly, neurological deficit developed in 8/8 interferon-β treated animals, all of which displayed paralysis of both hind limbs; the mean disease onset and duration were 12.4 dpi and 4.5 days respectively (FIG. 1 and Table 1). Once daily treatment from day 7 to 16 post immunisation using the compound of example 7 significantly delayed disease onset, shortened disease duration and reduced peak and cumulative disease score compared to both vehicle and interferon-β treated animals (FIG. 1 and Table 1). The compound in combination with interferon-β, provided pronounced protection, greater than that observed with either vehicle, interferon-β or the compound treatment alone. Once daily treatment from day 7 to 16 post immunisation using the compound in combination with interferon-β completely prevented the development of paralysis in 7 out of 8 rats, with only one animal exhibiting incomplete loss of tail tone (score 0.75) for one day only. Thus the compound of example 7 in combination with interferon-β significantly reduced disease duration (p<0.0001), and peak and cumulative disease score (p<0.01) relative to vehicle, interferon-β and the compound treatment alone. The compound in combination with interferon-β also conferred protection on weight loss, significantly decreasing the percent body weight lost at 18 dpi compared to vehicle treated animals (p<0.05 FIG. 2 and Table 1).

TABLE 1

Parameters of disease activity during Lewis rat acute EAE

| Treatment | Incidence (%) | [a]Onset (d.p.i.) | Duration (days) | Peak Disease Score | [b]Cumulative Disease Score | [c]Weight Loss (%) |
|---|---|---|---|---|---|---|
| Vehicle | 8/8 (100) | 11.8 (11-13) | 4.3 (4-5) | 3.1 (3-3.25) | 10.0 (8.25-12.25) | 20 (1-22) |
| Interferon-β | 8/8 (100) | 12.4 (11-13) | 4.5 (4-5) | 3.0 (2.75-3) | 10.3 (8.5-12.75) | 19 (11-25) |
| Example 7 | 7/8 (87.5) | 11.8 (11-15) | 3.0 (0-4) | 1.8 (0-3) | 4.8 (0-10) | 17 (10-23) |
| Interferon-β + Example 7 | 1/8 (12.5) | 18 (18) | 0.1† (0-1) | 0.1** (0-0.75) | 0.1** (0-0.75) | 13* (11-16) |

Values in the table represent the mean and range where n=8; **p<0.01 and †p<0.0001 vs vehicle, interferon-β and Example 7; *p<0.05 vs vehicle; Student t-test or Mann-Whitney U-test for parametric and non-parametric data respectively. Key: "a"; n=1 for the compound+interferon-β. "b"; Cumulative disease score calculated by summation of individual daily disease scores. "c"; Calculated as the weight on 18 dpi expressed as a percent of the maximum weight before disease onset.

Test Example 1

The suppressing action of the compounds of the present invention to calcium influx into nerve cells induced by AMPA was investigated using the primary culture system of nerve cells of cerebral cortex of embryo of rat.

Culturing Conditions:

Cerebral cortex was cut out from the brain of rat of gestational 18 days and treated with trypsin and DNase to disperse the cells. The cells were flown by MEM containing 10% of serum, sown in a culture bottle and astrocytes were proliferated. The astrocytes were re-dispersed by trypsin and sown in a 96-well plate. After incubation for one week, it was confirmed that the astrocytes covered all over the bottom and then the nerve cells of cerebral cortex which was dispersed by the above method were sown thereupon. After incubation for 24 hours, the medium was changed, the incubation was carried out for one week and, after that, the medium was changed to that containing 1 μM of MK-801. Nerve cells which were incubated for not shorter than 8 to 10 days were used.

Suppressing Action to Calcium Influx into Nerve Cells Induced by AMPA

Calcium influx into the cells was measured using Fura2-AM which was a calcium-sensitive fluorescent dye. It was treated in a medium containing Fura2-AM for 1 hour, incorporated into the cells, exchanged to a Tyrode solution containing 1 μM MK-801 and stimulation was carried out using 2 μM AMPA. Change in the amount of calcium flown into the cells were measured as the change in the fluorescent intensity at the exciting wave length of 340/380 nm. Effect of the test compound was evaluated using the reaction resulted in the AMPA added to a Tyrode solution containing no compound as a control. Results are shown in Tables 1 to 3.

GYKI 52446 (Le Peillet, et al., Brain Res., 571, 115, 1992) was used as a control compound. $IC_{50}$ of GYKI 52466 was 9.02 μM.

Test Example 2

Anticonvulsant Action Induced by AMPA

A test compound was suspended in a 0.5% methyl cellulose solution or in sesame oil and was orally administered (25 mg/kg) to male mice of ddy strain. After 30 minutes or 1 hour from the oral administration, AMPA was continuously injected (2 nmole/5 μl/minute/mouse) into lateral ventricle to induce the convulsions. The effect was judged by a time-extending action until the convulsion takes place by a continuous injection of AMPA.

Results

The compound represented by the above formula (I) according to the present invention showed an excellent anti-convulsant action. For example, the compounds of Examples 4, 7, 9, 12, 16, 32, 41, 47, 57, 61, 76, 78, 91, 126, 128, 137, 139, 164, 199, 261, 262, 264, 270 and 298 showed a significant anticonvulsant action.

Test Example 3

Occlusion Model of Mid-Cerebral Arteries

The usefulness of the compound related to the present invention in the remedy of acute stroke was confirmed by the test below. Namely, the cerebral bloodstream of mid-cerebral arteries was blocked by inserting a nylon suture thread of 4-0 specification whose edge was crashed with flame, by 17 mm from the branch of internal carotid artery, through internal carotid artery from the external carotid artery of a male Sprange Dawley rat, and cerebral infarction was prepared (Zea Longa et al., Stroke 20:84-91, 1989). The size of the cerebral infarction was evaluated by preparing the intersection slice of brain having a thickness of 2 mm and measuring the area of a portion which was not stained by TTC staining. The effect of the tested substance was carried out in this model by comparing the infarction nidus size between a group treated with a solvent and a group treated with the tested substance.

As a result, the compound related to the present invention revealed an excellent effect as the therapeutic agent of acute stroke.

Test Example 4

Antimethamphetamine Effect (S)-(+)-N,α-dimethylphenetylamine (hereinafter, referred to as "methamphetamine") was dosed intraperitoneal administration to a rat or mouse to which the tested compound was dosed, and a quantity of active movement was measured using an active movement measuring apparatus (SCANET SV-10; manufactured by TOYO Sangyo Co., Ltd.). The activity as the therapeutic agent of schizophrenia was evaluated using the hyperdynamic effect control of active movement caused by methamphetamine as an index (K. E. Vanover, Psychopharmacology 136: 123-131, 1998). The effect of the tested substance was confirmed by the control effect of a quantity of active movement accentuation in comparison with the group dosed with a solvent.

As a result, the compound related to the present invention revealed an excellent methamphetamine effect.

Test Example 5

Rigidity Model of Intercaruncle Ablatio Provocative Muscle

An animal model in which the myotony of anteroposterior limbs was provoked was prepared by electrically freezing between the upper cumulus and the lower cumulus of a rat. Myorelaxation effect was evaluated based on the effect of controlling the increase of muscle discharge which is generated when the posterior limbs in this model are moved back and forth. The effect of the tested substance was confirmed by the changes of muscle discharge amount before dosing the tested substance and muscle discharge amount after dosing it.

The compound related to the present invention revealed an excellent myorelaxation effect.

Test Example 6

Light Dark Test

A mouse is put in a dark box which is composed of two light and dark boxes which are linked by a tunnel, and items below were recorded concerning the behavior of the mouse for 5 minutes after that.
1. A time for remaining in the light and dark boxes.
2. Times by which the mouse went and came back between the light box and the dark box.
3. Times by which the mouse went until the entrance of the light box.

The antianxiety effect of the tested compound was detected as the elongation of the time remaining in the light and dark boxes, the increase of times by which the mouse went and came back between the light and the dark box, and the increase of times by which the mouse went until the entrance of the light box, for the group dosed with a solvent (Hascoet M., Bourin M., Pharm. Biochem. Behav. 60:645-653, 1998).

According to the present test, it was confirmed that the compound related to the present invention has an excellent antianxiety effect.

Test Example 7

Destruction Model of 6-hydroxydopamine-inductive Nigrostriaton

10 Mg/kg of L-dihydroxyphenylalanine (L-DOPA) (twice per day) was dosed every day in the abdomen of a rat whose one side of nigra neurocyte was destroyed by injecting 6-hydroxydopamine (6-OHDA) into nigra, therefore the increase of rotational motion to the reverse side of encephalopathy was provoked (C. Marin et al, Synapse 36(4):267-274, 2000). After the solvent or the tested compound was dosed to the rat, influence on the provoked rotational motion was studied. The tested compound delayed the time until primitive rotational motion shows the maximum value after dosing L-DOPA, and increased the time of showing rotation which is a half or more of the maximum rotational number.

Test Example 8

Acetic Acid Writhing Method

Anguishing condition under which the lower half of rat's body was twisted, its abdomen was dented and its hind legs were extended was provoked by injection 0.6% acetic acid saline in the abdomen of the rats. After the tested compound and the solvent were dosed, the acetic acid saline was injected in the abdomen, and analgesic effect was evaluated by comparing the times of these abnormal actions within an observation time (5 to 15 minutes after the dose of acetic acid) which occur after the dosing (Basic Pharmacology Experiment, edited by Kazuhiko Kubota, pages 45-47, Nankoh-do).

As a result, it could be confirmed that the compound related to the present invention controls the times of the abnormal actions significantly and has an excellent analgesic effect.

Test Example 9

Vomiting Model Induced by Cisplatin

A catheter for venoclysis was buried in a ferret, and the rat was postoperatively recovered. Then, vomiting reaction was provoked by injecting 10 mg/kg of cis-diaminedichloroplatinum (cisplatin) (A. Fink-Jensen et al., Neuroscience Letters 137:173-177, 1992). Cisplatin (10 mg/kg) was injected a ferret which was preliminarily treated with the tested compound or the solvent, then the ferret was put in an observation cage, and the time (latent time) and times until the rhythmical contraction of abdomen (defined as vomiting) occurs during the observation period of 240 minutes were measured.

As a result, the compound related to the present invention extended the latent time and reduced the vomiting times significantly.

Test Example 10

Experimental Autoimmune Encephalomyelitis Model

Female Lewis rats (205±10 g) obtained from Charles River, Kent UK, were housed in pairs under environmentally controlled conditions (6:00a.m.-6:00p.m. light/dark cycle; 22-24° C.; 45-55% humidity) and allowed free access to food and water. Experimental groups consisted of 9-12 animals. Rats were immunised in each hind foot with 20-50 μl of inoculum containing 50 μg guinea pig myelin basic protein (MBP; final concentration 2 mg/ml), emulsified in Freund's complete adjuvant (CFA; Sigma, UK) containing *Mycobacterium tuberculosis* H37Ra (final concentration 5.5 mg/ml; Difco Laboratories, UK). Animals were weighed and monitored daily and clinical disease scored as (0) no clinical signs; (1) flaccid tail and weight loss; (2) hind limb hypotonia with further weight loss; (3) complete hind limb paralysis; (4) paraplegia and (5) death. In addition, intermediate scores were assigned to animals which showed a loss of tonicity in the distal half of the tail (score=0.5), paralysis of one hind limb (score=2.5) or complete hind limb paralysis with fore-limb weakness (score=3.5). During the period of compound administration (10-16 days post immunisation; dpi) animals were scored 15 h after injection of vehicle or compound to avoid any acute effect of treatment on disease score. Compounds were dissolved/suspended in 0.5% methyl cellulose using a hand held Polytron homogeniser (PT1200; 2 min). Rats were dosed p.o. with either methyl cellulose vehicle (2.5 ml/kg) or compound at 5, 10 and 20 mg/kg.

Results: the compound of the invention is improved in view of EAE. The compounds of Examples 7, 32, 76, 139, 164, 261, 262 and 264 are for example provided with a superior effect to the vehicle-administered group.

TABLE 1

| Example | $IC_{50}$ (µM) |
|---|---|
| 1 | 0.8 |
| 2 | 1.8 |
| 3 | 0.3 |
| 4 | 0.1 |
| 5 | 0.6 |
| 6 | 9.3 |
| 7 | 0.1 |
| 8 | 0.1 |
| 9 | 0.03 |
| 10 | 0.05 |
| 11 | 0.06 |
| 12 | 0.1 |
| 13 | 0.2 |
| 14 | 0.1 |
| 15 | 0.05 |
| 16 | 0.1 |
| 17 | 0.7 |
| 18 | 0.02 |
| 19 | 0.08 |
| 20 | 0.04 |
| 21 | 0.03 |
| 22 | 0.06 |
| 23 | 0.2 |
| 24 | 0.2 |
| 25 | 0.03 |
| 26 | 0.02 |
| 27 | 0.05 |
| 28 | 0.2 |
| 29 | 0.1 |
| 30 | 0.04 |
| 31 | 0.1 |
| 32 | 0.1 |
| 33 | 0.7 |
| 34 | 3.7 |
| 35 | 3.1 |
| 36 | 1.1 |
| 37 | 0.7 |
| 38 | 6.3 |
| 39 | 0.3 |
| 41 | 0.08 |
| 42 | 0.2 |
| 43 | 0.5 |
| 44 | 0.3 |
| 45 | 0.2 |
| 46 | 0.4 |
| 47 | 0.6 |
| 48 | 0.04 |
| 49 | 0.2 |
| 52 | 1.1 |
| 55 | 0.8 |
| 56 | 3.2 |
| 57 | 0.2 |
| 58 | 0.1 |
| 60 | 1.7 |
| 61 | 0.2 |
| 62 | 3.1 |
| 63 | 1.1 |
| 64 | 2.8 |
| 65 | 0.6 |
| 66 | 2.4 |
| 67 | 6.5 |
| 69 | 0.9 |
| 70 | 3.1 |
| 71 | 0.05 |
| 72 | 0.7 |
| 73 | 1.2 |
| 74 | 0.2 |
| 76 | 0.1 |

TABLE 1-continued

| Example | $IC_{50}$ (µM) |
|---|---|
| 77 | 0.02 |
| 78 | 1.4 |
| 79 | 2.6 |
| 80 | 0.3 |
| 81 | 2.7 |
| 82 | 0.8 |
| 84 | 0.9 |
| 86 | 1.9 |
| 87 | 1.2 |
| 88 | 0.3 |
| 90 | 0.7 |
| 91 | 0.05 |
| 92 | 0.05 |
| 93 | 1.9 |
| 94 | 1.5 |
| 95 | 0.3 |
| 96 | 0.06 |
| 97 | 0.4 |
| 98 | 0.6 |
| 99 | 0.1 |
| 100 | 0.4 |
| 101 | 0.2 |
| 102 | 0.02 |
| 103 | 0.03 |
| 104 | 0.2 |
| 105 | 0.03 |
| 106 | 0.07 |
| 107 | 0.07 |
| 108 | 0.03 |
| 109 | 0.01 |
| 110 | 2.0 |
| 111 | 0.4 |
| 112 | 0.6 |
| 113 | 1.2 |
| 114 | 0.6 |
| 115 | 0.06 |
| 116 | 0.2 |
| 117 | 0.4 |
| 118 | 0.1 |
| 119 | 1.7 |
| 120 | 0.2 |
| 121 | 0.6 |
| 123 | 0.2 |
| 124 | 0.7 |
| 126 | 0.3 |
| 127 | 0.4 |
| 128 | 0.07 |
| 129 | 2.6 |
| 130 | 0.9 |
| 131 | 37 |
| 132 | 3.1 |
| 133 | 0.3 |

TABLE 2

| Example | $IC_{50}$ (µM) |
|---|---|
| 135 | 0.04 |
| 137 | 0.05 |
| 139 | 0.3 |
| 140 | 6.6 |
| 141 | 0.7 |
| 142 | 2.2 |
| 143 | 0.1 |
| 144 | 0.01 |
| 146 | 0.2 |
| 147 | 1.6 |
| 148 | 0.8 |
| 149 | 0.1 |
| 150 | 0.3 |
| 151 | 0.3 |
| 152 | 4.0 |
| 154 | 5.0 |
| 157 | 0.5 |

TABLE 2-continued

| Example | IC$_{50}$ (μM) |
|---|---|
| 159 | 1.6 |
| 163 | 8.2 |
| 164 | 0.08 |
| 165 | 0.4 |
| 166 | 0.3 |
| 171 | 2.3 |
| 173 | 4.2 |
| 174 | 3.3 |
| 176 | 5.4 |
| 178 | 2.0 |
| 180 | 0.5 |
| 182 | 6.0 |
| 184 | 2.3 |
| 185 | 1.7 |
| 187 | 6.1 |
| 188 | 8.5 |
| 190 | 0.6 |
| 192 | 1.1 |
| 193 | 0.4 |
| 195 | 0.2 |
| 196 | 0.3 |
| 197 | 2.9 |
| 198 | 0.3 |
| 199 | 0.7 |
| 200 | 2.0 |
| 201 | 0.2 |
| 202 | 0.7 |
| 204 | 1.6 |
| 206 | 0.5 |
| 209 | 7.0 |
| 210 | 5.2 |
| 211 | 3.6 |
| 215 | 0.1 |
| 216 | 2.4 |
| 217 | 1.3 |
| 218 | 0.1 |
| 219 | 3.7 |
| 220 | 0.6 |
| 221 | 7.1 |
| 222 | 0.2 |
| 226 | 9.5 |
| 227 | 1.8 |
| 228 | 2.7 |
| 229 | 4.2 |
| 230 | 4.0 |
| 232 | 4.3 |
| 234 | 0.9 |
| 235 | 4.4 |
| 236 | 0.6 |
| 237 | 1.5 |
| 238 | 0.6 |
| 239 | 0.3 |
| 240 | 0.1 |
| 241 | 0.4 |
| 242 | 0.5 |
| 243 | 1.2 |
| 244 | 1.8 |
| 245 | 1.2 |
| 246 | 1.1 |
| 247 | 3.6 |
| 248 | 3.4 |
| 249 | 0.3 |
| 250 | 0.9 |
| 251 | 0.9 |
| 252 | 0.3 |
| 253 | 4.7 |
| 255 | 0.5 |
| 256 | 1.2 |
| 257 | 3.7 |
| 259 | 2.0 |
| 260 | 2.7 |
| 261 | 0.08 |
| 262 | 0.3 |
| 263 | 1.0 |
| 264 | 0.05 |
| 265 | 0.7 |
| 266 | 0.1 |

TABLE 2-continued

| Example | IC$_{50}$ (μM) |
|---|---|
| 267 | 1.0 |
| 268 | 4.2 |
| 269 | 1.9 |
| 270 | 0.14 |
| 272 | 3.3 |
| 275 | 6.1 |
| 276 | 1.9 |
| 277 | 0.6 |
| 278 | 2.8 |
| 279 | 3.71 |
| 280 | 1.3 |
| 282 | 9.0 |
| 284 | 2.8 |
| 285 | 7.2 |
| 286 | 0.3 |
| 287 | 5.6 |
| 288 | 1.2 |
| 290 | 0.2 |
| 291 | 0.14 |
| 292 | 3.3 |
| 293 | 3.3 |
| 294 | 0.6 |
| 297 | 4.2 |
| 298 | 0.3 |
| 299 | 4.4 |
| 300 | 0.3 |

TABLE 3

| Example | IC$_{50}$ (μM) |
|---|---|
| 302 | 0.3 |
| 303 | 0.9 |
| 307 | 2.0 |
| 308 | 1.6 |
| 309 | 4.1 |
| 313 | 5.9 |
| 314 | 4.6 |
| 315 | 0.08 |
| 316 | 2.1 |
| 317 | 0.6 |
| 318 | 3.1 |
| 319 | 2.0 |
| 320 | 2.3 |
| 321 | 4.0 |
| 326 | 0.9 |
| 327 | 8.0 |
| 330 | 0.4 |
| 333 | 0.3 |
| 334 | 0.6 |
| 337 | 0.7 |
| 338 | 0.4 |
| 341 | 0.2 |
| 342 | 1.3 |
| 342 | 3.2 |
| 344 | 4.7 |
| 346 | 3.7 |
| 351 | 3.3 |
| 352 | 1.6 |
| 354 | 1.5 |
| 355 | 0.2 |
| 356 | 2.1 |
| 358 | 1.4 |
| 359 | 2.3 |
| 360 | 3.1 |
| 362 | 3.7 |
| 365 | 2.7 |
| 367 | 0.6 |
| 371 | 0.6 |
| 379-B | 6.4 |
| 381 | 0.4 |
| 382-B | 2.3 |
| 385 | 1.1 |
| 386 | 3.5 |

TABLE 3-continued

| Example | IC$_{50}$ (μM) |
| --- | --- |
| 387 | 7.0 |
| 388 | 2.9 |
| 390 | 1.0 |
| 391 | 0.1 |
| 392 | 0.1 |
| 393 | 0.3 |
| 394 | 1.4 |
| 395 | 0.9 |
| 398 | 0.2 |

The foregoing description of the invention is merely illustrative thereof and it should therefore be appreciated that various variations and modification can be made without departing from the spirit or scope of the invention as set forth in the accompanying claims.

Where preferred or optional features are described in connection with particular aspects of the present invention, they shall be deemed to apply mutatis mutandis to other aspects of the invention unless the context indicates otherwise.

All documents cited herein are hereby incorporated by reference, as are any citations referred to in said documents.

The invention claimed is:

1. A pharmaceutical composition comprising
    I) a compound represented by the following formula or a salt thereof:

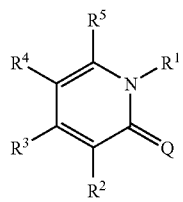

wherein,
    Q indicates O;
    $R^1$ indicates $X^1$-$A^1$;
    $R^2$ indicates $X^2$-$A^2$;
    $R^3$ indicates hydrogen;
    $R^4$ indicates $X^3$-$A^3$; and
    $R^5$ indicates hydrogen,
    wherein $X^1$, $X^2$, and $X^3$ each indicates a single bond and $A^1$, $A^2$, and $A^3$ are the same as or different from each other and each indicates a $C_{6-14}$ aromatic hydrocarbocyclic group or a 5 to 14 membered aromatic heterocyclic group, wherein each of $A^1$, $A^2$, and $A^3$ is optionally substituted with a hydroxyl group, a halogen atom, an amino group, or a nitrile group; and
    II) β-interferon.

2. A composition as claimed in claim 1, wherein the compound is one or more of:
    3-(2-cyanophenyl)-1-phenyl-5-(2-pyridyl)-1,2-dihydropyridin-2-one, 3-(2-cyanophenyl)-5-(2-pyridyl)-1-(3-pyridyl)-1,2-dihydropyridin-2-one, 3-(2-fluoro-3-pyridyl)-5-(2-pyridyl)-1-phenyl-1,2-dihydropyridin-2-one, 3-(2-fluoro-3-pyridyl)-5-(2-pyridyl)-1-(3-pyridyl)-1,2-dihydropyridin-2-one, 3-(2-cyanophenyl)-1-phenyl-5-(2-pyrimidinyl)-1,2-dihydropyridin-2-one, 3-(2-cyanophenyl)-1-(3-pyridyl)-5-(2-pyrinidinyl)-1,2-dihydropyridin-2-one, 3-(2-fluoropyridin-3-yl)-1-phenyl-5-(2-pyrimidinyl)-1,2-dihydropyridin-2-one, and 3-(2-cyanopyridin-3-yl)-1-phenyl-5-(2-pyrimidinyl)-1,2-dihydropyridin-2-one.

3. A composition, as claimed in claim 1, wherein the β-interferon is IFN-beta-1a or IFN-beta-1b.

4. A composition, as claimed in claim 3, wherein the IFN-beta-1a is Rebif or Avonex and the IFN-beta-1b is Betaseron or Betaferon.

5. A pharmaceutical composition for the treatment of a demyelinating disorder comprising a therapeutically effective amount of a composition for treating said demyelinating disorder according to claim 1 in combination with a pharmaceutically acceptable carrier or excipient.

6. The pharmaceutical composition according to claim 5, wherein the demyelinating disorder is encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV-myelopathy, HTLV-myelopathy, progressive multifocal leucoencephalopathy, or a secondary demyelinating disorder.

7. The pharmaceutical composition as claimed in claim 6, wherein the demyelinating disorder is a secondary demyelinating disease which is CNS lupus erythematodes, polyarteritis nodosa, Sjoegren's syndrome, sarcoid granuloma or isolated cerebral vasculitis.

8. A method for the treatment of a demyelinating disorder, the method comprising administering to a patient a composition as claimed in claim 1.

9. A method for the treatment of a demyelinating disorder, the method comprising administering to a patient a composition comprising
    I) a compound represented by the following formula or a salt thereof:

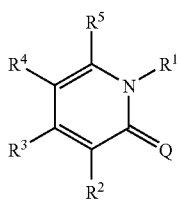

wherein, Q indicates O; $R^1$ indicates $X^1$-$A^1$; $R^2$ indicates $X^2$-$A^2$; $R^3$ indicates hydrogen; $R^4$ indicates $X^3$-$A^3$; and $R^5$ indicates hydrogen, wherein $X^1$, $X^2$, and $X^3$ each indicates a single bond and $A^1$, $A^2$, and $A^3$ are the same as or different from each other and each indicates a $C_{6-14}$ aromatic hydrocarbocyclic group or a 5 to 14 membered aromatic heterocyclic group, wherein each of $A^1$, $A^2$, and $A^3$ is optionally substituted with a hydroxyl group, a halogen atom, an amino group, or a nitrile group; and
    II) β-interferon
    wherein the compound and the β-interferon are administered separately, simultaneously or sequentially.

10. A kit comprising, a first container comprising
    a compound represented by the following formula or a salt thereof:

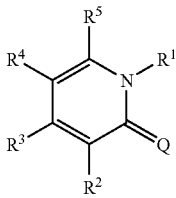

wherein, Q indicates O; $R^1$ indicates $X^1$-$A^1$; $R^2$ indicates $X^2$-$A^2$; $R^3$ indicates hydrogen; $R^4$ indicates $X^3$-$A^3$; and $R^5$ indicates hydrogen, wherein $X^1$, $X^2$, and $X^3$ each indicates a single bond and $A^1$, $A^2$, and $A^3$ are the same as or different from each other and each indicates a $C_{6-14}$ aromatic hydrocarbocyclic group or a 5 to 14 membered aromatic heterocyclic group, wherein each of $A^1$, $A^2$, and $A^3$ is optionally substituted with a hydroxyl group, a halogen atom, an amino group, or a nitrile group, and a second container comprising β-interferon,
optionally with instructions for use.

11. A kit comprising:
a first container comprising therein a compound represented by the following formula or a salt thereof:

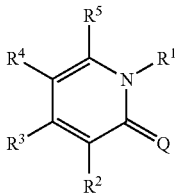

wherein,
Q indicates O;
$R^1$ indicates $X^1$-$A^1$;
$R^2$ indicates $X^2$-$A^2$;
$R^3$ indicates hydrogen;
$R^4$ indicates $X^3$-$A^3$; and
$R^5$ indicates hydrogen,
wherein $X^1$, $X^2$, and $X^3$ each indicates a single bond and $A^1$, $A^2$, and $A^3$ are the same as or different from each other and each indicates a $C_{6-14}$ aromatic hydrocarbocyclic group or a 5 to 14 membered aromatic heterocyclic group, wherein each of $A^1$, $A^2$, and $A^3$ is optionally substituted with a hydroxyl group, a halogen atom, an amino group, or a nitrile group; and
a second container comprising therein β-interferon,
optionally with instructions for use, wherein one or both of the first container and the second container further comprise a pharmaceutically acceptable carrier or excipient.

12. A kit, as claimed in claim 10, for use in the treatment of a demyelinating disorder.

13. A kit, as claimed in claim 10, wherein the compound and the β-interferon, are administered separately, simultaneously, or sequentially.

14. A pharmaceutical composition comprising:
3-(2-cyanophenyl)-1-phenyl-5-(2-pyridyl)-1,2-dihydropyridin-2-one or a salt thereof;
β-interferon; and
at least one pharmaceutically acceptable carrier or excipient.

15. The pharmaceutical composition of claim 14, wherein 3-(2-cyanophenyl)-1-phenyl-5-(2-pyridyl)-1,2-dihydropyridin-2-one or a salt thereof and β-interferon are formulated for separate, simultaneous, or sequential administration.

16. A method of treating a demyelinating disorder which comprises administering to a patient in need thereof a pharmaceutically effective amount of a composition of claim 14 or 15.

17. The method of claim 16, wherein 3-(2-cyanophenyl)-1-phenyl-5-(2-pyridyl)-1,2-dihydropyridin-2-one or a salt thereof and β-interferon are administered sequentially.

18. A composition as claimed in claim 1, wherein the compound and the immunoregulatory or anti-inflammatory agent are for separate, simultaneous, or sequential administration.

19. A combination comprising:
3-(2-cyanophenyl)-1-phenyl-5-(2-pyridyl)-1,2-dihydropyridin-2-one or a salt thereof; and
β-interferon.

20. The combination of claim 19, wherein 3-(2-cyanophenyl)-1-phenyl-5-(2-pyridyl)-1,2-dihydropyridin-2-one or a salt thereof and β-interferon are for separate, simultaneous, or sequential administration.

21. The method of claim 8, wherein the demyelinating disorder is encephalitis, acute disseminated encephalomyelitis, acute demyelinating polyneuropathy (Guillain Bane syndrome), chronic inflammatory demyelinating polyneuropathy, multiple sclerosis, Marchifava-Bignami disease, central pontine myelinolysis, Devic syndrome, Balo disease, HIV-myelopathy, HTLV-myelopathy, progressive multifocal leucoencephalopathy, or a secondary demyelinating disorder.

22. The method of claim 8, wherein the demyelinating disorder is a secondary demyelinating disease which is CNS lupus erythematodes, polyarteritis nodosa, Sjoegren's syndrome, sarcoid granuloma or isolated cerebral vasculitis.

* * * * *